United States Patent
Takeuchi et al.

(10) Patent No.: US 12,013,637 B2
(45) Date of Patent: Jun. 18, 2024

(54) OXIME ESTER COMPOUND AND PHOTOPOLYMERIZATION INITIATOR CONTAINING SAME

(71) Applicant: ADEKA CORPORATION, Tokyo (JP)

(72) Inventors: Yoshitomo Takeuchi, Tokyo (JP); Taiki Mihara, Tokyo (JP); Naomi Sato, Tokyo (JP); Kazushi Matsukawa, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 709 days.

(21) Appl. No.: 17/256,320

(22) PCT Filed: Jun. 27, 2019

(86) PCT No.: PCT/JP2019/025755
§ 371 (c)(1),
(2) Date: Dec. 28, 2020

(87) PCT Pub. No.: WO2020/004601
PCT Pub. Date: Jan. 2, 2020

(65) Prior Publication Data
US 2021/0271163 A1    Sep. 2, 2021

(30) Foreign Application Priority Data

Jun. 29, 2018  (JP) .................................. 2018-125614
Mar. 25, 2019  (JP) .................................. 2019-057429

(51) Int. Cl.
*G03F 7/031* (2006.01)
*C07D 209/14* (2006.01)
*C07D 209/86* (2006.01)
*C08F 2/50* (2006.01)
*G02B 5/22* (2006.01)
*G03F 7/00* (2006.01)

(52) U.S. Cl.
CPC .......... *G03F 7/031* (2013.01); *C07D 209/14* (2013.01); *C07D 209/86* (2013.01); *C08F 2/50* (2013.01); *G02B 5/223* (2013.01); *G03F 7/0007* (2013.01)

(58) Field of Classification Search
CPC .. C07D 209/14; C07D 209/86; C07D 333/54; C07D 307/91
See application file for complete search history.

(56) References Cited

U.S. PATENT DOCUMENTS

| 5,994,359 | A | 11/1999 | Grote et al. |
| 7,534,880 | B2 * | 5/2009 | Norcini ................... G03F 7/031 544/170 |
| 2010/0136467 | A1 | 6/2010 | Matsumoto et al. |
| 2010/0136491 | A1 | 6/2010 | Matsumoto et al. |
| 2012/0149833 | A1 | 6/2012 | Luo |
| 2017/0003589 | A1 | 1/2017 | Yoo et al. |
| 2017/0240755 | A1 * | 8/2017 | Nesvadba ............ C09D 11/107 |
| 2018/0086717 | A1 * | 3/2018 | Hikida ................... B01J 20/262 |
| 2018/0275514 | A1 | 9/2018 | Nara et al. |
| 2019/0018282 | A1 | 1/2019 | Kitajima |
| 2021/0132496 | A1 | 5/2021 | Nara et al. |

FOREIGN PATENT DOCUMENTS

| CN | 103282386 A | 9/2013 |
| DE | 195 48 370 A1 | 7/1997 |
| JP | 2008-94770 A | 4/2008 |
| JP | 2010-526846 A | 8/2010 |
| JP | 2010-527338 A | 8/2010 |
| JP | 2011-225484 A | 11/2011 |
| JP | 2016-79158 A | 5/2016 |
| JP | 2016079158 A * | 5/2016 |
| JP | 2016-206488 A | 12/2016 |
| JP | 2017-179211 A | 10/2017 |
| WO | WO 2015/080503 A1 | 6/2015 |
| WO | WO 2017/033880 A1 | 3/2017 |
| WO | WO 2017/051680 A1 | 3/2017 |
| WO | WO 2017/099019 A1 | 6/2017 |
| WO | WO 2017/164161 A1 | 9/2017 |
| WO | WO 2017/169819 A1 | 10/2017 |
| WO | WO 2017/170473 A1 | 10/2017 |

OTHER PUBLICATIONS

English translation of JP2016079158. (Year: 2016).*

(Continued)

*Primary Examiner* — Chanceity N Robinson
*Assistant Examiner* — Anna Malloy
(74) *Attorney, Agent, or Firm* — Birch, Stewart, Kolasch & Birch, LLP

(57) ABSTRACT

An oxime ester compound is useful as a photopolymerization initiator used in a polymerizable composition. A photopolymerization initiator contains the oxime ester compound. The oxime ester compound contains, in the same molecule: a group represented by the following Formula (I); and a photoradical cleavable group containing no oxime ester group.

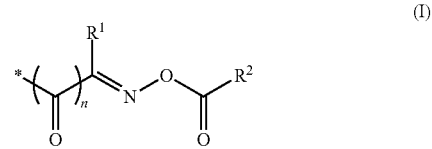

(I)

13 Claims, No Drawings

(56) References Cited

OTHER PUBLICATIONS

Extended European Search Report for corresponding European Application No. 19825412.0, dated Mar. 28, 2022.
Chang et al., "Facile Synthesis of Nitriles From Primary Nitro Compounds Via Nitrolic Acids and Their Esters," Tetrahedron Letters, vol. 37, No. 43, 1996, pp. 7791-7794.
International Search Report, issued in PCT/JP2019/025755, dated Sep. 10, 2019.
Written Opinion of the International Searching Authority, issued in PCT/JP2019/025755, dated Sep. 10, 2019.

* cited by examiner

OXIME ESTER COMPOUND AND PHOTOPOLYMERIZATION INITIATOR CONTAINING SAME

TECHNICAL FIELD

The present invention relates to an oxime ester compound, and a photopolymerization initiator containing the same. More particularly, the present invention relates to: an oxime ester compound that is useful as a photopolymerization initiator used in a polymerizable composition; and a photopolymerization initiator containing the oxime ester compound.

BACKGROUND ART

Polymerizable compositions are obtained by adding a polymerization initiator to an ethylenically unsaturated compound and can be polymerized and cured by irradiation with an energy beam (light); therefore, polymerizable compositions are used in photocurable inks, photosensitive printing boards, various photoresists, and the like.

As polymerization initiators to be used in these polymerizable compositions, Patent Document 1 proposes an oxime ester photopolymerization initiator having a carbazole skeleton, and Patent Document 2 proposes a polymerization initiator that contains an oxime ester compound having a triarylamine skeleton. Colorant-containing polymerizable compositions for color filters and the like are demanded to have a high sensitivity, and resists are required to contain a polymerization initiator at a high concentration.

RELATED ART DOCUMENTS

Patent Documents

[Patent Document 1] JP2010-527338A
[Patent Document 2] WO 2017/033880A1

SUMMARY OF THE INVENTION

Problems to be Solved by the Invention

However, the oxime ester compounds proposed in Patent Documents 1 and 2 cannot attain satisfactory levels of sensitivity, heat resistance (low sublimation) and transparency (high brightness of a color filter) at the same time. A problem to be solved is that a polymerization initiator having a satisfactory sensitivity and a high transmittance in a visible-light region is yet to be developed.

In view of the above, an object of the present invention is to provide: an oxime ester compound that is useful as a photopolymerization initiator used in a polymerizable composition; and a photopolymerization initiator containing the oxime ester compound. The oxime ester compound of the present invention is particularly useful as a polymerization initiator having a high sensitivity and excellent transparency.

Means for Solving the Problems

The present inventors intensively studied to solve the above-described problem and consequently discovered that a compound having the below-described structure solves the problem, thereby completing the present invention.

That is, an oxime ester compound of the present invention is characterized by containing, in the same molecule: a group represented by the following Formula (I); and a photoradical cleavable group containing no oxime ester group:

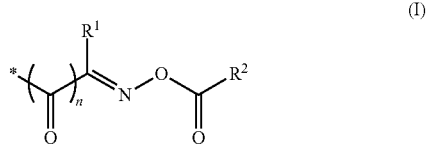
(I)

In Formula (I),
$R^1$ and $R^2$ each independently represent a hydrogen atom, a halogen atom, a nitro group, a cyano group, a hydrocarbon group having 1 to 20 carbon atoms, or a heterocycle-containing group having 2 to 20 carbon atoms;
one or more hydrogen atoms in the groups represented by $R^1$ and $R^2$ are optionally substituted with a halogen atom, a nitro group, a cyano group, a hydroxy group, an amino group, a carboxyl group, a methacryloyl group, an acryloyl group, an epoxy group, a vinyl group, a vinyl ether group, a mercapto group, an isocyanate group, or a heterocycle-containing group having 2 to 20 carbon atoms;
one or more methylene groups in the groups represented by $R^1$ and $R^2$ are optionally substituted with —O—, —CO—, —COO—, —OCO—, —NR$^3$—, —NR$^3$CO—, —S—, —CS—, —SO$_2$—, —SCO—, —COS—, —OCS—, or CSO—, provided that oxygen atoms are not arranged adjacent to one another;
$R^3$ represents a hydrogen atom or a hydrocarbon group having 1 to 20 carbon atoms;
n represents 0 or 1; and
* represents a bond.

The oxime ester compound of the present invention preferably has a structure represented by the following Formula (II):

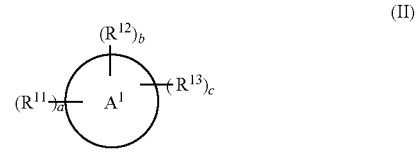
(II)

In Formula (II),
$A^1$ represents an aromatic ring having 6 to 20 carbon atoms;
$R^{11}$ represents a group represented by Formula (I);
$R^{12}$ represents the photoradical cleavable group containing no oxime ester group, a hydrocarbon group having 1 to 20 carbon atoms which is substituted with the photoradical cleavable group containing no oxime ester group, or a heterocycle-containing group having 2 to 20 carbon atoms which is substituted with the photoradical cleavable group containing no oxime ester group;
$R^{13}$ each independently represents a halogen atom, a nitro group, a cyano group, a hydrocarbon group having 1 to 20 carbon atoms, or a heterocycle-containing group having 2 to 20 carbon atoms;
one or more hydrogen atoms in the groups represented by $R^{12}$ and $R^{13}$ are optionally substituted with a halogen atom, a nitro group, a cyano group, a hydroxy group, an amino group, a carboxyl group, a methacryloyl group, an acryloyl group, an epoxy group, a vinyl group, a vinyl ether group, a mercapto group, an isocyanate group, or a heterocycle-containing group having 2 to 20 carbon atoms;

one or more methylene groups in the groups represented by $R^{12}$ and $R^{13}$ are optionally substituted with —O—, —CO—, —COO—, —OCO—, —NR$^{14}$—, —NR$^{14}$CO—, —S—, —CS—, —SO$_2$—, —SCO—, —COS—, —OCS—, or CSO—, provided that oxygen atoms are not arranged adjacent to one another;

$R^{14}$ represents a hydrogen atom or a hydrocarbon group having 1 to 20 carbon atoms;

a represents an integer of 1 to 20 and, when a is an integer of 2 or larger, plural $R^{11}$s are optionally the same or different;

b represents an integer of 1 to 20 and, when b is an integer of 2 or larger, plural $R^{12}$s are optionally the same or different;

c represents an integer of 0 to 20 and, when c is an integer of 2 or larger, plural $R^{13}$s are optionally the same or different; and (a+b+c) is 20 or less.

In the oxime ester compound of the present invention, $A^1$ is preferably a structure represented by the following Formula (IIIα) or (IIIβ):

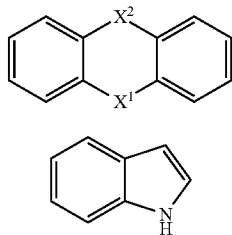

In Formula (IIIα), $X^1$ represents an oxygen atom, a sulfur atom, a selenium atom, $C^{21}R^{22}$, CO, NR$^{23}$ or PR$^{24}$;

$X^2$ represents a single bond, no bond, an oxygen atom, a sulfur atom, a selenium atom, CR$^{21}$R$^{22}$, CO, NR$^{23}$, or PR$^{24}$;

$R^{21}$, $R^{22}$, $R^{23}$ and $R^{24}$ each independently represent a hydrogen atom, a hydrocarbon group having 1 to 20 carbon atoms, or a heterocycle-containing group having 2 to 20 carbon atoms;

hydrogen atoms in the groups represented by $R^{21}$, $R^{22}$, $R^{23}$ and $R^{24}$ are optionally substituted with a halogen atom, a nitro group, a cyan group, a hydroxy group, a carboxyl group, or a heterocyclic group having 2 to 20 carbon atoms; and one or more methylene groups in the groups represented by $R^{21}$, $R^{22}$, $R^{23}$ and $R^{24}$ are optionally substituted with —O—, provided that oxygen atoms are not arranged adjacent to one another.

Further, in the oxime ester compound of the present invention, $R^{12}$ in Formula (II) is preferably the photoradical cleavable group containing no oxime ester group.

Still further, in the oxime ester compound of the present invention, the photoradical cleavable group containing no oxime ester group is a group represented by the following Formula (IVα), (IVβ), (IVγ), (IVδ), (IVε), (IVζ), or (IVθ):

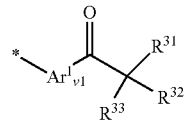

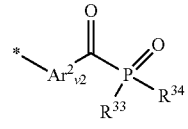

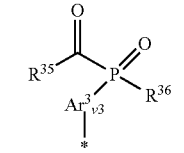

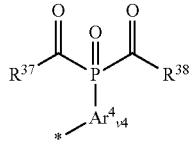

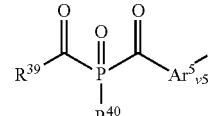

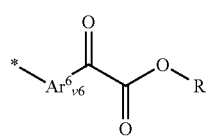

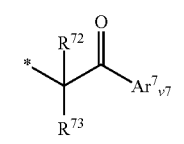

In Formulae (IVα) to (IVθ), $R^{31}$ represents OR$^{41}$, NR$^{42}$R$^{43}$, or a heterocycle-containing group having 2 to 20 carbon atoms;

$R^{32}$ and $R^{33}$ each represent $R^{41}$ or OR$^{41}$;

$R^{32}$ and $R^{33}$ are optionally bound together to form a ring;

$R^{41}$ represents a hydrogen atom or a hydrocarbon group having 1 to 20 carbon atoms;

$R^{42}$ and $R^{43}$ each represent a hydrocarbon group having 1 to 20 carbon atoms;

$R^{71}$ represents a hydrocarbon group having 1 to 20 carbon atoms;

$R^{72}$ and $R^{73}$ each represent $R^{41}$ or OR$^{41}$;

$R^{34}$, $R^{35}$, $R^{36}$, $R^{37}$, $R^{38}$, $R^{39}$, $R^{40}$, Ar$^1$, Ar$^2$, Ar$^3$, Ar$^4$, Ar$^5$, Ar$^6$, and Ar$^7$ each represent an aryl group having 6 to 20 carbon atoms;

v1, v2, v3, v4, v5, v6, and v7 each represent 0 or 1; and

* represents a bond.

A polymerization initiator of the present invention is characterized by containing the oxime ester compound of the present invention.

A polymerizable composition of the present invention is characterized by containing: (A) the polymerization initiator of the present invention; and (B) an ethylenically unsaturated compound.

The polymerizable composition of the present invention preferably further contains (C) a colorant.

A cured product of the present invention is characterized in that it is obtained from the polymerizable composition of the present invention.

A color filter of the present invention is characterized by including the cured product of the present invention.

A display device of the present invention is characterized by including the color filter of the present invention.

A method of producing a cured product according to the present invention is characterized by including irradiating the polymerizable composition of the present invention with light, or curing the polymerizable composition of the present invention by heating.

Effects of the Invention

According to the present invention, an oxime ester compound that is useful as a photopolymerization initiator used in a polymerizable composition, and a photopolymerization initiator containing the oxime ester compound can be provided. The oxime ester compound of the present invention is a novel compound that has a high sensitivity and excellent transparency and is thus useful as a polymerization initiator. By using a polymerizable composition containing this polymerization initiator, a color filter having a high brightness and a display device including the color filter can be provided, which is useful.

MODE FOR CARRYING OUT THE INVENTION

The oxime ester compound of the present invention and a photopolymerization initiator containing the same, as well as a polymerizable composition containing the photopolymerization initiator, a cured product thereof, a color filter, and a display device will now be described in detail based on preferred embodiments.

The oxime ester compound of the present invention is a compound that contains, in the same molecule: a group represented by the following Formula (I); and a photoradical cleavable group containing no oxime ester group:

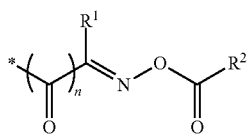

(I)

The oxime ester compound of the present invention has geometric isomers with respect to the double bond of oxime; however, these geometric isomers are not distinguished from one another. In other words, in the present specification, the oxime ester compound of the present invention and exemplary compounds thereof each represent a mixture of one or more of the geometric isomers and are not restricted to a structure of a specific isomer. The term "photoradical cleavable group containing no oxime ester group" used herein means a group other than an oxime ester group that is cleaved and generates a radical when irradiated with light (active energy) such as ultraviolet radiation.

In Formula (I), $R^1$ and $R^2$ each independently represent a hydrogen atom, a halogen atom, a nitro group, a cyano group, a hydrocarbon group having 1 to 20 carbon atoms, or a heterocycle-containing group having 2 to 20 carbon atoms;

one or more hydrogen atoms in the groups represented by $R^1$ and $R^2$ are optionally substituted with a halogen atom, a nitro group, a cyano group, a hydroxy group, an amino group, a carboxyl group, a methacryloyl group, an acryloyl group, an epoxy group, a vinyl group, a vinyl ether group, a mercapto group, an isocyanate group, or a heterocycle-containing group having 2 to 20 carbon atoms;

one or more methylene groups in the groups represented by $R^1$ and $R^2$ are optionally substituted with —O—, —CO—, —COO—, —OCO—, —NR$^3$—, —NR$^3$CO—, —S—, —CS—, —SO$_2$—, —SCO—, —COS—, —OCS—, or CSO—, provided that oxygen atoms are not arranged adjacent to one another;

$R^3$ represents a hydrogen atom or a hydrocarbon group having 1 to 20 carbon atoms;

n represents 0 or 1; and

* represents a bond.

The hydrocarbon group having 1 to 20 carbon atoms which is represented by $R^1$ to $R^3$ in Formula (I) is not particularly restricted; however, it is preferably, for example, an alkyl group having 1 to 20 carbon atoms, an alkenyl group having 2 to 20 carbon atoms, a cycloalkyl group having 3 to 20 carbon atoms, a cycloalkylalkyl group having 4 to 20 carbon atoms, an aryl group having 6 to 20 carbon atoms, or an arylalkyl group having 7 to 20 carbon atoms.

Examples of the alkyl group having 1 to 20 carbon atoms include methyl, ethyl, propyl, isopropyl, butyl, isobutyl, s-butyl, t-butyl, amyl, isoamyl, t-amyl, hexyl, heptyl, octyl, isooctyl, 2-ethylhexyl, t-octyl, nonyl, isononyl, decyl, isodecyl, undecyl, dodecyl, tetradecyl, hexadecyl, octadecyl, and icosyl.

Examples of the alkenyl group having 2 to 20 carbon atoms include vinyl, ethylene, 2-propenyl, 3-butenyl, 2-butenyl, 4-pentenyl, 3-pentenyl, 2-hexenyl, 3-hexenyl, 5-hexenyl, 2-heptenyl, 3-heptenyl, 4-heptenyl, 3-octenyl, 3-nonenyl, 4-decenyl, 3-undecenyl, 4-dodecenyl, and 4,8,12-tetradecatrienylallyl.

The "cycloalkyl group having 3 to 20 carbon atoms" means a saturated monocyclic or saturated polycyclic alkyl group having 3 to 20 carbon atoms. Examples thereof include cyclopropyl, cyclobutyl, cyclopentyl, cyclohexyl, cycloheptyl, cyclooctyl, cyclononyl, cyclodecyl, adamantly, decahydronaphthyl, octahydropentalene, and bicyclo[1.1.1]pentanyl.

The "cycloalkylalkyl group having 4 to 20 carbon atoms" means a group having 4 to 20 carbon atoms in which a hydrogen atom of an alkyl group is substituted with a cycloalkyl group. Examples thereof include cyclopropylmethyl, 2-cyclobutylethyl, 3-cyclopentylpropyl, 4-cyclohexylbutyl, cycloheptylmethyl, cyclooctylmethyl, 2-cyclononylethyl, 2-cyclodecylethyl, 3-3-adamantylpropyl, and decahydronaphthylpropyl.

Examples of the aryl group having 6 to 20 carbon atoms include phenyl, tolyl, xylyl, ethylphenyl, naphthyl, anthryl and phenanthrenyl, as well as phenyl, biphenylyl, naphthyl and anthryl which are substituted with at least one of the above-described alkyl groups.

The "arylalkyl group having 7 to 20 carbon atoms" means a group having 7 to 20 carbon atoms in which a hydrogen atom of an alkyl group is substituted with an aryl group. Examples thereof include benzyl, α-methylbenzyl, α,α-dimethylbenzyl, phenylethyl, and naphthylpropyl.

Among the hydrocarbon groups having 1 to 20 carbon atoms, from the standpoint of attaining good sensitivity as a polymerization initiator, alkyl groups having 1 to 12 carbon atoms, alkenyl groups having 2 to 10 carbon atoms, cycloalkyl groups having 3 to 10 carbon atoms, cycloalkylalkyl groups having 4 to 15 carbon atoms, aryl groups having 6 to 15 carbon atoms, and arylalkyl groups having 7 to 15 carbon atoms are particularly preferred.

In Formula (I), examples of the heterocycle-containing group having 2 to 20 carbon atoms which is represented by $R^1$ and $R^2$ and examples of the heterocycle-containing group having 2 to 20 carbon atoms which is represented by $R^1$ and $R^2$ in which a hydrogen atom is optionally substituted include pyrrolyl, pyridyl, pyridylethyl, pyrimidyl, pyridazyl, piperadyl, piperidyl, pyranyl, pyranylethyl, pyrazolyl, triazyl, triazylmethyl, pyrrolyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, julolidyl, morpholinyl, thiomorpholinyl, 2-pyrrolidinon-1-yl, 2-piperidon-1-yl, 2,4-dioxyimidazolidin-3-yl, and 2,4-dioxyoxazolidin-3-yl.

The methylene groups in the groups represented by $R^1$ and $R^2$ in Formula (I) are optionally substituted with —O—, —CO—, —COO—, —OCO—, —NR$^3$—, —NR$^3$CO—, —S—, —CS—, —SO$_2$—, —SCO—, —COS—, —OCS—, or CSO—, and this substitution may be made with one or more substituents. In the case of groups that can be substituted consecutively, two or more of such groups are optionally substituted consecutively, provided that oxygen atoms are not arranged adjacent to one another.

Examples of the halogen atom in Formula (I) include fluorine, chlorine, bromine, and iodine.

A cured product using a compound in which n=1 in Formula (I) as (A) a polymerization initiator is preferred since it has excellent transparency and brightness.

A compound in which $R^1$ of Formula (I) is an alkyl group having 1 to 12 carbon atoms is preferred since it has a high solubility in organic solvents, and a compound in which $R^2$ of Formula (I) is a methyl group, an ethyl group or a phenyl group is preferred since it has a high reactivity.

Among the heterocycle-containing group having 2 to 20 carbon atoms, heterocycle-containing groups having 2 to 10 carbon atoms are particularly preferred from the standpoint of attaining good sensitivity as a polymerization initiator.

The oxime ester compound of the present invention preferably has a structure represented by the following Formula (II):

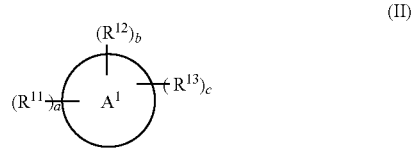

(II)

In Formula (II), $A^1$ represents an aromatic ring having 6 to 20 carbon atoms;

$R^{11}$ represents a group represented by Formula (I);

$R^{12}$ represents the photoradical cleavable group containing no oxime ester group, a hydrocarbon group having 1 to 20 carbon atoms which is substituted with the photoradical cleavable group containing no oxime ester group, or a heterocycle-containing group having 2 to 20 carbon atoms which is substituted with the photoradical cleavable group containing no oxime ester group;

$R^{13}$ each independently represents a halogen atom, a nitro group, a cyano group, a hydrocarbon group having 1 to 20 carbon atoms, or a heterocycle-containing group having 2 to 20 carbon atoms;

one or more hydrogen atoms in the groups represented by $R^{12}$ and $R^{13}$ are optionally substituted with a halogen atom, a nitro group, a cyano group, a hydroxy group, an amino group, a carboxyl group, a methacryloyl group, an acryloyl group, an epoxy group, a vinyl group, a vinyl ether group, a mercapto group, an isocyanate group, or a heterocycle-containing group having 2 to 20 carbon atoms;

one or more methylene groups in the groups represented by $R^{12}$ and $R^{13}$ are optionally substituted with —O—, —CO—, —COO—, —OCO—, —NR$^{14}$—, —NR$^{14}$CO—, —S—, —CS—, —SO$_2$—, —SCO—, —COS—, —OCS—, or CSO—, provided that oxygen atoms are not arranged adjacent to one another;

$R^{14}$ represents a hydrogen atom or a hydrocarbon group having 1 to 20 carbon atoms;

a represents an integer of 1 to 20 and, when a is an integer of 2 or larger, plural $R^{11}$s are optionally the same or different;

b represents an integer of 1 to 20 and, when b is an integer of 2 or larger, plural $R^{12}$s are optionally the same or different;

c represents an integer of 0 to 20 and, when c is an integer of 2 or larger, plural $R^{13}$s are optionally the same or different; and (a+b+c) is 20 or less.

The "aromatic ring having 6 to 20 carbon atoms" represented by $A^1$ in Formula (II) means an aromatic ring-containing structure having 6 to 20 carbon atoms, and it is a group that contains an aromatic hydrocarbon ring or an aromatic heterocycle.

The term "aromatic hydrocarbon ring" used herein means a structure that contains an aromatic hydrocarbon ring but not an aromatic heterocycle, and examples thereof include cyclobutadiene, benzene, cyclooctatetraene, cyclotetradecaheptaene, cyclooctadecanonaene, naphthalene, anthracene, triphenylamine, diphenyl sulfide, and fluorene.

The term "aromatic heterocycle" used herein means a structure that contains an aromatic heterocycle, and examples thereof include furan, thiophene, pyrrole, pyrazole, imidazole, pyridine, pyridazine, pyrimidine, pyrazine, carbazole and indole, as well as the above-exemplified structures.

Examples of the hydrocarbon group having 1 to 20 carbon atoms which is represented by $R^{12}$ and $R^{13}$ in Formula (II) include the same ones as those exemplified above for the hydrocarbon group having 1 to 20 carbon atoms which is represented by $R^1$ and the like of Formula (I).

In Formula (II), examples of the heterocycle-containing group having 2 to 20 carbon atoms which is represented by $R^{12}$ and $R^{13}$ and examples of the heterocycle-containing group having 2 to 20 carbon atoms which is represented by $R^{12}$ and $R^{13}$ in which a hydrogen atom is optionally substituted include the same ones as those exemplified above for the heterocycle-containing group having 2 to 20 carbon atoms which is represented by $R^1$ and the like of Formula (I).

The methylene groups in the groups represented by $R^{12}$ and $R^{13}$ in Formula (II) are optionally substituted with —O—, —CO—, —COO—, —OCO—, —NR$^{14}$—, —NR$^{14}$CO—, —S—, —CS—, —SO$_2$—, —SCO—, —COS—, —OCS—, or CSO—, and this substitution may be made with one or more substituents. In the case of groups that can be substituted consecutively, two or more of such groups are optionally substituted consecutively, provided that oxygen atoms are not arranged adjacent to one another.

In Formula (II), $R^{14}$ represents a hydrogen atom or a hydrocarbon group having 1 to 20 carbon atoms, and examples of the hydrocarbon group having 1 to 20 carbon atoms include the same ones as those exemplified above for $R^1$ to $R^3$.

Examples of the halogen atom in Formula (II) include fluorine, chlorine, bromine, and iodine.

A compound in which $A^1$ of Formula (II) is diphenyl sulfide is preferred since it shows a high sensitivity and excellent transparency when used as a polymerization initiator.

A compound in which $A^1$ of Formula (II) is fluorene is preferred since it shows a high sensitivity and excellent transparency when used as a polymerization initiator.

A compound in which $A^1$ of Formula (II) is carbazole is preferred since it not only shows a high sensitivity to a light source having a long wavelength of 360 nm or longer when used as a polymerization initiator, but also maintains a high sensitivity even when used in combination with a pigment and the like.

A compound in which $A^1$ of Formula (II) is indole is preferred since it shows a high sensitivity and excellent transparency when used as a polymerization initiator.

In Formula (II), a represents an integer of 1 to 20 and, when a is an integer of 2 or larger, plural $R^{11}$s are optionally the same or different; b represents an integer of 1 to 20 and, when b is an integer of 2 or larger, plural $R^{12}$s are optionally the same or different; c represents an integer of 0 to 20 and, when c is an integer of 2 or larger, plural $R^{13}$s are optionally the same or different; and (a+b+c) is 20 or less. In the oxime ester compound of the present invention, a compound in which a and b of Formula (II) are each 1 to 3 is preferred since it has excellent transparency and sensitivity when used as a polymerization initiator, and a compound in which a and b are both 1 is particularly preferred. In the oxime ester compound of the present invention, a compound in which $R^{12}$ of Formula (II) is the above-described photoradical cleavable group containing no oxime ester group is also preferred since it has excellent sensitivity.

A compound in which c of Formula (II) is 0 to 3 is preferred since it has excellent transparency and sensitivity when used as a polymerization initiator, and a compound in which c is 0 or 1 is particularly preferred.

In the oxime ester compound of the present invention, $A^1$ is preferably a structure represented by the following Formula (IIIα) or (IIIβ):

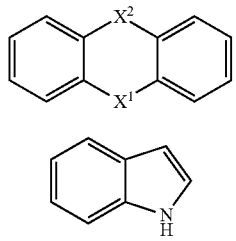

(IIIα)

(IIIβ)

In Formula (IIIα), $X^1$ represents an oxygen atom, a sulfur atom, a selenium atom, $CR^{21}R^{22}$, CO, $NR^{23}$, or $PR^{24}$; $X^2$ represents a single bond, no bond, an oxygen atom, a sulfur atom, a selenium atom, $CR^{21}R^{22}$, CO, $NR^{23}$, or $PR^{24}$; $R^{21}$, $R^{22}$, $R^{23}$ and $R^{24}$ each independently represent a hydrogen atom, a hydrocarbon group having 1 to 20 carbon atoms, or a heterocycle-containing group having 2 to 20 carbon atoms; hydrogen atoms in the groups represented by $R^{21}$, $R^{22}$, $R^{23}$ and $R^{24}$ are optionally substituted with a halogen atom, a nitro group, a cyan group, a hydroxy group, a carboxyl group, or a heterocyclic group having 2 to 20 carbon atoms; and one or more methylene groups in the groups represented by $R^{21}$, $R^{22}$, $R^{23}$ and $R^{24}$ are optionally substituted with —O—, provided that oxygen atoms are not arranged adjacent to one another.

Examples of the hydrocarbon group having 1 to 20 carbon atoms which is represented by $R^{21}$ and $R^{24}$ in Formula (IIIα) include the same ones as those exemplified above for the hydrocarbon group having 1 to 20 carbon atoms which is represented by $R^1$ and the like of Formula (1).

In Formula (IIIα), examples of the heterocycle-containing group having 2 to 20 carbon atoms which is represented by $R^{21}$ to $R^{24}$ and examples of the heterocycle-containing group having 2 to 20 carbon atoms which is represented by $R^{21}$ to $R^{24}$ in which a hydrogen atom is optionally substituted include the same ones as those exemplified above for the heterocycle-containing group having 2 to 20 carbon atoms which is represented by $R^1$ and the like of Formula (1).

Preferred structures represented by Formula (IIIα) are, for example, diphenyl sulfide (wherein, $X^1$ is a sulfur atom, and $X^2$ represents no bond), fluorene (wherein, $X^1$ is $C^{21}R^{22}$, and $X^2$ is a single bond), and carbazole (wherein, $X^1$ is a sulfur atom, and $X^2$ is a single bond), since these structures provide good sensitivity.

A compound in which $X^2$ of Formula (IIIα) is a single bond is preferred since it shows excellent sensitivity when used as a polymerization initiator.

Examples of the halogen atom in Formula (IIIα) include fluorine, chlorine, bromine, and iodine.

When $X^2$ in Formula (IIIα) represents no bond, the structure represented by Formula (IIIα) means a group represented by the following Formula (IIIα'):

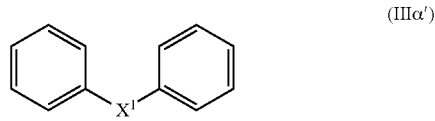

(IIIα')

The photoradical cleavable group is not particularly restricted; however, it is preferably a group represented by any of the following Formulae (IVα) to (IVθ) since such a group has a high activity to ultraviolet radiation.

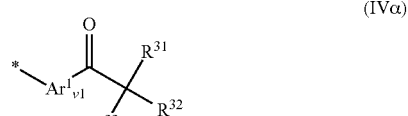

(IVα)

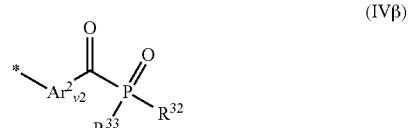

(IVβ)

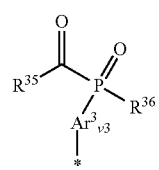 (IVγ)

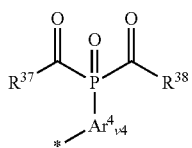 (IVδ)

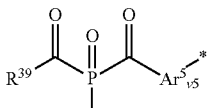 (IVε)

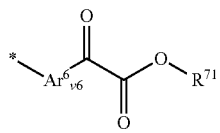 (IVζ)

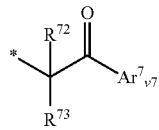 (IVθ)

In Formulae (IVα) to (IVθ), $R^{31}$ represents $OR^{41}$, $NR^{42}R^{43}$, or a heterocycle-containing group having 2 to 20 carbon atoms; $R^{32}$ and $R^{33}$ each represent $R^{41}$ or $OR^{41}$; $R^{32}$ and $R^{33}$ are optionally bound together to form a ring; $R^{41}$ represents a hydrogen atom or a hydrocarbon group having 1 to 20 carbon atoms; $R^{42}$ and $R^{43}$ each represent a hydrocarbon group having 1 to 20 carbon atoms; $R^{71}$ represents a hydrocarbon group having 1 to 20 carbon atoms; $R^{72}$ and $R^{73}$ each represent $R^{41}$ or $OR^{41}$; $R^{34}$, $R^{35}$, $R^{36}$, $R^{37}$, $R^{38}$, $R^{39}$, $R^{40}$, $Ar^1$, $Ar^2$, $Ar^3$, $Ar^4$, $Ar^5$, $Ar^6$, and $Ar^7$ each represent an aryl group having 6 to 20 carbon atoms; v1, v2, v3, v4, v5, v6, and v7 each represent 0 or 1; and * represents a bond.

Examples of the heterocycle-containing group having 2 to 20 carbon atoms which is represented by $R^{31}$ in Formula (IVα) include the same ones as those exemplified above for $R^1$ and the like of Formula (1). The heterocycle-containing group having 2 to 20 carbon atoms is preferably, for example, a nitrogen atom-containing heterocycle. Examples of the nitrogen atom-containing heterocycle include an aziridine ring, an azetidine ring, an azolidine ring, an azole ring, an azinane ring, an azepane ring, a morpholine ring, and a thiazine ring. From the standpoint of attaining excellent photocleavability, a morpholine ring and a thiazine ring are particularly preferred, and a morpholine ring is especially preferred.

Examples of the ring formed by $R^{32}$ and $R^{33}$ in Formula (IVα) include: saturated alicyclic rings, such as a cyclopentane ring, a cyclohexane ring, a cycloheptane ring, and a cyclooctane ring; the above-described aromatic hydrocarbon rings; and the above-described heterocycles. The ring is preferably a saturated alicyclic ring from the standpoint of attaining a high transparency and a high solubility in solvents, particularly preferably a cyclohexane ring from the standpoint of attaining a high safety of the compound.

Examples of the hydrocarbon group having 1 to 20 carbon atoms which is represented by $R^{41}$ to $R^{43}$ and $R^{71}$ in Formula (IVα) include the same ones as those exemplified above for $R^1$ and the like of Formula (1).

Examples of the aryl group having 6 to 20 carbon atoms which is represented by $R^{34}$ to $R^{40}$ and $Ar^1$ to $Ar^7$ in Formulae (IVα) to (IVθ) include the same ones as those exemplified above for $R^1$ and the like of Formula (1).

A compound in which the photoradical cleavable group containing no oxime ester group is a group represented by Formula (IVα) has excellent sensitivity and is thus preferred. A compound in which $R^{31}$ of Formula (IVα) is $OR^{41}$ or $NR^{42}R^{43}$ is more preferred, and a compound in which $R^{31}$ of Formula (IVα) is $NR^{42}R^{43}$ is particularly preferred.

Examples of preferred photoradical cleavable groups include the following (IVα1) to (IVα5), (IVβ1), (IVγ1), (IVδ1), and (IVε1). Thereamong, the photoradical cleavable groups represented by (IVα1) to (IVα5) are preferred because of their high sensitivity. When a light source including a UV light in a long-wavelength range of 365 nm or longer is used, the photoradical cleavable groups represented by (IVβ1), (IVγ1), (IVδ1) and (IVε1) are preferred.

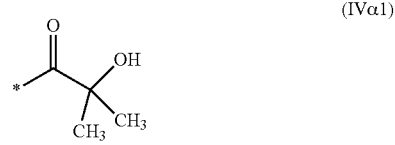 (IVα1)

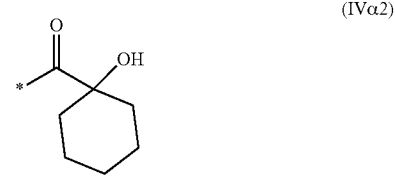 (IVα2)

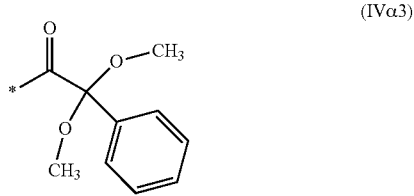 (IVα3)

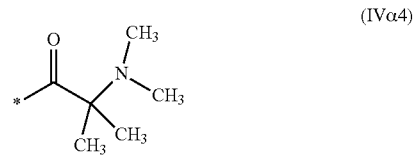 (IVα4)

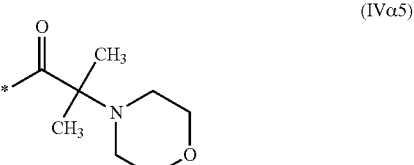 (IVα5)

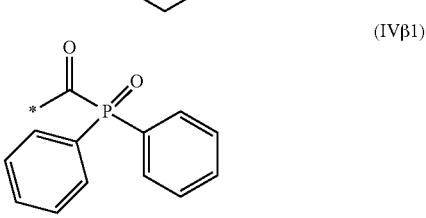 (IVβ1)

-continued

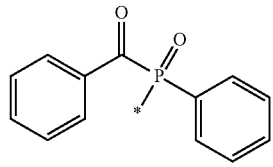
(IVγ1)

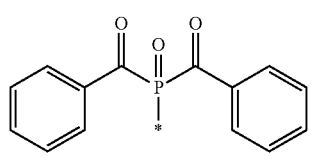
(IVδ1)

-continued

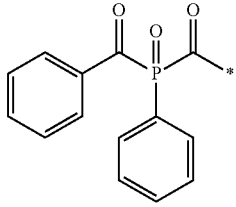
(IVε1)

Preferred specific examples of the oxime ester compound of the present invention include the following compounds No. 1-1 to No. 1-76, No. 2-1 to No. 2-100, No. 3-1 to No. 3-70, No. 4-1 to No. 4-72, No. 5-1 to No. 5-68, and No. 6-1 to No. 6-11. It is noted here, however, that the oxime ester compound of the present invention is not restricted to the following compounds by any means.

Compound No. 1-1

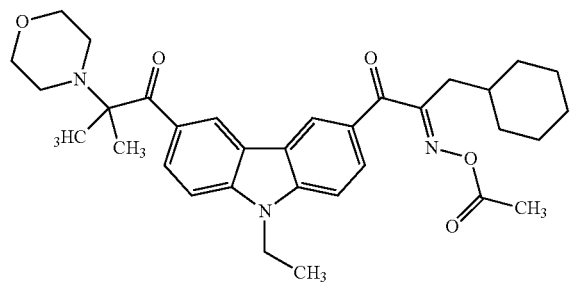

Compound No. 1-2

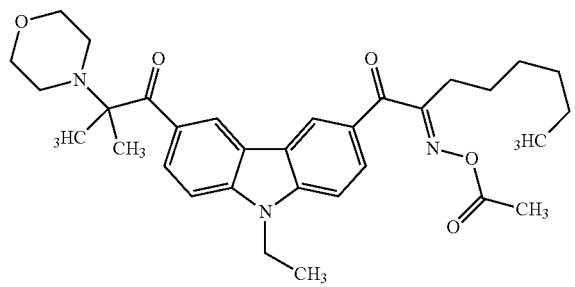

Compound No. 1-3

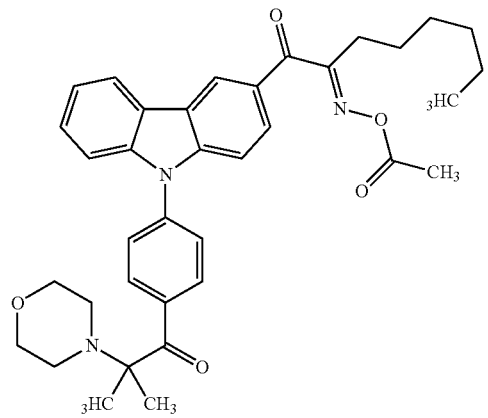

Compound No. 1-4

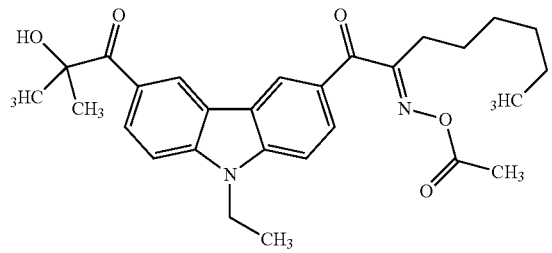

-continued
Compound No. 1-5
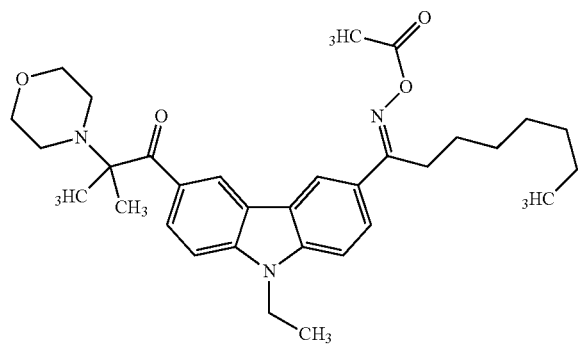
Compound No. 1-6
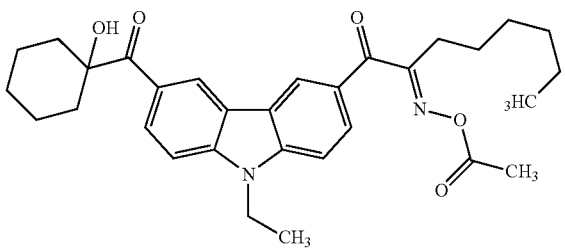
Compound No. 1-7
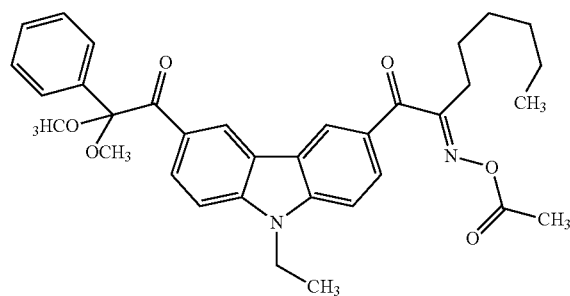
Compound No. 1-8
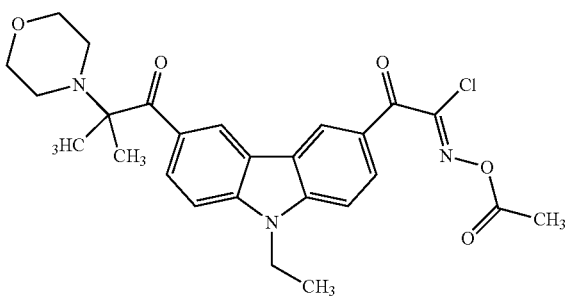
Compound No. 1-9
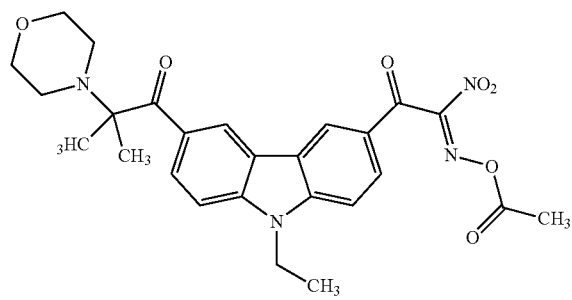
Compound No. 1-10
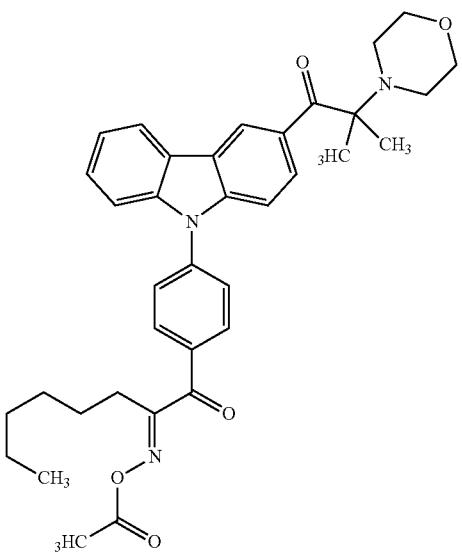

-continued
Compound No. 1-11
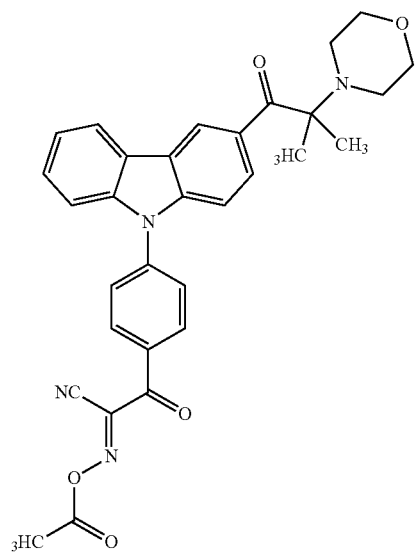
Compound No. 1-12
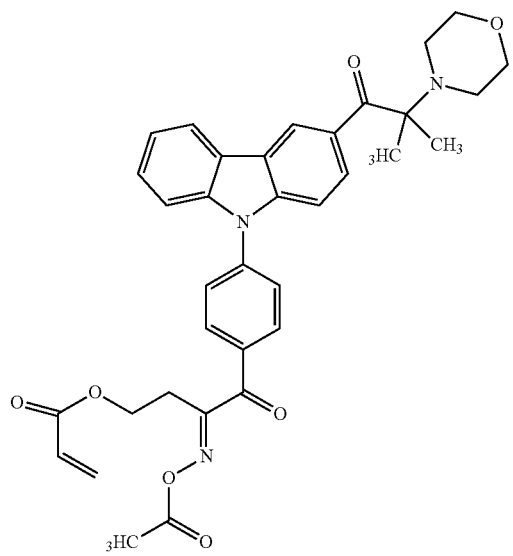
Compound No. 1-13
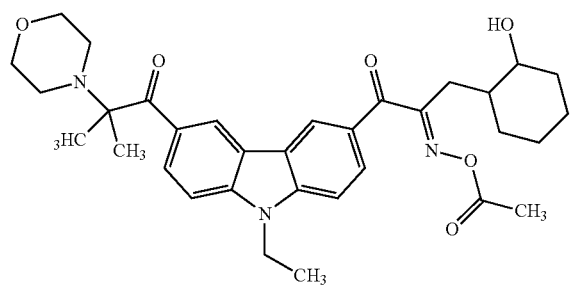
Compound No. 1-14
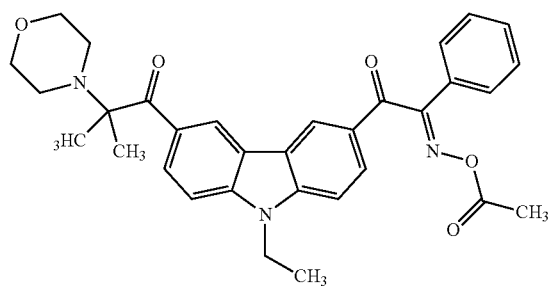
Compound No. 1-15
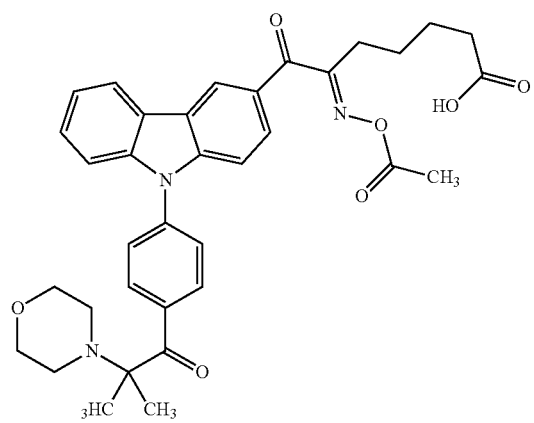
Compound No. 1-16
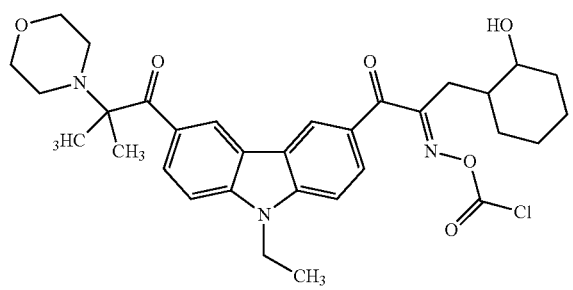

-continued
Compound No. 1-17
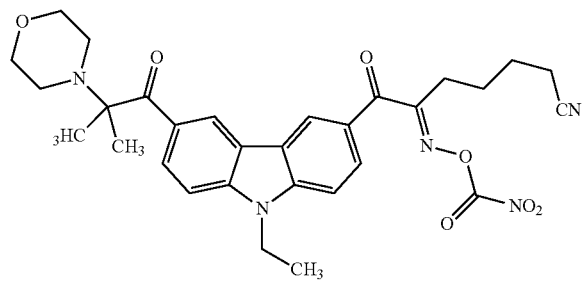
Compound No. 1-18
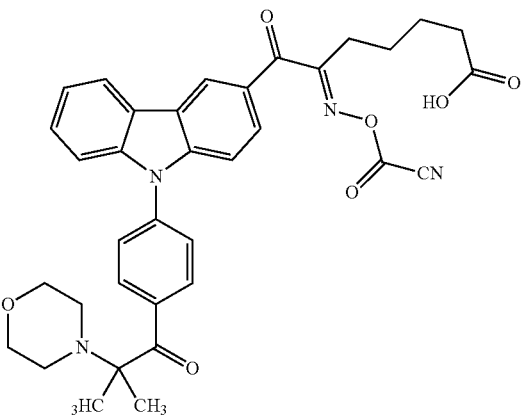
Compound No. 1-19
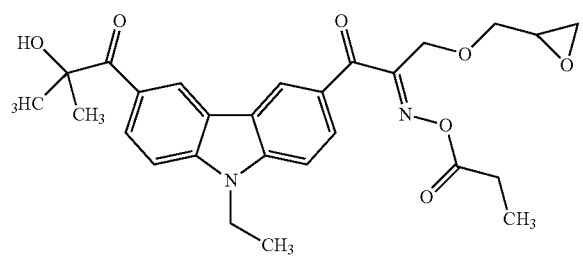
Compound No. 1-20
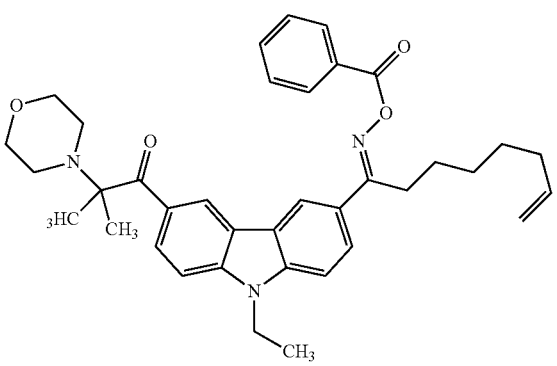
Compound No. 1-21
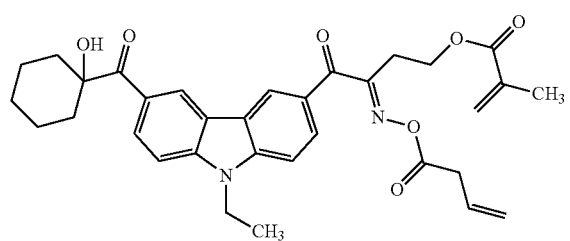
Compound No. 1-22
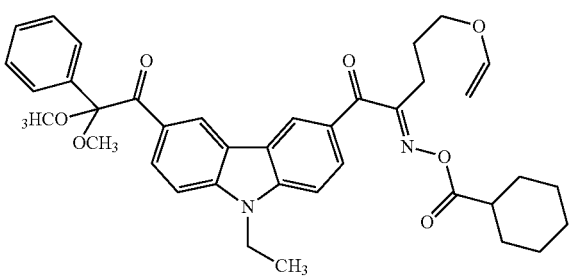
Compound No. 1-23
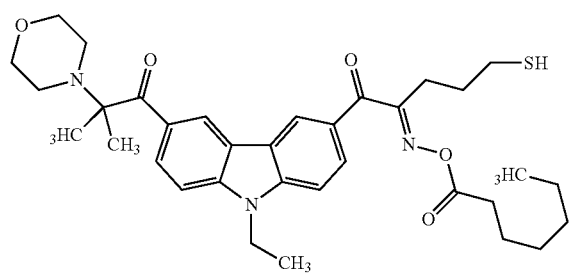
Compound No. 1-24
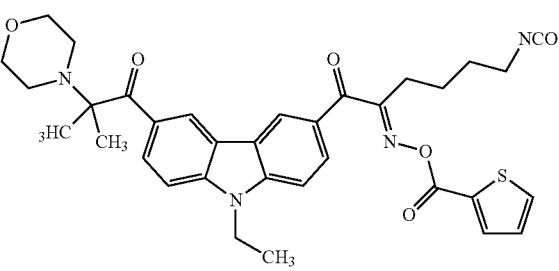

Compound No. 1-25
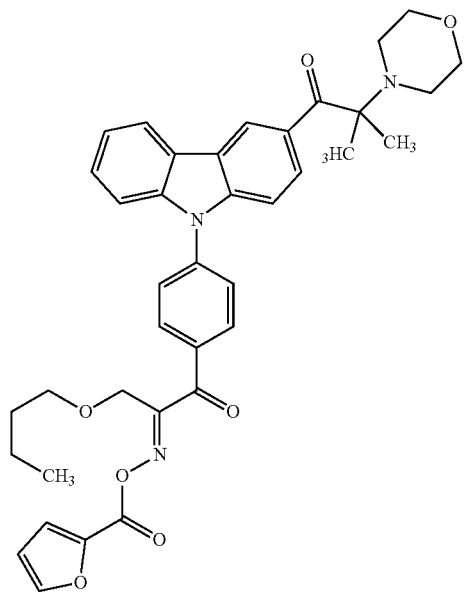
Compound No. 1-26
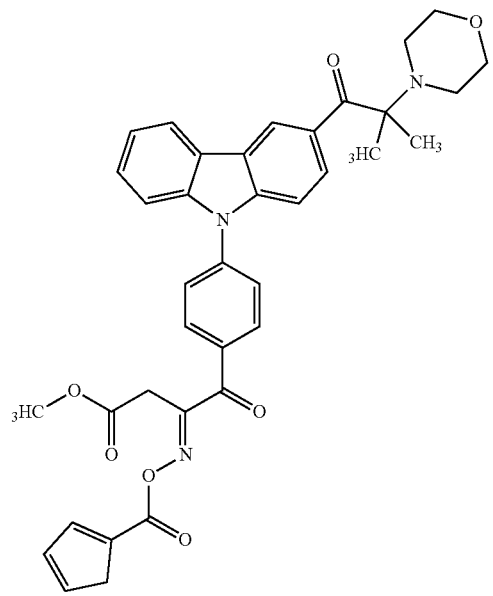
Compound No. 1-27
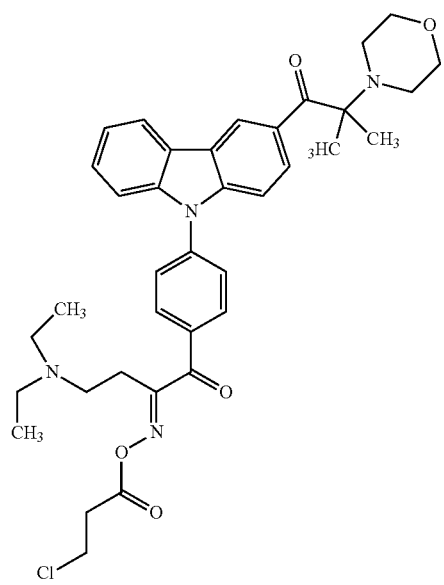
Compound No. 1-28
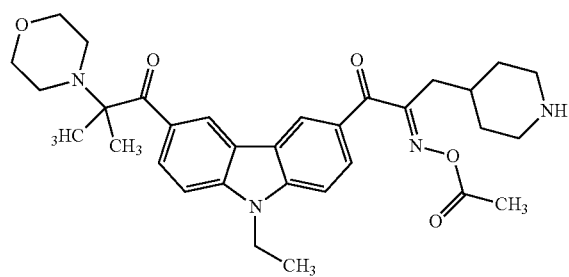

-continued
Compound No. 1-29
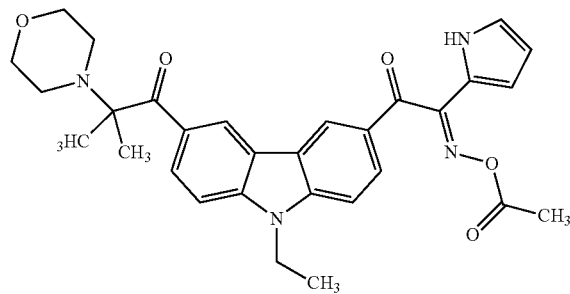
Compound No. 1-30
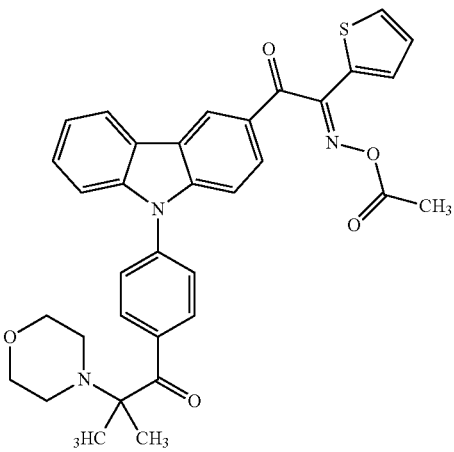
Compound No. 1-31
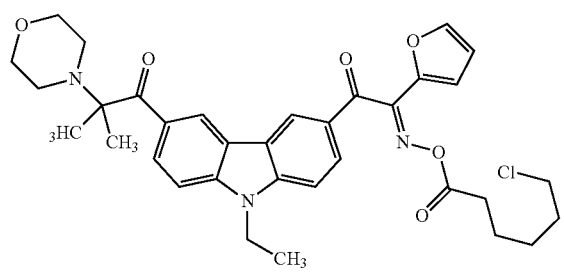
Compound No. 1-32
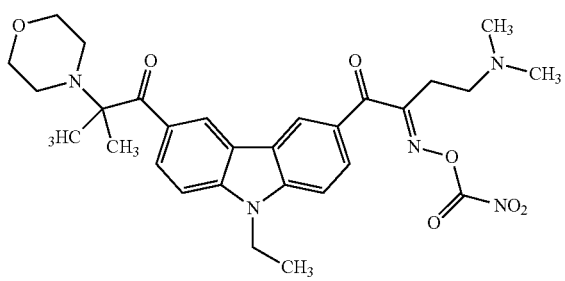
Compound No. 1-33
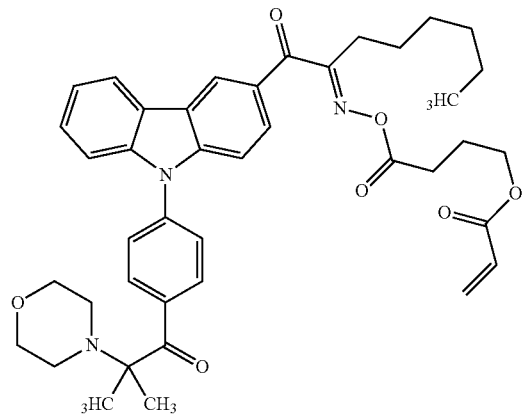
Compound No. 1-34
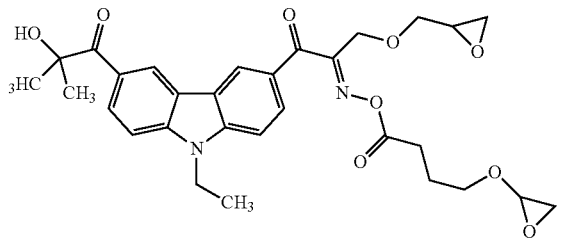
Compound No. 1-35
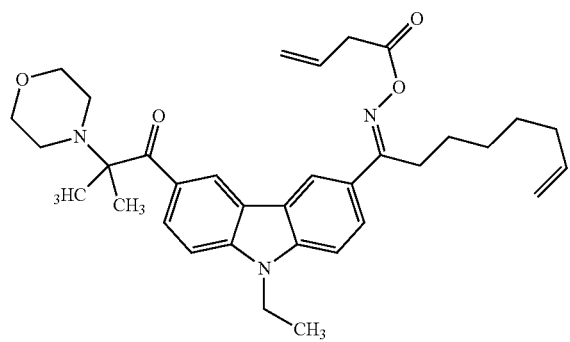
Compound No. 1-36
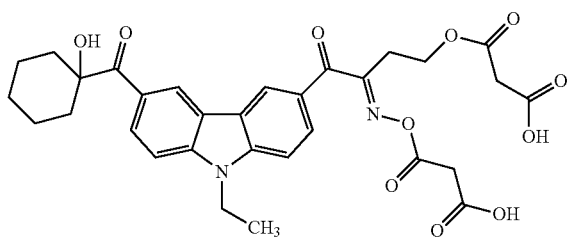

Compound No. 1-37
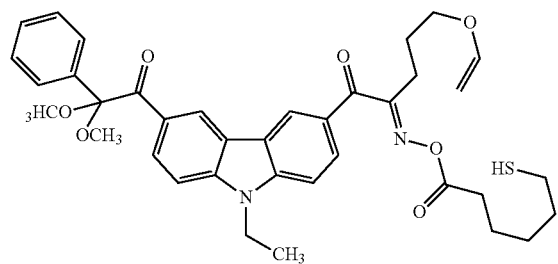
Compound No. 1-38
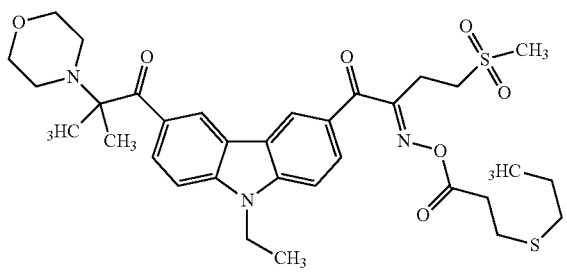
Compound No. 1-39
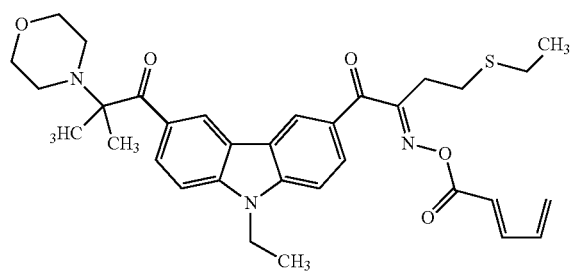
Compound No. 1-40
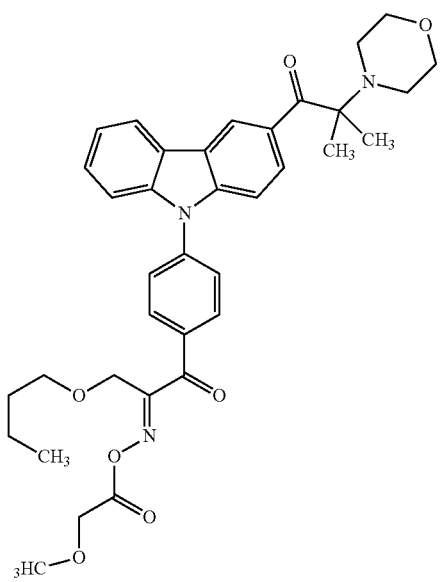
Compound No. 1-41
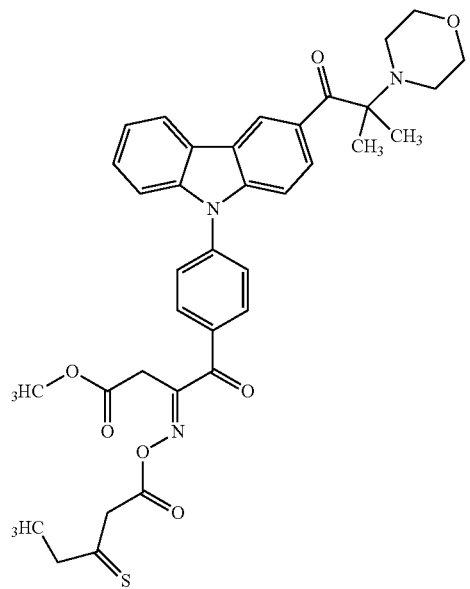
Compound No. 1-42
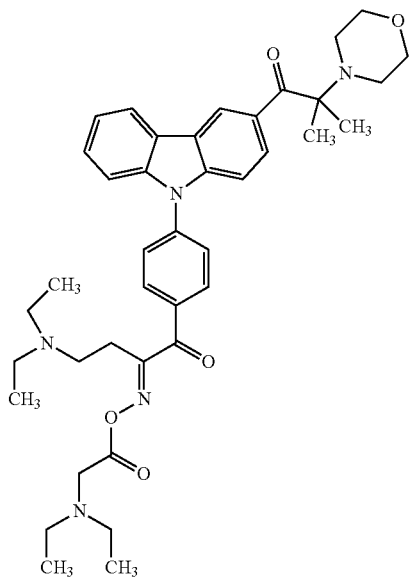

-continued
Compound No. 1-43
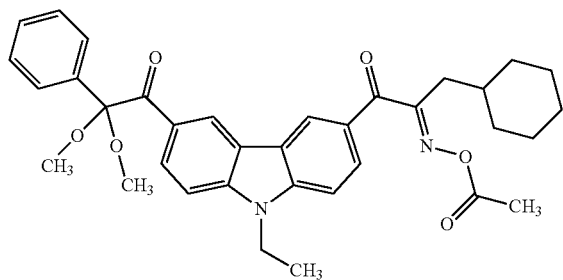
Compound No. 1-44
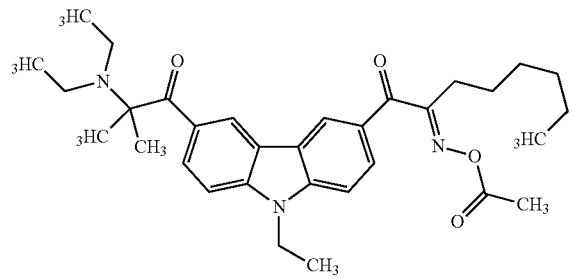
Compound No. 1-45
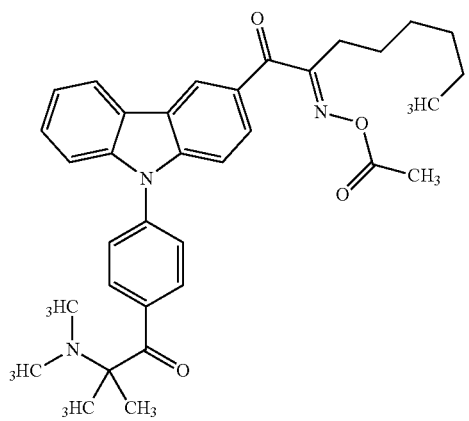
Compound No. 1-46
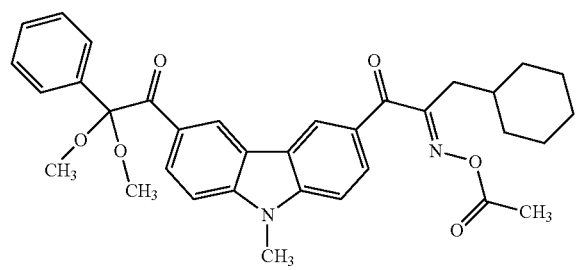
Compound No. 1-47
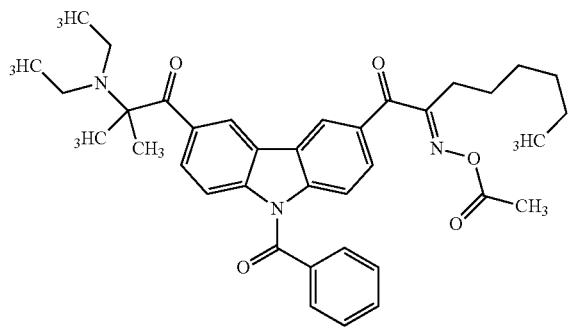
Compound No. 1-48
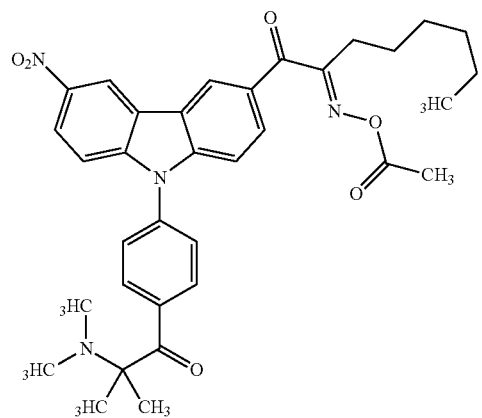
Compound No. 1-49
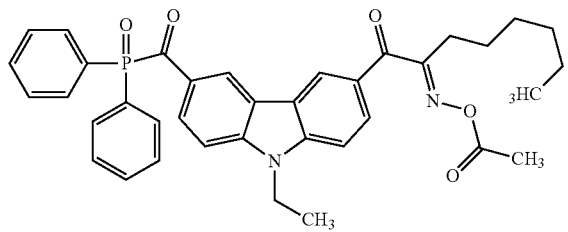
Compound No. 1-50
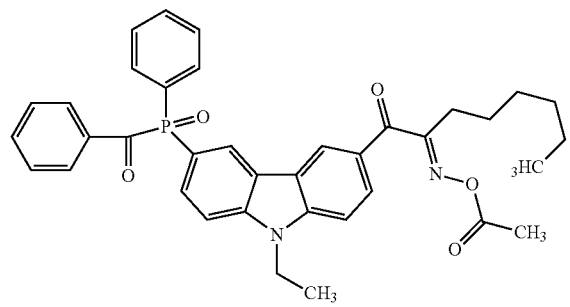

Compound No. 1-51
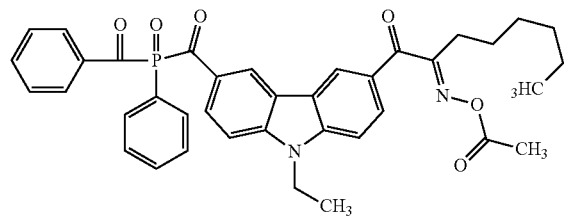
Compound No. 1-52
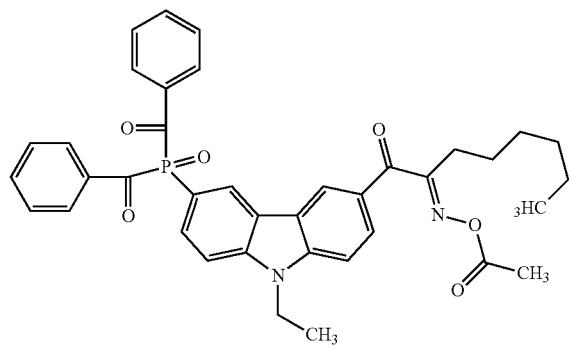
Compound No. 1-53
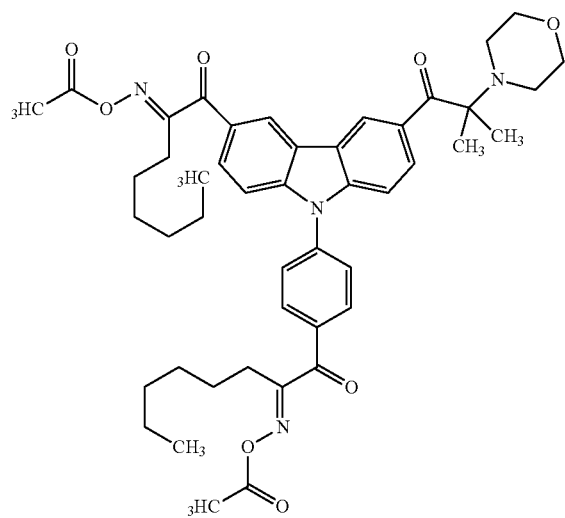
Compound No. 1-54
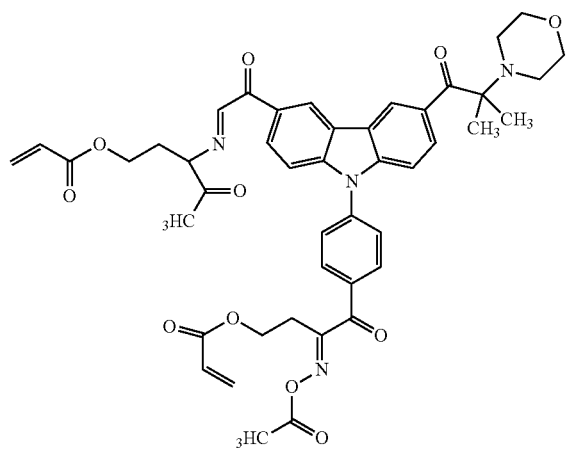
Compound No. 1-55
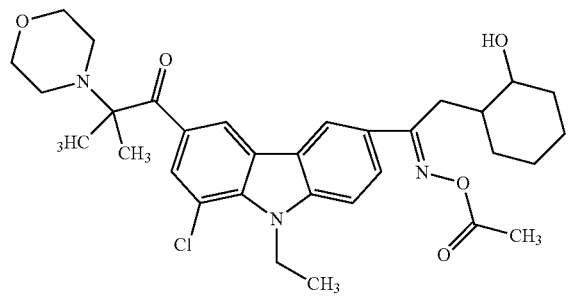
Compound No. 1-56
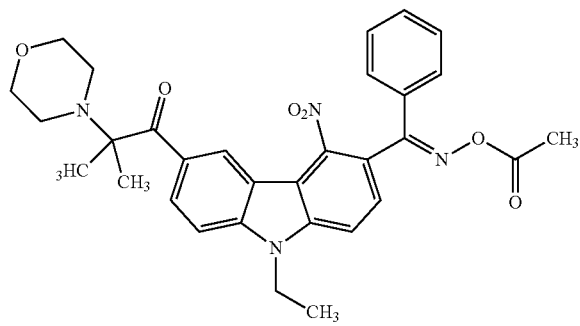

-continued
Compound No. 1-57
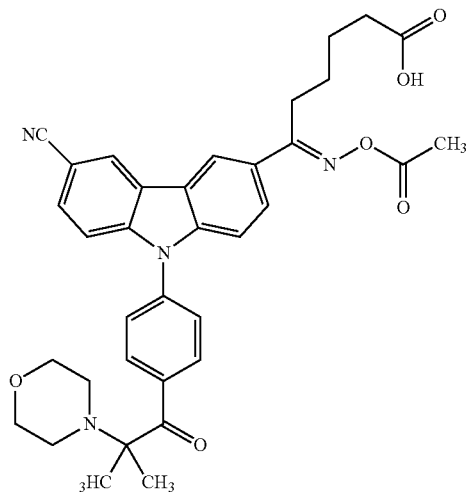
Compound No. 1-58
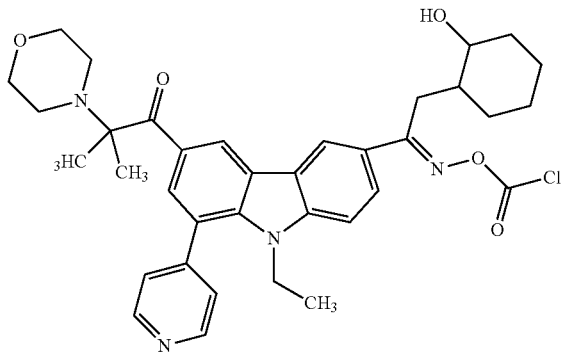
Compound No. 1-59
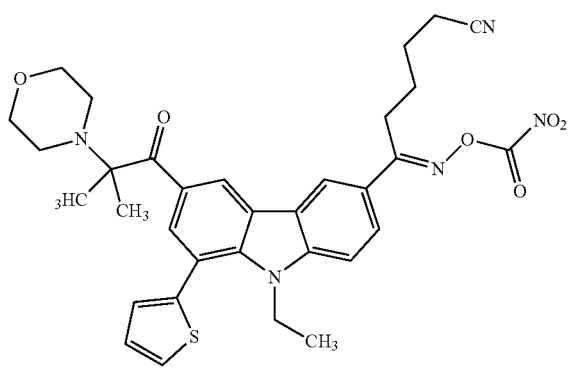
Compound No. 1-60
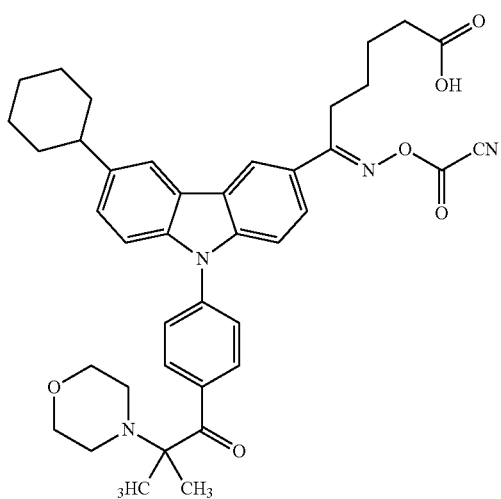
Compound No. 1-61
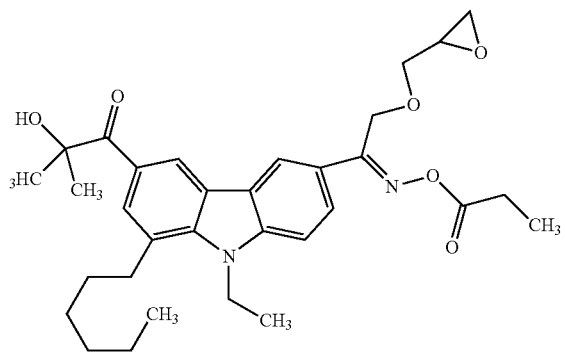
Compound No. 1-62
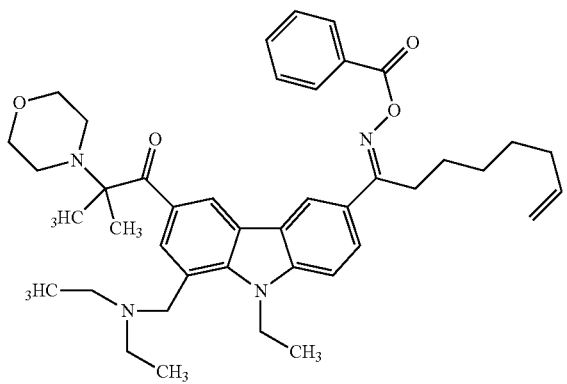

-continued
Compound No. 1-63
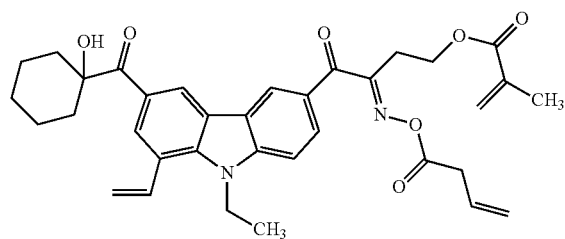
Compound No. 1-64
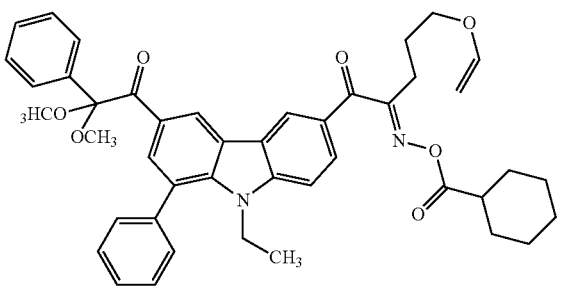
Compound No. 1-65
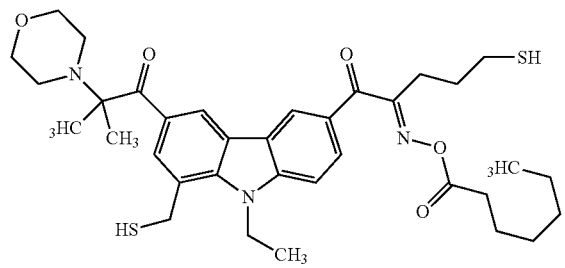
Compound No. 1-66
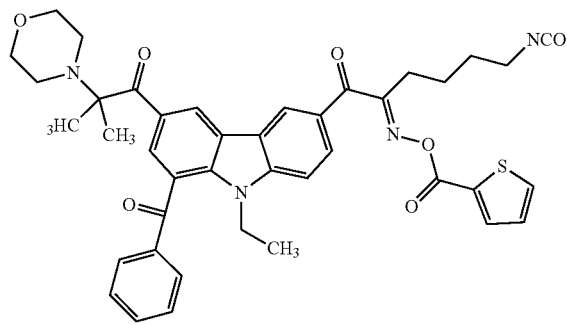
Compound No. 1-67
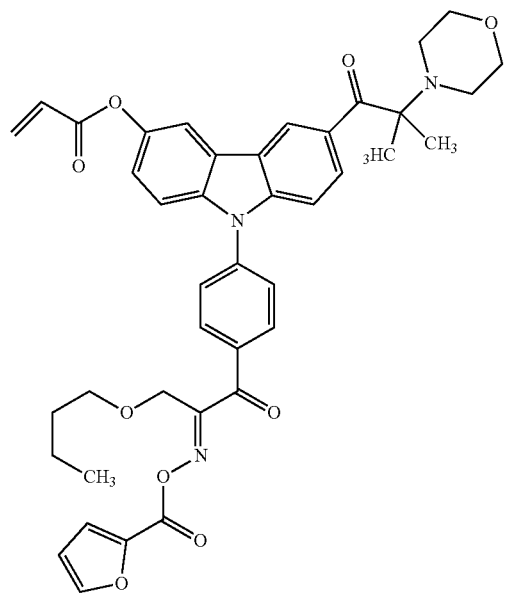
Compound No. 1-68
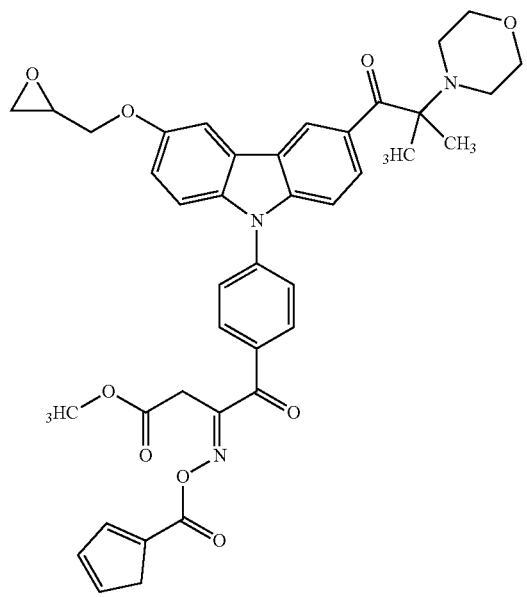

Compound No. 1-69
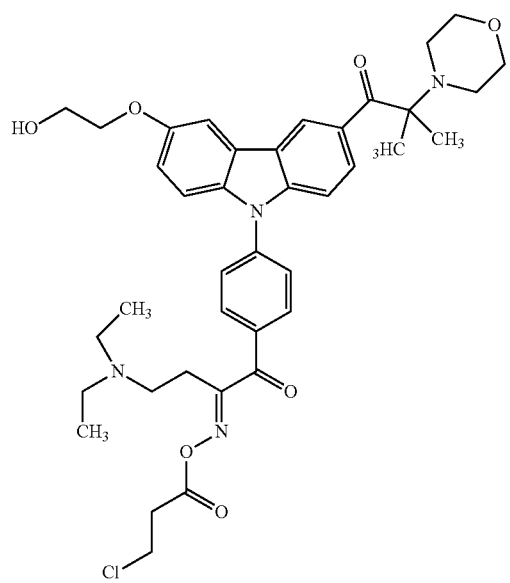
Compound No. 1-70
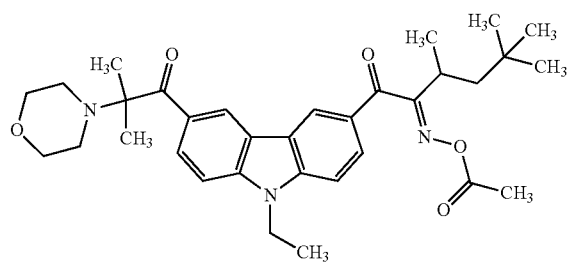
Compound No. 1-71
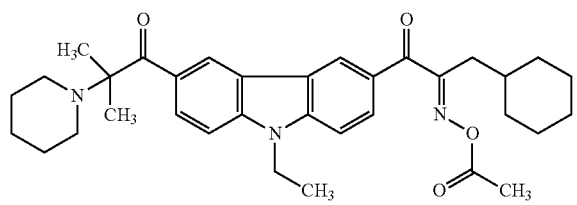
Compound No. 1-72
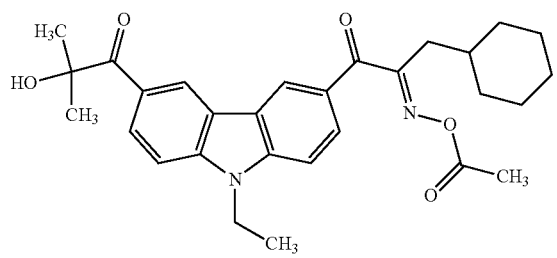
Compound No. 1-73
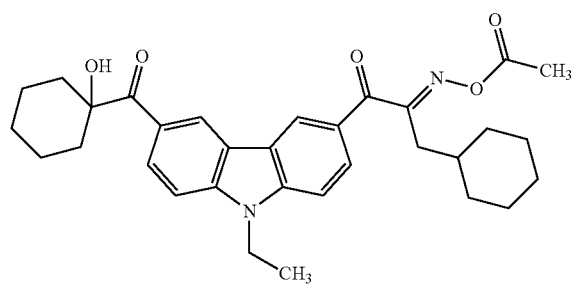
Compound No. 1-74
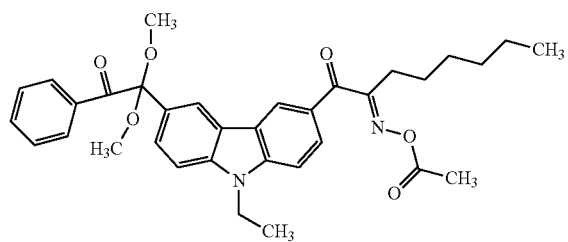
Compound No. 1-75
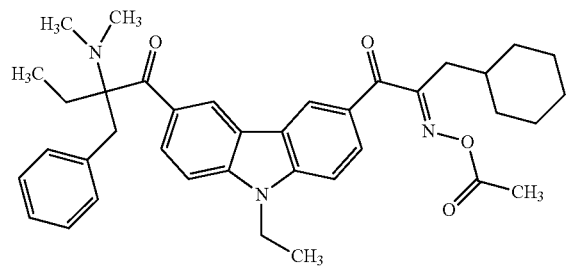
Compound No. 1-76
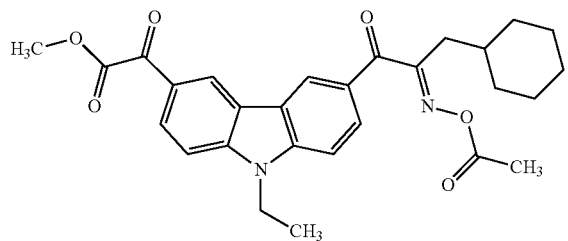

-continued
Compound No. 2-1
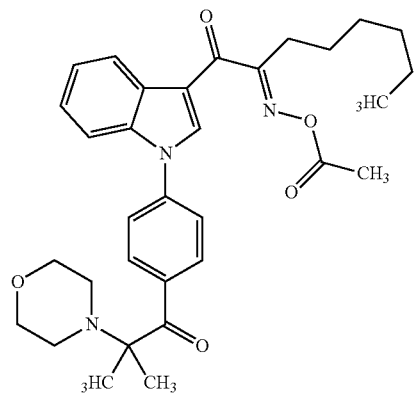
Compound No. 2-2
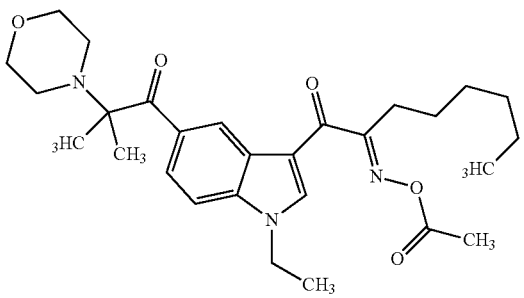
Compound No. 2-3
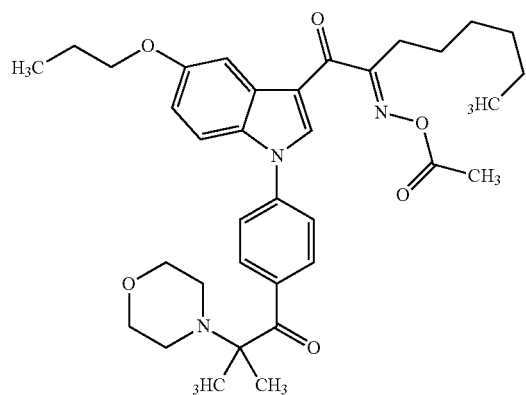
Compound No. 2-4
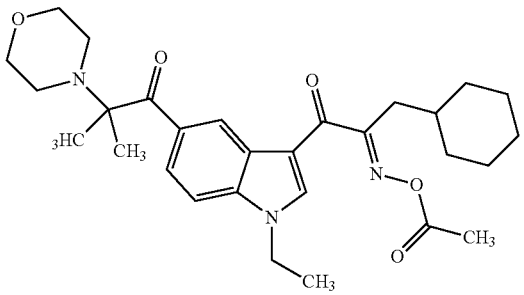
Compound No. 2-5
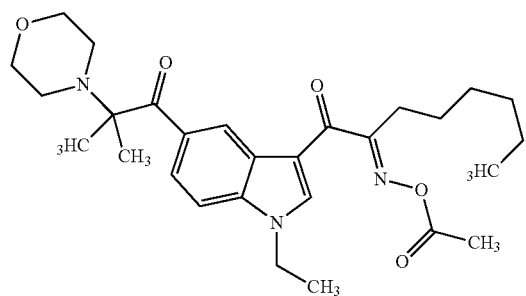
Compound No. 2-6
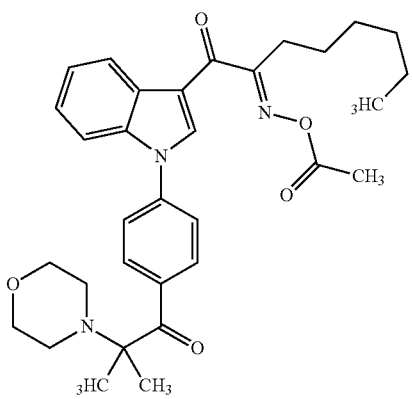
Compound No. 2-7
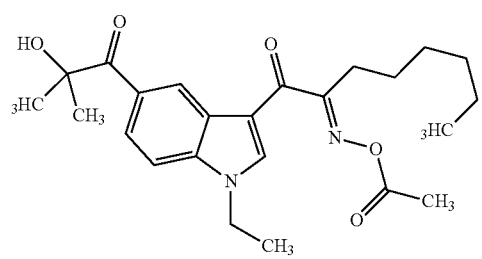
Compound No. 2-8
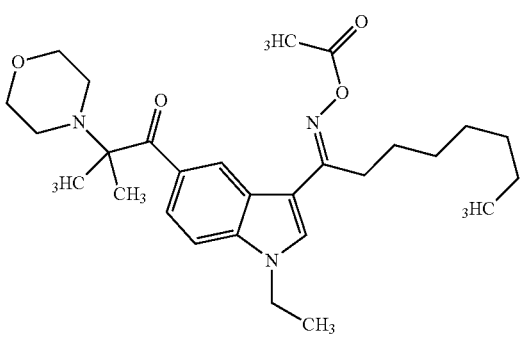

-continued
Compound No. 2-9
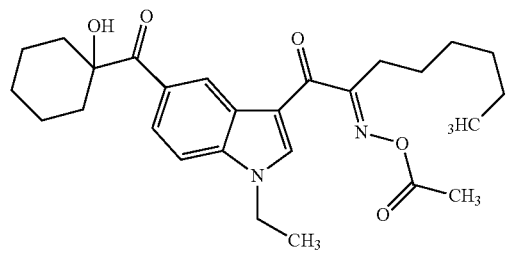
Compound No. 2-10
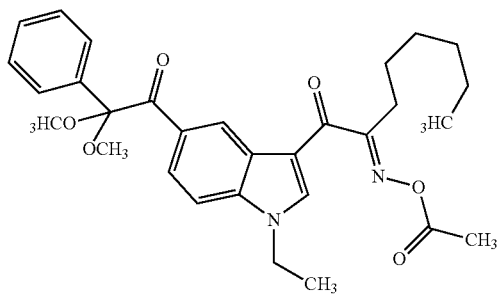
Compound No. 2-11
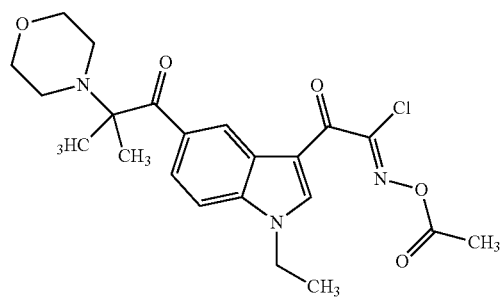
Compound No. 2-12
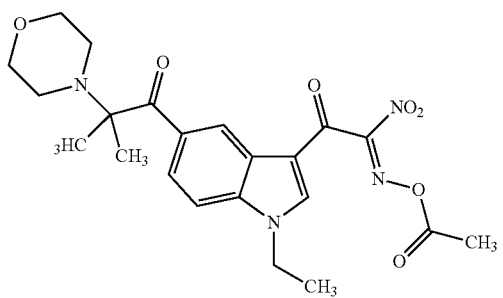
Compound No. 2-13
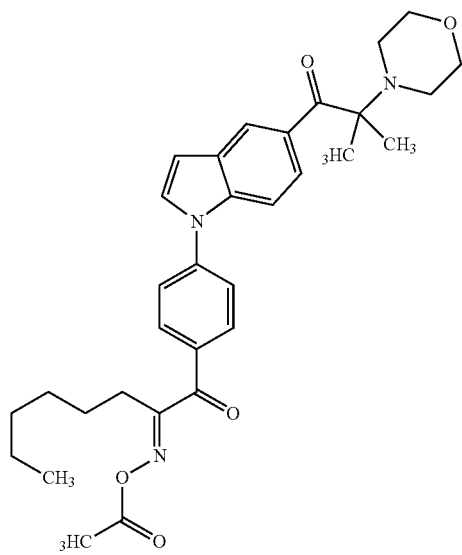
Compound No. 2-14
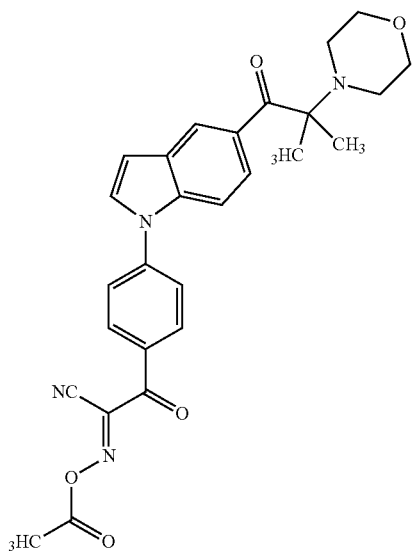

Compound No. 2-15
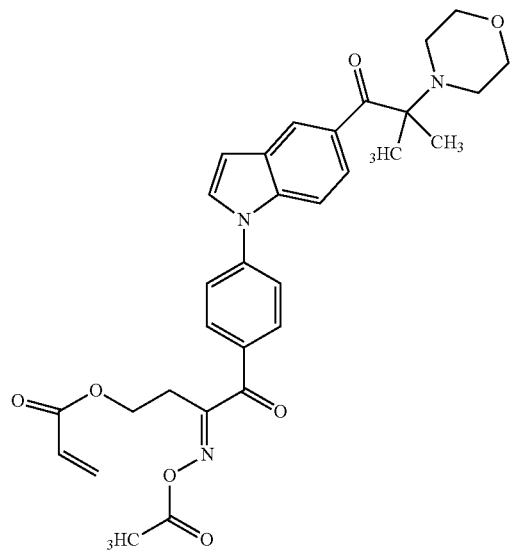
Compound No. 2-16
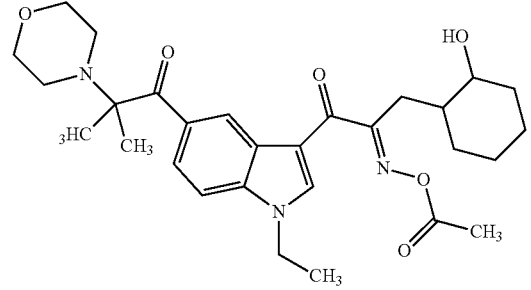
Compound No. 2-17
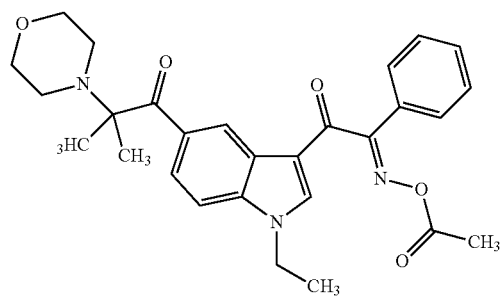
Compound No. 2-18
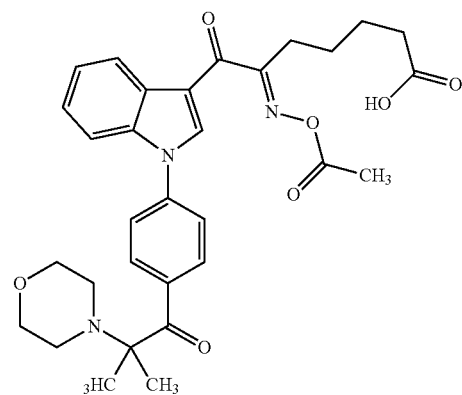
Compound No. 2-19
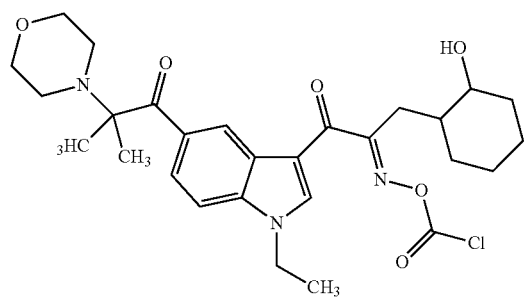
Compound No. 2-20
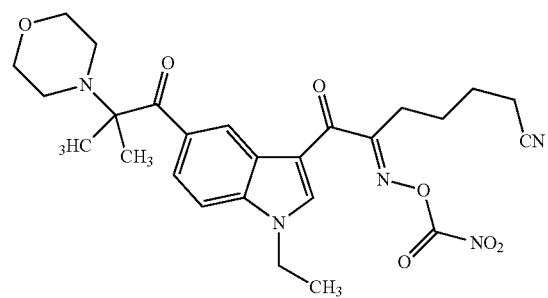

Compound No. 2-21
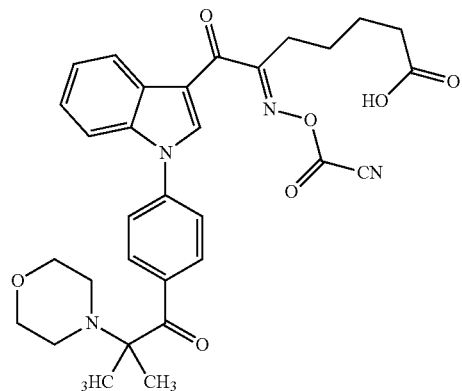
Compound No. 2-22
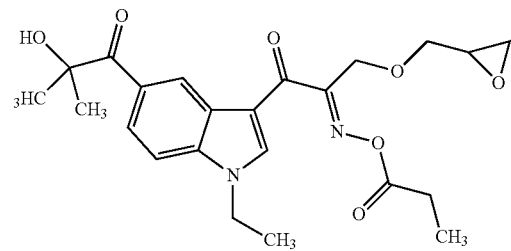
Compound No. 2-23
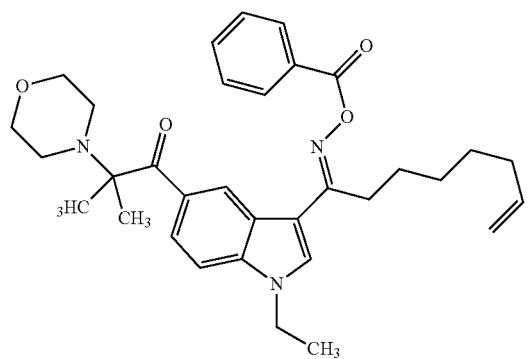
Compound No. 2-24
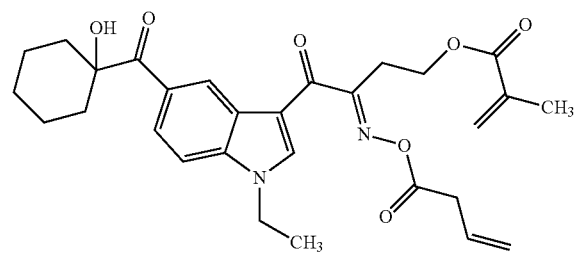
Compound No. 2-25
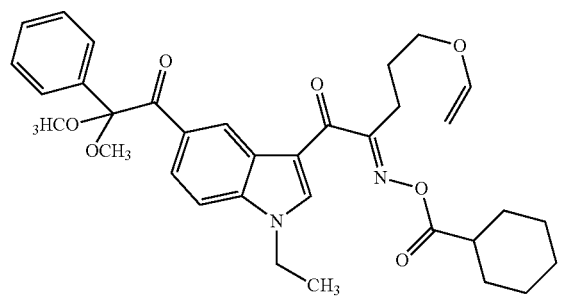
Compound No. 2-26
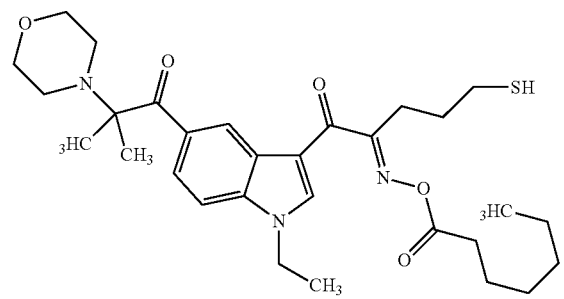

Compound No. 2-27
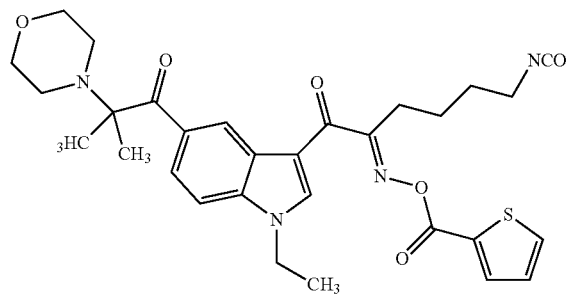
Compound No. 2-28
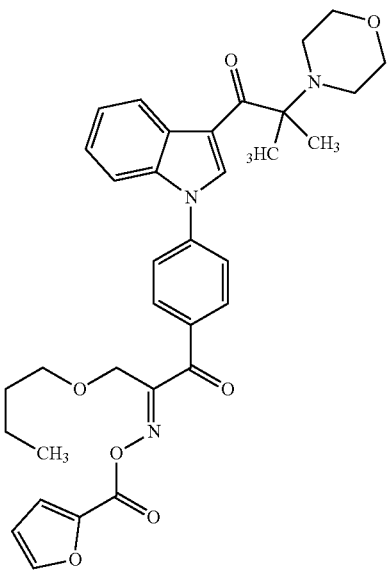
Compound No. 2-29
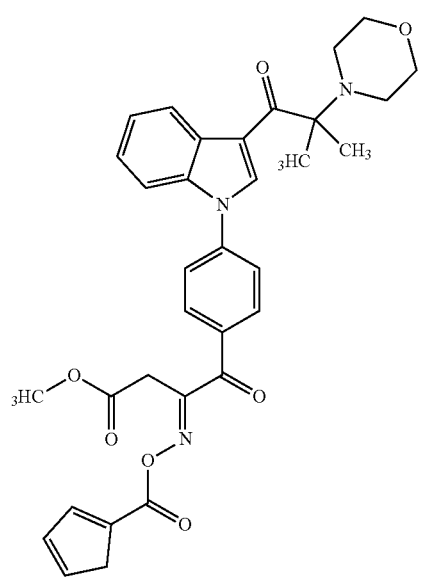
Compound No. 2-30
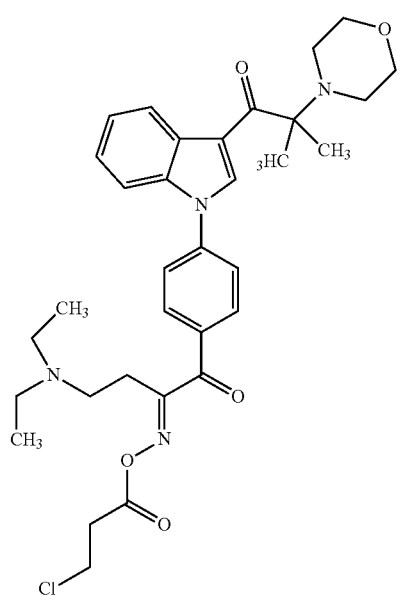
Compound No. 2-31
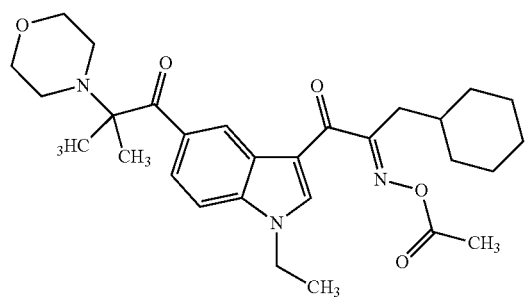
Compound No. 2-32
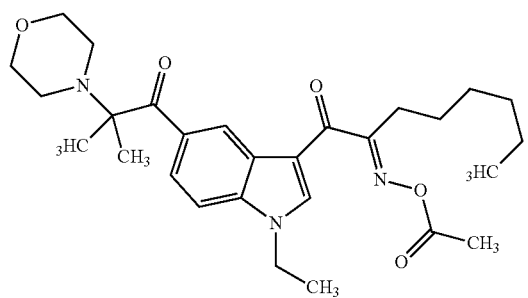

-continued
Compound No. 2-33
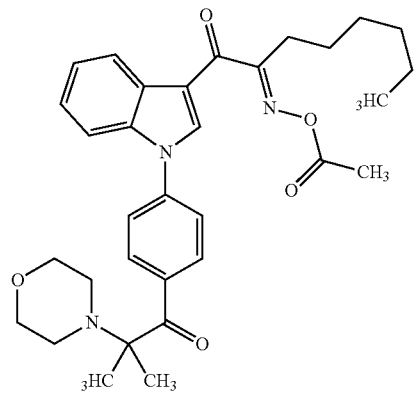
Compound No. 2-34
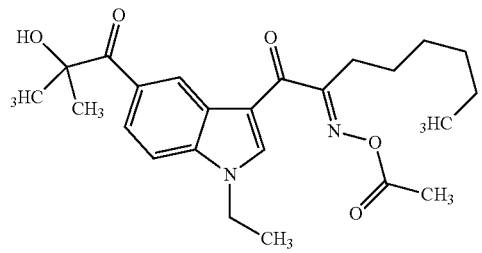
Compound No. 2-35
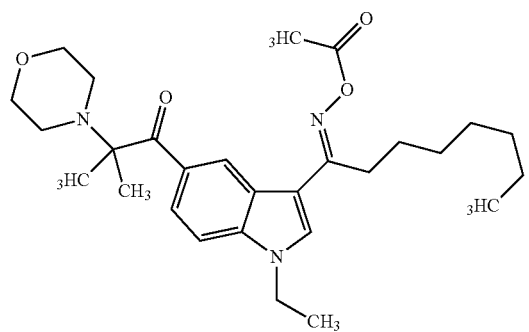
Compound No. 2-36
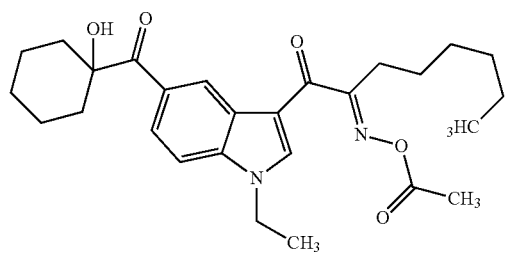
Compound No. 2-37
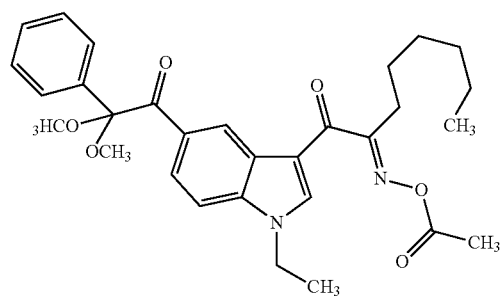
Compound No. 2-38
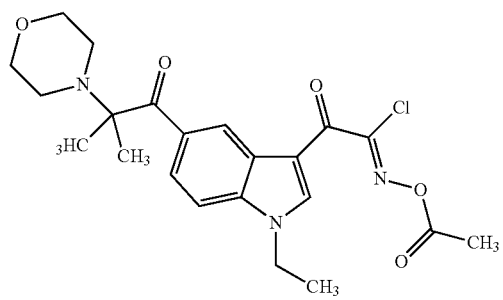
Compound No. 2-39
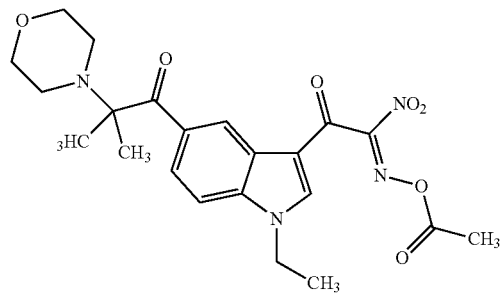
Compound No. 2-40
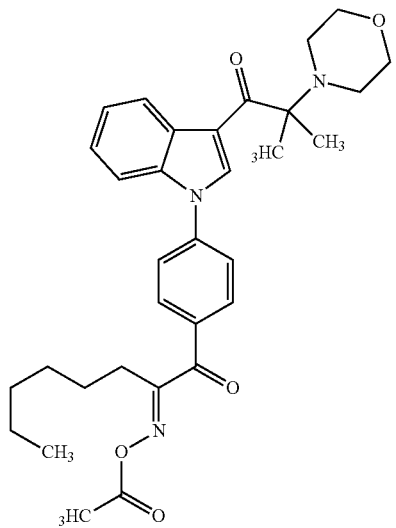

-continued
Compound No. 2-41
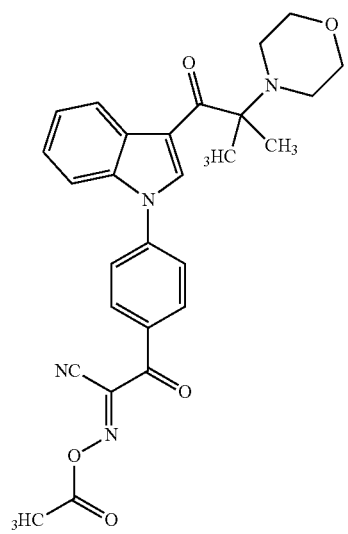
Compound No. 2-42
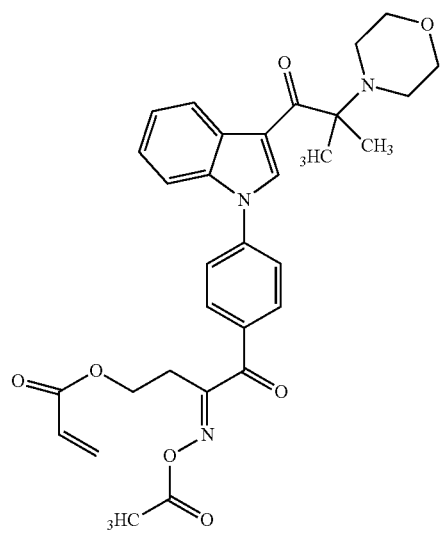
Compound No. 2-43
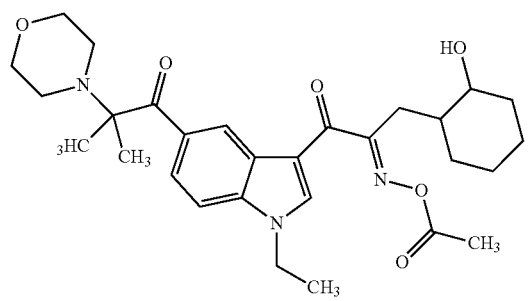
Compound No. 2-44
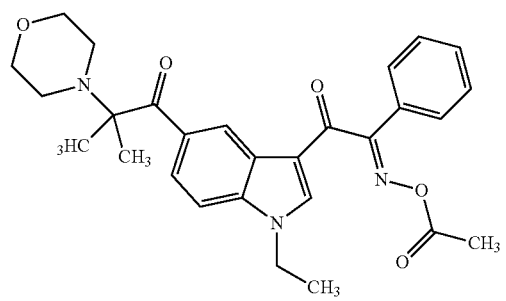
Compound No. 2-45
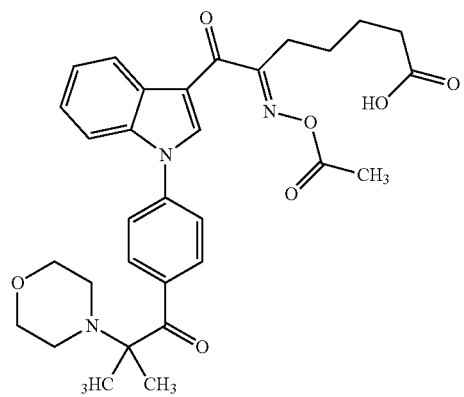
Compound No. 2-46
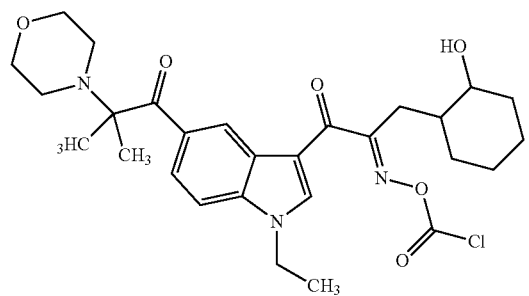

Compound No. 2-47
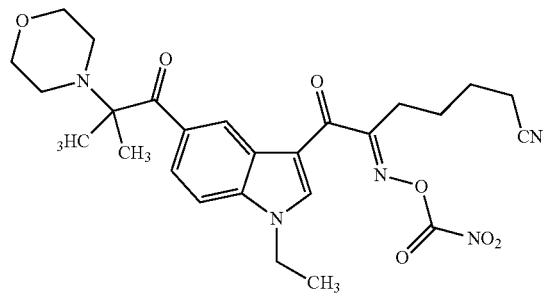
Compound No. 2-48
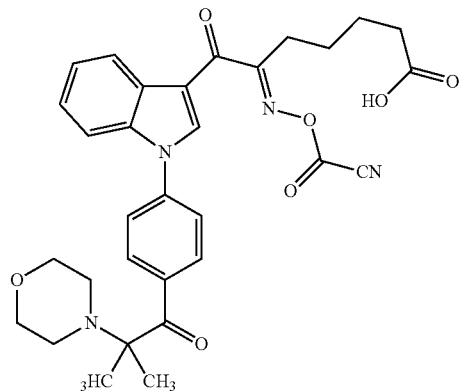
Compound No. 2-49
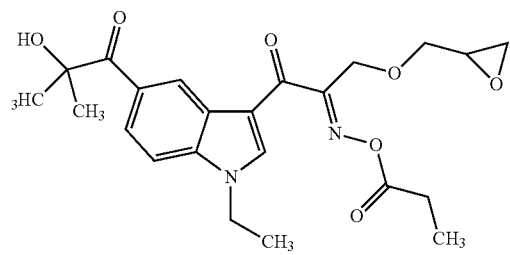
Compound No. 2-50
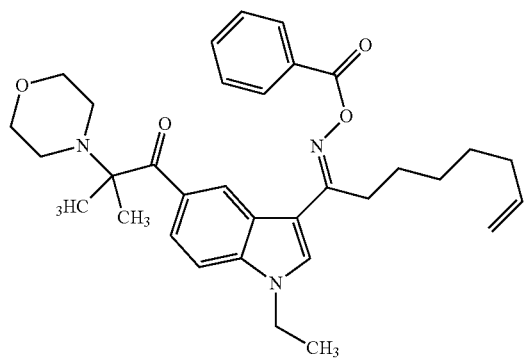
Compound No. 2-51
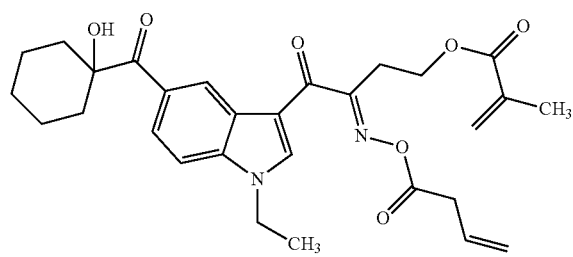
Compound No. 2-52
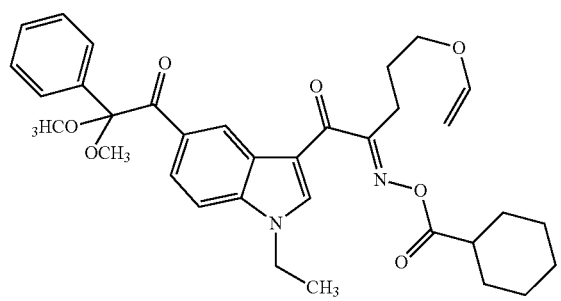
Compound No. 2-53
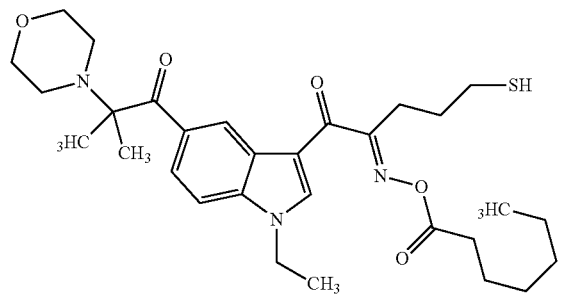
Compound No. 2-54
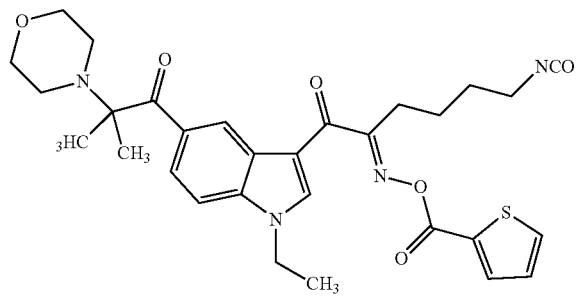

Compound No. 2-55
Compound No. 2-56
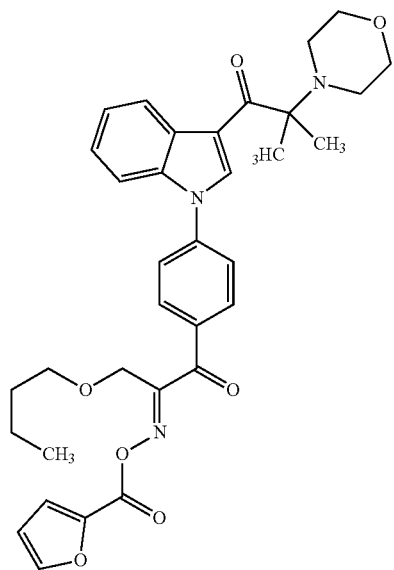
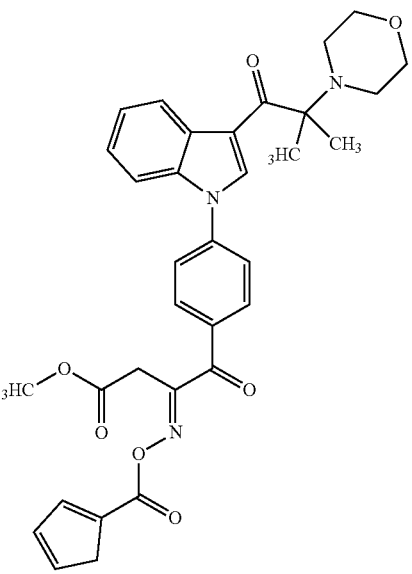
Compound No. 2-57
Compound No. 2-58
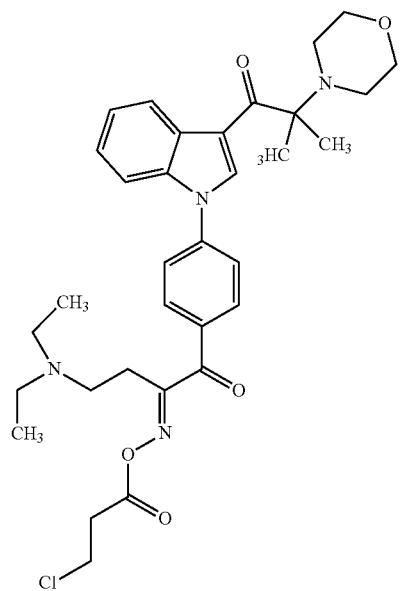
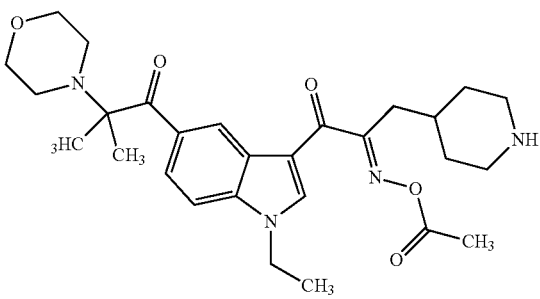
Compound No. 2-59
Compound No. 2-60
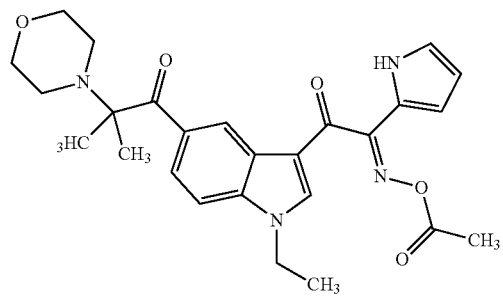
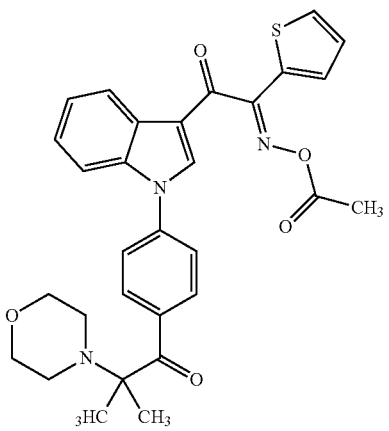

Compound No. 2-61
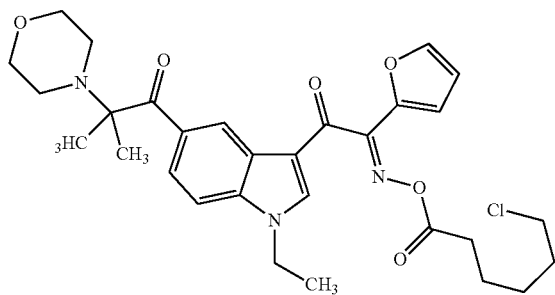
Compound No. 2-62
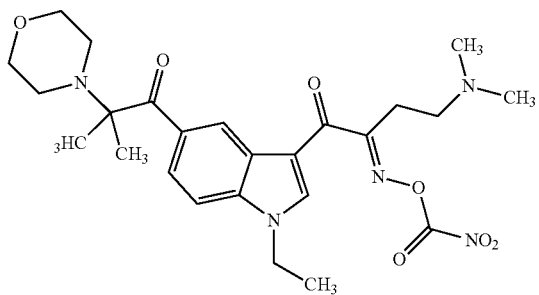
Compound No. 2-63
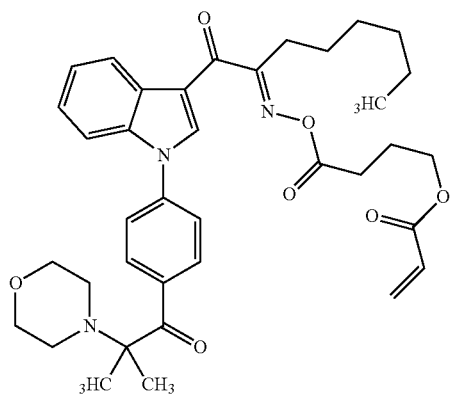
Compound No. 2-64
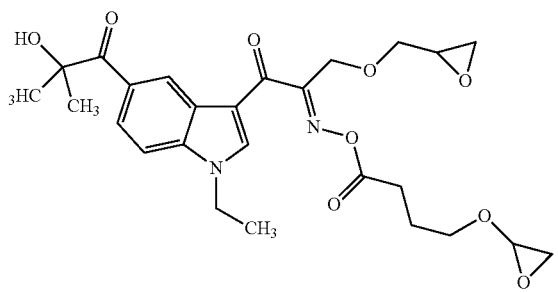
Compound No. 2-65
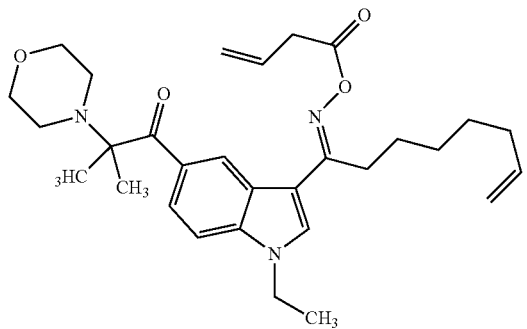
Compound No. 2-66
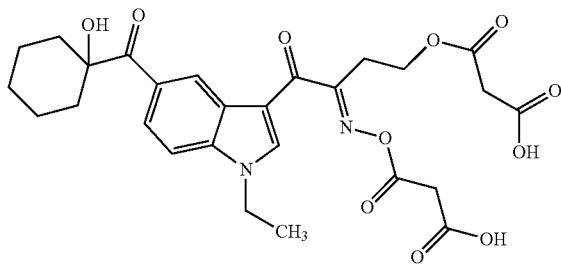
Compound No. 2-67
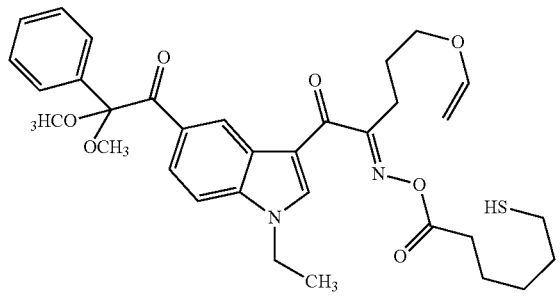
Compound No. 2-68
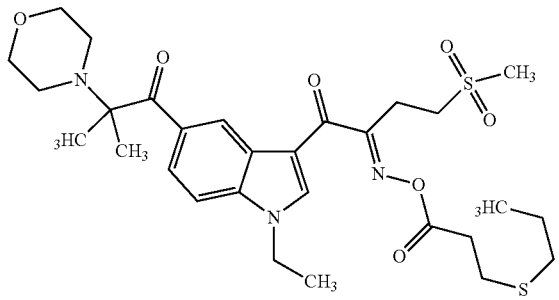

-continued
Compound No. 2-69
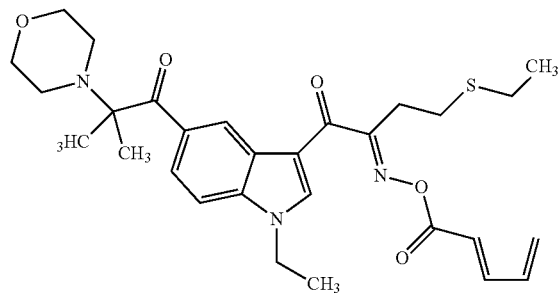
Compound No. 2-70
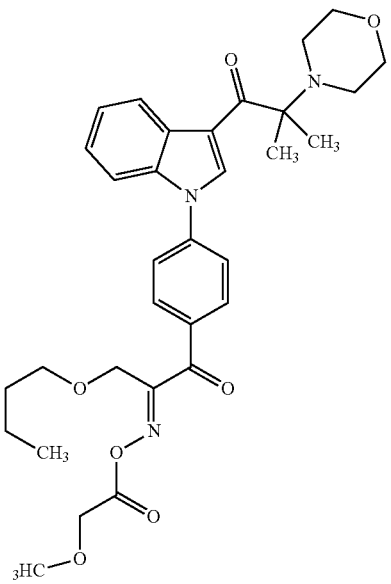
Compound No. 2-71
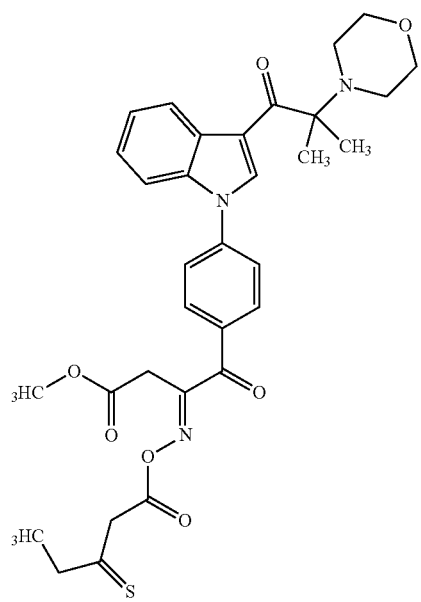
Compound No. 2-72
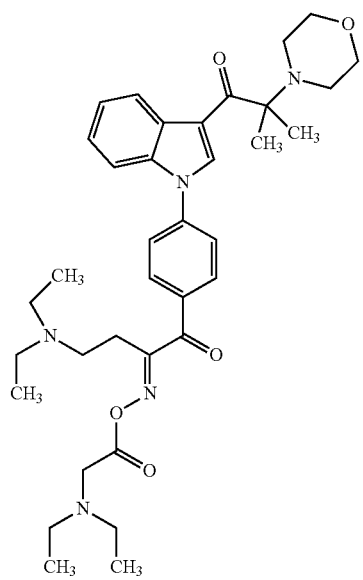
Compound No. 2-73
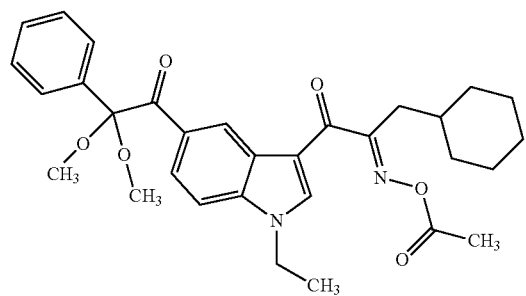
Compound No. 2-74
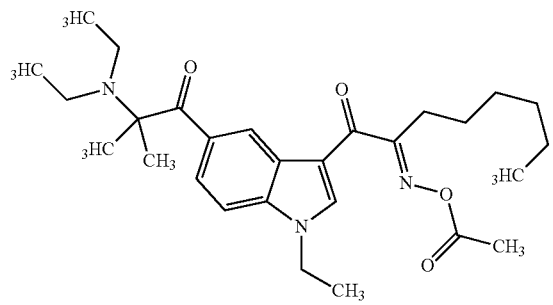

-continued
Compound No. 2-75
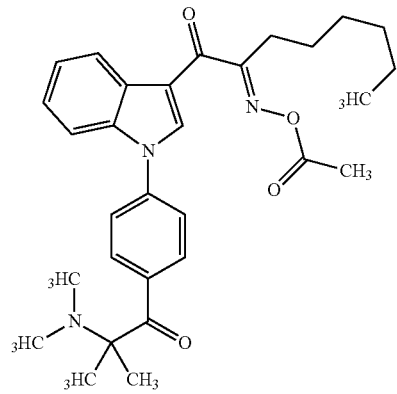
Compound No. 2-76
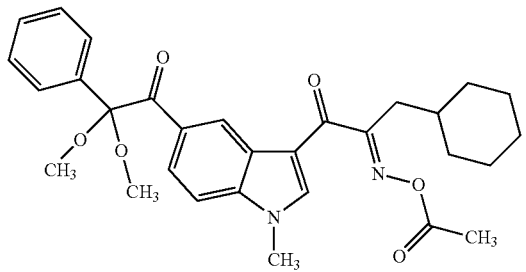
Compound No. 2-77
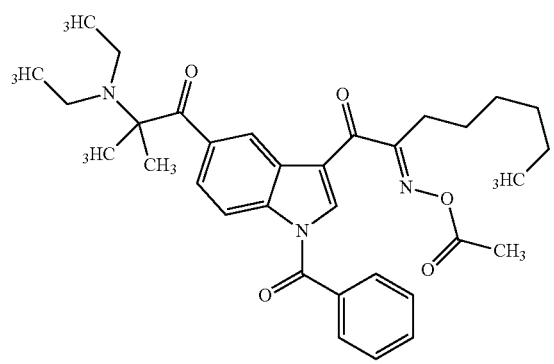
Compound No. 2-78
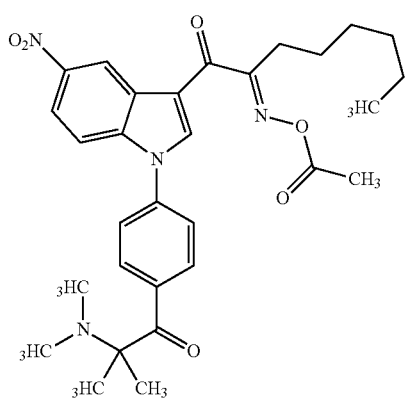
Compound No. 2-79
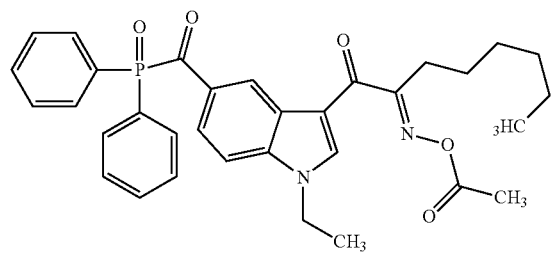
Compound No. 2-80
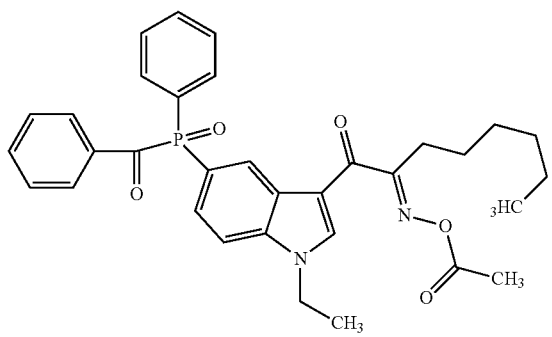
Compound No. 2-82
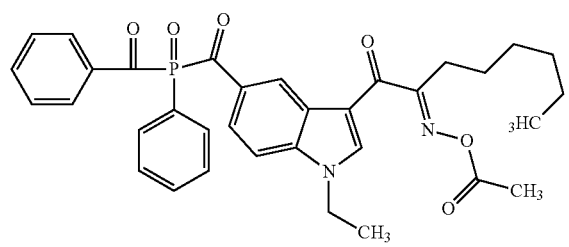
Compound No. 2-83
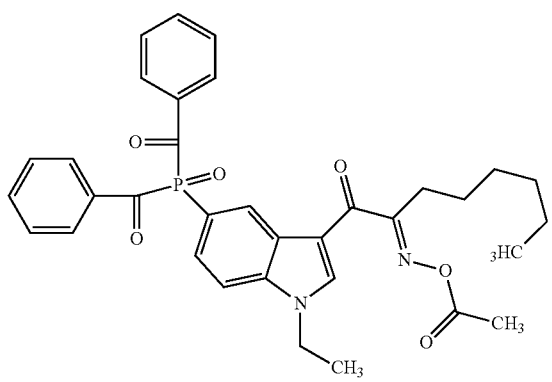

-continued
Compound No. 2-84
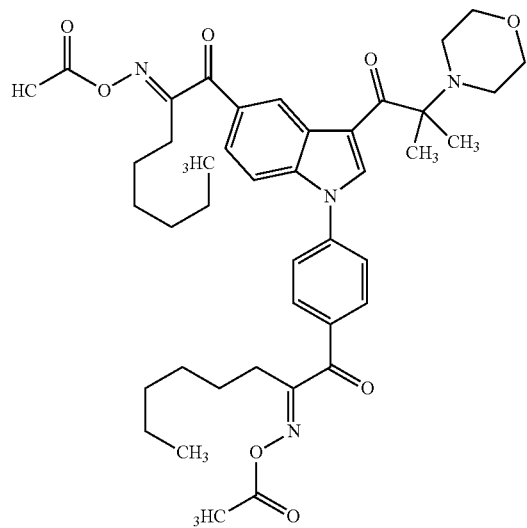
Compound No. 2-85
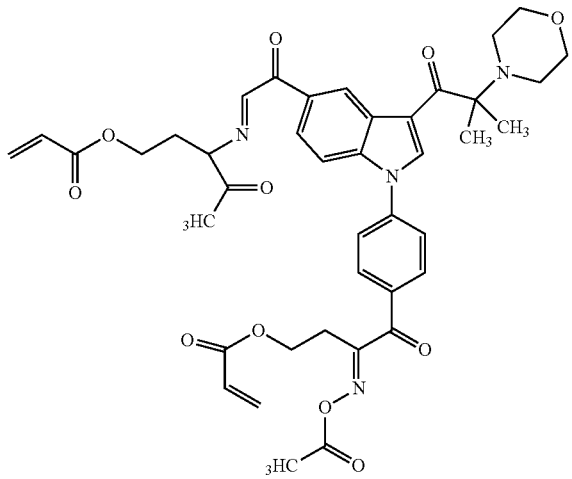
Compound No. 2-86
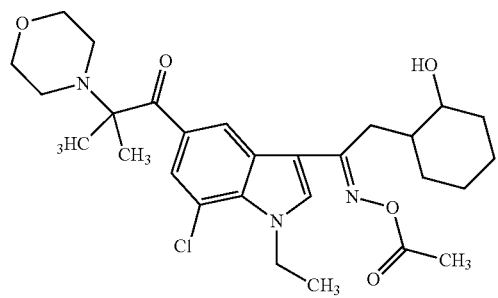
Compound No. 2-87
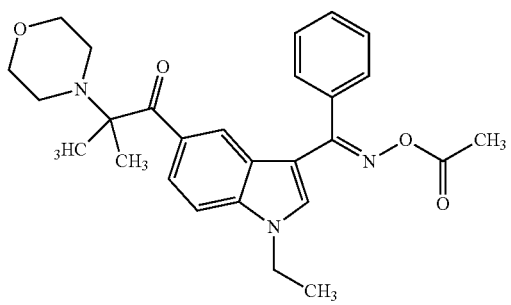
Compound No. 2-88
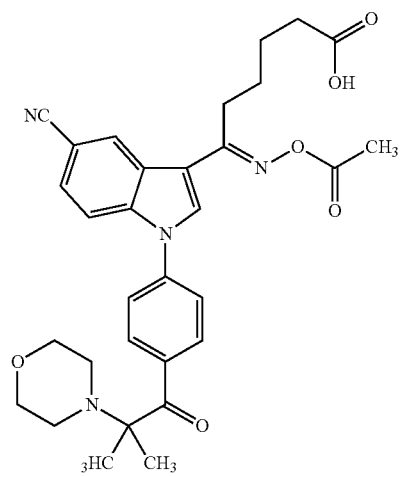
Compound No. 2-89
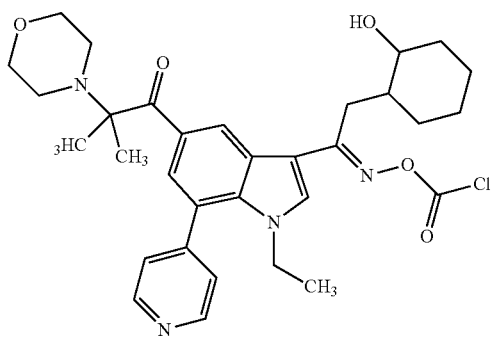

Compound No. 2-90
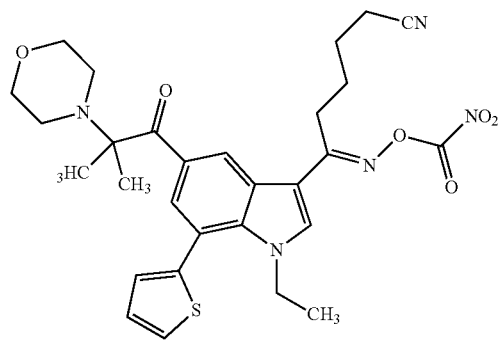
Compound No. 2-91
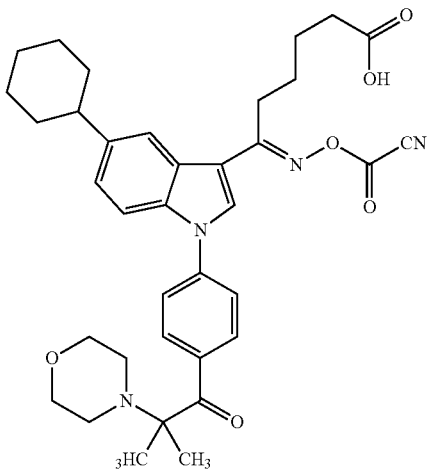
Compound No. 2-92
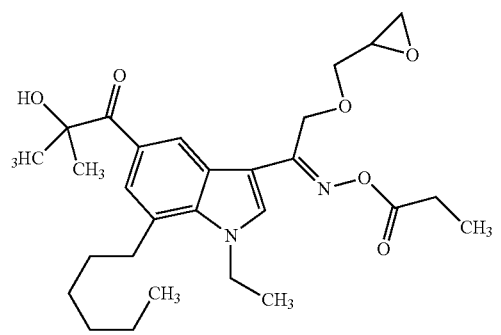
Compound No. 2-93
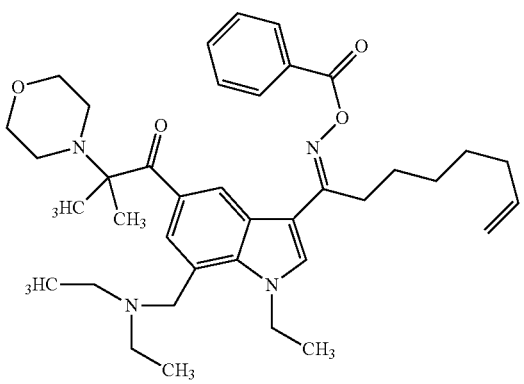
Compound No. 2-94
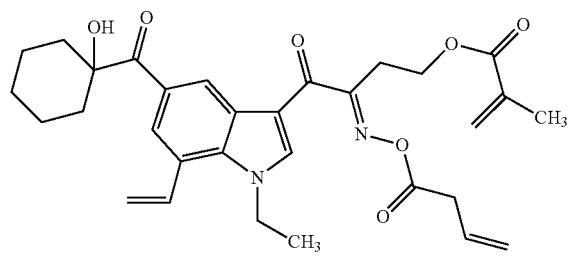
Compound No. 2-95
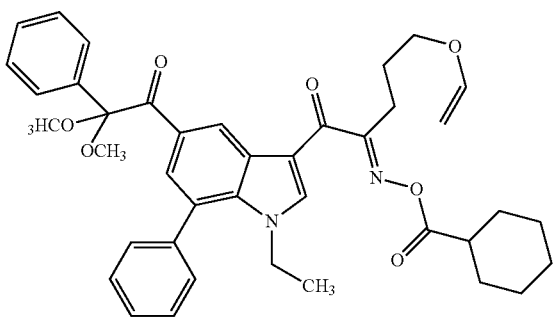
Compound No. 2-96
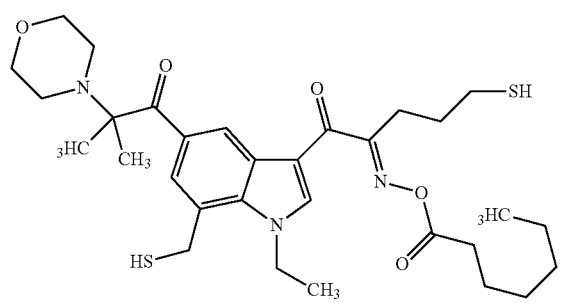
Compound No. 2-97
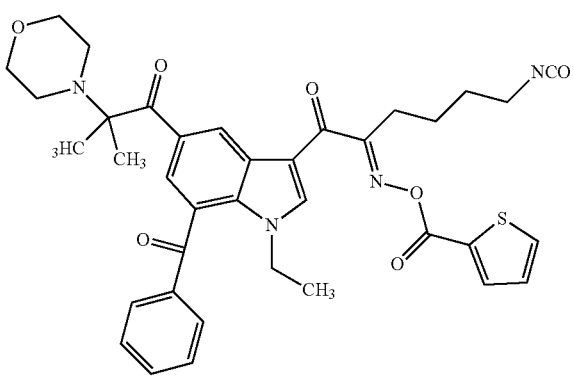

Compound No. 2-98
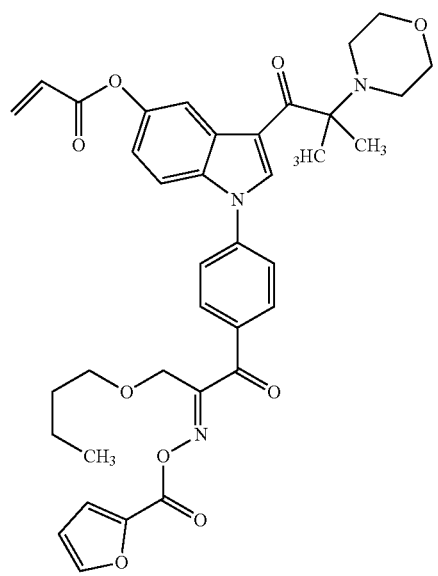
Compound No. 2-99
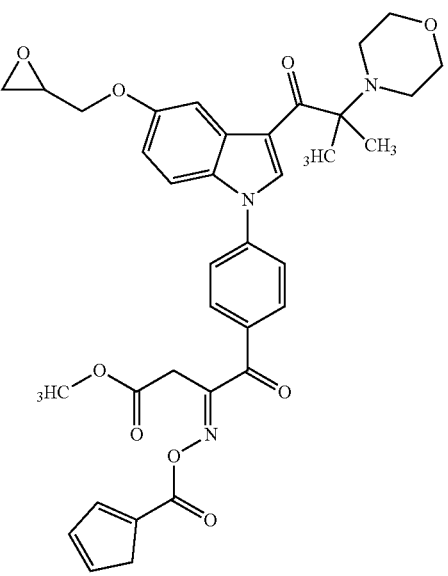
Compound No. 2-100
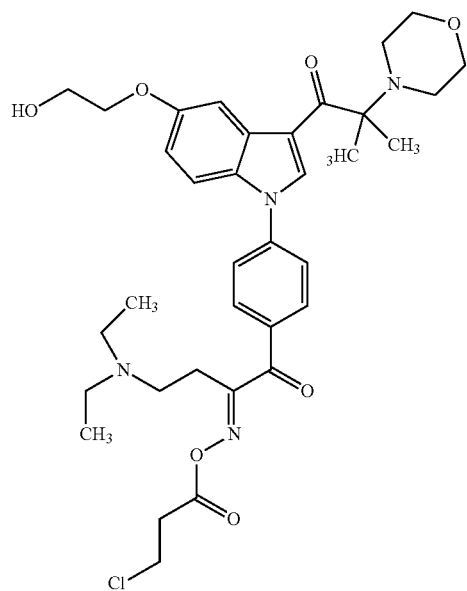
Compound No. 3-1
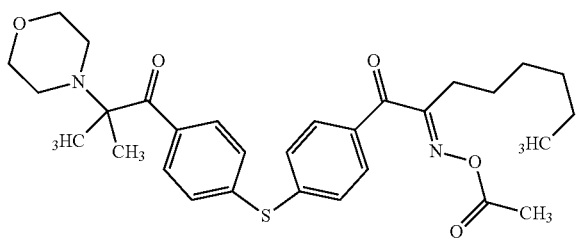
Compound No. 3-2
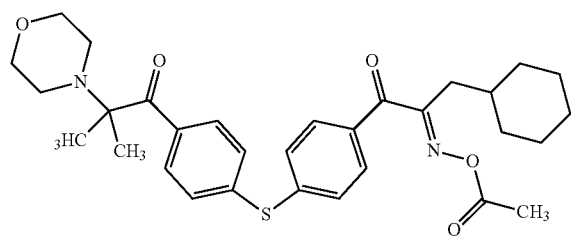
Compound No. 3-3
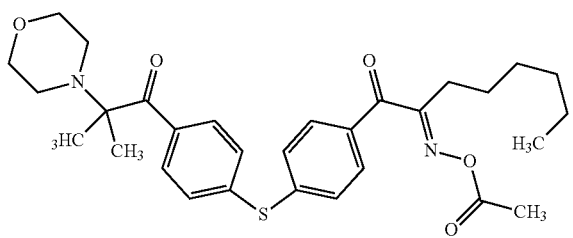

Compound No. 3-4
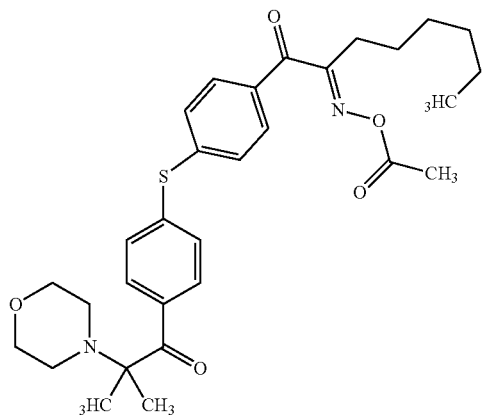
Compound No. 3-5
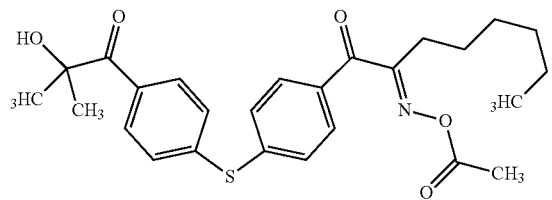
Compound No. 3-6
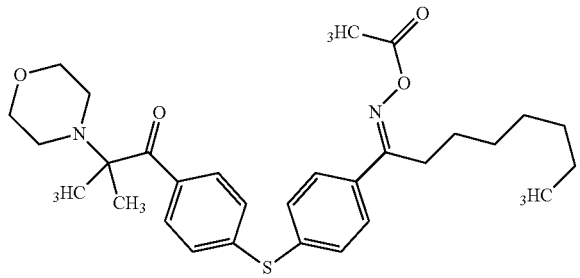
Compound No. 3-7
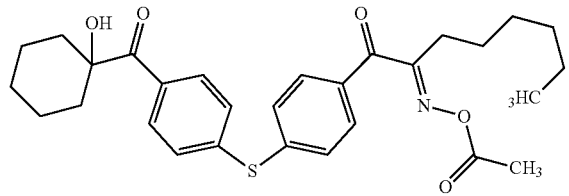
Compound No. 3-8
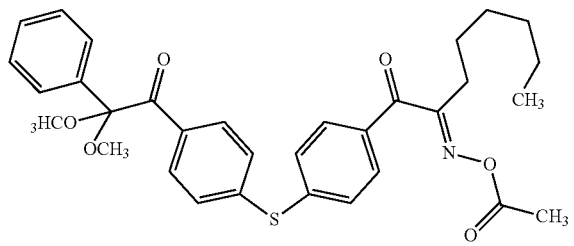
Compound No. 3-9
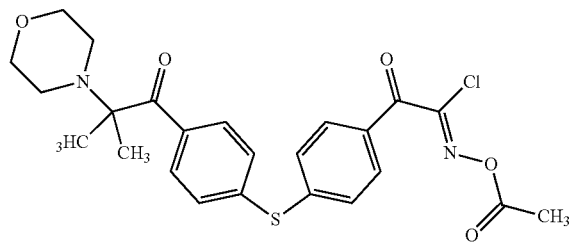
Compound No. 3-10
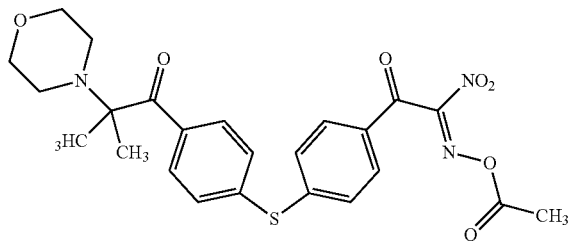
Compound No. 3-11
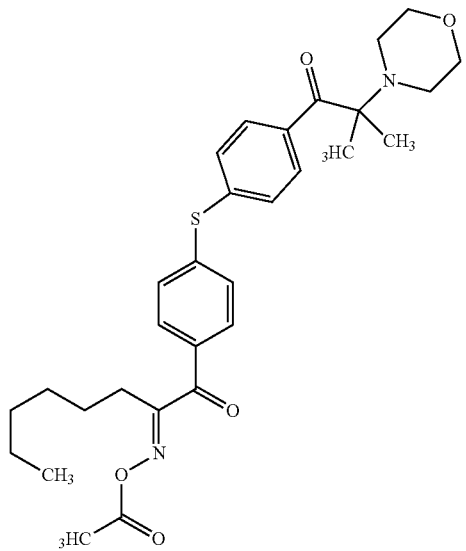

-continued
Compound No. 3-12
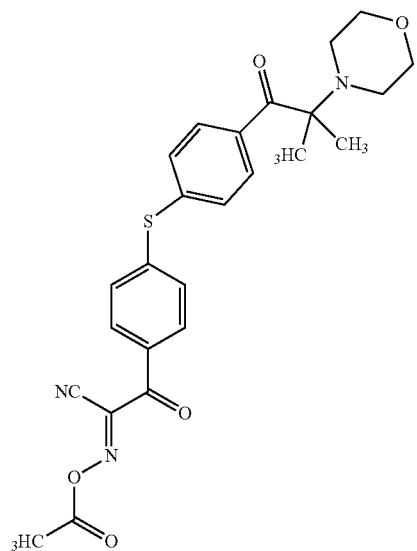
Compound No. 3-13
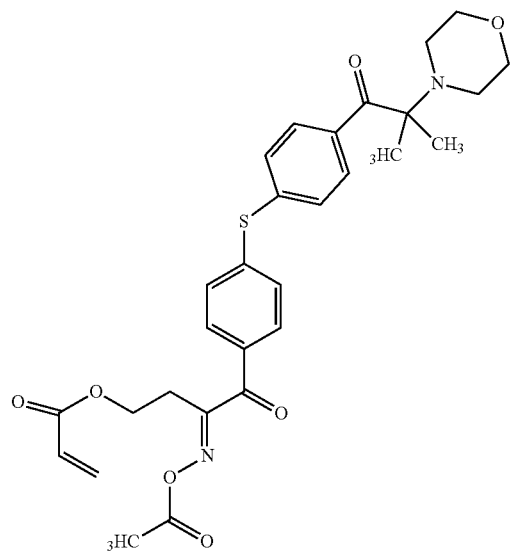
Compound No. 3-14
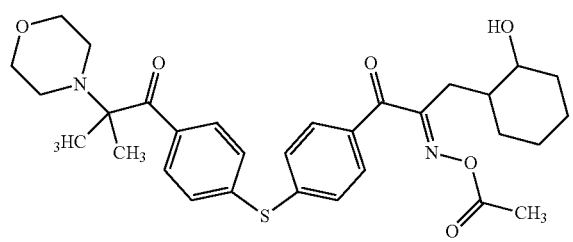
Compound No. 3-15
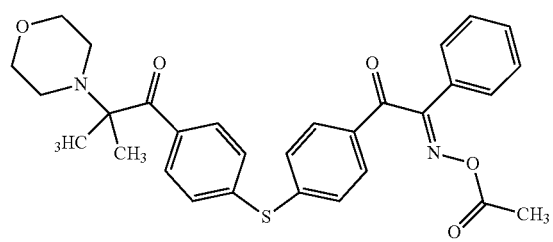
Compound No. 3-16
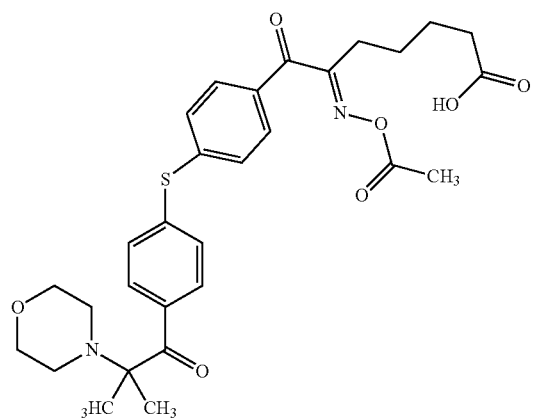
Compound No. 3-17
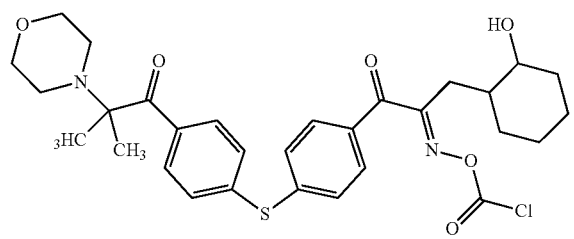

-continued
Compound No. 3-18
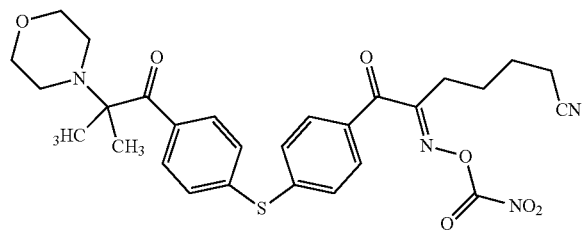
Compound No. 3-19
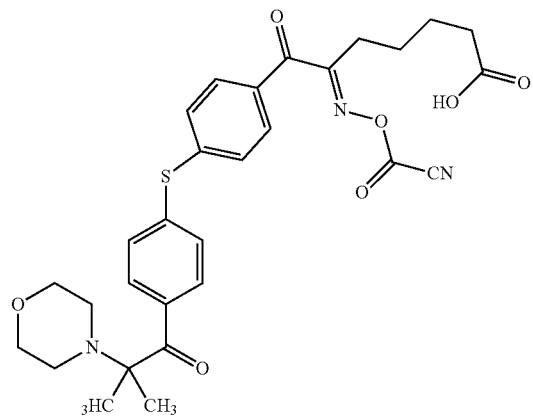
Compound No. 3-20
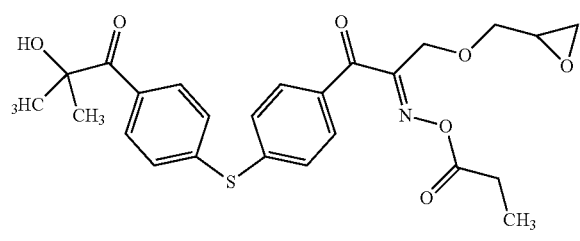
Compound No. 3-21
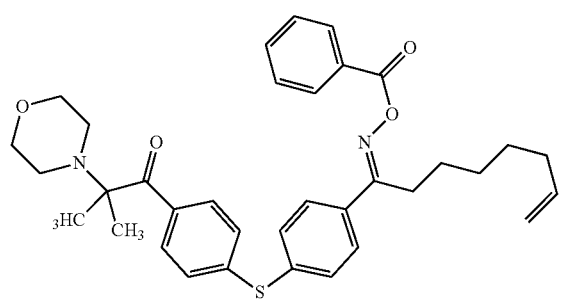
Compound No. 3-22
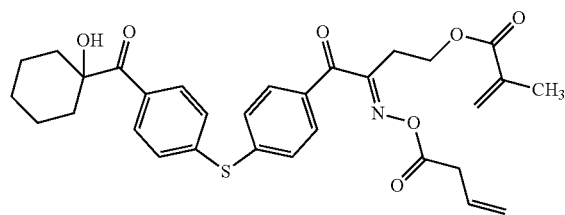
Compound No. 3-23
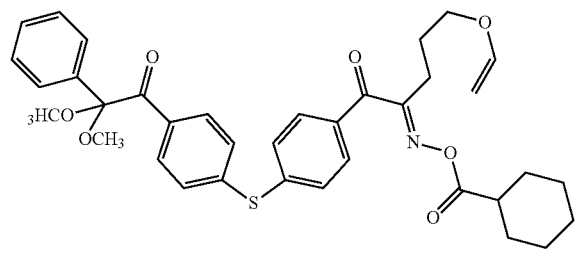
Compound No. 3-24
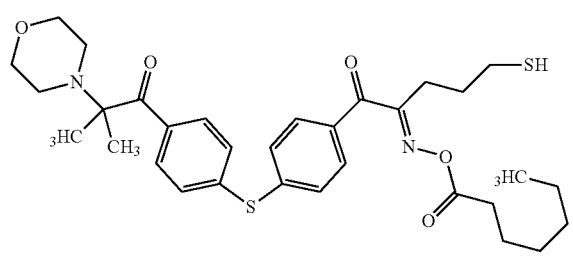
Compound No. 3-25
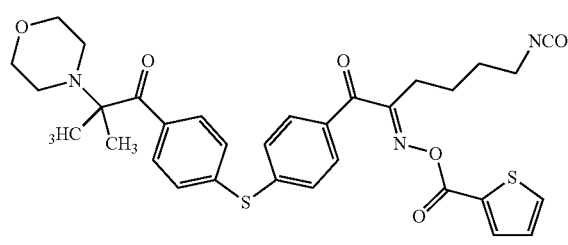

-continued
Compound No. 3-26
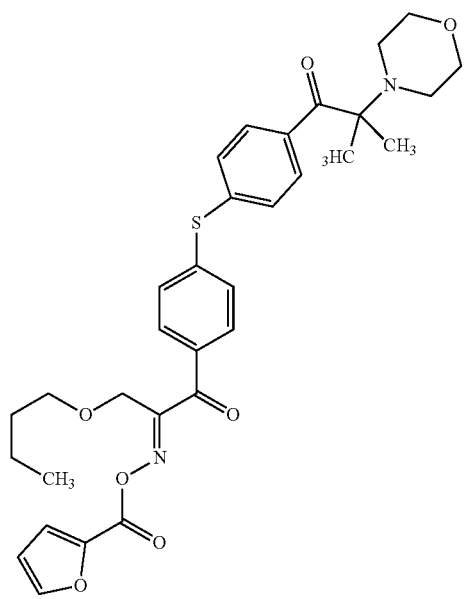
Compound No. 3-27
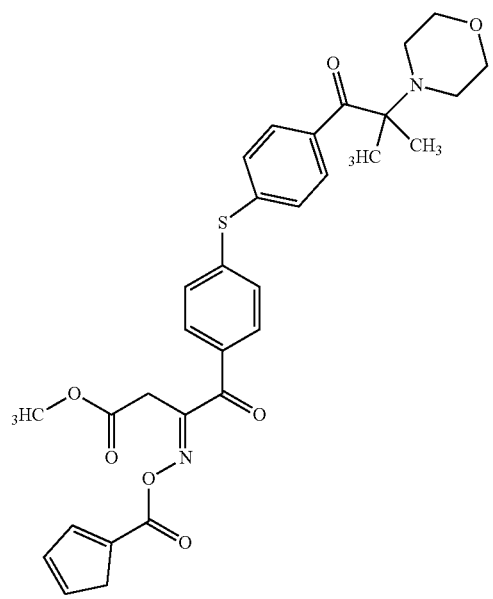
Compound No. 3-28
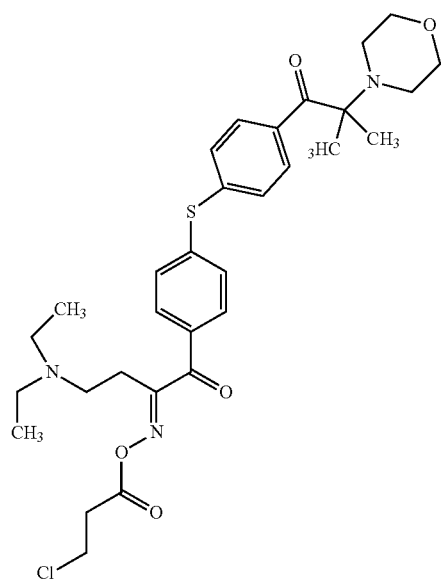
Compound No. 3-29
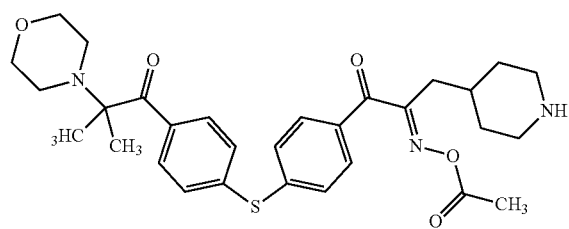

-continued
Compound No. 3-30
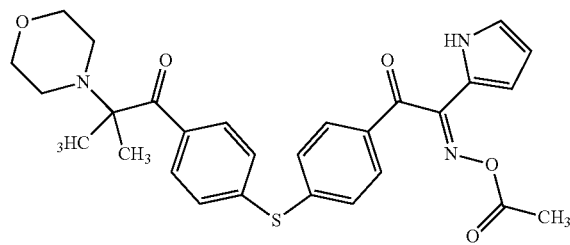
Compound No. 3-31
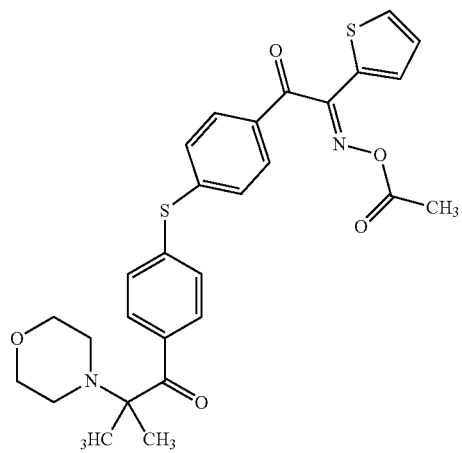
Compound No. 3-32
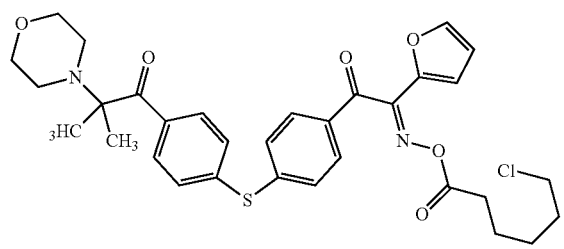
Compound No. 3-33
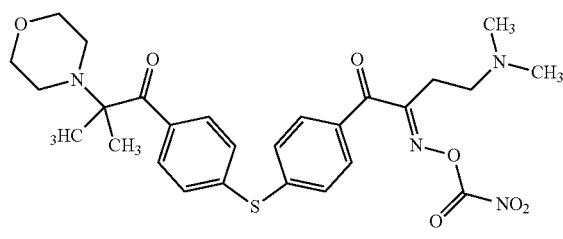
Compound No. 3-34
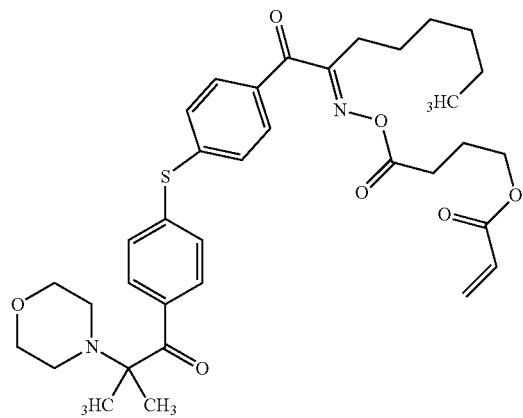
Compound No. 3-35
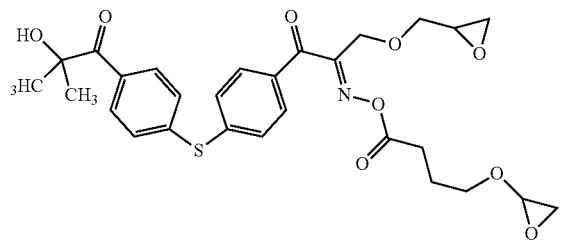
Compound No. 3-36
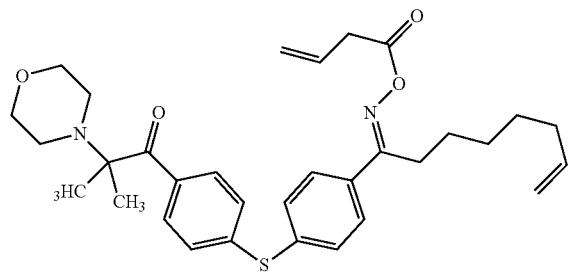
Compound No. 3-37
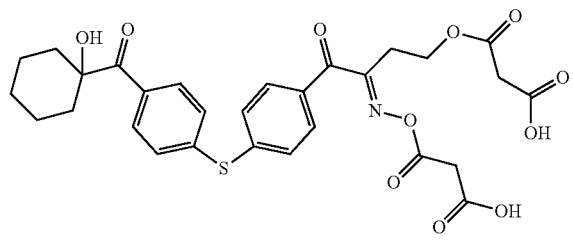

Compound No. 3-38
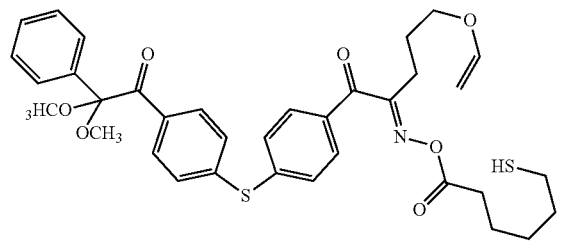
Compound No. 3-39
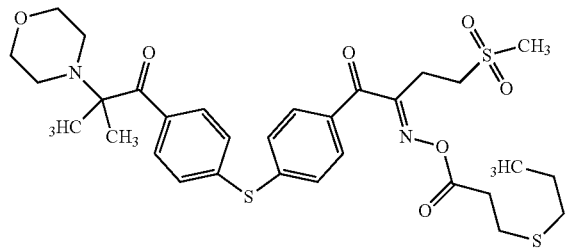
Compound No. 3-40
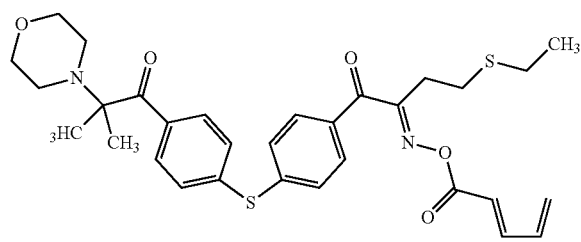
Compound No. 3-41
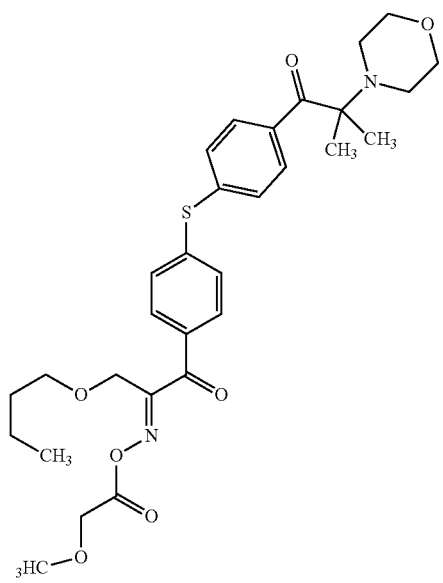
Compound No. 3-42
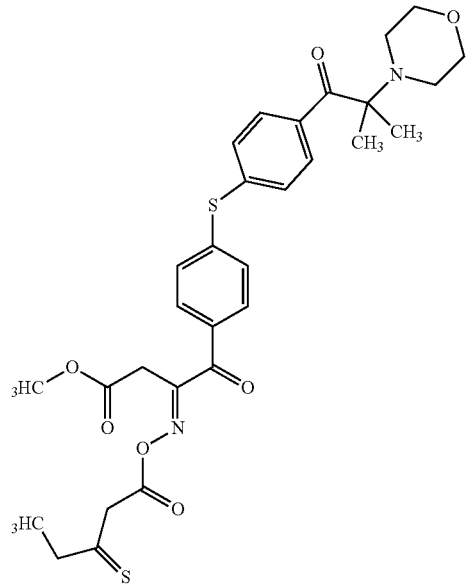
Compound No. 3-43
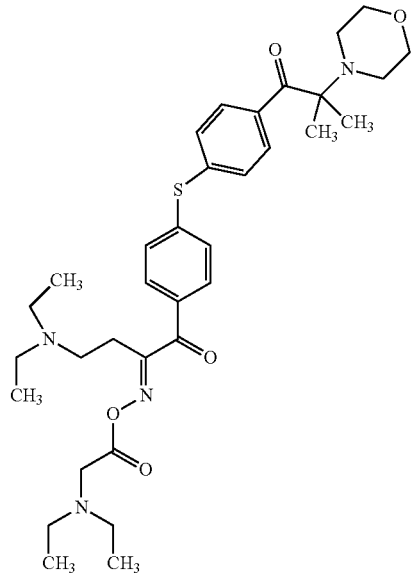

Compound No. 3-44
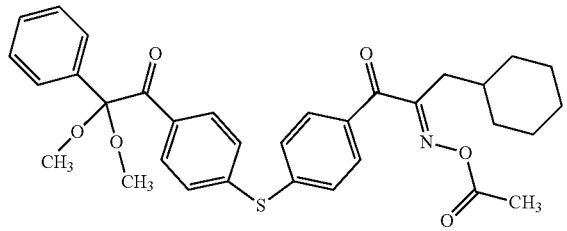
Compound No. 3-45
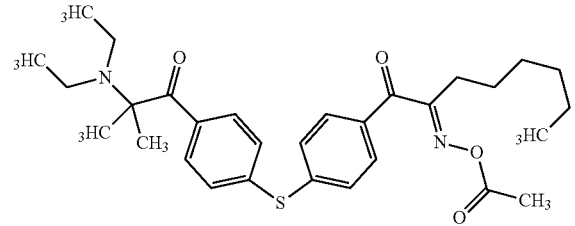
Compound No. 3-46
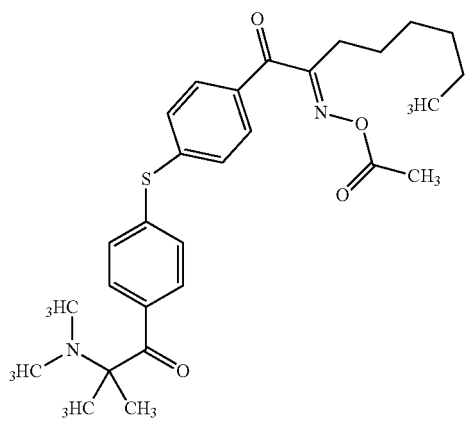
Compound No. 3-47
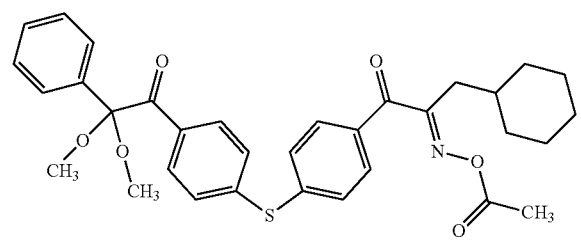
Compound No. 3-48
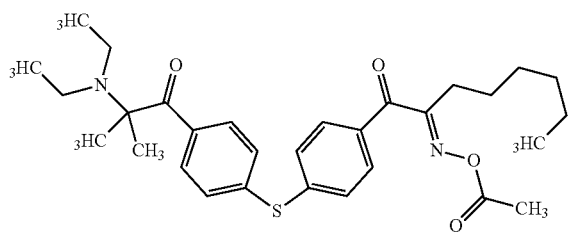
Compound No. 3-49
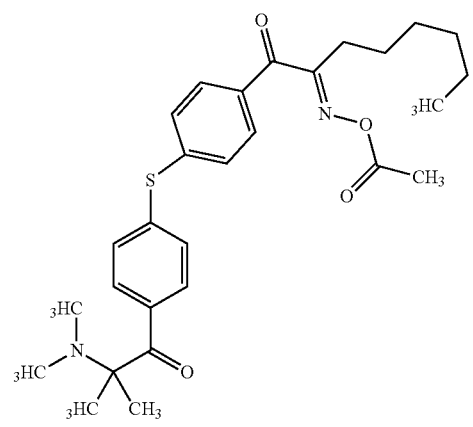
Compound No. 3-50
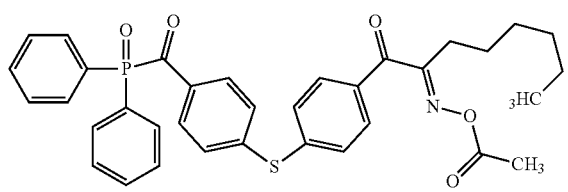
Compound No. 3-51
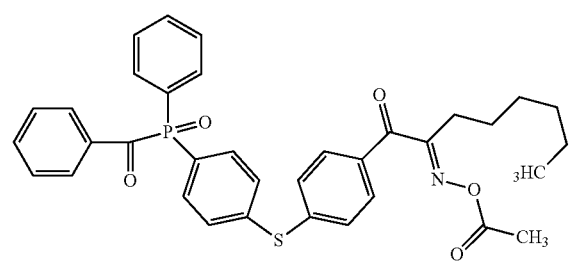

Compound No. 3-52
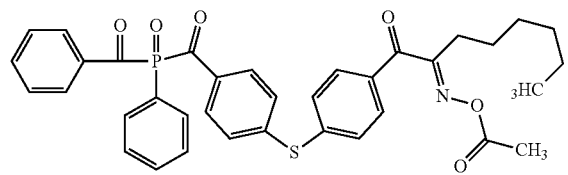
Compound No. 3-53
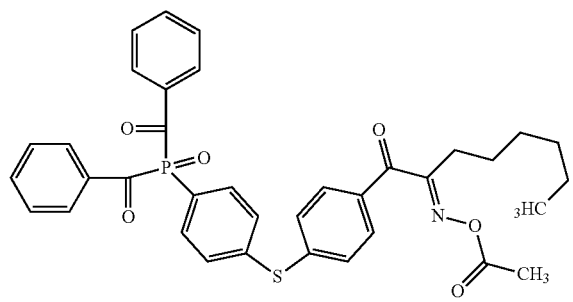
Compound No. 3-54
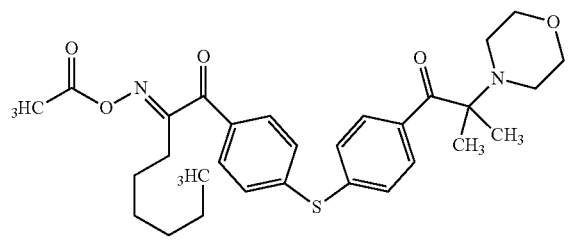
Compound No. 3-55
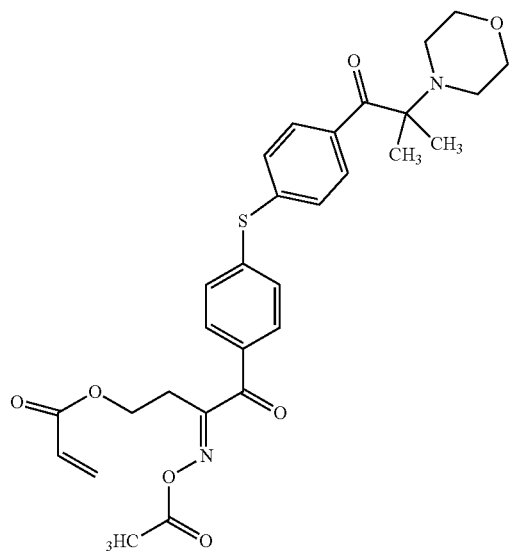
Compound No. 3-56
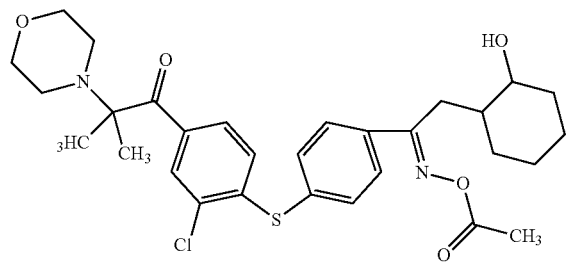
Compound No. 3-57
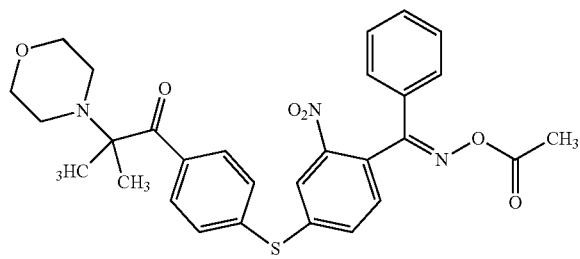

Compound No. 3-58
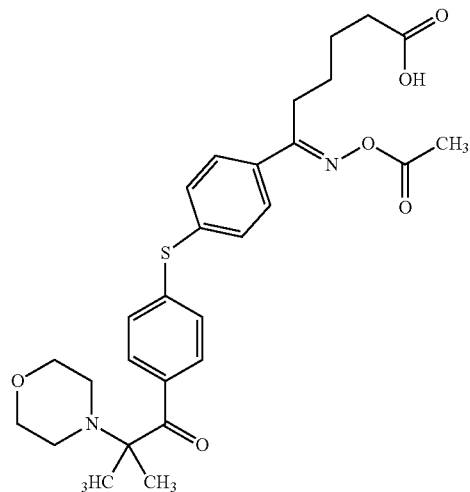
Compound No. 3-59
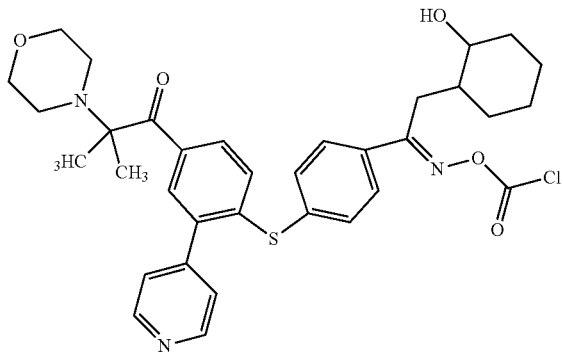
Compound No. 3-60
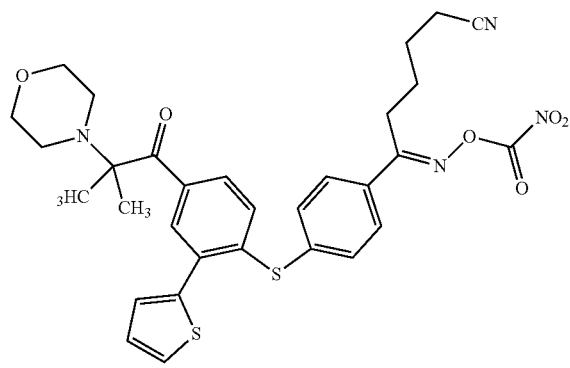
Compound No. 3-61
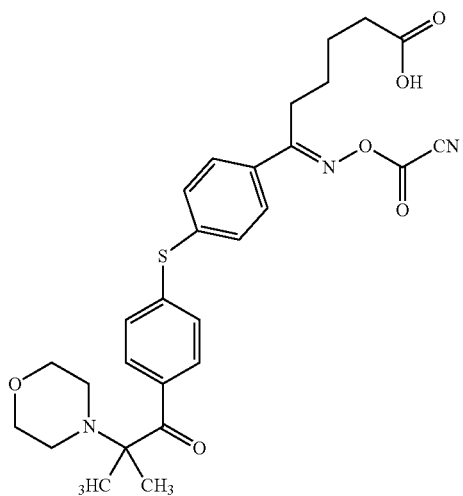
Compound No. 3-62
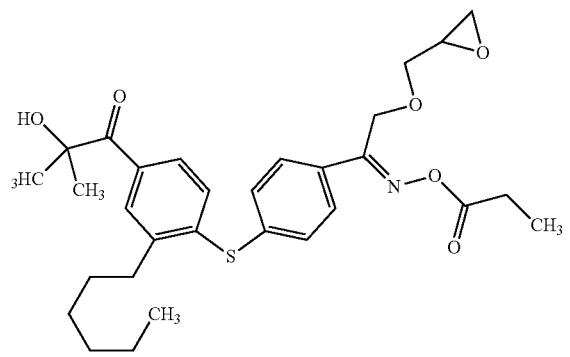
Compound No. 3-63
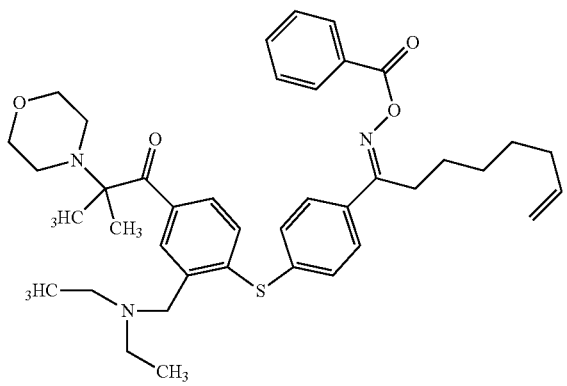

-continued
Compound No. 3-64
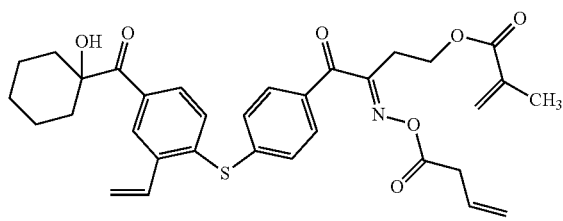
Compound No. 3-65
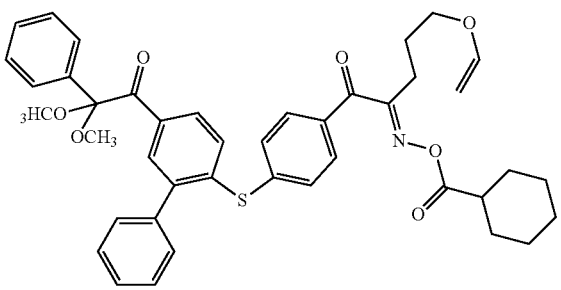
Compound No. 3-66
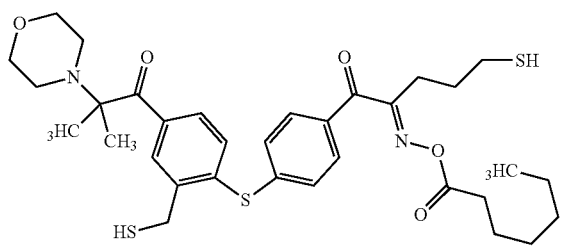
Compound No. 3-67
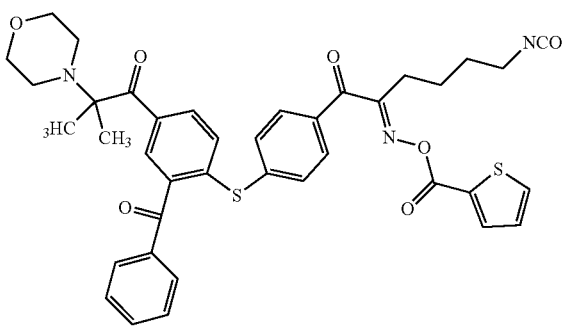
Compound No. 3-68
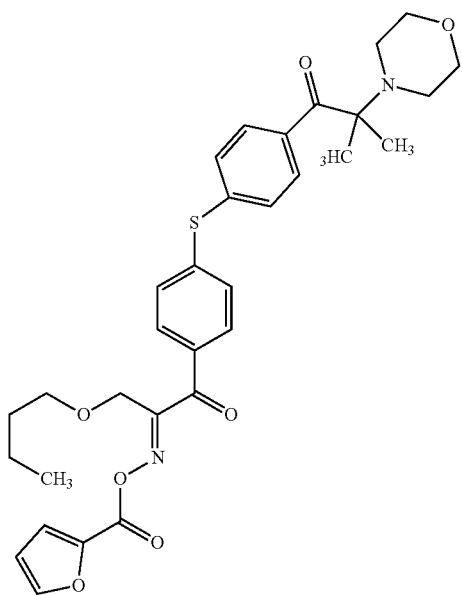
Compound No. 3-69
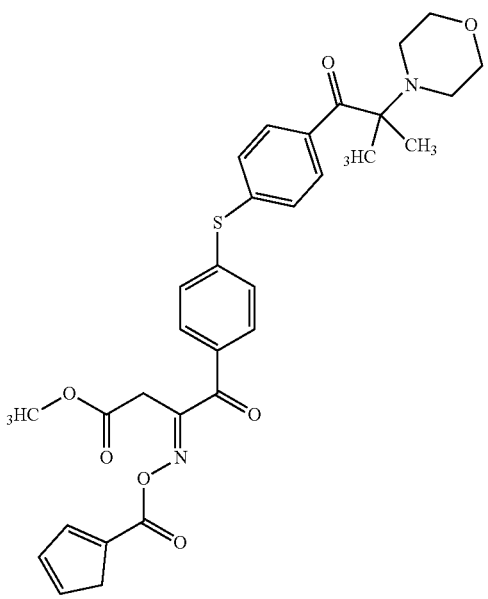

87 88
-continued
Compound No. 3-70
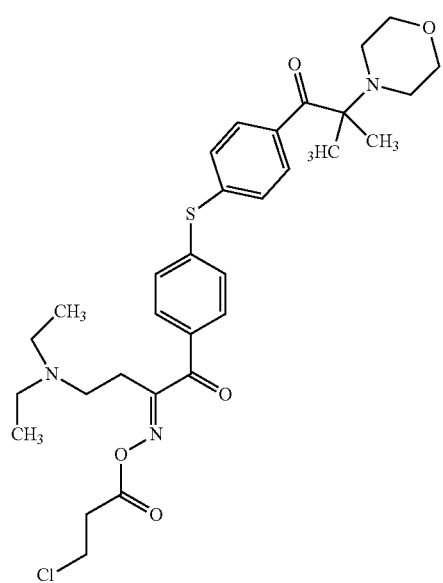
Compound No. 4-1
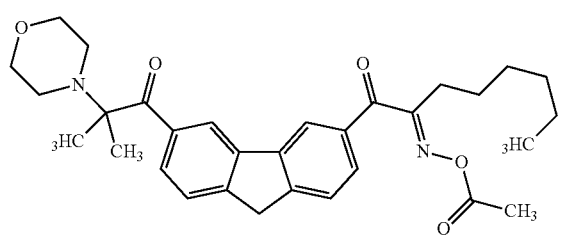
Compound No. 4-2
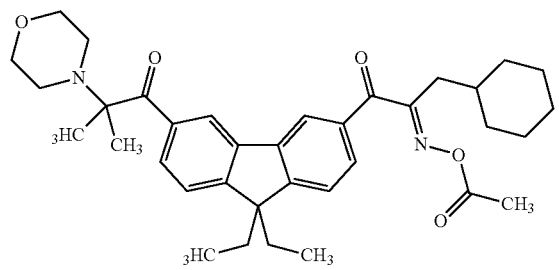
Compound No. 4-3
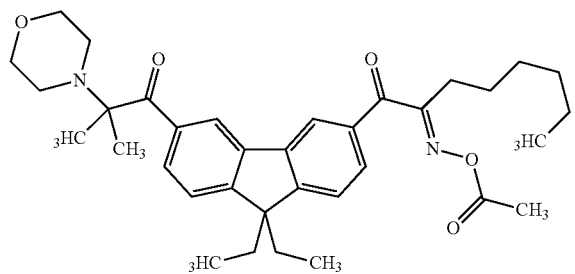
Compound No. 4-4
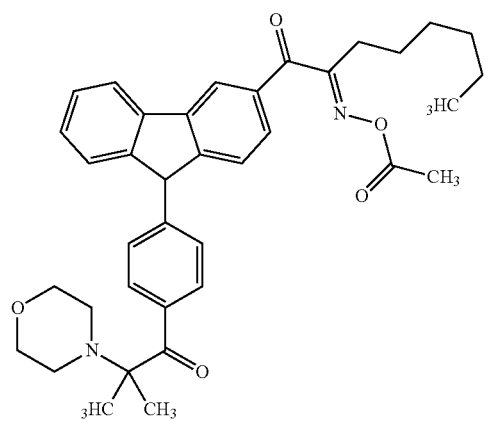
Compound No. 4-5
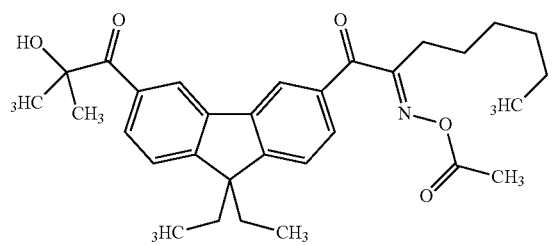

Compound No. 4-6
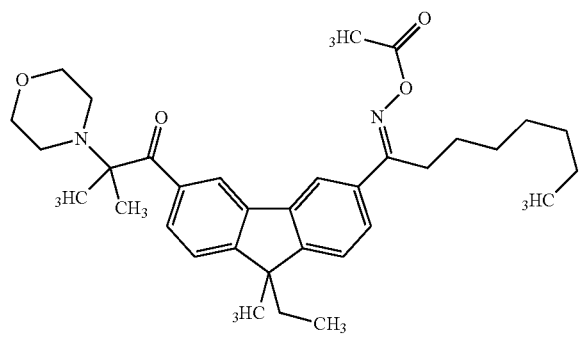
Compound No. 4-7
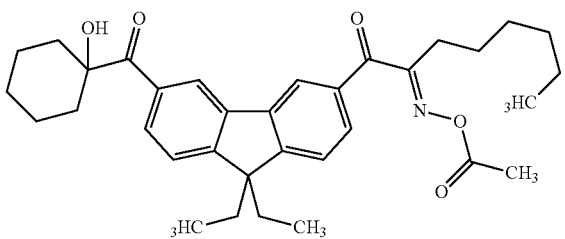
Compound No. 4-8
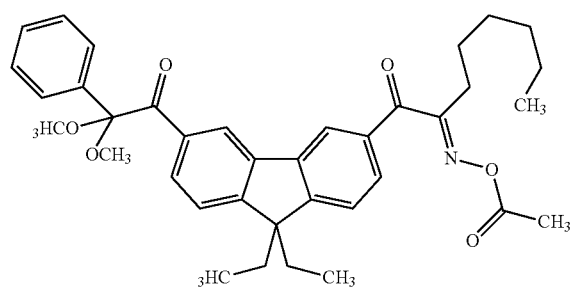
Compound No. 4-9
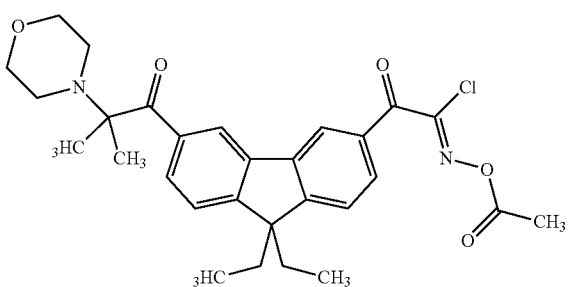
Compound No. 4-10
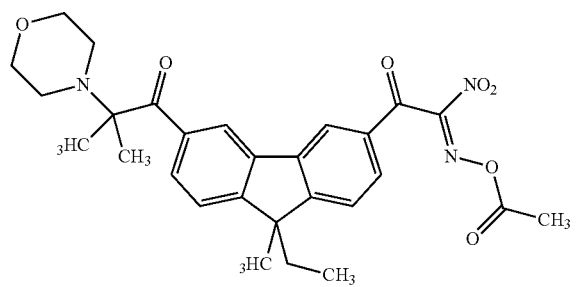
Compound No. 4-11
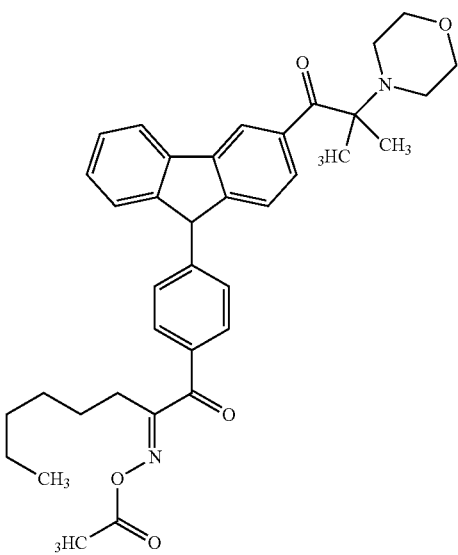

-continued
Compound No. 4-12
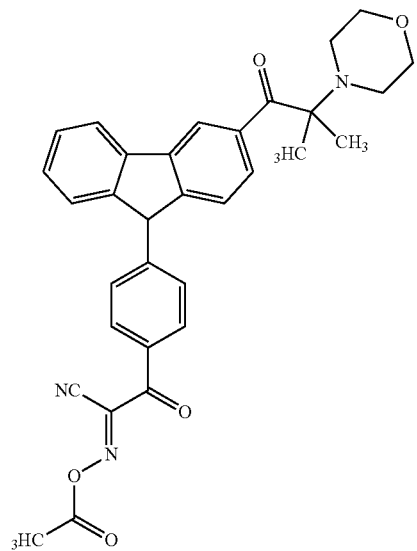
Compound No. 4-13
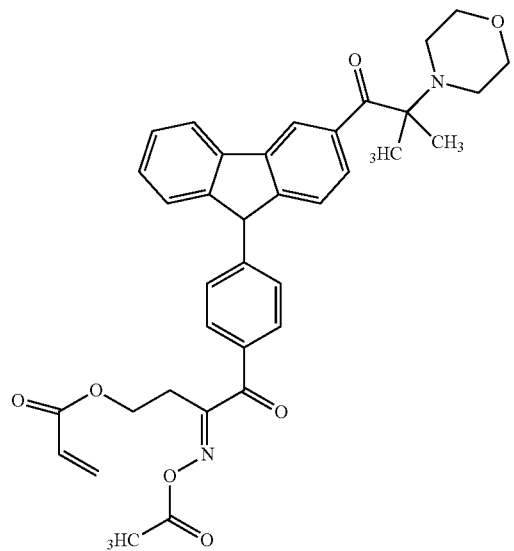
Compound No. 4-14
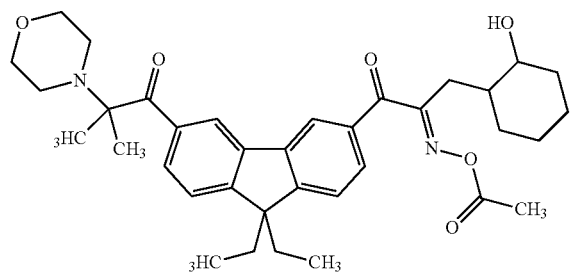
Compound No. 4-15
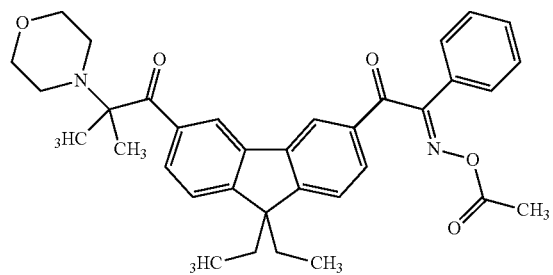
Compound No. 4-16
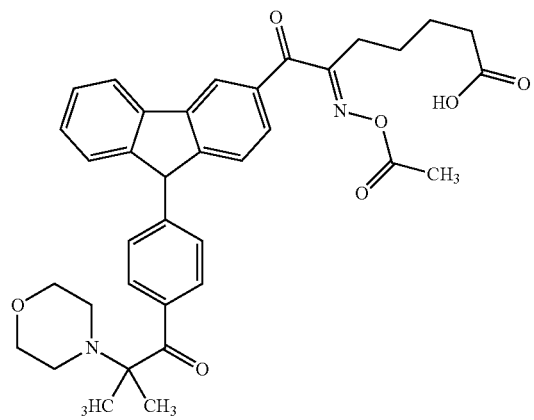
Compound No. 4-17
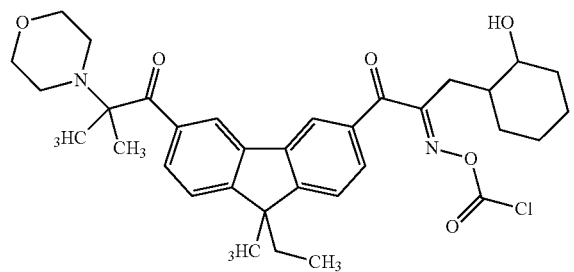

-continued
Compound No. 4-18
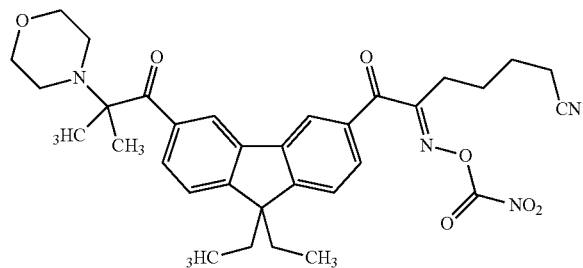
Compound No. 4-19
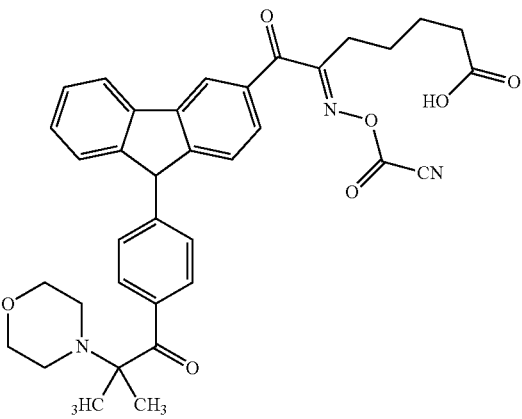
Compound No. 4-20
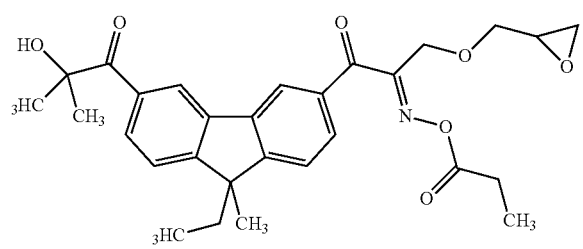
Compound No. 4-21
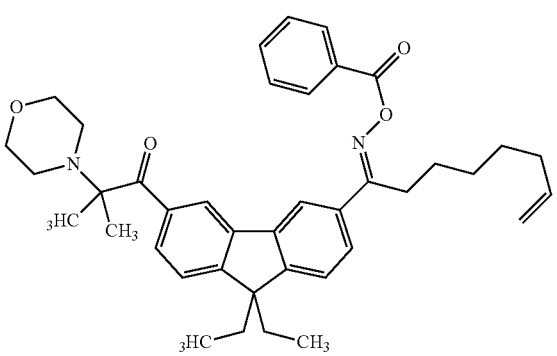
Compound No. 4-22
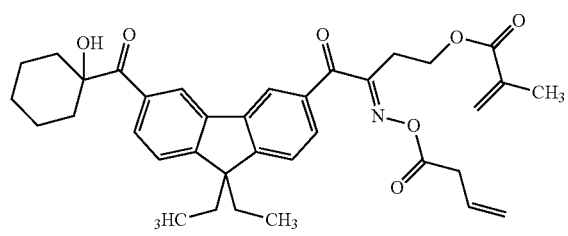
Compound No. 4-23
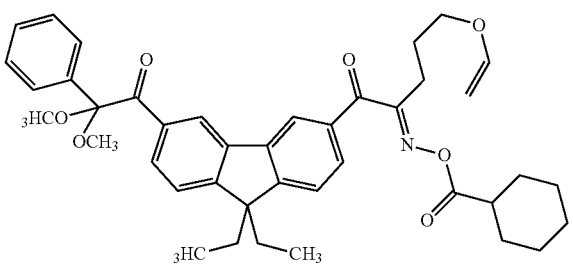
Compound No. 4-24
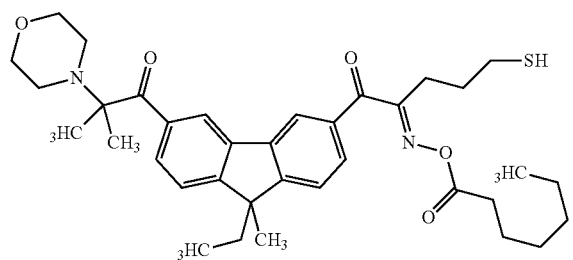
Compound No. 4-25
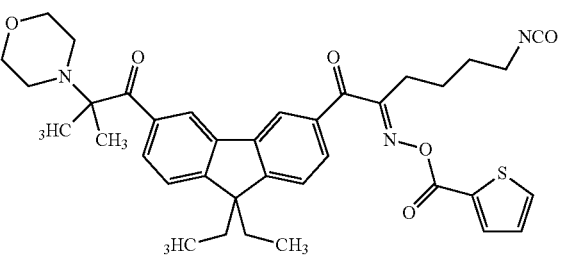

Compound No. 4-26
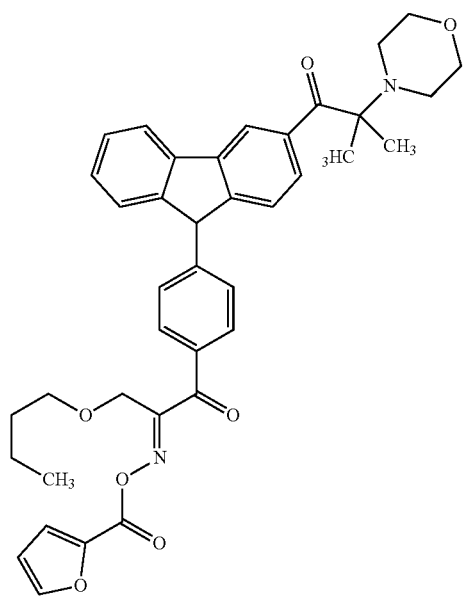
Compound No. 4-27
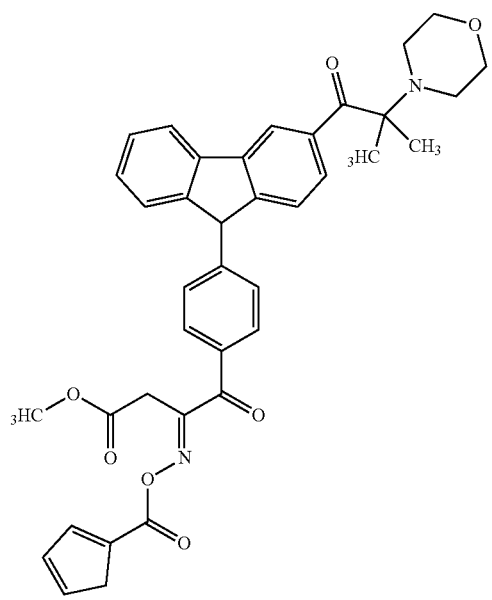
Compound No. 4-28
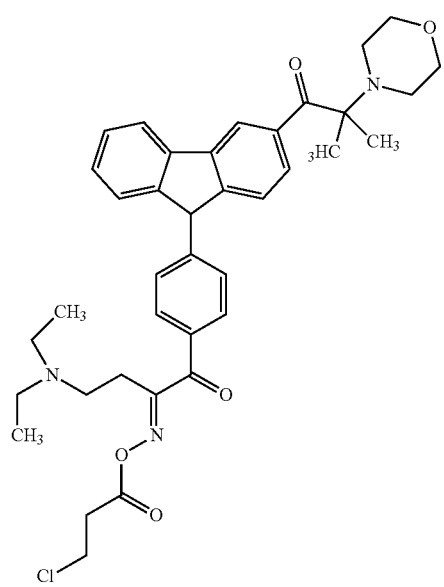
Compound No. 4-29
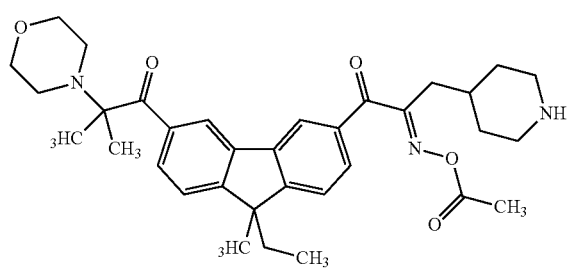

-continued
Compound No. 4-30
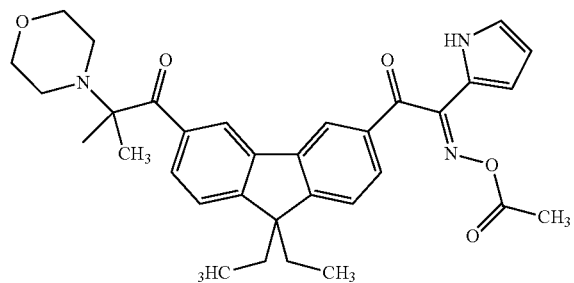
Compound No. 4-31
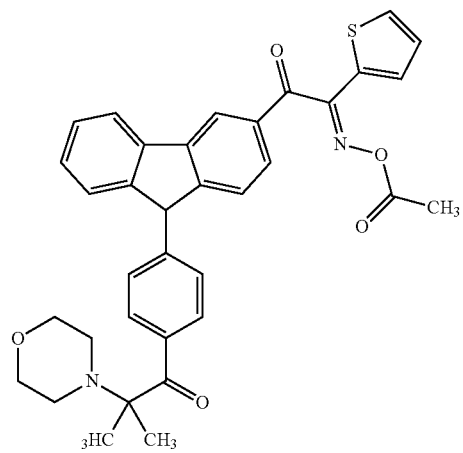
Compound No. 4-32
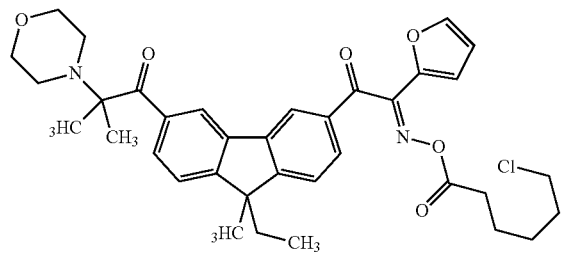
Compound No. 4-33
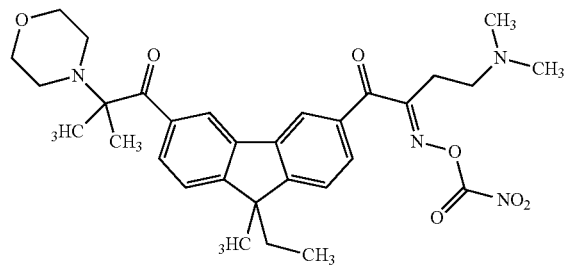
Compound No. 4-34
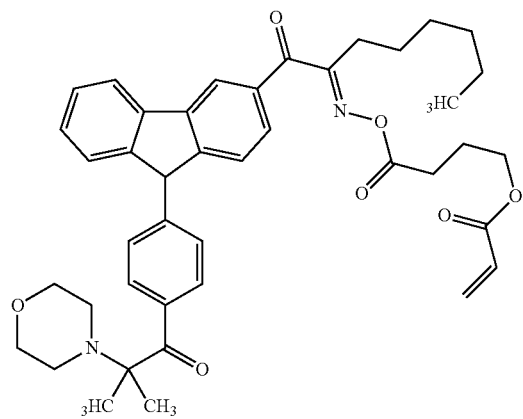
Compound No. 4-35
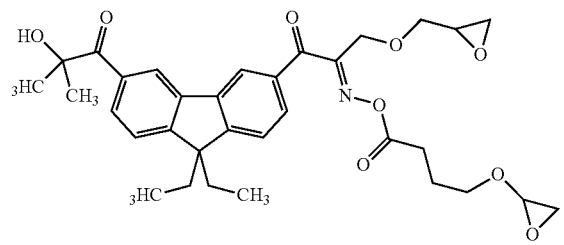
Compound No. 4-36
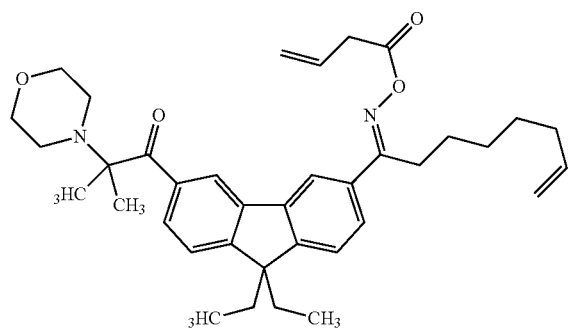
Compound No. 4-37
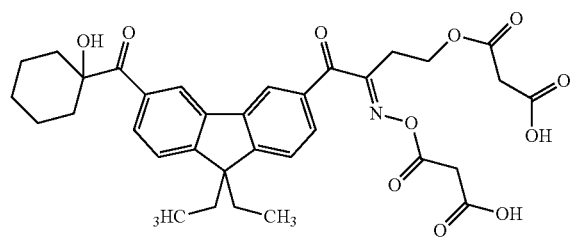

Compound No. 4-38
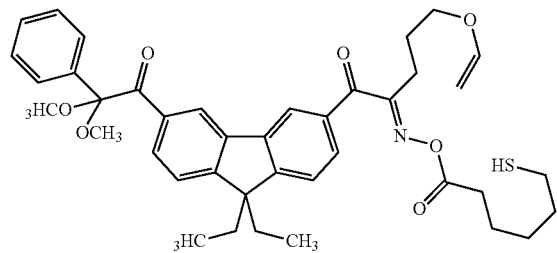
Compound No. 4-39
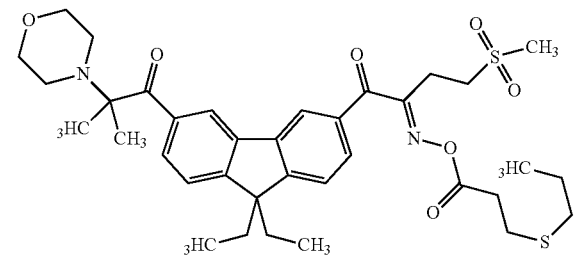
Compound No. 4-40
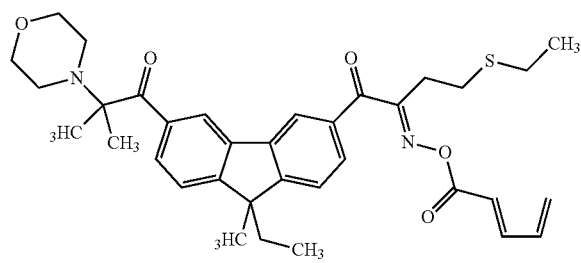
Compound No. 4-41
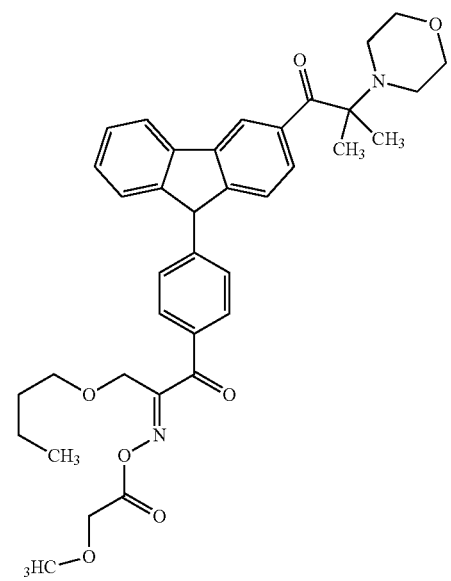
Compound No. 4-42
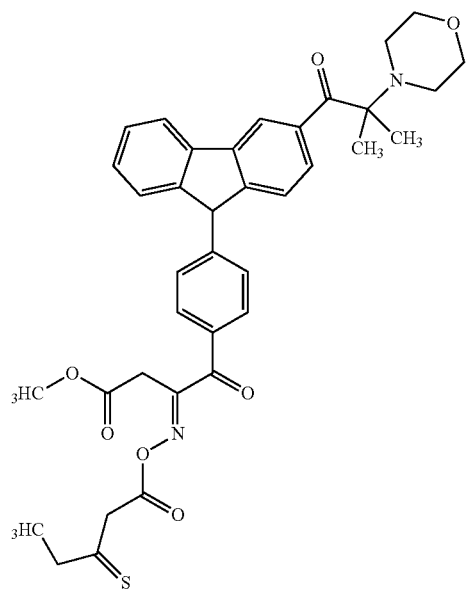
Compound No. 4-43
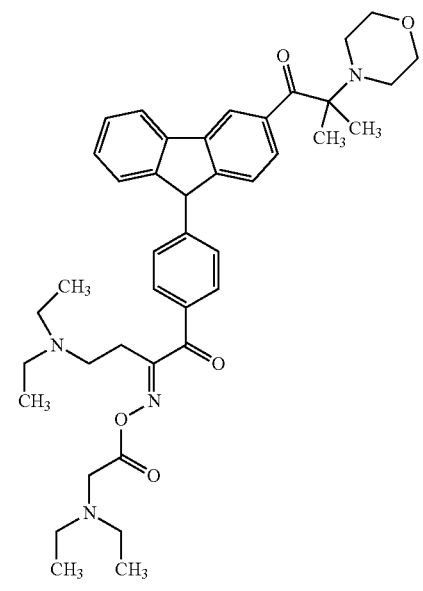

-continued
Compound No. 4-44
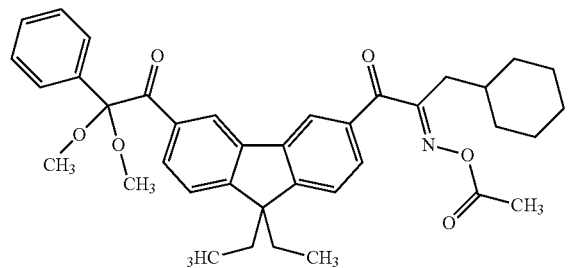
Compound No. 4-45
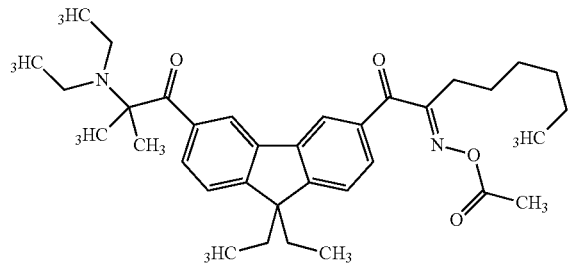
Compound No. 4-46
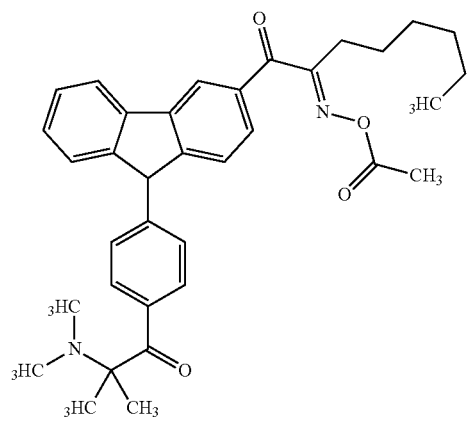
Compound No. 4-47
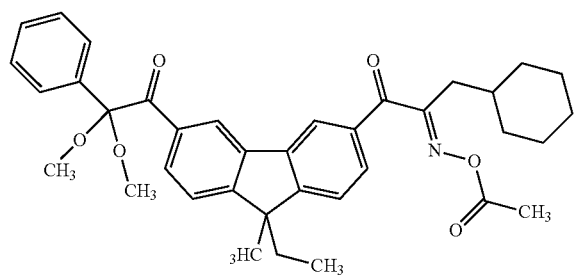
Compound No. 4-48
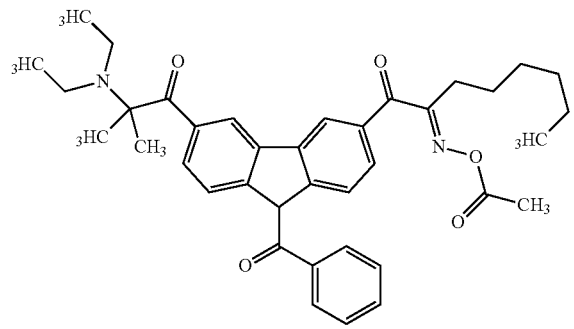
Compound No. 4-49
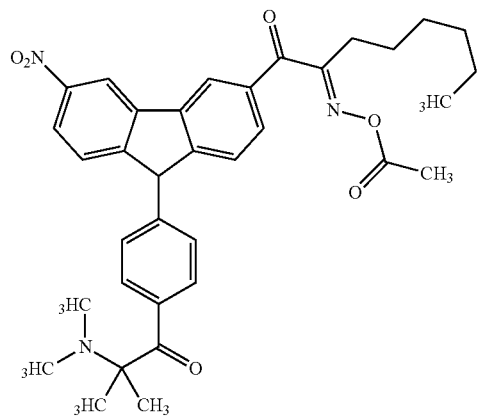
Compound No. 4-50
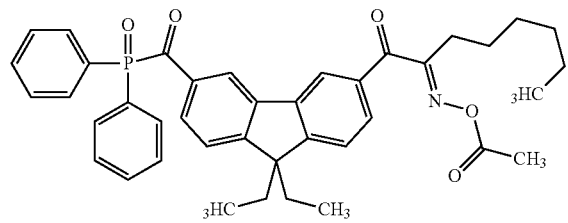
Compound No. 4-51
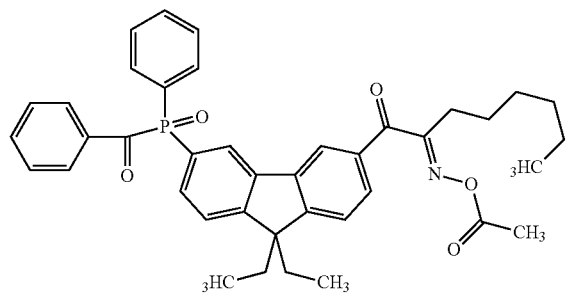

-continued
Compound No. 4-52
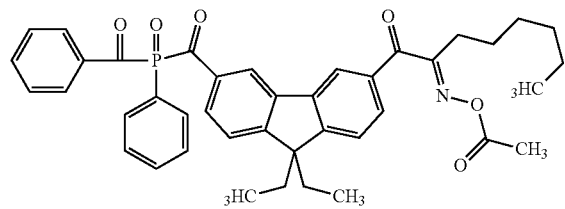
Compound No. 4-53
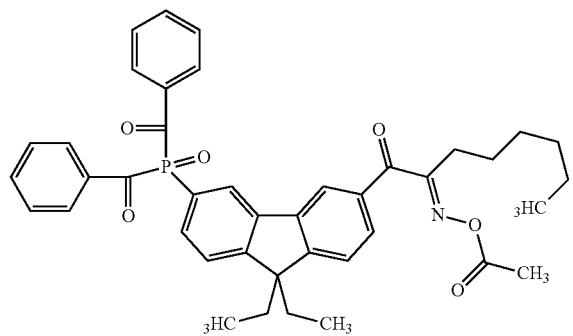
Compound No. 4-54
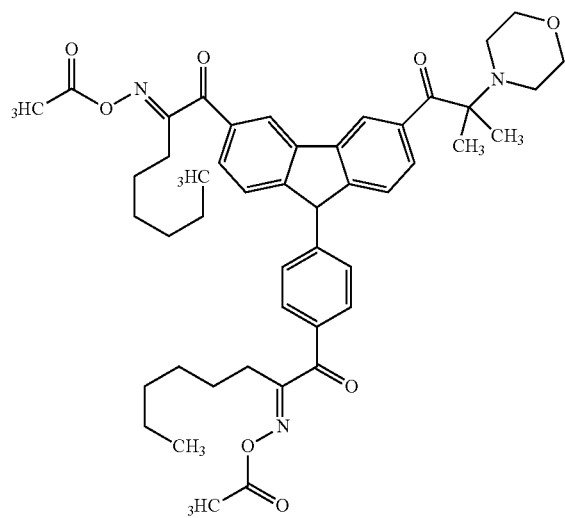
Compound No. 4-55
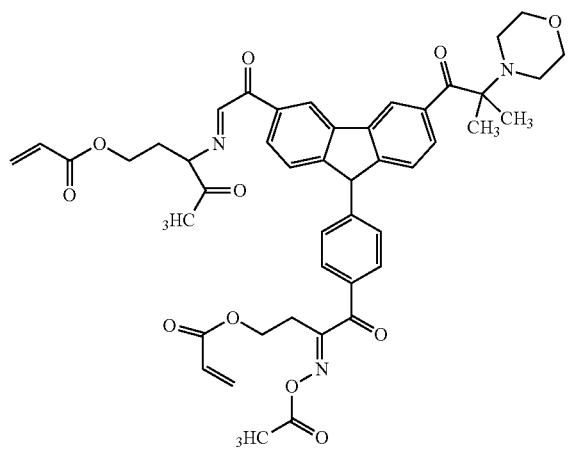
Compound No. 4-56
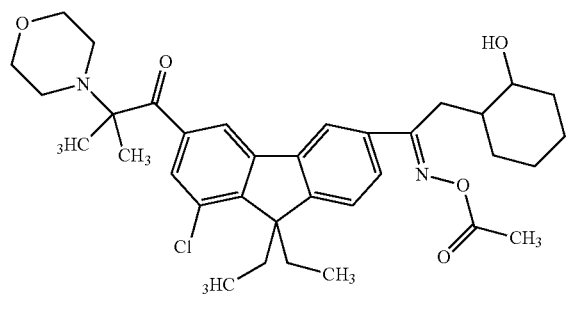
Compound No. 4-57
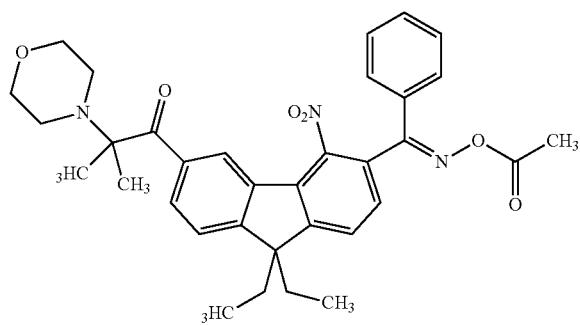

Compound No. 4-58
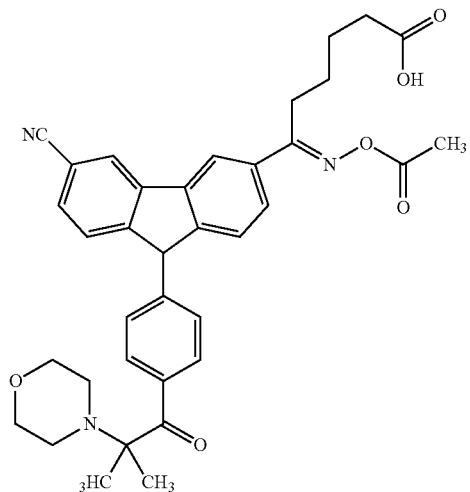
Compound No. 4-59
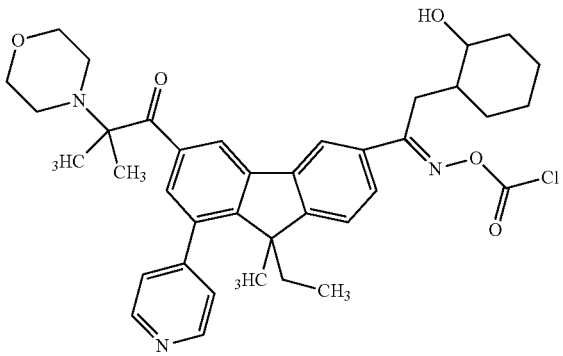
Compound No. 4-60
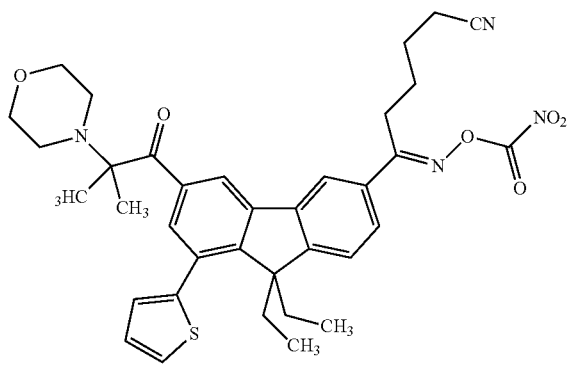
Compound No. 4-61
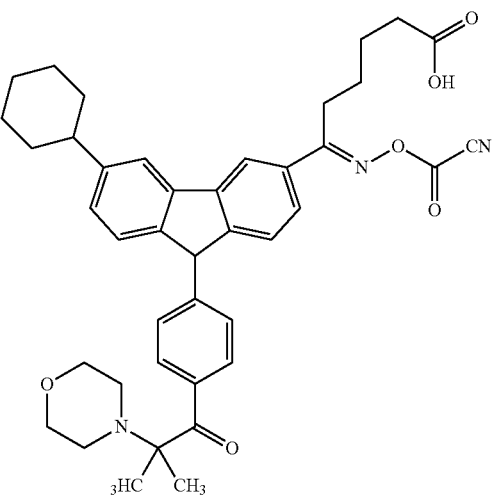
Compound No. 4-62
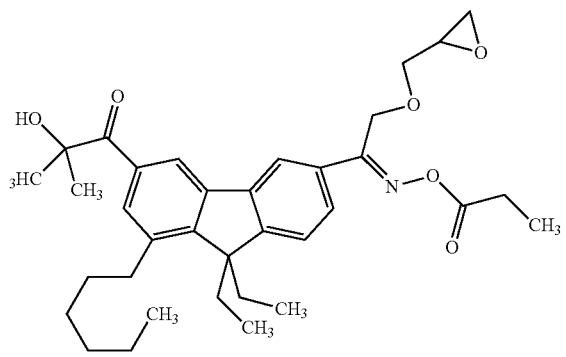
Compound No. 4-63
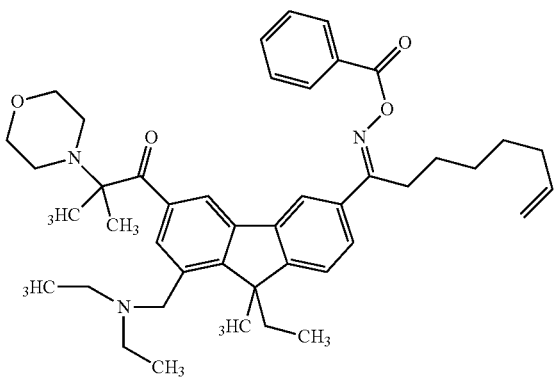

Compound No. 4-64
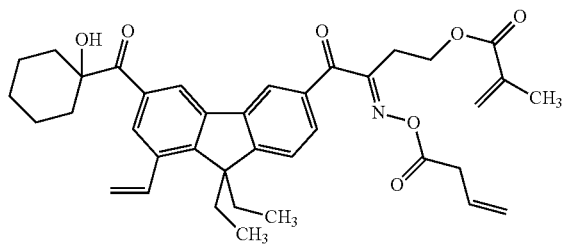
Compound No. 4-65
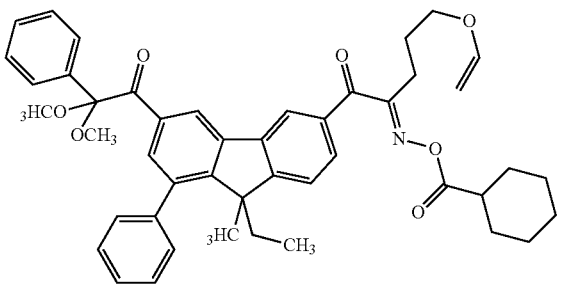
Compound No. 4-66
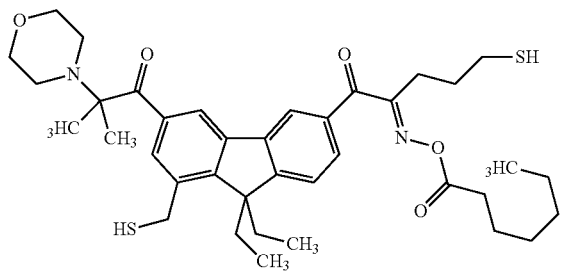
Compound No. 4-67
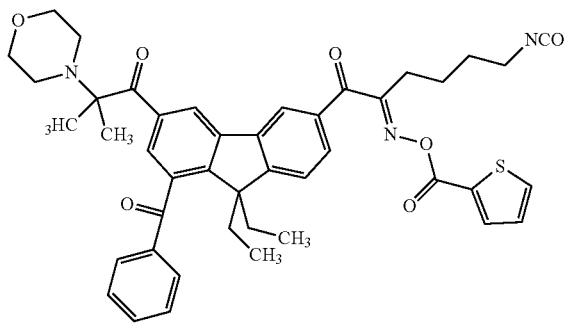
Compound No. 4-68
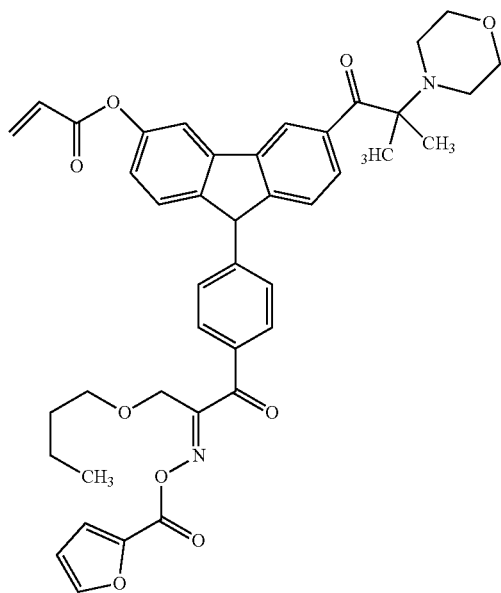
Compound No. 4-69
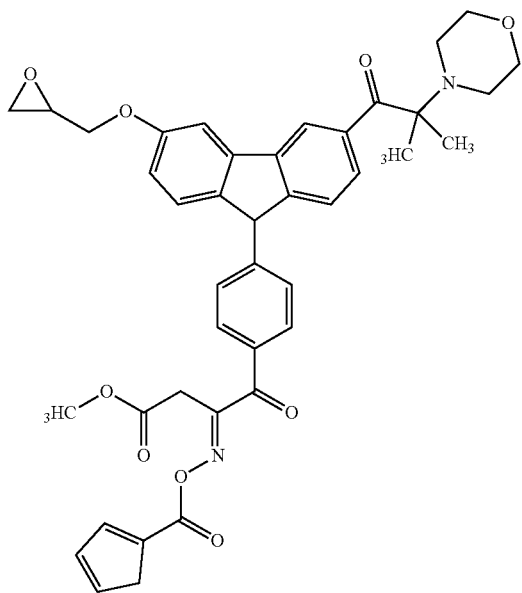

Compound No. 4-70
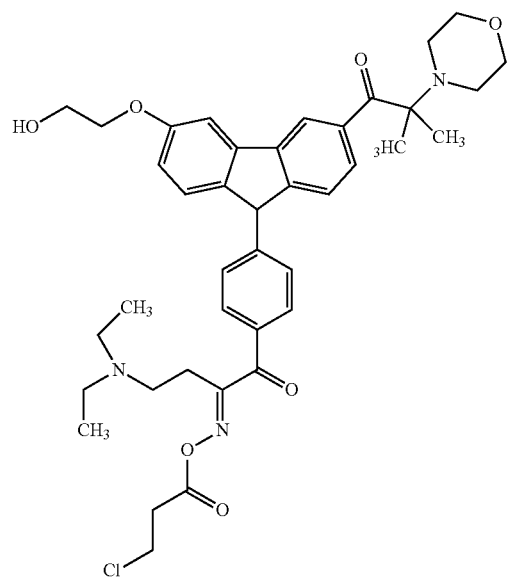
Compound No. 4-71
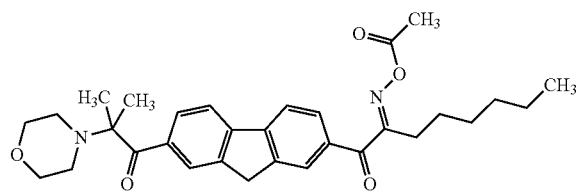
Compound No. 4-72
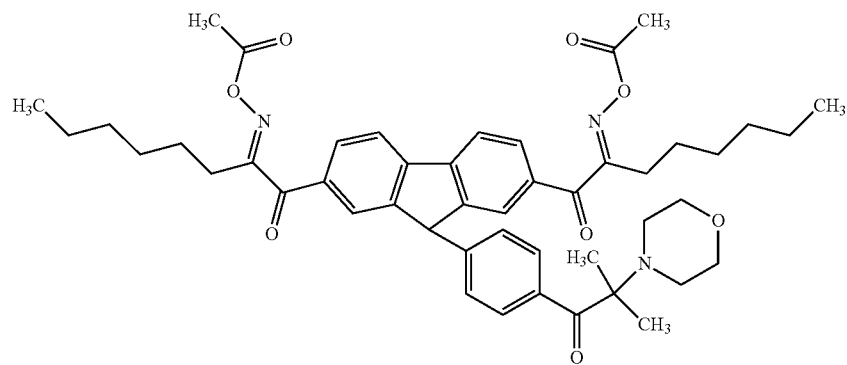
Compound No. 5-1
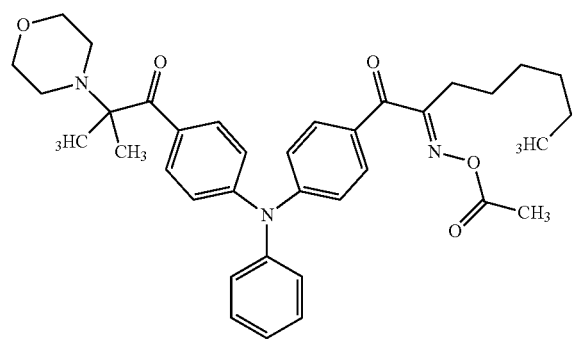
Compound No. 5-2
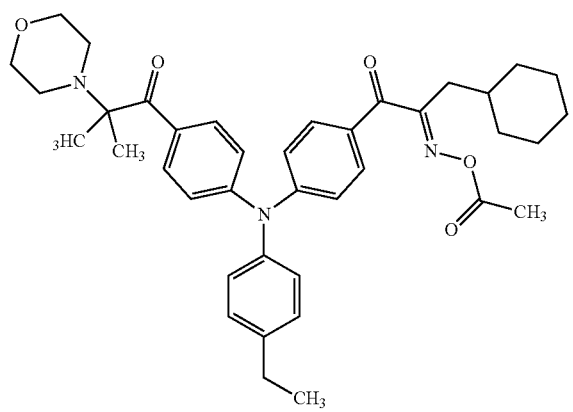

-continued
Compound No. 5-3
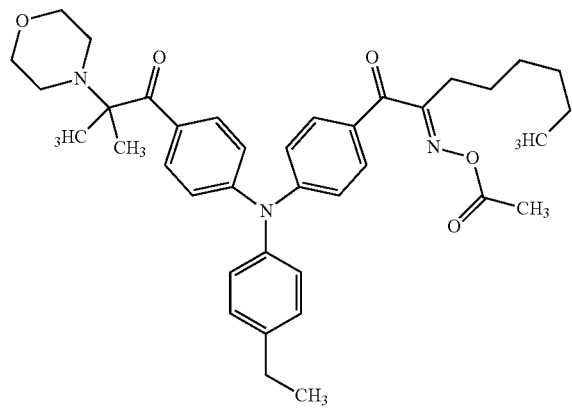
Compound No. 5-4
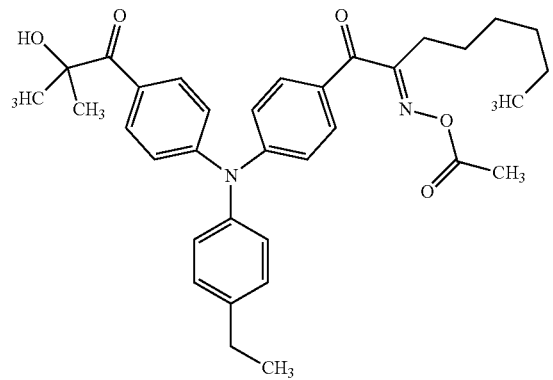
Compound No. 5-5
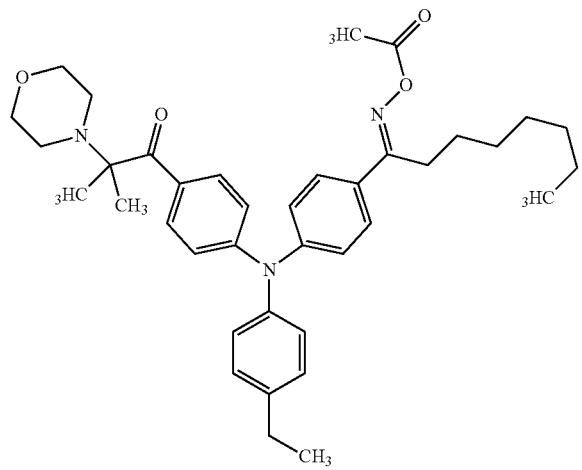
Compound No. 5-6
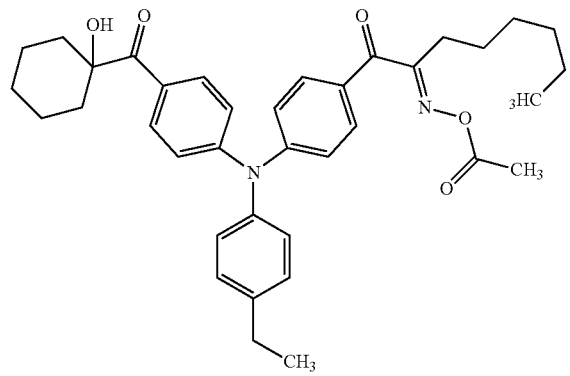
Compound No. 5-7
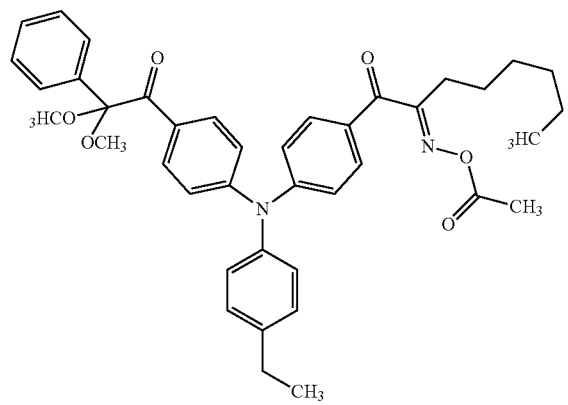
Compound No. 5-8
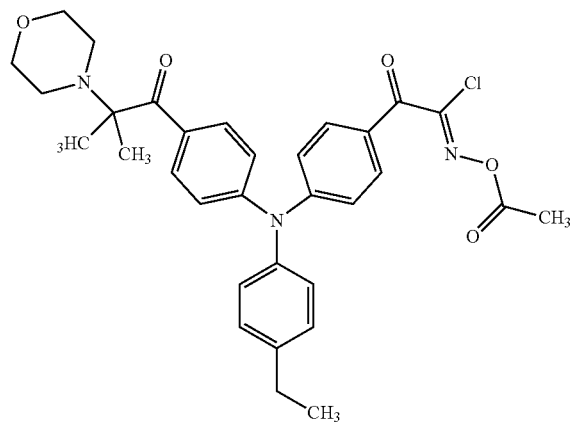

-continued
Compound No. 5-9
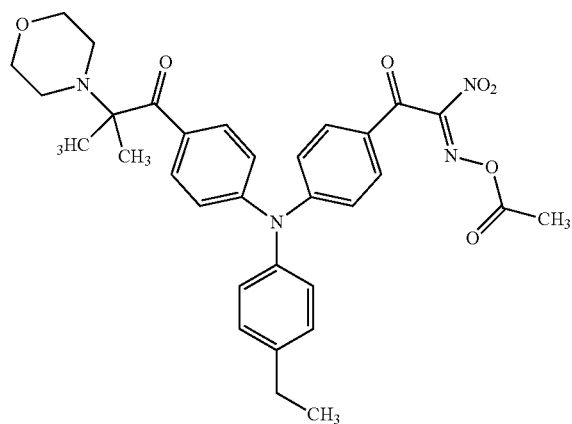
Compound No. 5-10
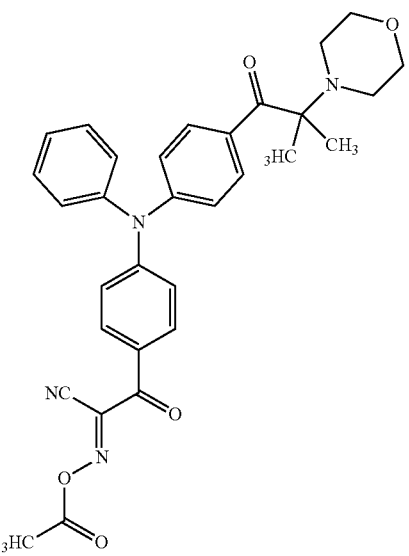
Compound No. 5-11
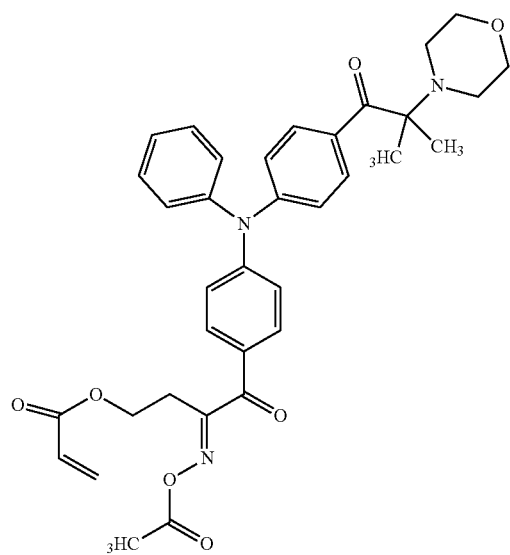
Compound No. 5-12
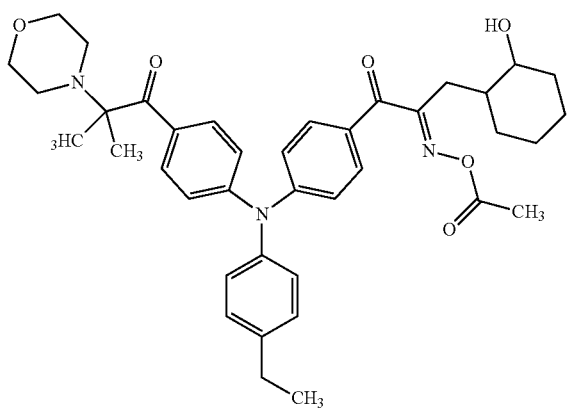
Compound No. 5-13
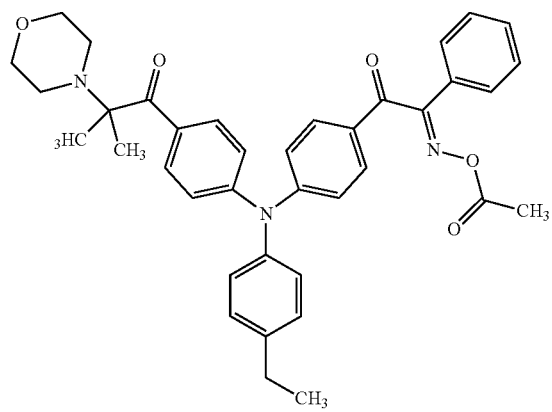
Compound No. 5-14
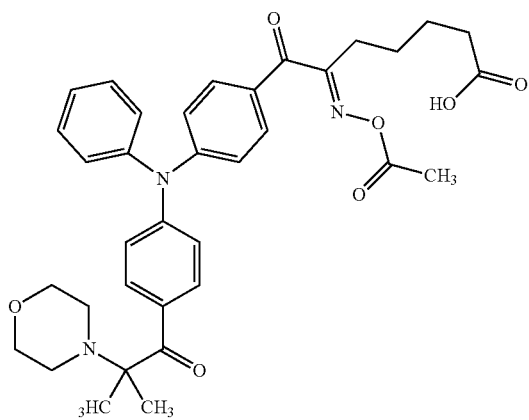

-continued
Compound No. 5-15
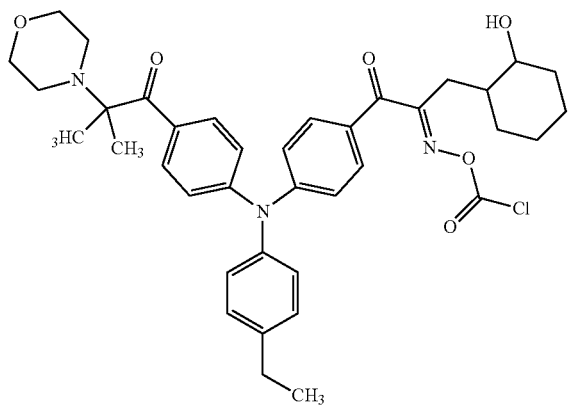
Compound No. 5-16
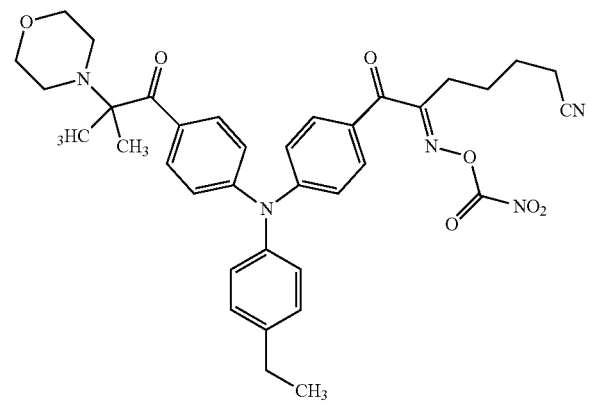
Compound No. 5-17
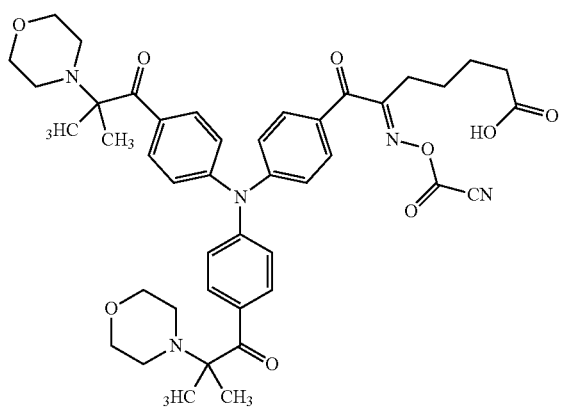
Compound No. 5-18
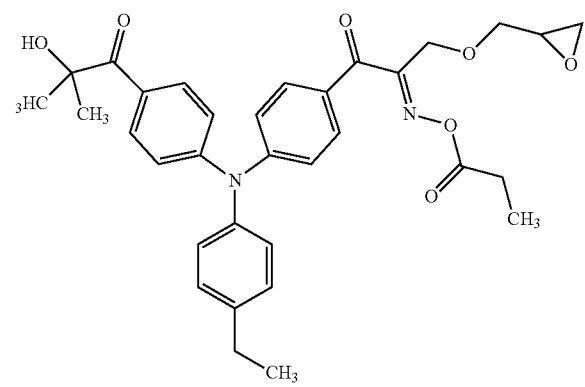
Compound No. 5-19
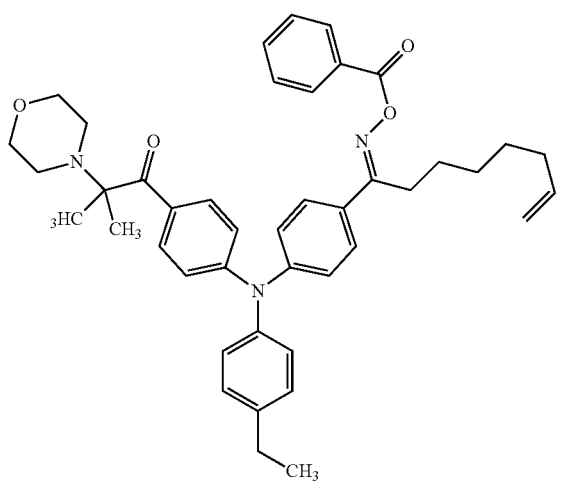
Compound No. 5-20
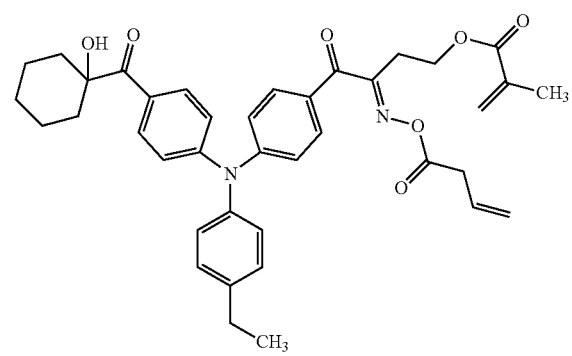

-continued
Compound No. 5-21
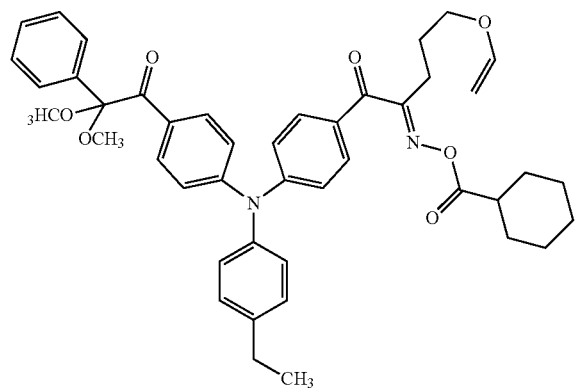
Compound No. 5-22
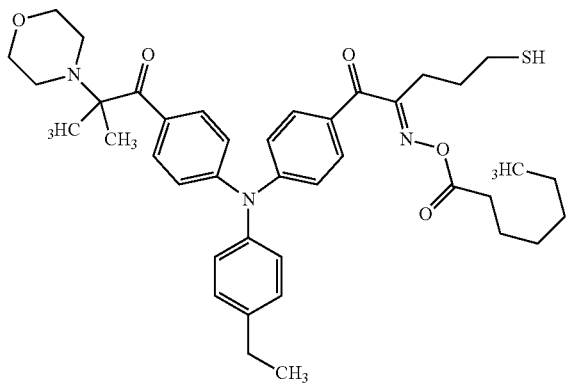
Compound No. 5-23
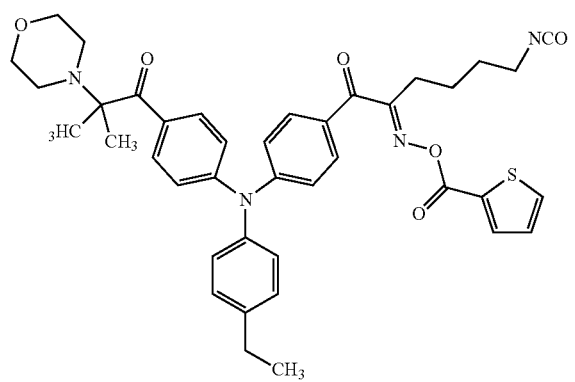
Compound No. 5-24
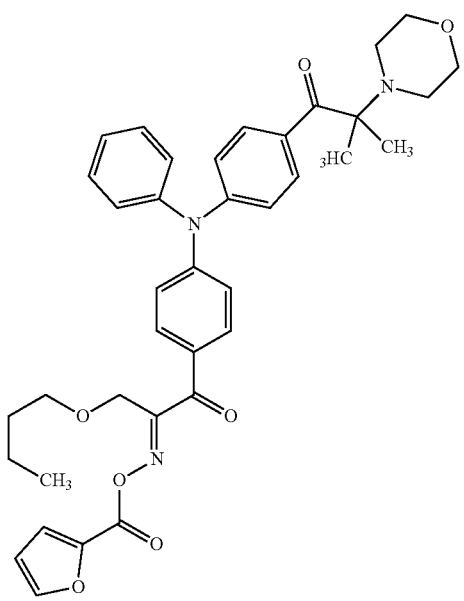
Compound No. 5-25
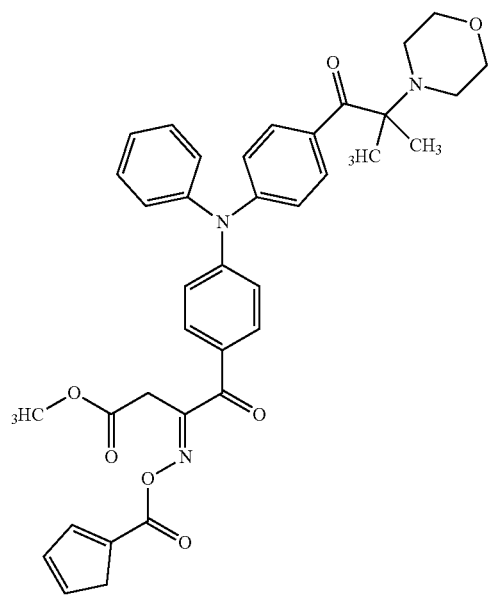
Compound No. 5-26
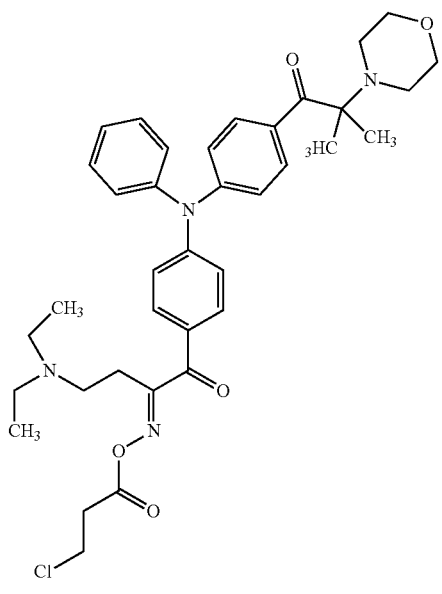

-continued
Compound No. 5-27
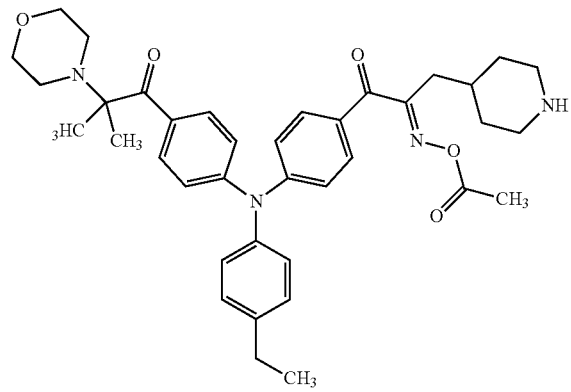
Compound No. 5-28
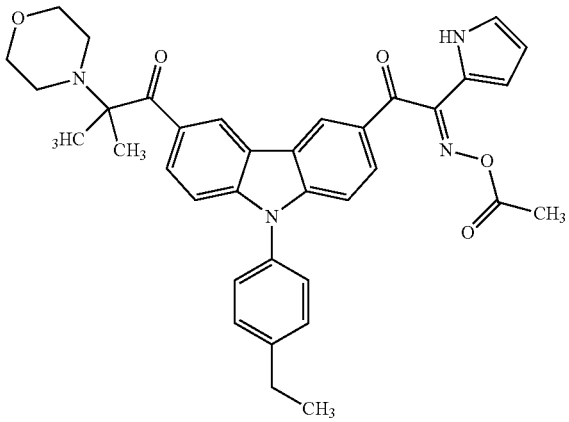
Compound No. 5-29
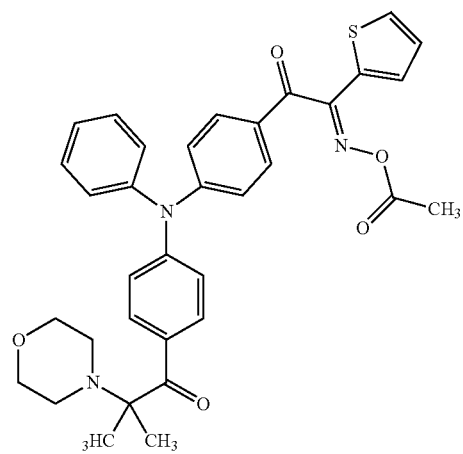
Compound No. 5-30
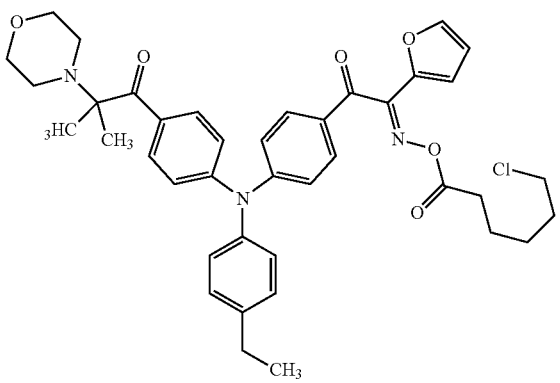
Compound No. 5-31
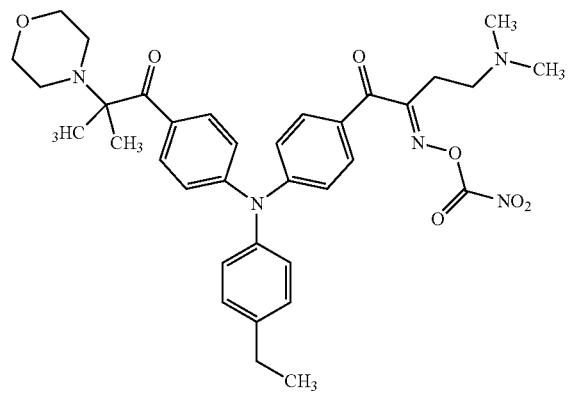
Compound No. 5-32
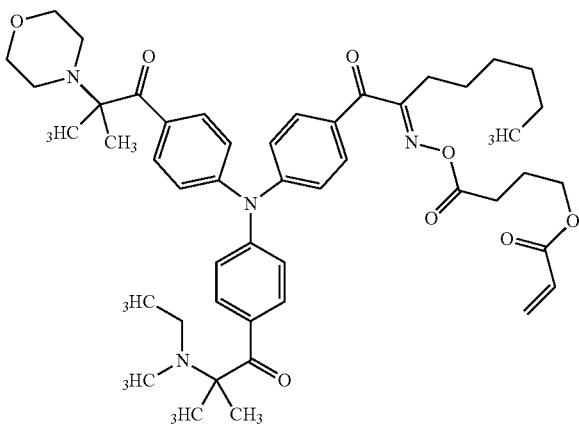

-continued
Compound No. 5-33
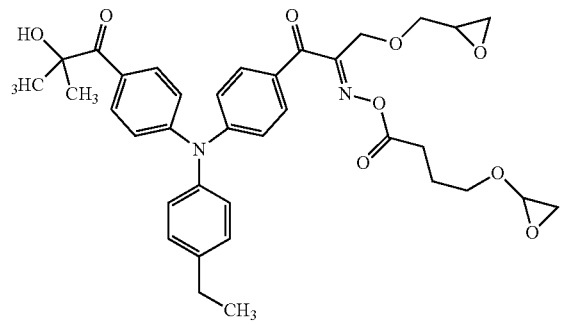
Compound No. 5-34
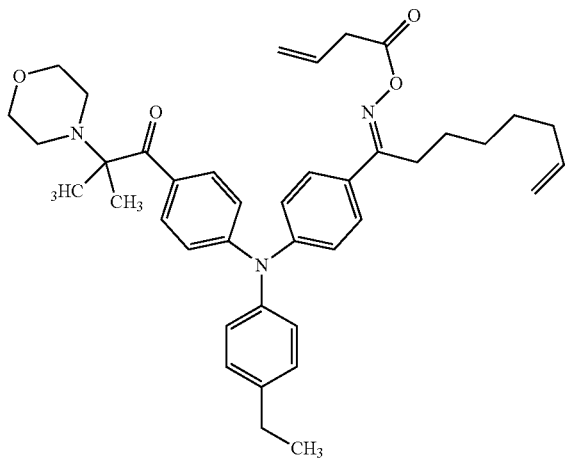
Compound No. 5-35
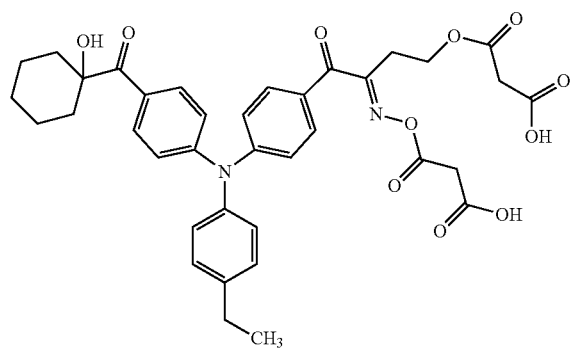
Compound No. 5-36
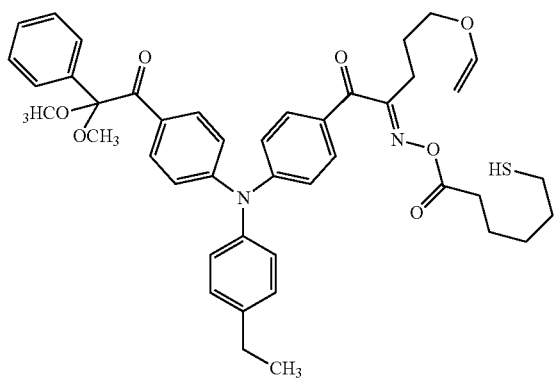
Compound No. 5-37
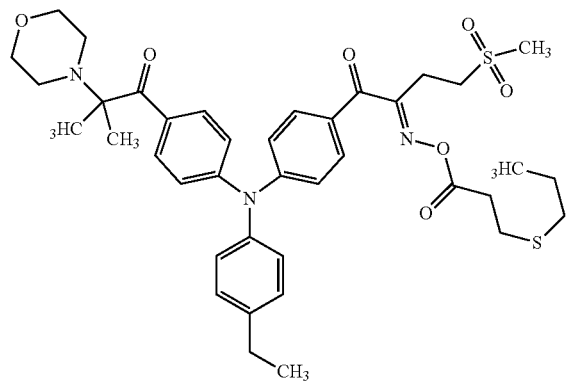
Compound No. 5-38
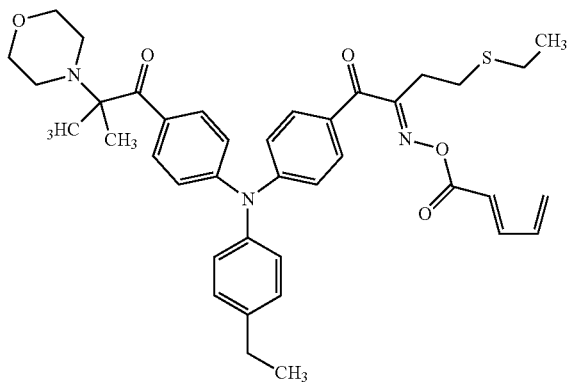

123
124
-continued
Compound No. 5-39
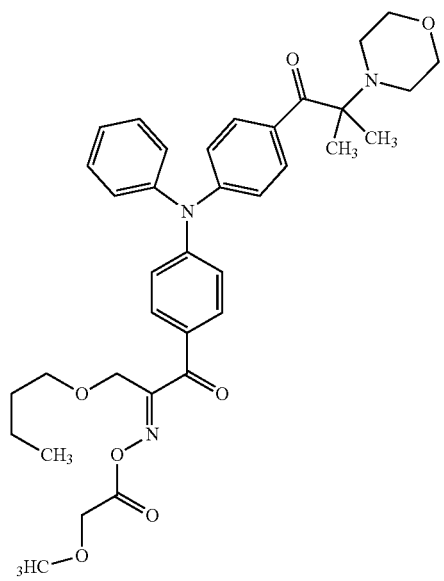
Compound No. 5-40
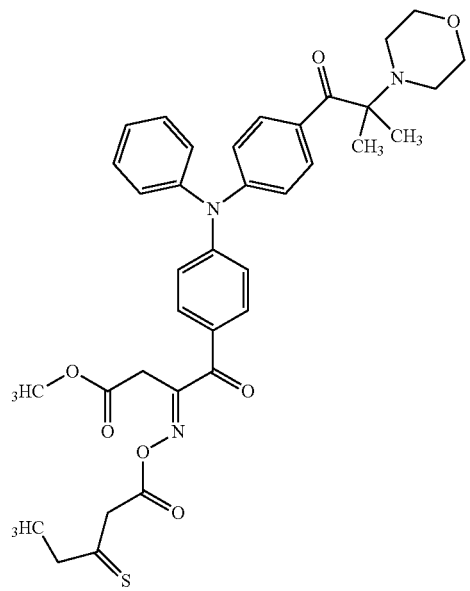
Compound No. 5-41
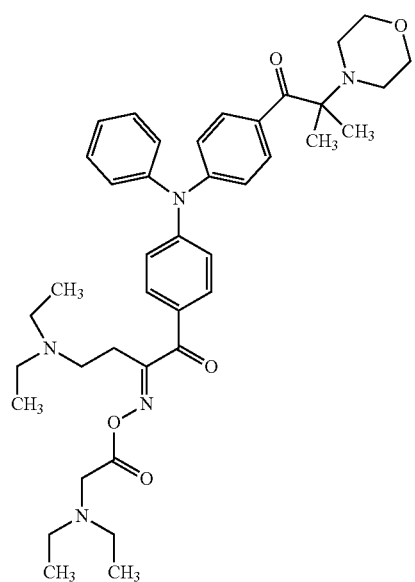
Compound No. 5-42
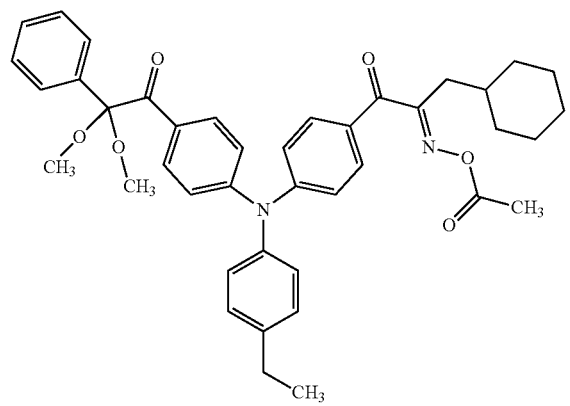
Compound No. 5-43
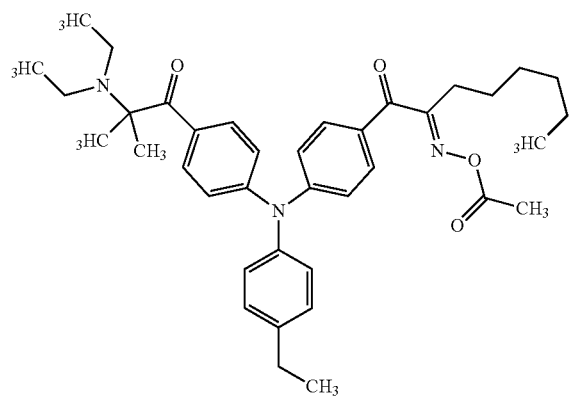
Compound No. 5-44
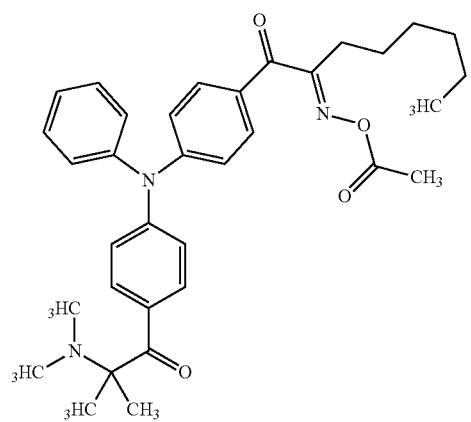

Compound No. 5-45
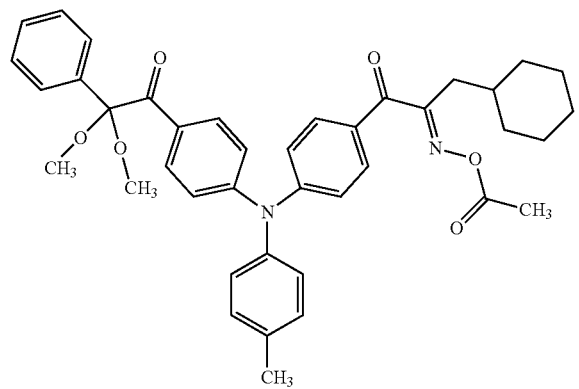
Compound No. 5-46
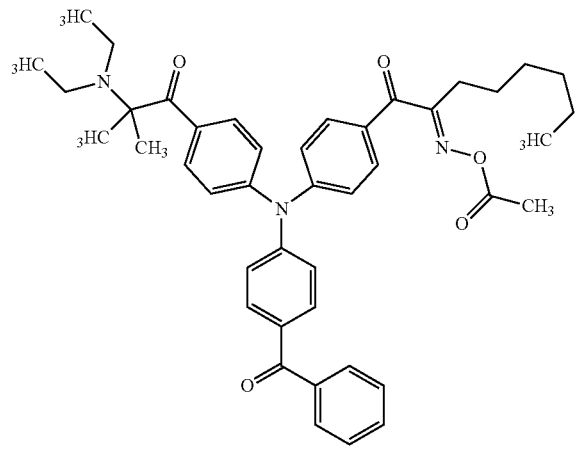
Compound No. 5-47
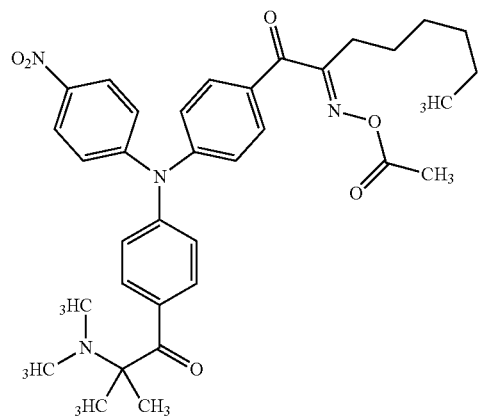
Compound No. 5-48
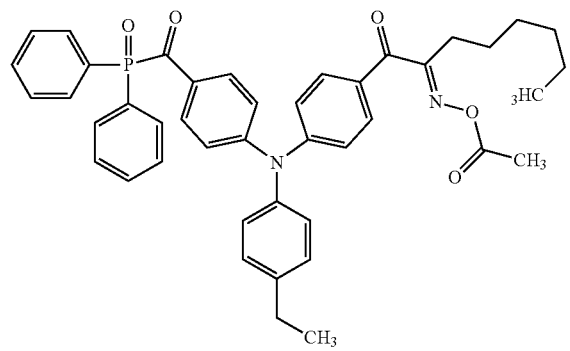
Compound No. 5-49
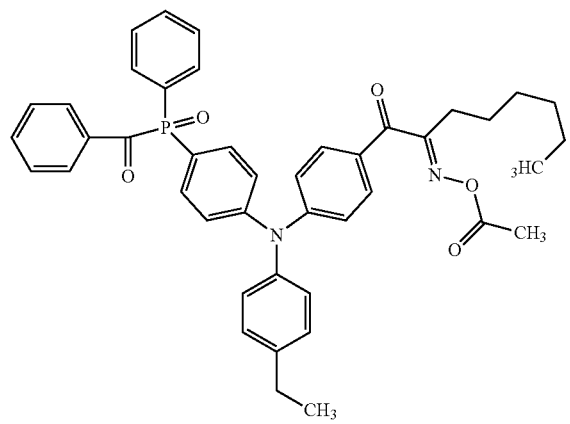
Compound No. 5-50
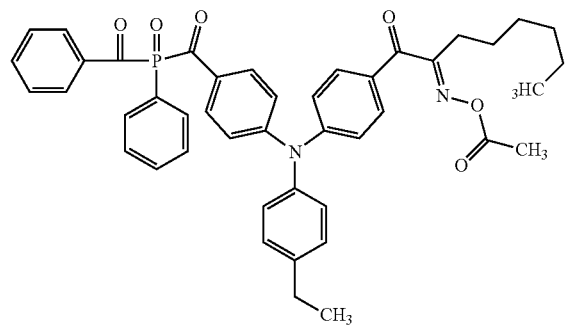

-continued
Compound No. 5-51
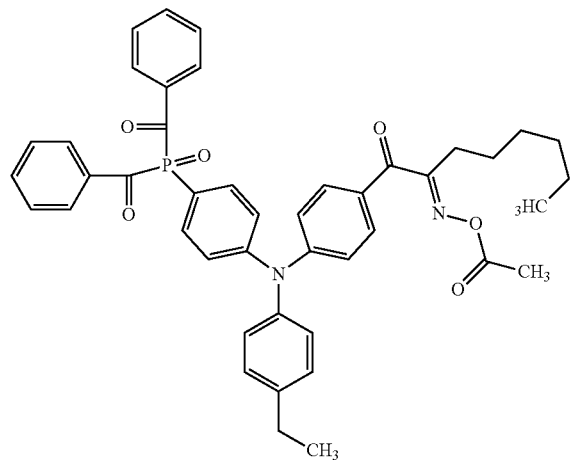
Compound No. 5-52
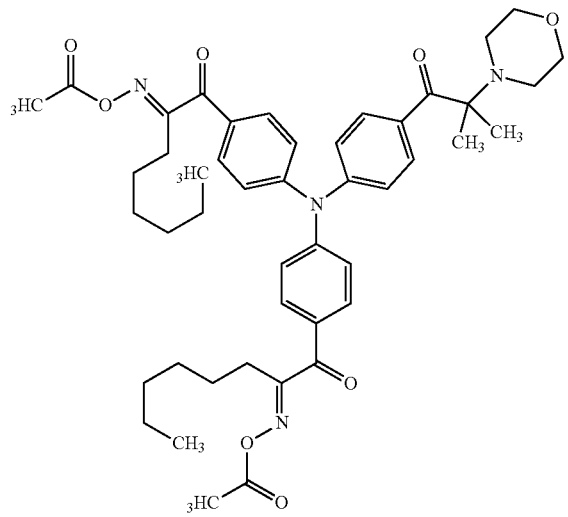
Compound No. 5-53
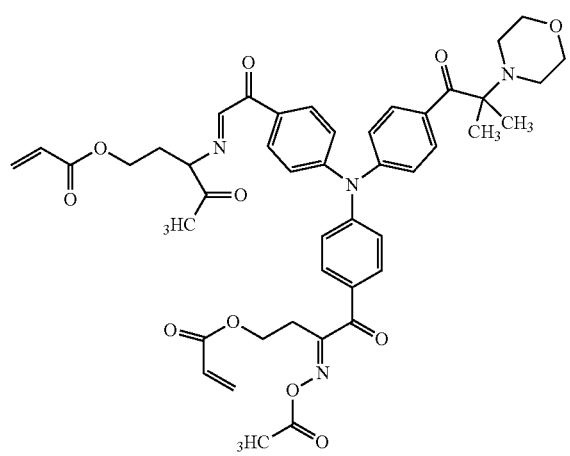
Compound No. 5-54
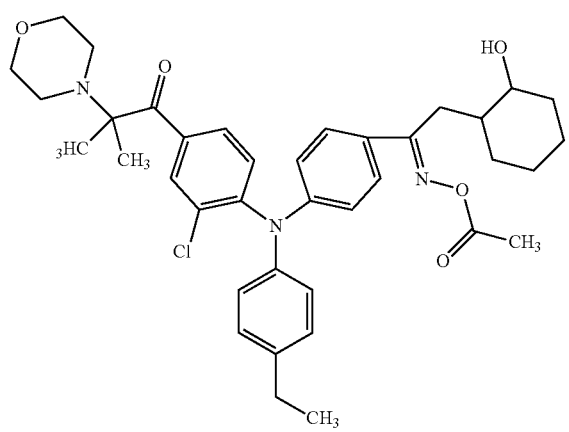
Compound No. 5-55
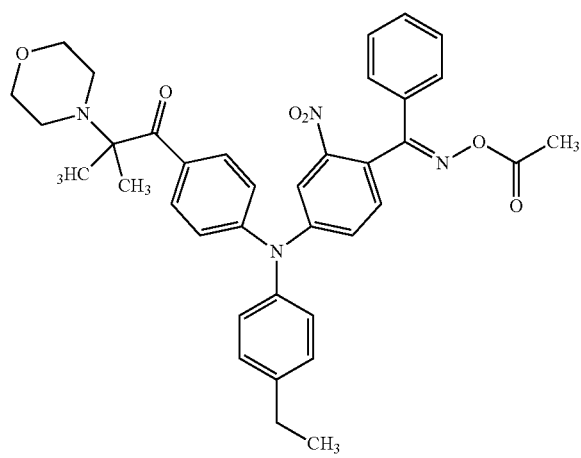
Compound No. 5-56
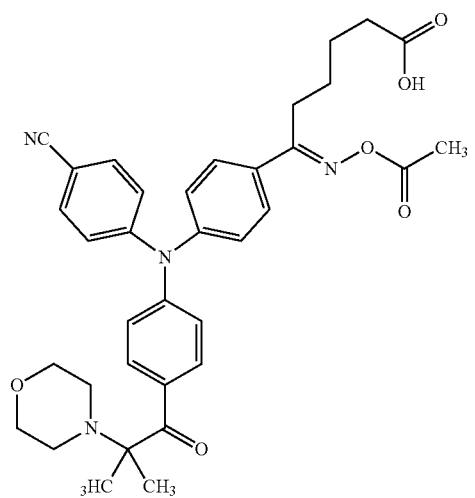

129 130
-continued
Compound No. 5-57
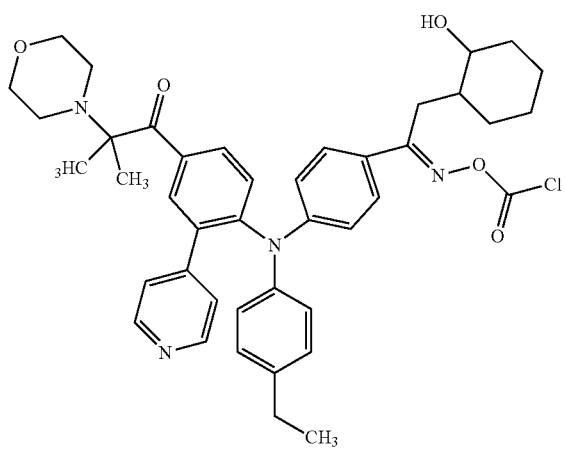
Compound No. 5-58
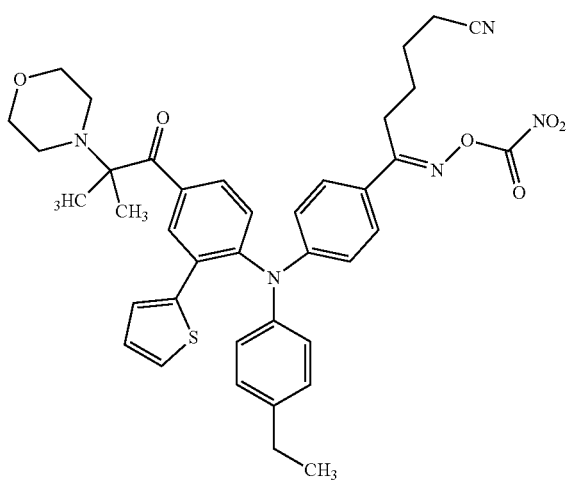
Compound No. 5-59
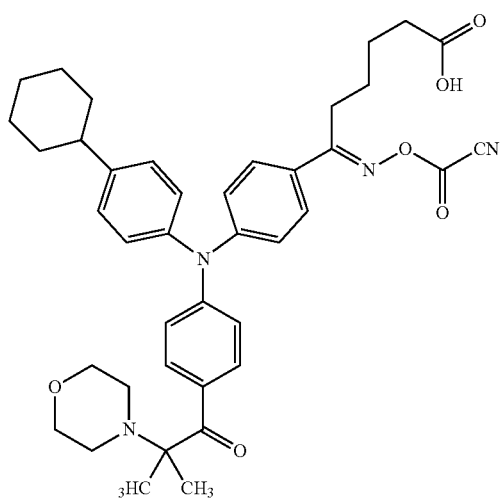
Compound No. 5-60
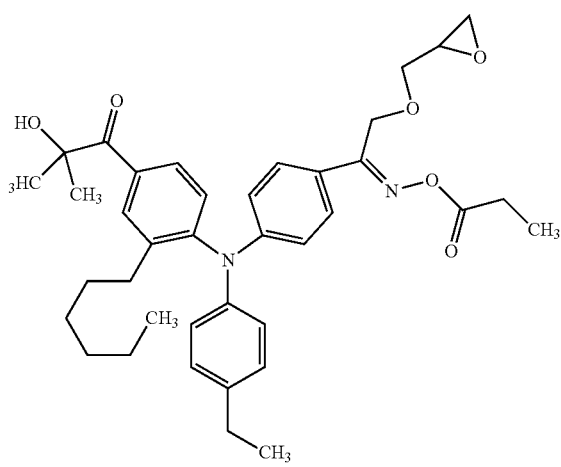
Compound No. 5-61
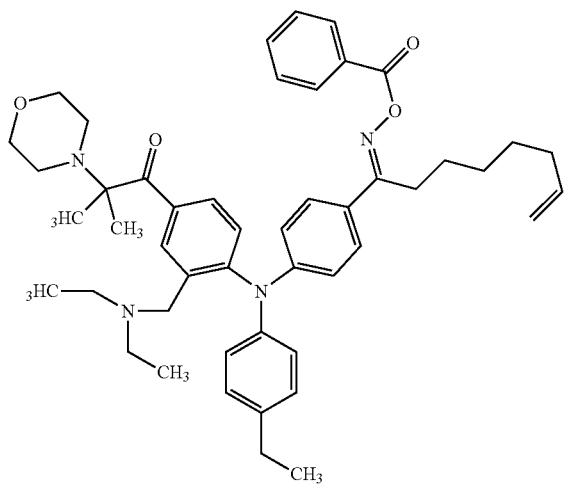
Compound No. 5-62
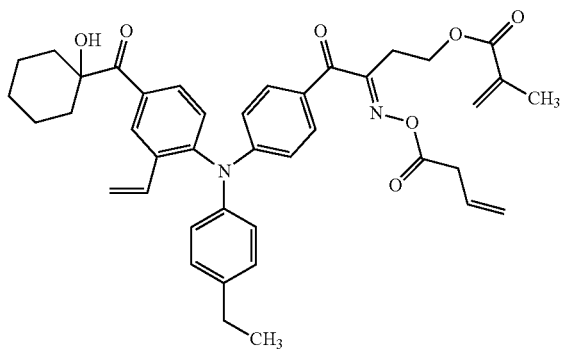

Compound No. 5-63
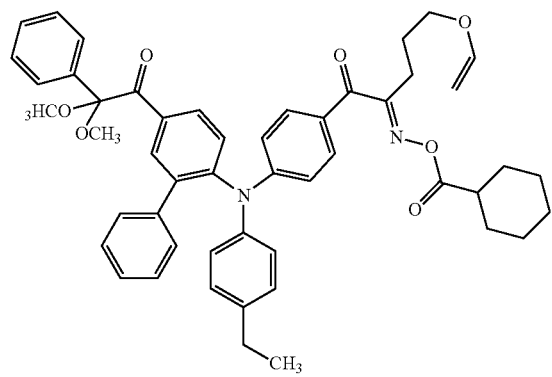
Compound No. 5-64
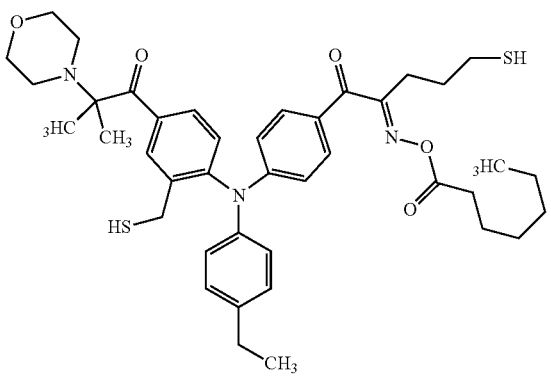
Compound No. 5-65
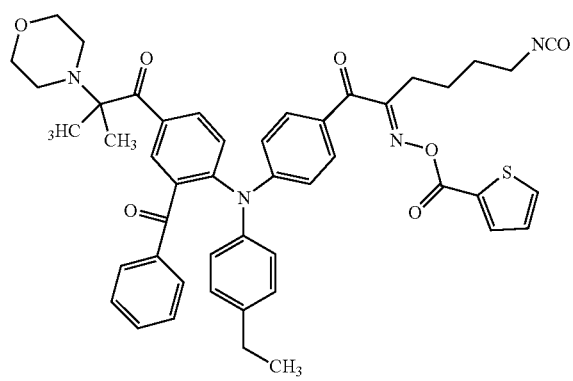
Compound No. 5-66
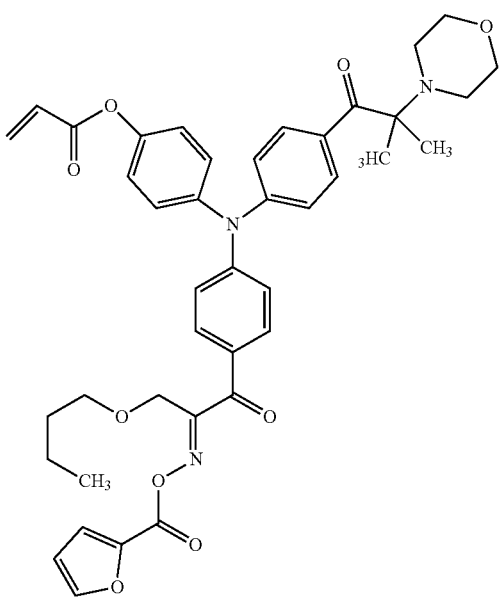
Compound No. 5-67
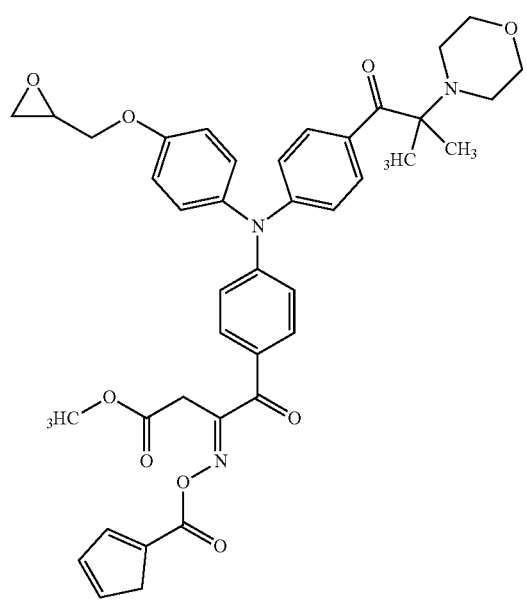
Compound No. 5-68
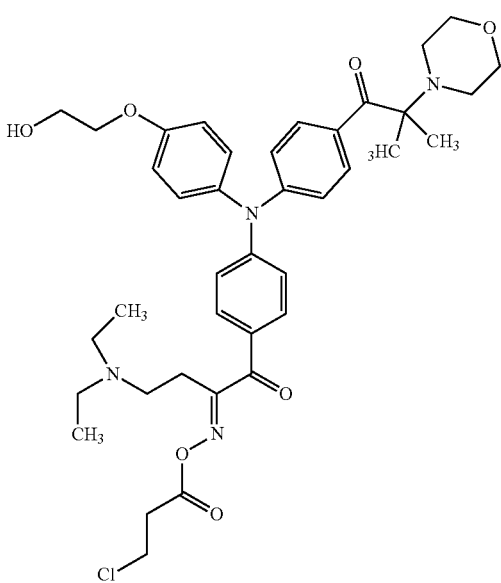

Examples of the oxime ester compound of the present invention also include the following compounds.
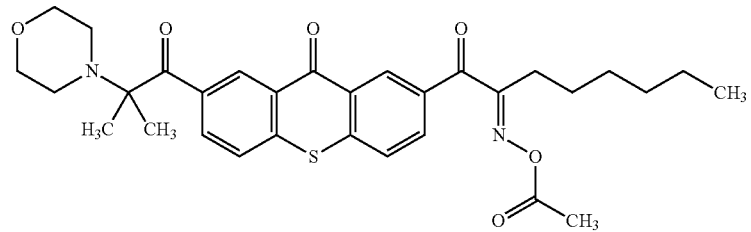
Compound No. 6-1
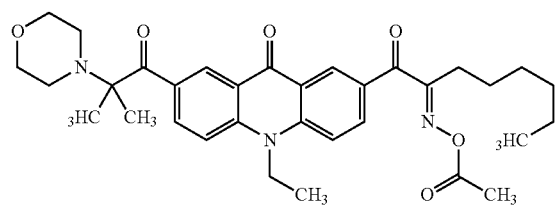
Compound No. 6-2
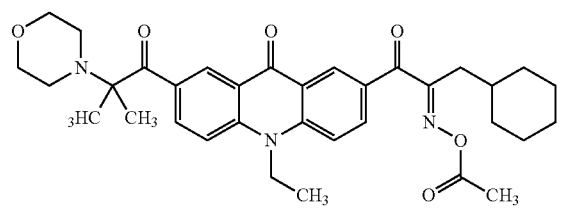
Compound No. 6-3
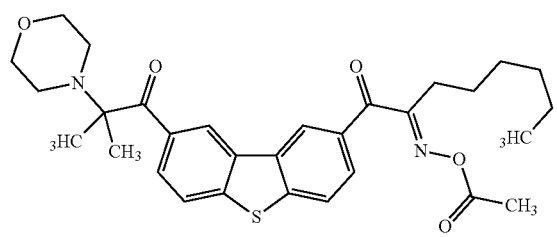
Compound No. 6-4
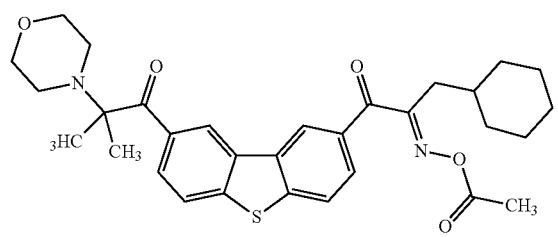
Compound No. 6-5
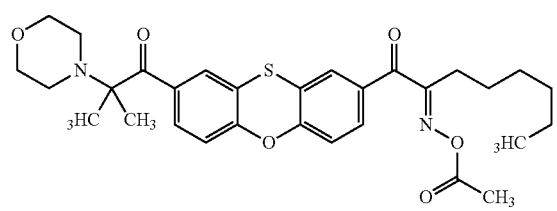
Compound No. 6-6
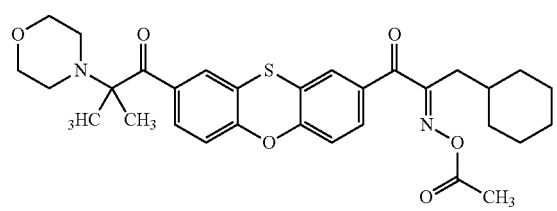
Compound No. 6-7
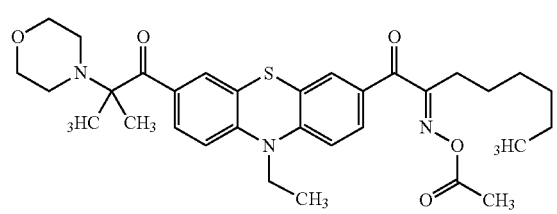
Compound No. 6-8
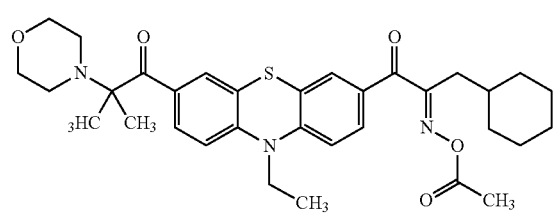
Compound No. 6-9
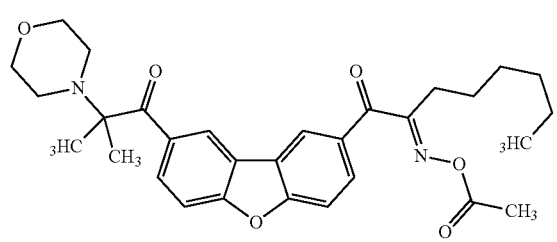
Compound No. 6-10
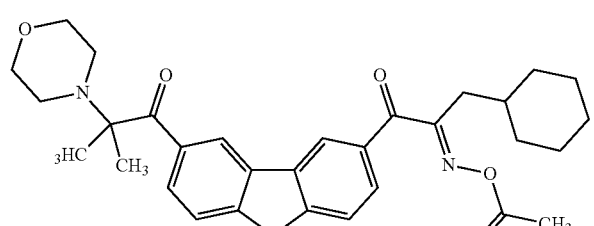
Compound No. 6-11

A compound containing a group represented by Formula (I) and the above-described photoradical cleavable group in the same molecule can be synthesized by, for example, but not particularly limited to, the following method.

When n=0 in Formula (I), a ketone compound 1 is obtained by allowing a known aromatic ring-containing compound and a known and commercially available acid chloride to react with each other; a ketone compound 1' is obtained by allowing the ketone compound 1 and a photoradical cleavable group-containing bromide to react with each other; and an oxime compound 1 is obtained by allowing the ketone compound 1' with hydroxylamine hydrochloride. Subsequently, the oxime compound 1 is allowed to react with an acid chloride in the presence of triethylamine (TEA), whereby an oxime ester compound A of the present invention, which is represented by Formula (I), is obtained. The oxime compound and the oxime ester compound can also be produced by the method described in JP4223071B2.

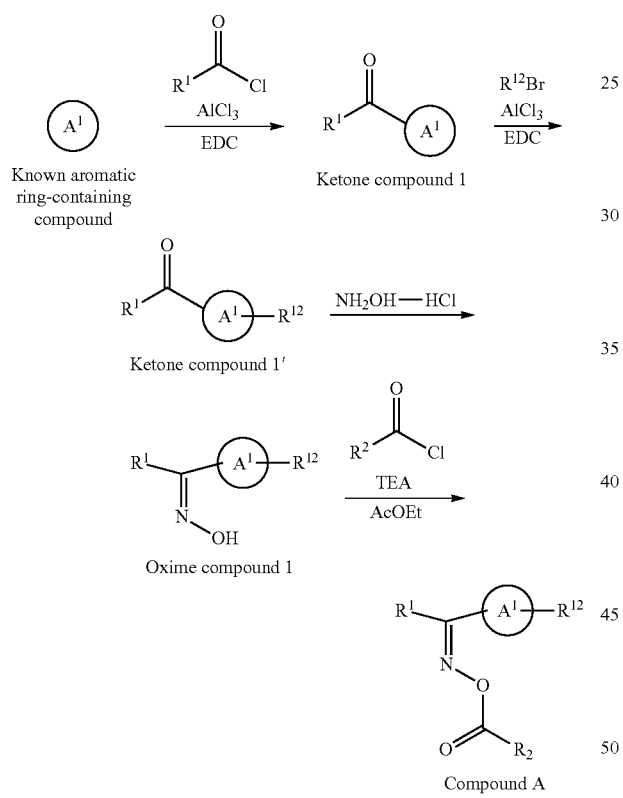

When n=1 in Formula (I) and c=0 in Formula (II), for example, the following production method can be employed in accordance with the below-described reaction formula That is, a ketone compound 2 is obtained by allowing a known aromatic ring-containing compound and an acid chloride to react with each other; a ketone compound 2' is obtained by allowing the ketone compound 2 and a photoradical cleavable group-containing bromide to react with each other; and an oxime compound 2 is obtained by allowing the ketone compound 2' with isobutyl nitrite. Subsequently, the oxime compound 2 is allowed to react with an acid anhydride or an acid chloride in the presence TEA, whereby an oxime ester compound B of the present invention, which is represented by Formula (I), is obtained.

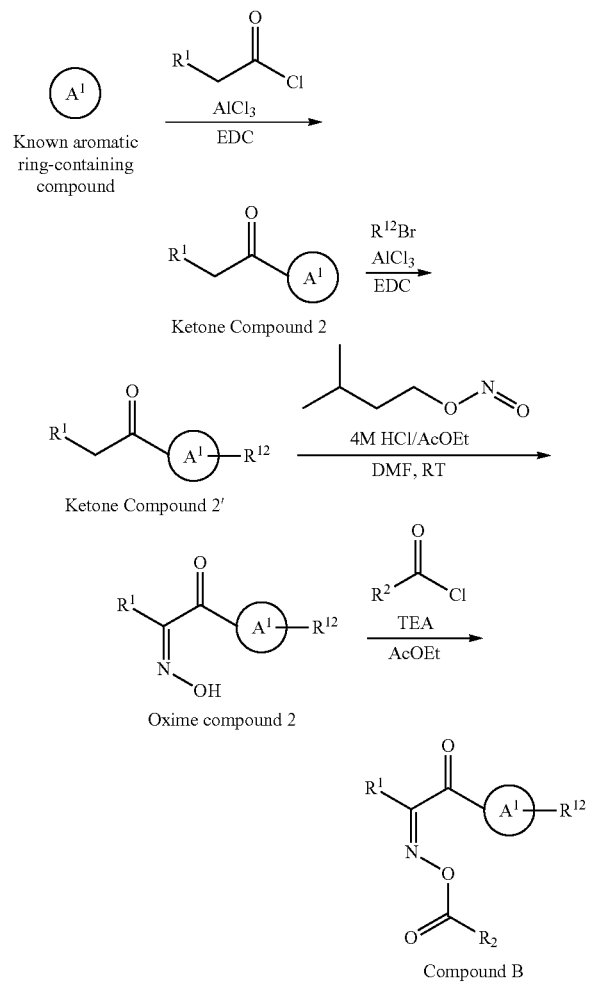

The above-described novel oxime ester compound of the present invention is useful in pharmaceuticals, agricultural chemicals, base generators, polymerization initiators and the like, and is particularly useful as a polymerization initiator (a photopolymerization initiator or a thermal polymerization initiator). The novel oxime ester compound of the present invention can also be suitability used as a sensitizer.

The polymerizable composition of the present invention contains (A) the polymerization initiator of the present invention and (B) an ethylenically unsaturated compound, and may further contain, as optional components, a combination of components such as (C) a colorant, (D) an alkali-developable compound, an inorganic compound, and a solvent.

The (A) polymerization initiator of the present invention contains at least one compound having a group represented by Formula (I) and the above-described photoradical cleavable group in the same molecule, and may be used in combination with other polymerization initiator. The content of the oxime ester compound of the present invention in the (A) polymerization initiator of the present invention is preferably 30 to 100% by mass, more preferably 50 to 100% by mass. The (A) polymerization initiator of the present invention is useful as a polymerization initiator of the (B) ethylenically unsaturated compound.

Other photopolymerization initiator not corresponding to the oxime ester compound of the present invention is not particularly restricted as long as it generates a radical when irradiated with light, and any conventionally known can be used. Preferred examples thereof include oxime ester-based compounds, acetophenone-based compounds, benzyl-based compounds, benzophenone-based compounds, and thioxanthone-based compounds.

Examples of the oxime ester-based compounds include compounds having a group represented by Formula (I), and such compounds can be preferably used in the polymerizable composition of the present invention since they have good sensitivity among photopolymerization initiators.

Among these oxime ester-based compounds, a compound represented by the following Formula (V) is preferably used in the polymerizable composition of the present invention since it has a particularly high sensitivity.

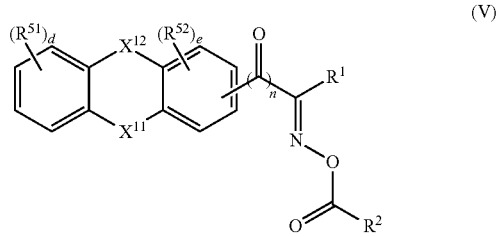

In Formula (V), $R^1$, $R^2$ and n are the same as $R^1$, $R^2$ and n in Formula (I), respectively;

$R^{51}$ and $R^{52}$ each independently represent a hydrogen atom, a nitro group, a cyano group, a hydrocarbon group having 1 to 20 carbon atoms, or a heterocycle-containing group having 2 to 20 carbon atoms, the hydrocarbon group having 1 to 20 carbon atoms being preferably an alkyl group having 1 to 20 carbon atoms, an aryl group having 6 to 20 carbon atoms, or an arylalkyl group having 7 to 20 carbon atoms;

$X^{11}$ represents an oxygen atom, a sulfur atom, a selenium atom, $CR^{53}R^{54}$, CO, $NR^{55}$, or $PR^{56}$;

$X^{12}$ represents no bond, a direct bond, a hydrocarbon group having 1 to 20 carbon atoms, or CO;

$R^{53}$ to $R^{56}$ each independently represent a hydrogen atom, a hydrocarbon group having 1 to 20 carbon atoms, or a heterocycle-containing group having 2 to 20 carbon atoms;

hydrogen atoms in the groups represented by $R^{53}$ to $R^{56}$ are optionally substituted with a halogen atom, a nitro group, a cyano group, a hydroxy group, an amino group, a carboxyl group, a methacryloyl group, an acryloyl group, an epoxy group, a vinyl group, a mercapto group, an isocyanate group, or a heterocycle-containing group;

methylene groups in the groups represented by $R^{51}$ to $R^{56}$ are optionally substituted with —O—, —CO—, —COO—, —OCO—, —S—, —SO$_2$—, —SCO—, or —COS—, provided that oxygen atoms are not arranged adjacent to one another;

$R^{51}$ to $R^{56}$ each independently and optionally form a ring with either one of the benzene rings adjacent thereto;

d represents the number of 0 to 4; and e represents the number of 0 to 3.

Examples of the hydrocarbon group having 1 to 20 carbon atoms which is represented by $R^{51}$ to $R^{56}$ in Formula (V) include the same ones as those exemplified above for $R^1$ and the like.

Examples of the heterocycle-containing group having 2 to 20 carbon atoms which is represented by $R^{51}$ to $R^{56}$ in Formula (V) include the same ones as those exemplified above for $R^1$ and the like.

Examples of a preferred oxime ester-based compound represented by Formula (V) include the following compounds No. A2-1 to No. A2-28. It is noted here, however, that the (A) polymerization initiator used in the polymerizable composition of the present invention is not restricted to the following compounds by any means.

Compound No. A 2-1

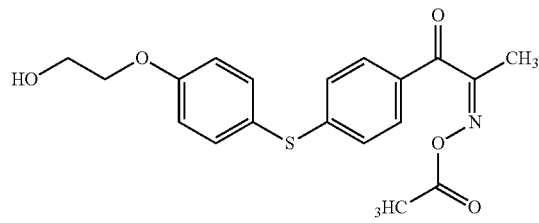

Compound No. A 2-2

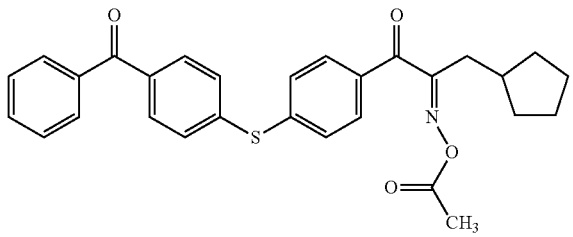

Compound No. A 2-3

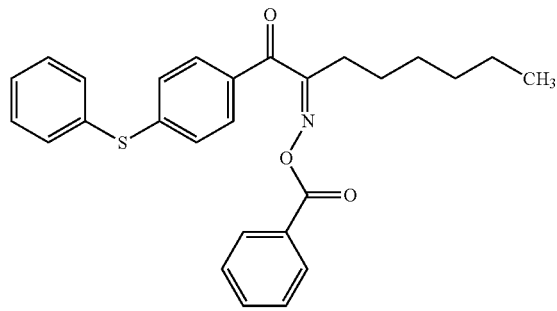

Compound No. A 2-4

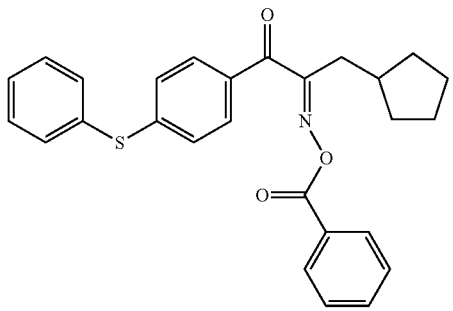

-continued
Compound No. A 2-5
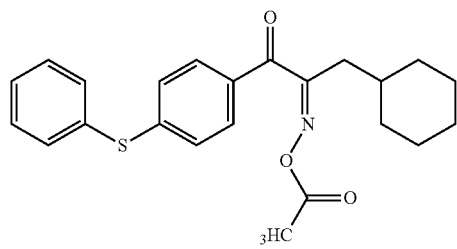
Compound No. A 2-6
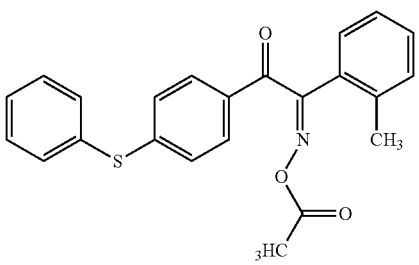
Compound No. A 2-7
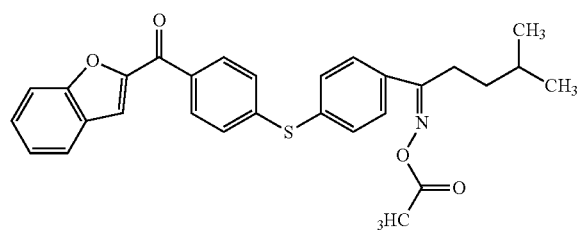
Compound No. A 2-8
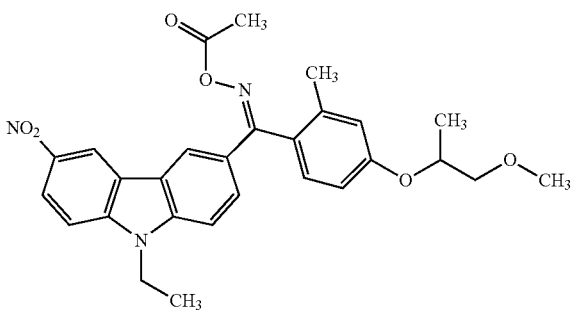
Compound No. A 2-9
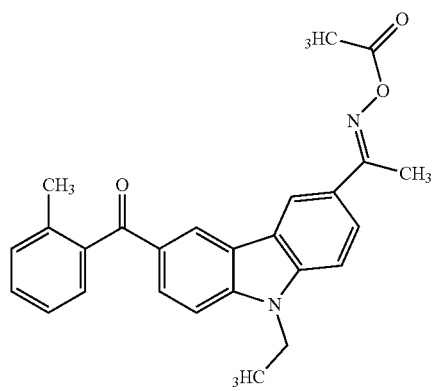
Compound No. A 2-10
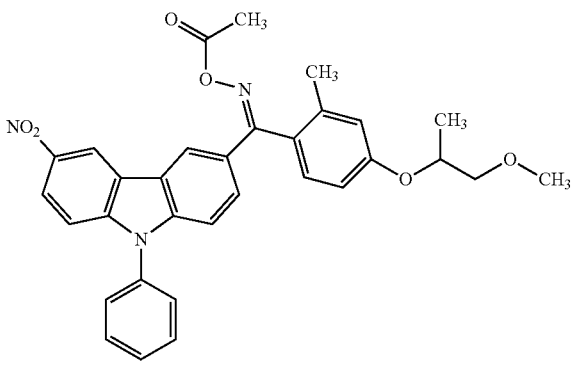
Compound No. A 2-11
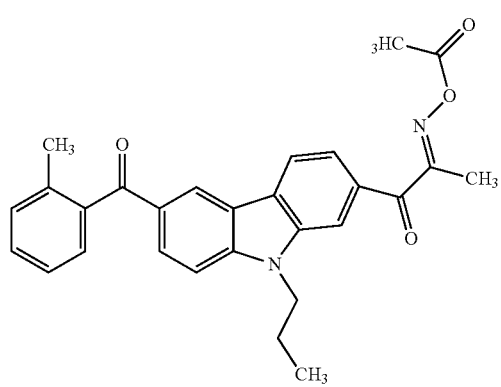
Compound No. A 2-12
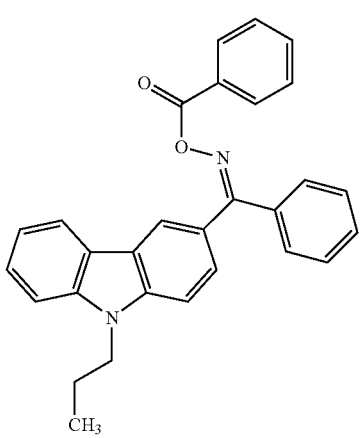

Compound No. A 2-13
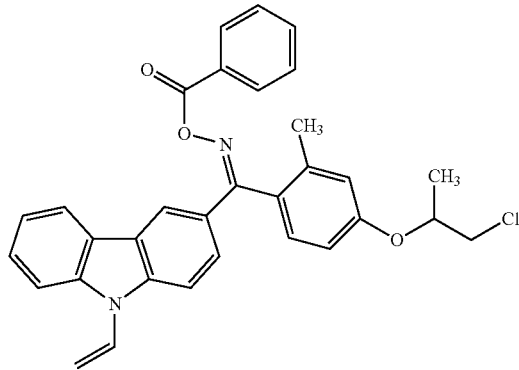
Compound No. A 2-14
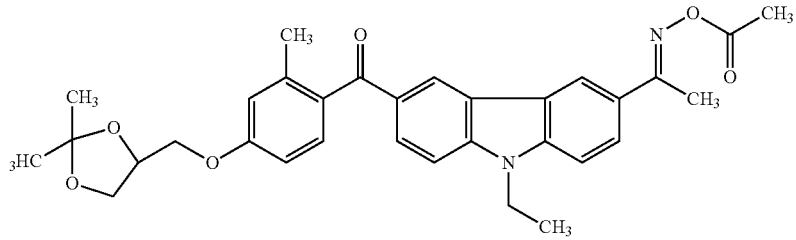
Compound No. A 2-15
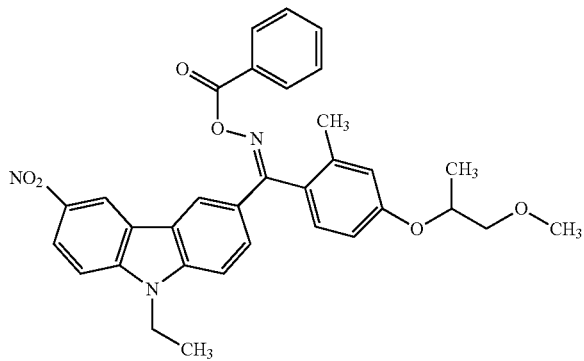
Compound No. A 2-16
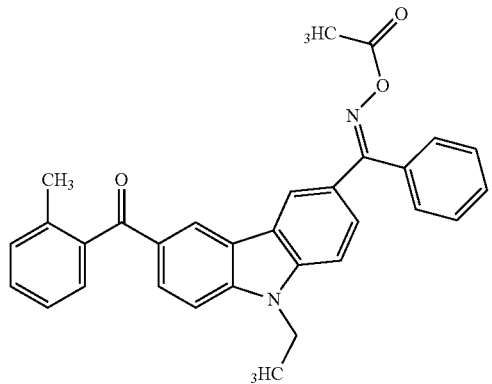
Compound No. A 2-17
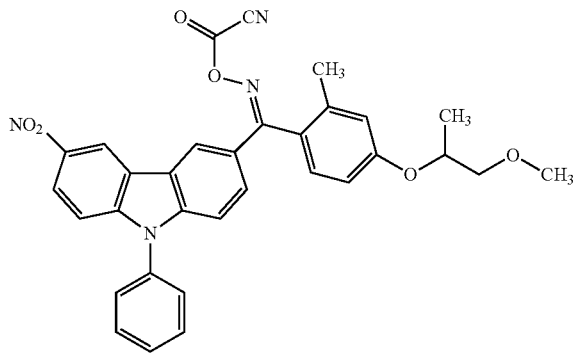
Compound No. A 2-18
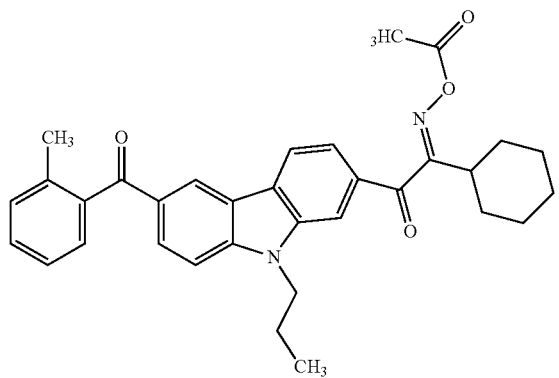

Compound No. A 2-19
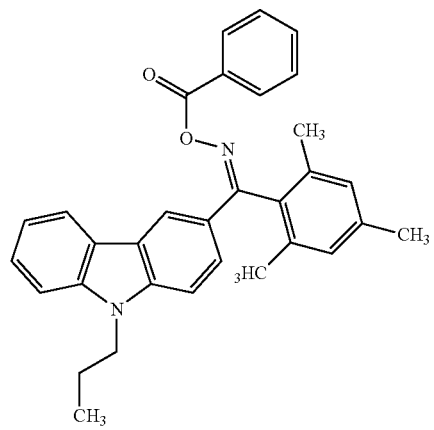
Compound No. A 2-20
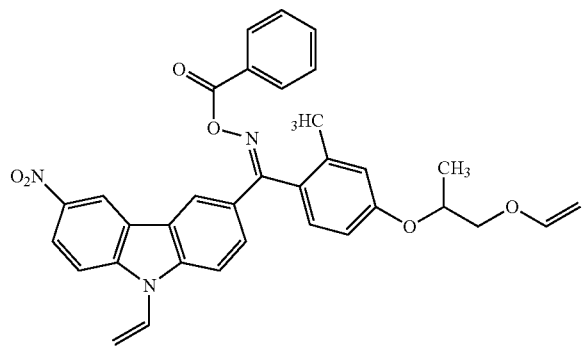
Compound No. A 2-21
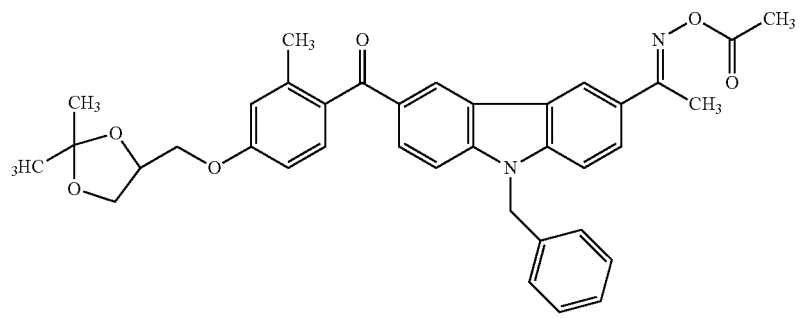
Compound No. A 2-22
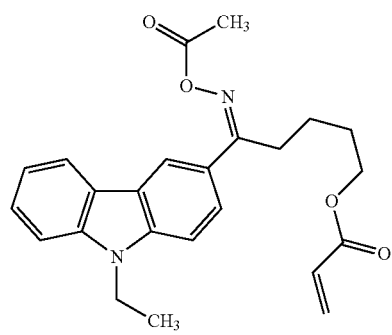
Compound No. A 2-23
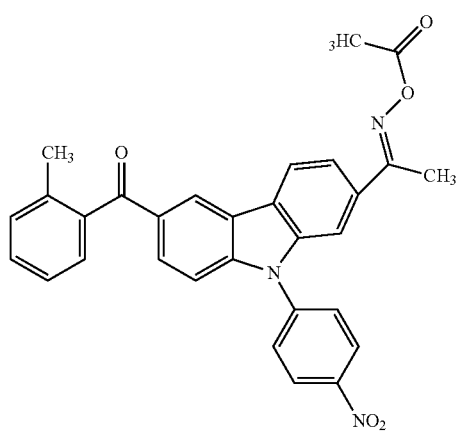
Compound No. A 2-24
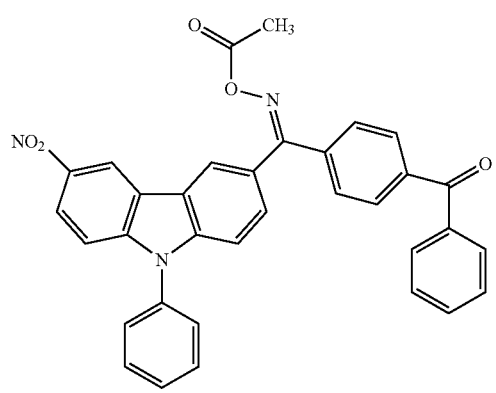
Compound No. A 2-25
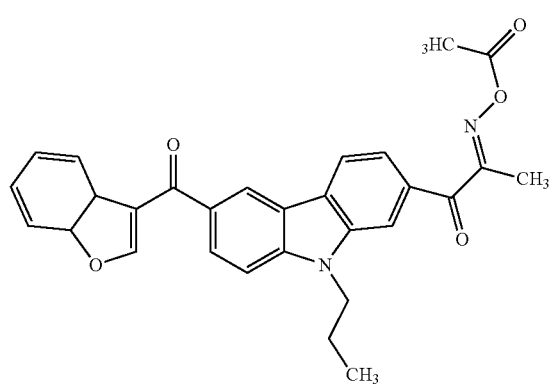

-continued

Compound No. A 2-26

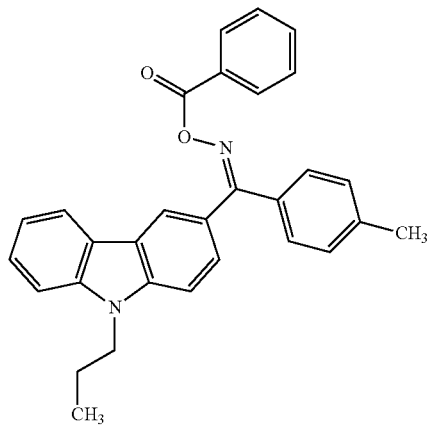

Compound No. A 2-27

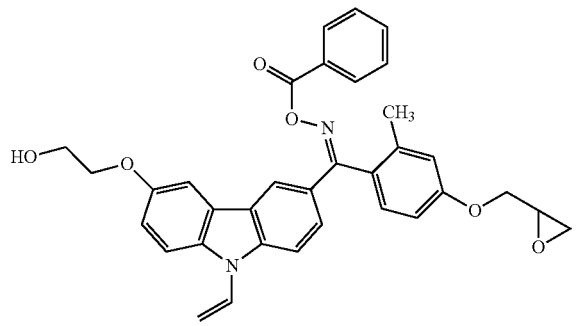

Compound No. A 2-28

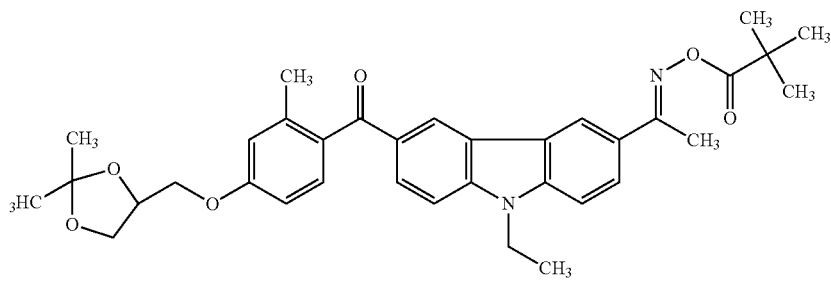

When $X^{11}$ is a sulfur atom and $X^{12}$ represents no bond in Formula (V), the oxime ester-based compound has a diphenyl sulfide skeleton as represented by the compounds No. A2-1 to A2-7, and such an oxime ester-based compound is preferred since the use thereof in combination as a polymerization initiator yields a polymerizable composition having good sensitivity.

When $X^{11}$ is $NR^{55}$ and $X^{12}$ is a direct bond in Formula (V), the oxime ester-based compound has a carbazole skeleton as represented by the compounds No. A2-8 to A2-28, and such an oxime ester-based compound is particularly preferred from the standpoint of obtaining a polymerizable composition having good sensitivity.

Examples of the acetophenone-based compounds include diethoxyacetophenone, 2-hydroxy-2-methyl-1-phenylpropan-1-one, 4'-isopropyl-2-hydroxy-2-methylpropiophenone, 2-hydroxymethyl-2-methylpropiophenone, 2,2-dimethoxy-1,2-diphenylethane-1-one, p-dimethylaminoacetophenone, p-tert-butyldichloroacetophenone, p-tert-butyltrichloroacetophenone, p-azidobenzalacetophenone, 1-hydroxycyclohexyl phenyl ketone, 2-methyl-1-[4-(methylthio)phenyl]-2-morpholinopropanon-1, 2-benzyl-2-dimethylamino-1-(4-morpholinophenyl)-butanone-1, benzoin, benzoin methyl ether, benzoin ethyl ether, benzoin isopropyl ether, benzoin-n-butyl ether, benzoin isobutyl ether, and 1-[4-(2-hydroxyethoxy)-phenyl]-2-hydroxy-2-methyl-1-propan-1-one.

Examples of the benzyl-based compounds include benzyl.

Examples of the benzophenone-based compounds include benzophenone, methyl o-benzoylbenzoate, Michler's ketone, 4,4'-bisdiethylaminobenzophenone, 4,4'-dichlorobenzophenone, and 4-benzoyl-4'-methyldiphenyl sulfide.

Examples of the thioxanthone-based compounds include thioxanthone, 2-methylthioxanthone, 2-ethylthioxanthone, 2-chlorothioxanthone, 2-isopropylthioxanthone, and 2,4-diethylthioxanthone.

Examples of other photopolymerization initiators include phosphine oxide-based compounds such as 2,4,6-trimethylbenzoyldiphenyl phosphine oxide, and titanocene-based compounds such as bis(cyclopentadienyl)-bis[2,6-difluoro-3-(pyrr-1-yl)]titanium.

Examples of commercially available radical initiators include ADEKA OPTOMER N-1414, N-1717 and N-1919, as well as ADEKA ARKLS NCI-831 and NCI-930 (which are manufactured by ADEKA Corporation); IRGACURE 184, IRGACURE 369, IRGACURE 651, IRGACURE 907, IRGACURE OXE01, IRGACURE OXE02, and IRGACURE 784 (which are manufactured by BASF Japan, Ltd.); and TR-PBG-304, TR-PBG-305, TR-PBG-309, and TR-PBG-314 (which are manufactured by Changzhou Tronly New Electronic Materials Co., Ltd.).

In the polymerizable composition of the present invention, the content of the (A) polymerization initiator is not particularly restricted; however, it is preferably 1 to 70 parts by mass, more preferably 1 to 50 parts by mass, most preferably 5 to 30 parts by mass, with respect to 100 parts by mass of the (B) ethylenically unsaturated compound.

The (B) ethylenically unsaturated compound may be any compound having an ethylenically unsaturated bond. The (B) ethylenically unsaturated compound is not particularly restricted and may be one that is conventionally used in a polymerizable composition, and examples thereof include: unsaturated aliphatic hydrocarbons, such as ethylene, propylene, butylene, isobutylene, vinyl chloride, vinylidene chloride, vinylidene fluoride, and tetrafluoroethylene; (meth)acrylic acid, α-chloroacrylic acid, itaconic acid, maleic acid, citraconic acid, fumaric acid, himic acid, crotonic acid, isocrotonic acid, vinylacetic acid, allylacetic acid, cinnamic acid, sorbic acid, mesaconic acid, mono[2-(meth)acryloyloxyethyl]succinate, mono[2-(meth)acryloyloxyethyl]phthalate, and mono(meth)acrylates of polymers having a carboxy group and a hydroxy group at both terminals, such as ω-carboxypolycaprolactone mono(meth)acrylate; unsaturated polybasic acids, such as hydroxyethyl (meth) acrylate-malate, hydroxypropyl (meth)acrylate-malate, dicyclopentadiene-malate, and polyfunctional (meth)acrylates having one carboxyl group and two or more (meth) acryloyl groups; esters formed between an unsaturated monobasic acid and a polyhydric alcohol or a polyhydric phenol, such as 2-hydroxyethyl (meth)acrylate, 2-hydroxypropyl (meth)acrylate, glycidyl (meth)acrylate, the below-described compounds No. A1 to No. A4, methyl (meth) acrylate, butyl (meth)acrylate, isobutyl (meth)acrylate, t-butyl (meth)acrylate, cyclohexyl (meth)acrylate, n-octyl (meth)acrylate, isooctyl (meth)acrylate, isononyl (meth) acrylate, stearyl (meth)acrylate, lauryl (meth)acrylate, methoxyethyl (meth)acrylate, dimethylaminomethyl (meth) acrylate, dimethylaminoethyl (meth)acrylate, aminopropyl (meth)acrylate, dimethylaminopropyl (meth)acrylate, ethoxyethyl (meth)acrylate, poly(ethoxy)ethyl (meth)acrylate, butoxyethoxyethyl (meth)acrylate, ethylhexyl (meth) acrylate, phenoxyethyl (meth)acrylate, tetrahydrofuryl (meth)acrylate, vinyl (meth)acrylate, allyl (meth)acrylate, benzyl (meth)acrylate, ethylene glycol di(meth)acrylate, diethylene glycol di(meth)acrylate, triethylene glycol di(meth)acrylate, polyethylene glycol di(meth)acrylate, propylene glycol di(meth)acrylate, 1,4-butanediol di(meth)acrylate, 1,6-hexanediol di(meth)acrylate, trimethylolethane tri (meth)acrylate, trimethylolpropane tri(meth)acrylate, dipentaerythritol hexa(meth)acrylate, dipentaerythritol penta(meth)acrylate, pentaerythritol tetra(meth)acrylate, pentaerythritol tri(meth)acrylate, tricyclodecane dimethylol di(meth)acrylate, tri[(meth)acryloylethyl]isocyanurate, and polyester (meth)acrylate oligomers; metal salts of unsaturated polybasic acids, such as zinc (meth)acrylate and magnesium (meth)acrylate; unsaturated polybasic acid anhydrides, such as maleic anhydride, itaconic anhydride, citraconic anhydride, methyltetrahydrophthalic anhydride, tetrahydrophthalic anhydride, trialkyltetrahydrophthalic anhydride, 5-(2,5-dioxotetrahydrofuryl)-3-methyl-3-cyclohexene-1,2-dicarboxylic acid anhydride, trialkyltetrahydrophthalic anhydride-maleic anhydride adducts, dodecenylsuccinic anhydride, and methylhimic anhydride; amides formed by an unsaturated monobasic acid and a multivalent amine, such as (meth)acrylamide, methylene-bis(meth)acrylamide, diethylenetriamine-tris(meth)acrylamide, xylylene-bis(meth)acrylamide, α-chloroacrylamide, and N-2-hydroxyethyl (meth)acrylamide; unsaturated aldehydes, such as acrolein; unsaturated aldehydes, such as acrolein; unsaturated nitriles, such as (meth)acrylonitrile, α-chloroacrylonitrile, vinylidene cyanide, and allyl cyanide; unsaturated aromatic compounds, such as styrene, 4-methylstyrene, 4-ethylstyrene, 4-methoxystyrene, 4-hydroxystyrene, 4-chlorostyrene, divinylbenzene, vinyltoluene, vinylbenzoic acid, vinylphenol, vinylsulfonic acid, 4-vinylbenzenesulfonic acid, vinylbenzyl methyl ether, and vinylbenzyl glycidyl ether; unsaturated ketones, such as methyl vinyl ketone; unsaturated amine compounds, such as vinylamine, allylamine, N-vinylpyrrolidone, and vinylpiperidine; vinyl alcohols, such as allyl alcohol and crotyl alcohol; vinyl ethers, such as vinyl methyl ether, vinyl ethyl ether, n-butyl vinyl ether, isobutyl vinyl ether, and allyl glycidyl ether; unsaturated imides, such as maleimide, N-phenylmaleimide, and N-cyclohexylmaleimide; indenes, such as indene and 1-methylindene; aliphatic conjugated dienes, such as 1,3-butadiene, isoprene, and chloroprene; macromonomers having a mono (meth)acryloyl group at a terminal of a polymer molecular chain, such as polystyrene, polymethyl (meth)acrylate, poly-n-butyl (meth)acrylate, and polysiloxanes; vinyl chloride; vinylidene chloride; divinyl succinate; diallyl phthalate; triallyl phosphate; triallyl isocyanurate; vinyl thioether; vinylimidazole; vinyloxazoline; vinylcarbazole; vinylpyrrolidone; vinylpyridine; vinylurethane compounds formed by a hydroxy group-containing vinyl monomer and a polyisocyanate compound; and vinylepoxy compounds formed by a hydroxy group-containing vinyl monomer and a polyepoxy compound.

As the (B) ethylenically unsaturated compound, a commercially available product can be used, and examples thereof include KAYARAD DPHA, DPEA-12, PEG400DA, THE-330, RP-1040, NPGDA, and PET30 (which are manufactured by Nippon Kayaku Co., Ltd.); SPC-1000 and SPC-3000 (which are manufactured by Showa Denko K.K.); ARONIX M-140, M-215, and M-350 (which are manufactured by Toagosei Co., Ltd.); and NK ESTER A-DPHA-TMPT, A-DCP, A-HD-N, A-9300, TMPT, DCP, NPCS and HD-N (which are manufactured by Shin-Nakamura Chemical Co., Ltd.).

Thereamong, mono(meth)acrylates of polymers having a carboxy group and a hydroxy group at both terminals, polyfunctional (meth)acrylates having one carboxyl group and two or more (meth)acryloyl groups, and esters formed between an unsaturated monobasic acid and a polyhydric alcohol or a polyhydric phenol are preferred when the polymerizable composition of the present invention is used as the below-described alkali-developable photosensitive resin composition.

These ethylenically unsaturated compounds may be used individually or in combination of two or more thereof and, when two or more ethylenically unsaturated compounds are used in combination, they may be copolymerized in advance to be used as a copolymer.

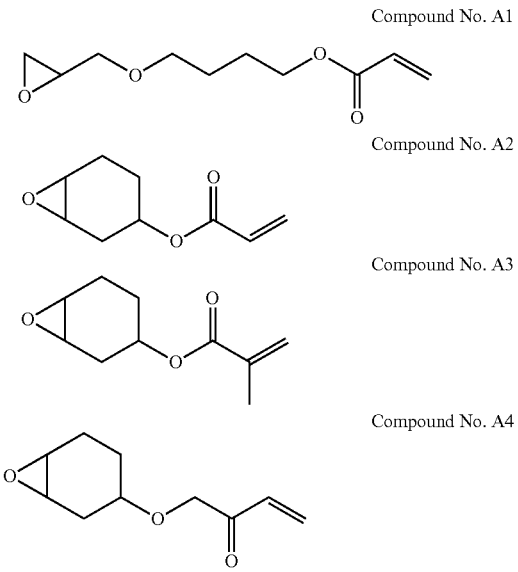

Compound No. A1

Compound No. A2

Compound No. A3

Compound No. A4

A colorant (C) may be further incorporated into the polymerizable composition of the present invention to obtain a colored polymerizable composition. Examples of the colorant (C) include pigments, dyes, and natural dyes. These colorants (C) may be used individually, or in combination of two or more thereof.

Examples of the pigments that can be used include nitroso compounds; nitro compounds; azo compounds; diazo compounds; xanthene compounds; quinoline compounds; anthraquinone compounds; coumarin compounds; phthalocyanine compounds; isoindolinone compounds; isoindoline compounds; quinacridone compounds; anthanthrone compounds; perinone compounds; perylene compounds; diketopyrrolopyrrole compounds; thioindigo compounds; dioxazine compounds; triphenylmethane compounds; quinophthalone compounds; naphthalene tetracarboxylic acids; metal complex compounds of azo dyes and cyanine dyes; lake pigments; carbon blacks, such as those obtained by a furnace process, a channel process or a thermal process, acetylene black, Ketjen black, and lamp black; the above-described carbon blacks which have been adjusted or coated with an epoxy resin; the above-described carbon blacks which have been dispersed with a resin in a solvent and to which 20 to 200 mg/g of the resin have been adsorbed in advance; the above-described carbon blacks which have been subjected to an acidic or alkaline surface treatment; carbon blacks having an average particle size of 8 nm or larger and a DBP oil absorption amount of 90 ml/100 g or less; carbon blacks having a total oxygen content, which is calculated from CO and $CO_2$ in a volatile component at 950° C., of not less than 9 mg per 100 $m^2$ of the surface area; graphites; graphitized carbon blacks; activated carbons; carbon fibers; carbon nanotubes; carbon microcoils; carbon nanohorns; carbon aerogels; fullerene; aniline black; PIGMENT BLACK 7; titanium black; and organic or inorganic pigments, such as chromium oxide green, Milori blue, cobalt green, cobalt blue, manganese-based pigments, ferrocyanides, phosphate ultramarine blue, Prussian blue, ultramarine, cerulean blue, viridian, emerald green, lead sulfate, lead yellow, zinc yellow, Indian red (red iron (III) oxide), cadmium red, synthetic iron black, and amber. These pigments may be used individually, or a plurality thereof may be used in combination.

As the pigments, commercially available pigments can be used as well, and examples thereof include PIGMENT RED 1, 2, 3, 9, 10, 14, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 228, 240, and 254; PIGMENT ORANGE 13, 31, 34, 36, 38, 43, 46, 48, 49, 51, 52, 55, 59, 60, 61, 62, 64, 65, and 71; PIGMENT YELLOW 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180, and 185; PIGMENT GREEN 7, 10, and 36; PIGMENT BLUE 15, 15:1, 15:2, 15:3, 15:4, 15:5, 15:6, 22, 24, 56, 60, 61, 62, and 64; and PIGMENT VIOLET 1, 19, 23, 27, 29, 30, 32, 37, 40, and 50.

Examples of the dyes include azo dyes, anthraquinone dyes, indigoid dyes, triarylmethane dyes, xanthene dyes, alizarin dyes, acridine dyes, stilbene dyes, thiazole dyes, naphthol dyes, quinoline dyes, nitro dyes, indamine dyes, oxazine dyes, phthalocyanine dyes and cyanine dyes, and a plurality of these dyes may be used in combination.

In the polymerizable composition of the present invention, the content of the (C) colorant is preferably 50 to 350 parts by mass, more preferably 100 to 250 parts by mass, with respect to 100 parts by mass of the (B) ethylenically unsaturated compound.

An alkali-developable compound (D) may be further incorporated into the polymerizable composition of the present invention to obtain an alkali-developable photosensitive resin composition. A composition containing the (C) colorant and the (D) alkali-developable compound at the same time is also referred to as "colored alkali-developable photosensitive resin composition".

The (D) alkali-developable compound is not particularly restricted as long as it is soluble in an aqueous alkali solution, and examples thereof include the resins described in JP2004-264414A.

As the (D) alkali-developable compound, an acrylate copolymer or a resin obtained by allowing an unsaturated monobasic acid to act on an epoxy group of an epoxy compound and further allowing a polybasic acid anhydride to act on the resultant, such as a phenol and/or cresol-novolac epoxy resin, a polyphenylmethane-type epoxy resin having a polyfunctional epoxy group, or an epoxy acrylate resin, can be used. The term "epoxy acrylate resin" used herein refers to a resin obtained by allowing (meth)acrylic acid to act on an epoxy compound, and examples thereof include RIPOXY SPC-2000, DICLITE UE-777 manufactured by DIC Corporation, and U-PICA 4015 manufactured by Japan U-Pica Co., Ltd.

The alkali-developable compound optionally having an ethylenically unsaturated bond preferably contains 0.2 to 1.0 equivalent of an unsaturated group. Among such compounds, an epoxy acrylate resin and a carboxyl group-containing polymer are preferred.

The carboxyl group-containing polymer is not particularly restricted as long as it contains a structural unit having a carboxyl group (hereinafter, referred to as "structural unit (U1)"), and the carboxyl group-containing polymer preferably contains a structural unit having a crosslinkable group, such as a methacryloyl group, an acryloyl group, an epoxy group, a vinyl group, a vinyl ether group, a mercapto group, an oxetanyl group, or an isocyanate group (hereinafter, referred to as "structural unit (U2)"), and a structural unit having a silyl group (hereinafter, referred to as "structural unit (U3)"). The carboxyl group-containing polymer may also contain a structural unit other than the above-described structural units (U1) to (U3) (hereinafter, referred to as "structural unit (U4)").

The structural unit (U1) is preferably a structural unit derived from at least one selected from the group consisting of unsaturated carboxylic acids and unsaturated carboxylic acid anhydrides (hereinafter, referred to as "compound (u1)").

The compound (u1) is, for example, a monocarboxylic acid, a dicarboxylic acid, or a dicarboxylic acid anhydride. Examples of the monocarboxylic acid include acrylic acid, methacrylic acid, crotonic acid, 2-acryloyloxyethyl succinic acid, 2-methacryloyloxyethyl succinic acid, 2-acryloyloxyethyl hexahydrophthalic acid, and 2-methacryloyloxyethyl hexahydrophthalic acid; examples of the dicarboxylic acid include maleic acid, fumaric acid, and citraconic acid; and examples of the dicarboxylic acid anhydride include anhydrides of the above-described dicarboxylic acids.

Thereamong, from the standpoints of the copolymerization reactivity and the solubility of the resulting copolymer in a developer, the compound (u1) is preferably acrylic acid, methacrylic acid, 2-acryloyloxyethyl succinic acid, 2-methacryloyloxyethyl succinic acid, or maleic anhydride. The compound (u1) may be used individually, or two or more thereof may be used in combination.

The structural unit (U2) is preferably a structural unit derived from a polymerizable unsaturated compound having an epoxy group or an oxetanyl group (hereinafter, referred to as "compound (u2)").

The compound (u2) is preferably at least one selected from the group consisting of polymerizable unsaturated compounds having an epoxy group and polymerizable unsaturated compounds having an oxetanyl group.

Examples of the polymerizable unsaturated compounds having an epoxy group include (meth)acrylic acid oxiranyl (cyclo)alkyl esters, α-alkyl acrylic acid oxiranyl(cyclo)alkyl esters, and glycidyl ether compounds having a polymerizable unsaturated bond; and examples of the polymerizable unsaturated compounds having an oxetanyl group include (meth)acrylic acid esters having an oxetanyl group.

As for specific examples of the compound (u2), examples of the (meth)acrylic acid oxiranyl(cyclo)alkyl esters include glycidyl (meth)acrylate, 2-methylglycidyl (meth)acrylate, 4-hydroxybutyl (meth)acrylate glycidyl ether, 3,4-epoxybutyl (meth)acrylate, 6,7-epoxyheptyl (meth)acrylate, 3,4-epoxycyclohexyl (meth)acrylate, 3,4-epoxycyclohexylmethyl (meth)acrylate, and 3,4-epoxytricyclo[5.2.1.0$^{2.6}$]decyl (meth)acrylate.

Examples of the α-alkyl acrylic acid oxiranyl(cyclo)alkyl esters include glycidyl α-ethylacrylate, glycidyl α-n-propylacrylate, glycidyl α-n-butylacrylate, 6,7-epoxyheptyl α-ethylacrylate, and 3,4-epoxycyclohexyl α-ethylacrylate.

Examples of the glycidyl ether compounds having a polymerizable unsaturated bond include o-vinylbenzyl glycidyl ether, m-vinylbenzyl glycidyl ether, and p-vinylbenzyl glycidyl ether.

Examples of the (meth)acrylic acid esters having an oxetanyl group include 3-((meth)acryloyloxymethyl)oxetane, 3-((meth)acryloyloxymethyl)-3-ethyloxetane, 3-((meth)acryloyloxymethyl)-2-methyloxetane, 3-((meth)acryloyloxyethyl)-3-ethyloxetane, 2-ethyl-3-((meth)acryloyloxyethyl)oxetane, 3-methyl-3-(meth)acryloyloxymethyloxetane, and 3-ethyl-3-(meth)acryloyloxymethyloxetane.

Among these specific examples, glycidyl methacrylate, 2-methylglycidyl methacrylate, 3,4-epoxycyclohexyl methacrylate, 3,4-epoxycyclohexylmethyl methacrylate, 3,4-epoxytricyclo[5.2.1.0$^{2.6}$]decyl methacrylate, 3,4-epoxytricyclo[5.2.1.0$^{2.6}$]decyl acrylate, 3-methacryloyloxymethyl-3-ethyloxetane, 3-methyl-3-methacryloyloxymethyloxetane, or 3-ethyl-3-methacryloyloxymethyloxetane is preferred from the standpoint of polymerizability.

The compound (u2) may be used individually, or two or more thereof may be used in combination.

As the structural unit (U2) having a methacryloyl group or an acryloyl group as a crosslinkable group, a structural unit having a (meth)acryloyloxy group can be preferably used.

The structural unit having a (meth)acryloyloxy group can be obtained by allowing a carboxyl group in a polymer to react with a (meth)acrylic acid ester having an epoxy group. The structural unit having a (meth)acryloyloxy group that is obtained after the reaction is desirably a structural unit represented by the following Formula (U):

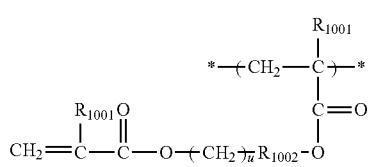

(U)

In Formula (U), $R^{1000}$ and $R^{1001}$ each independently represent a hydrogen atom or a methyl group; u represents an integer of 1 to 6; $R^{1002}$ represents a divalent group represented by the following Formula (Uα) or (Uβ); and * represents a bond.

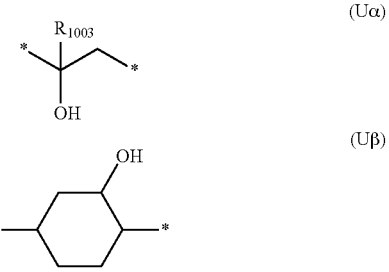

In Formula (Uα), $R^{1003}$ represents a hydrogen atom or a methyl group. In Formulae (Uα) and (Uβ), * represents a bond.

With regard to the structural unit represented by Formula (U), for example, when a compound such as glycidyl methacrylate or 2-methylglycidyl methacrylate is allowed to react with a carboxyl group-containing copolymer, $R^{1002}$ in Formula (U) is Formula (Uα). Meanwhile, when a compound such as 3,4-epoxycyclohexylmethyl methacrylate is allowed to react with a carboxyl group-containing copolymer, $R^{1002}$ in Formula (U) is Formula (Uβ).

For the reaction between the carboxyl group of the above-described polymer and an unsaturated compound such as a (meth)acrylic acid ester having an epoxy group, the unsaturated compound having an epoxy group is added to a solution of the polymer that preferably contains a polymerization inhibitor in the presence of an appropriate catalyst as required, and the resultant is stirred with heating for a prescribed time. The catalyst is, for example, tetrabutyl ammonium bromide. The polymerization inhibitor is, for example, p-methoxyphenol. The reaction temperature is preferably 70° C. to 100° C. The reaction time is preferably 8 hours to 12 hours.

With regard to the structural unit ratio of the carboxyl group-containing polymer, the content ratio of the structural unit having a (meth)acryloyloxy group as a crosslinkable group is preferably 10% by mole to 70% by mole, more preferably 20% by mole to 50% by mole, with respect to all structural units of the carboxyl group-containing polymer.

By controlling the ratio of the structural unit having a (meth)acryloyloxy group to be in this range, the heat resistance is improved and defects in development are reduced, so that the generation of development residues can be inhibited.

The structural unit (U3) is preferably a structural unit derived from a polymerizable unsaturated compound having a silyl group (hereinafter, referred to as "compound (u3)").

Examples of the compound (u3) include 3-(meth)acryloyloxypropylmethyldimethoxysilane, 3-(meth)acryloyloxypropylethyldimethoxysilane, 3-(meth)acryloyloxypropyltrimethoxysilane, and 3-(meth)acryloyloxypropyltriethoxysilane.

The above-described compounds (u3) may be used individually, or two or more thereof may be used in combination.

The structural unit (U4), which is a structural unit other than the above-described structural units (U1) to (U3), is preferably a structural unit derived from a polymerizable unsaturated compound other than the above-described (u1) to (u3) (hereinafter, referred to as "compound (u4)"). Examples of the compound (u4) include alkyl (meth)acrylates, cycloalkyl (meth)acrylates, aryl (meth)acrylates, aralkyl (meth)acrylates, unsaturated dicarboxylic acid dialkyl esters, (meth)acrylic acid esters having an oxygen-containing 5-membered heterocyclic ring or an oxygen-containing 6-membered heterocyclic ring, vinyl aromatic compounds, conjugated diene compounds, and other polymerizable unsaturated compounds.

Examples of the alkyl (meth)acrylates include methyl acrylate, n-propyl (meth)acrylate, i-propyl (meth)acrylate, n-butyl (meth)acrylate, sec-butyl (meth)acrylate, and t-butyl (meth)acrylate; and examples of the cycloalkyl (meth)acrylates include cyclohexyl (meth)acrylate, 2-methylcyclohexyl (meth)acrylate, tricyclo[5.2.1.0$^{2,6}$]decan-8-yl (meth)acrylate, 2-(tricyclo[5.2.1.0$^{2,6}$]decan-8-yloxy)ethyl (meth)acrylate, and isobornyl (meth)acrylate.

Examples of the aryl (meth)acrylates include phenyl acrylate; and examples of the aralkyl (meth)acrylates include benzyl (meth)acrylate.

Examples of the unsaturated dicarboxylic acid dialkyl esters include diethyl maleate, diethyl fumarate.

Examples of the (meth)acrylic acid esters having an oxygen-containing 5-membered heterocyclic ring or an oxygen-containing 6-membered heterocyclic ring include tetrahydrofuran-2-yl (meth)acrylate, tetrahydropyran-2-yl (meth)acrylate, and 2-methyltetrahydropyran-2-yl (meth)acrylate.

Examples of the vinyl aromatic compounds include styrene and α-methylstyrene.

Examples of the conjugated diene compounds include 1,3-butadiene and isoprene.

Examples of other polymerizable unsaturated compounds include 2-hydroxyethyl (meth)acrylate, acrylonitrile, methacrylonitrile, acrylamide, and methacrylamide.

Among the above-described compounds (u4), from the standpoint of the copolymerization reactivity, for example, n-butyl methacrylate, 2-methylglycidyl methacrylate, benzyl methacrylate, tricyclo[5.2.1.0$^{2,6}$]decan-8-yl methacrylate, styrene, p-methoxystyrene, tetrahydrofuan-2-yl methacrylate, and 1,3-butadiene are preferred.

These compounds (u4) may be used individually, or two or more thereof may be used in combination.

A preferred carboxyl group-containing polymer according to the present invention can be synthesized by copolymerizing a mixture of polymerizable unsaturated compounds including the above-described compounds (u1) to (u4) at the below-described respective ratios.

Further, by allowing a (meth)acrylic acid ester having an epoxy group to react with the carboxyl group of the structural unit derived from the compound (u1) in the resulting copolymer, a structural unit having a (meth)acryloyloxy group can be incorporated into the copolymer.

The compounds (u1) to (u4) are preferably used in the following ranges.

Compound (u1): preferably 0.1% by mole to 30% by mole, more preferably 1% by mole to 20% by mole, still more preferably 5% by mole to 15% by mole Compound (u2): preferably 1% by mole to 95% by mole, more preferably 10% by mole to 60% by mole, still more preferably 20% by mole to 30% by mole Compound (u3): preferably 50% by mole or less, more preferably 1% by mole to 40% by mole, still more preferably 10% by mole to 30% by mole Compound (u4): preferably 80% by mole or less, more preferably 1% by mole to 60% by mole, still more preferably 25% by mole to 50% by mole A polymerizable composition containing a carboxyl group-containing polymer, which is obtained by copolymerizing a mixture of polymerizable unsaturated compounds including the compounds (u1) to (u4) in the above-described respective ranges, is preferred since it achieves a high resolution without deterioration of good coating properties and is thus capable of yielding a cured film having a highly balanced properties even with a high-resolution pattern.

The weight-average molecular weight (Mw) of the carboxyl group-containing polymer is preferably 2,000 to 100,000, more preferably 5,000 to 50,000. By using a carboxyl group-containing polymer that has an Mw in this range, a high resolution is achieved without deterioration of good coating properties; therefore, a cured film having a highly balanced properties even with a high-resolution pattern can be provided. The term "weight-average molecular weight" used herein means a weight-average molecular weight (Mw) in terms of polystyrene that is determined by gel permeation chromatography (GPC).

A carboxyl group-containing polymer can be produced by polymerizing a mixture of the above-described polymerizable unsaturated compounds, preferably in an appropriate solvent and in the presence of a radical polymerization initiator.

Examples of the solvent used in the polymerization include diethylene glycol monoethyl ether acetate, diethylene glycol diethyl ether, diethylene glycol ethyl methyl ether, diethylene glycol dimethyl ether, propylene glycol monomethyl ether, ethylene glycol monobutyl ether acetate, propylene glycol monomethyl ether acetate (PGMEA), dipropylene glycol monomethyl ether acetate, 3-methoxybutyl acetate, cyclohexanol acetate, benzyl alcohol, and 3-methoxybutanol. These solvents may be used individually, or two or more thereof may be used in combination.

The radical polymerization initiator is not particularly restricted, and examples thereof include azo compounds, such as 2,2'-azobisisobutyronitrile, 2,2'-azobis-(2,4-dimethylvaleronitrile), 2,2'-azobis-(4-methoxy-2,4-dimethylvaleronitrile), 4,4'-azobis(4-cyanovaleric acid), dimethyl-2,2'-azobis(2-methyl propionate), and 2,2'-azobis(4-methoxy-2,4-dimethylvaleronitrile). These radical polymerization initiators may be used individually, or two or more thereof may be used in combination.

Among carboxyl group-containing polymers, those polymers described in JP2005-234362A as well as those polymers obtained by allowing an unsaturated monobasic acid to act on epoxy groups of an epoxy compound represented by the following Formula (VI) and further allowing a polybasic acid anhydride to act on the resultant are preferred.

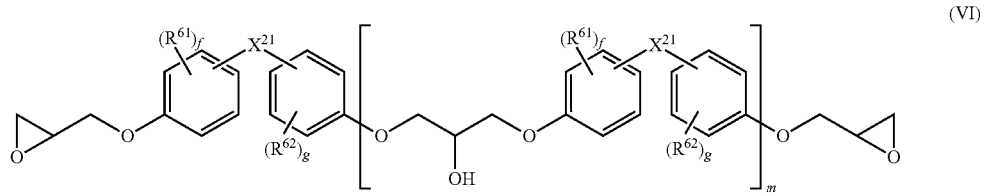

(VI)

In Formula (VI), $X^{21}$ represents a direct bond, a methylene group, an alkylidene group having 1 to 4 carbon atoms, an alicyclic hydrocarbon group having 3 to 20 carbon atoms, —O—, —S—, —SO$_2$—, —SS—, —SO—, —CO—, —OCO—, or a group represented by the below-described Formula (VIα), (VIβ) or (VIγ), which alkylidene group is optionally substituted with a halogen atom; $R^{61}$ and $R^{62}$ each independently represent an alkyl group having 1 to 5 carbon atoms, an alkoxy group having 1 to 8 carbon atoms, an alkenyl group having 2 to 5 carbon atoms, or a halogen atom, which alkyl group, alkoxy group and alkenyl group are optionally substituted with a halogen atom; when $R^{61}$ and $R^{62}$ each exist in a plural number, the plural $R^{61}$s and $R^{62}$s are each optionally the same or different; f represents an integer of 0 to 4; g represents an integer of 0 to 4; m represents an integer of 0 to 10; and an optical isomer that exists when m is not 0 may be any isomer.

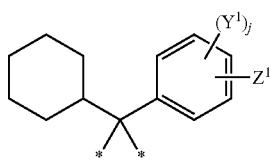

(VIα)

In Formula (VIα), $Z^1$ represents a hydrogen atom, a phenyl group which is optionally substituted with an alkyl group having 1 to 10 carbon atoms or an alkoxy group having 1 to 10 carbon atoms, or a cycloalkyl group having 3 to 10 carbon atoms which is optionally substituted with an alkyl group having 1 to 10 carbon atoms or an alkoxy group having 1 to 10 carbon atoms; $Y^1$ represents an alkyl group having 1 to 10 carbon atoms, an alkoxy group having 1 to 10 carbon atoms, an alkenyl group having 2 to 10 carbon atoms, or a halogen atom, which alkyl group, alkoxy group and alkenyl group are optionally substituted with a halogen atom; j represents an integer of 0 to 5; and * represents a bond.

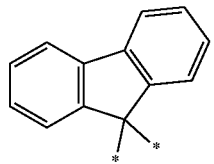

(VIβ)

In Formula (VIβ), * represents a bond.

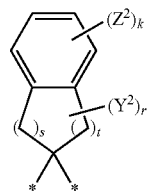

(VIγ)

In Formula (VIγ), $Y^2$ and $Z^2$ each independently represent an alkyl group having 1 to 10 carbon atoms which is optionally substituted with a halogen atom, an aryl group having 6 to 20 carbon atoms which is optionally substituted with a halogen atom, an aryloxy group having 6 to 20 carbon atoms which is optionally substituted with a halogen atom, an arylthio group having 6 to 20 carbon atoms which is optionally substituted with a halogen atom, an arylalkenyl group having 6 to 20 carbon atoms which is optionally substituted with a halogen atom, an arylalkyl group having 7 to 20 carbon atoms which is optionally substituted with a halogen atom, a heterocyclic group having 2 to 20 carbon atoms which is optionally substituted with a halogen atom, or a halogen atom; a methylene group in the group represented by $Y^2$ is optionally substituted with an unsaturated bond, —O—, or —S—; $Z^2$ optionally forms a ring with adjacent $Z^2$; k represents an integer of 0 to 4; r represents an integer of 0 to 8; s represents an integer of 0 to 4; t represents an integer of 0 to 4; a total of s and t is an integer of 2 to 4; and * represents a bond.

Examples of the above-described unsaturated monobasic acid that is allowed to act on the epoxy compound include acrylic acid, methacrylic acid, crotonic acid, cinnamic acid, sorbic acid, hydroxyethyl methacrylate-malate, hydroxyethyl acrylate-malate, hydroxypropyl methacrylate-malate, hydroxypropyl acrylate-malate, and dicyclopentadiene-malate.

Examples of the above-described polybasic acid anhydride that is allowed to act after the unsaturated monobasic acid include biphenyltetracarboxylic acid dianhydride, tetrahydrophthalic anhydride, succinic anhydride, biphthalic anhydride, maleic anhydride, trimellitic anhydride, pyromellitic anhydride, 2,2',3,3'-benzophenonetetracarboxylic anhydride, ethylene glycol bis-anhydrotrimellitate, glycerol tris-anhydrotrimellitate, hexahydrophthalic anhydride, methyltetrahydrophthalic anhydride, nadic anhydride, methylnadic anhydride, trialkyltetrahydrophthalic anhydrides, hexahydrophthalic anhydride, 5-(2,5-dioxotetrahydrofuryl)-3-methyl-3-cyclohexene-1,2-dicarboxylic anhydride, trialkyltetrahydrophthalic anhydride-maleic anhydride adducts, dodecenylsuccinic anhydride, and methylhymic anhydride.

The reaction molar ratio of the epoxy compound, the unsaturated monobasic acid and the polybasic acid anhydride is preferably as follows. That is, it is preferred to set the ratio such that, in the resulting epoxy adduct having a structure in which 0.1 to 1.0 carboxyl group of the unsaturated monobasic acid is added per epoxy group of the epoxy compound, 0.1 to 1.0 acid anhydride structure of the polybasic acid anhydride is incorporated per hydroxy group of the epoxy adduct. The reactions of the epoxy compound, the unsaturated monobasic acid and the polybasic acid anhydride can be carried out in accordance with a conventional method.

Preferred examples of the carboxyl group-containing polymer include the below-described [Polymer U1] and [Polymer U2].

[Polymer U1]

To a flask equipped with a condenser and a stirrer, 4 parts by mass of 2,2'-azobisisobutyronitrile and 190 parts by mass of propylene glycol monomethyl ether acetate were added. Subsequently, 55 parts by mass of methacrylic acid, 45 parts by mass of benzyl methacrylate, and 2 parts by mass of α-methylstyrene dimer as a molecular weight modifier were further added, the temperature of the resulting solution was increased to 80° C. with gentle stirring, and this temperature was maintained for 4 hours, after which the temperature was further increased to 100° C. and this temperature was maintained for 1 hour to perform polymerization, whereby a solution containing a copolymer was obtained. Then, 1.1 parts by mass of tetrabutyl ammonium bromide and 0.05 parts by mass of 4-methoxyphenol as a polymerization inhibitor were added to the thus obtained solution containing a copolymer, and the resultant was stirred in the atmosphere at 90° C. for 30 minutes, after which 74 parts by mass of glycidyl methacrylate was added and allowed to react for 10 hours at 90° C., whereby a polymer U1 having a weight-average molecular weight Mw of 9,000 was obtained. This polymer U1 has the structural unit (U1), the structural unit (U2), and the structural unit (U4).

[Polymer U2]

To a flask equipped with a condenser and a stirrer, 5 parts by mass of 2,2'-azobisisobutyronitrile and 250 parts by mass of 3-methoxybutyl acetate were added, and 18 parts by mass of methacrylic acid, 25 parts by mass of tricyclo[5.2.1.0$^{2.6}$] decan-8-yl methacrylate, 5 parts of styrene, 20 parts by mass of 3-acryloxypropyltrimethoxysilane, and 32 parts by mass of glycidyl methacrylate were further added. After purging the system with nitrogen, the temperature of the resulting solution was increased to 80° C. with gentle stirring. This temperature was maintained for 5 hours to perform polymerization, whereby a polymer U2 having a weight-average molecular weight Mw of 12,000 was obtained. This polymer U2 has the structural unit (U1), the structural unit (U2), the structural unit (U3), and the structural unit (U4).

The alkali-developable photosensitive resin composition of the present invention, which is one embodiment of the polymerizable composition of the present invention, contains (A) a polymerization initiator, (B) an ethylenically unsaturated compound, and (D) an alkali-developable compound as indispensable components, along with a combination of optional components such as an inorganic compound and a solvent. It is noted here that the alkali-developable photosensitive resin composition of the present invention which contains (C) a colorant is hereinafter particularly referred to as "the colored alkali-developable photosensitive resin composition of the present invention". The (B) ethylenically unsaturated compound and the (D) alkali-developable compound may be the same compound or different compounds, and may each be used individually or in combination of two or more thereof.

In order to adjust the acid value and thereby improve the developability of the (colored) alkali-developable photosensitive resin composition of the present invention, a monofunctional or polyfunctional epoxy compound can be further used together with the above-described alkali-developable compound optionally having an ethylenically unsaturated bond. The alkali-developable compound optionally having an ethylenically unsaturated bond preferably has a solid acid value in a range of 5 to 120 mgKOH/g, and the amount of the monofunctional or polyfunctional epoxy compound to be used is preferably selected such that the above-described acid value is satisfied.

Examples of the monofunctional epoxy compound include glycidyl methacrylate, methyl glycidyl ether, ethyl glycidyl ether, propyl glycidyl ether, isopropyl glycidyl ether, butyl glycidyl ether, isobutyl glycidyl ether, t-butyl glycidyl ether, pentyl glycidyl ether, hexyl glycidyl ether, heptyl glycidyl ether, octyl glycidyl ether, nonyl glycidyl ether, decyl glycidyl ether, undecyl glycidyl ether, dodecyl glycidyl ether, tridecyl glycidyl ether, tetradecyl glycidyl ether, pentadecyl glycidyl ether, hexadecyl glycidyl ether, 2-ethylhexyl glycidyl ether, allyl glycidyl ether, propargyl glycidyl ether, p-methoxyethyl glycidyl ether, phenyl glycidyl ether, p-methoxyglycidyl ether, p-butylphenol glycidyl ether, cresyl glycidyl ether, 2-methylcresyl glycidyl ether, 4-nonylphenyl glycidyl ether, benzyl glycidyl ether, p-cumylphenyl glycidyl ether, trityl glycidyl ether, 2,3-epoxypropyl methacrylate, epoxidized soybean oil, epoxidized linseed oil, glycidyl butyrate, vinylcyclohexane monoxide, 1,2-epoxy-4-vinylcyclohexane, styrene oxide, pinene oxide, methylstyrene oxide, cyclohexene oxide, propylene oxide, and the above-described compounds No. A2 and No. A3.

As the polyfunctional epoxy compound, it is preferred to use at least one compound selected from the group consisting of bisphenol-type epoxy compounds and glycidyl ethers since a (colored) alkali-developable photosensitive resin composition having more favorable properties can thereby be obtained. As the bisphenol-type epoxy compounds, in addition to epoxy compounds represented by Formula (VI), for example, bisphenol-type epoxy compounds such as hydrogenated bisphenol-type epoxy compounds can be used as well.

As the glycidyl ethers, for example, ethylene glycol diglycidyl ether, propylene glycol diglycidyl ether, 1,4-butanediol diglycidyl ether, 1,6-hexanediol diglycidyl ether, 1,8-octanediol diglycidyl ether, 1,10-decanediol diglycidyl ether, 2,2-dimethyl-1,3-propanediol diglycidyl ether, diethylene glycol diglycidyl ether, triethylene glycol diglycidyl ether, tetraethylene glycol diglycidyl ether, hexaethylene glycol diglycidyl ether, 1,4-cyclohexane dimethanol diglycidyl ether, 1,1,1-tri(glycidyloxymethyl)propane, 1,1,1-tri(glycidyloxymethyl)ethane, 1,1,1-tri(glycidyloxymethyl)methane, and 1,1,1,1-tetra(glycidyloxymethyl)methane can be used.

In addition, novolac-type epoxy compounds, such as phenol novolac-type epoxy compounds, biphenyl novolac-type epoxy compounds, cresol novolac-type epoxy compounds, bisphenol A novolac-type epoxy compounds, and dicyclopentadiene novolac-type epoxy compounds; alicyclic epoxy compounds, such as 3,4-epoxy-6-methylcyclohexylmethyl-3,4-epoxy-6-methylcyclohexane carboxylate, 3,4-epoxycyclohexylmethyl-3,4-epoxycyclohexane carboxylate, and 1-epoxyethyl-3,4-epoxycyclohexane; glycidyl esters, such as diglycidyl phthalate, diglycidyl tetrahydrophthalate, and glycidyl dimerate; glycidylamines, such as tetraglycidyl diaminodiphenylmethane, triglycidyl p-aminophenol, and N,N-diglycidylaniline; heterocyclic epoxy compounds, such as 1,3-diglycidyl-5,5-dimethylhydantoin and triglycidyl isocyanurate; dioxide compounds, such as dicyclopentadiene dioxide; naphthalene-type epoxy compounds; triphenylmethane-type epoxy compounds; and dicyclopentadiene-type epoxy compounds can also be used.

Particularly, when the polymerizable composition of the present invention is made into an alkali-developable photosensitive resin composition, the content of the alkali-developable compound optionally having an ethylenically unsaturated bond in the alkali-developable photosensitive resin composition of the present invention is preferably 1 to 20% by mass, particularly preferably 3 to 12% by mass.

A solvent may be further added to the polymerizable composition of the present invention. The solvent is usually one that is capable of dissolving or dispersing the above-described components as required (e.g., (A) polymerization initiator and (B) ethylenically unsaturated compound), and examples thereof include: ketones, such as methyl ethyl ketone, methyl amyl ketone, diethyl ketone, acetone, methyl isopropyl ketone, methyl isobutyl ketone, cyclohexanone, and 2-heptanone; ether-based solvents, such as ethyl ether, dioxane, tetrahydrofuran, 1,2-dimethoxyethane, 1,2-diethoxyethane, and dipropylene glycol dimethyl ether; ester-based solvents, such as methyl acetate, ethyl acetate, n-propyl acetate, isopropyl acetate, n-butyl acetate, cyclohexyl acetate, ethyl lactate, dimethyl succinate, and TEXANOL; cellosolve-based solvents, such as ethylene glycol monomethyl ether and ethylene glycol monoethyl ether; alcohol-based solvents, such as methanol, ethanol, iso- or n-propanol, iso- or n-butanol, and amyl alcohol; ether ester-based solvents, such as ethylene glycol monomethyl ether acetate, ethylene glycol monoethyl ether acetate, propylene glycol-1-monomethyl ether-2-acetate, dipropylene glycol monomethyl ether acetate, 3-methoxybutyl ether acetate, and ethoxyethyl ether propionate; BTX-based solvents, such as benzene, toluene, and xylene; aliphatic hydrocarbon-based solvents, such as hexane, heptane, octane, and cyclohexane; terpene-based hydrocarbon oils, such as turpentine oil, D-limonene, and pinene; paraffin-based solvents, such as mineral spirits, SWASOL #310 (manufactured by COSMO Matsuyama Oil Co., Ltd.) and SOLVESSO #100 (manufactured by Exon Chemical Co., Ltd.); halogenated aliphatic hydrocarbon-based solvents, such as carbon tetrachloride, chloroform, trichloroethylene, methylene chloride, and 1,2-dichloroethane; halogenated aromatic hydrocarbon-based solvents, such as chlorobenzene; carbitol-based solvents; aniline; triethylamine; pyridine; acetic acid; acetonitrile; carbon disulfide; N,N-dimethylformamide; N,N-dimethylacetamide (DMAc); N-methylpyrrolidone; dimethyl sulfoxide; and water. These solvents may be used individually, or two or more thereof may be used as a mixed solvent.

Among these solvents, for example, ketones and ether ester-based solvents, particularly glycol-1-monomethyl ether-2-acetate and cyclohexanone are preferred since they allow the polymerizable composition to have good compatibility between a resist and the (A) polymerization initiator.

Further, to the polymerizable composition of the present invention, commonly used additives such as p-anisole, hydroquinone, pyrocatechol, t-butylcatechol, an inorganic compound, a latent additive, an organic polymer, a chain transfer agent, a sensitizer, a surfactant, a silane coupling agent, a melamine compound, a thermal polymerization inhibitor, a plasticizer, an adhesion promoter, a filler, an antifoaming agent, a leveling agent. a surface modifier, an antioxidant, an ultraviolet absorber, a dispersion aid, an anti-coagulant, a catalyst, an effect promoter, a cross-linking agent, and thickener may be added as required.

To the polymerizable composition of the present invention, a dispersant for dispersing the (C) colorant and/or an inorganic compound may be added. The dispersant is not restricted as long as it is capable of dispersing and stabilizing the (C) colorant or an inorganic compound, and any commercially available dispersant such as BYK Series manufactured by BYK-Chemie GmbH can be used. Particularly, a polymeric dispersant composed of a polyester, polyether, or polyurethane having a basic functional group, in which the basic functional group has a nitrogen atom and the functional group having a nitrogen atom is an amine and/or a quaternary salt thereof and which has an amine value of 1 to 100 mgKOH/g, is preferably used.

The latent additive is represented by any of the following Formulae (A) to (C).

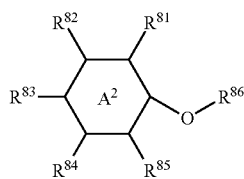
(A)

In Formula (A),
ring $A^2$ is a six-membered alicyclic, aromatic or heterocyclic ring;
$R^{81}$, $R^{82}$, $R^{83}$, $R^{84}$ and $R^{85}$ each represent a hydrogen atom, a halogen atom, a cyano group, a hydroxy group, a nitro group, a carboxyl group, an optionally substituted alkyl group having 1 to 40 atoms, aryl group having 6 to 20 carbon atoms, arylalkyl group having 7 to 20 carbon atoms or heterocycle-containing group having 2 to 20 carbon atoms, or —O—$R^{86}$.
at least one of $R^{81}$, $R^{82}$, $R^{83}$, $R^{84}$ and $R^{85}$ is not a hydrogen atom; and
$R^{86}$ represents an alkyl group having 1 to 20 carbon atoms, an alkenyl group having 2 to 20 carbon atoms, an aryl group having 6 to 20 carbon atoms, an arylalkyl group having 7 to 20 carbon atoms, a heterocycle-containing group having 2 to 20 carbon atoms, or a trialkylsilyl group.

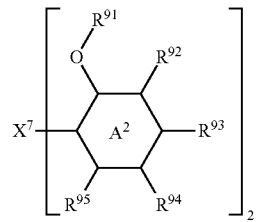
(B)

In Formula (B),
ring $A^2$ and $R^{91}$ are the same as the ring $A^2$ and $R^{86}$ of Formula (A);
$X^7$ is a group represented by the following Formula (2);
$R^{92}$, $R^{93}$, $R^{94}$ and $R^{95}$ each represent a hydrogen atom, a halogen atom, a cyano group, a hydroxy group, a nitro group, a carboxyl group, or an optionally substituted alkyl group having 1 to 40 atoms, aryl group having 6 to 20 carbon atoms, arylalkyl group having 7 to 20 carbon atoms, or heterocycle-containing group having 2 to 20 carbon atoms; and
at least one of $R^{92}$, $R^{93}$, $R^{94}$ and $R^{95}$ is not a hydrogen atom.

$$*\text{---}Z^5\text{---}X^8\text{---}Z^6\text{---}* \qquad (2)$$

In Formula (2),
$X^8$ represents —$CR^{97}R^{98}$—, —$NR^{99}$—, a divalent aliphatic hydrocarbon group having 1 to 35 carbon atoms, a divalent aromatic hydrocarbon group having 6 to 35 carbon atoms, a divalent heterocyclic group having 2 to 35 carbon atoms, or a group that is the same as the substituent represented by any one of Formulae (VIα), (VIβ) and (VIγ);
a methylene group in the aliphatic hydrocarbon group is optionally substituted with —O—, —S—, —CO—, —COO—, —OCO— or —NH—, or with a combination of these linking groups provided that oxygen atoms are not arranged adjacent to one another;
$R^{97}$ and $R^{98}$ each represent a hydrogen atom, an alkyl group having 1 to 8 carbon atoms, an aryl group having 6 to 20 carbon atoms, or an arylalkyl group having 7 to 20 carbon atoms;
$Z^5$ and $Z^6$ each independently represent a direct bond, —O—, —S—, >CO, —CO—O—, —O—CO—, —$SO_2$—, —SS—, —SO—, or >$NR^{100}$;

$R^{99}$ and $R^{100}$ each represent a hydrogen atom, an optionally substituted aliphatic hydrocarbon group having 1 to 35 carbon atoms, an optionally substituted aromatic hydrocarbon group having 6 to 35 carbon atoms, or an optionally substituted heterocyclic group having 2 to 35 carbon atoms; and

* represents a bond.

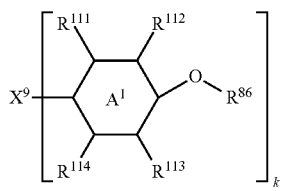
(C)

In Formula (C), k=2 to 6; $X^9$ is a group represented by the above-described Formula (2) when k=2, a group represented by the following Formula (3) when k=3, a group represented by the following Formula (4) when k=4, a group represented by the following Formula (5) when k=5, or a group represented by the following Formula (6) when k=6; $R^{111}$, $R^{112}$, $R^{113}$ and $R^{114}$ each represent a hydrogen atom, a halogen atom, a cyano group, a hydroxy group, a nitro group, a carboxyl group, or an optionally substituted alkyl group having 1 to 40 carbon atoms, aryl group having 6 to 20 carbon atoms, arylalkyl group having 7 to 20 carbon atoms, or heterocycle-containing group having 2 to 20 carbon atoms; at least one of $R^{111}$, $R^{112}$, $R^{113}$ and $R^{114}$ is not a hydrogen atom; and ring $A^1$ and $R^{86}$ are the same as in Formula (A).

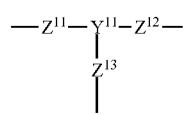
(3)

In Formula (3), $Y^{11}$ represents a trivalent aliphatic hydrocarbon group having 3 to 35 carbon atoms, a trivalent alicyclic hydrocarbon group having 3 to 35 carbon atoms, a trivalent aromatic hydrocarbon group having 6 to 35 carbon atoms, or a trivalent heterocyclic group having 2 to 35 carbon atoms; $Z^{11}$, $Z^{12}$ and $Z^{13}$ each independently represent a direct bond, —O—, —S—, >CO, —CO—O—, —O—CO—, —SO$_2$—, —SS—, —SO—, —NR$^{121}$—, —PR$^{121}$—, an optionally substituted aliphatic hydrocarbon group having 1 to 35 carbon atoms, an optionally substituted aromatic hydrocarbon group having 6 to 35 carbon atoms, or an optionally substituted heterocyclic group having 2 to 35 carbon atoms; $R^{121}$ represents a hydrogen atom, an optionally substituted aliphatic hydrocarbon group having 1 to 35 carbon atoms, an optionally substituted aromatic hydrocarbon group having 6 to 35 carbon atoms, or an optionally substituted heterocyclic group having 2 to 35 carbon atoms; and a methylene group in the aliphatic hydrocarbon group is optionally substituted with a carbon-carbon double bond, —O—, —CO—, —O—CO—, —CO—O—, or —SO$_2$—.

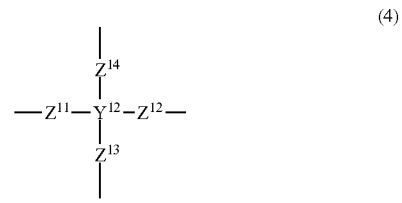
(4)

In Formula (4), $Y^{12}$ represents a carbon atom, a tetravalent aliphatic hydrocarbon group having 1 to 35 carbon atoms, a tetravalent aromatic hydrocarbon group having 6 to 35 carbon atoms, or a tetravalent heterocyclic group having 2 to 35 carbon atoms; a methylene group in the aliphatic hydrocarbon group is optionally substituted with —COO—, —O—, —OCO—, —NHCO—, —NH—, or —CONH—; and $Z^{11}$ to $Z^{14}$ each independently have the same meaning as the groups represented by $Z^{11}$ to $Z^{13}$ in Formula (3).

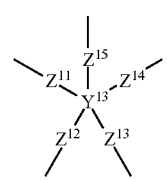
(5)

In Formula (5), $Y^{13}$ represents a pentavalent aliphatic hydrocarbon group having 2 to 35 carbon atoms, a pentavalent aromatic hydrocarbon group having 6 to 30 carbon atoms, or a pentavalent heterocyclic group having 2 to 30 carbon atoms, which aliphatic hydrocarbon group is optionally interrupted by —COO—, —O—, —OCO—, —NHCO—, —NH—, or —CONH—; and $Z^{11}$ to $Z^{15}$ each independently have the same meaning as the groups represented by $Z^{11}$ to $Z^{13}$ in Formula (3).

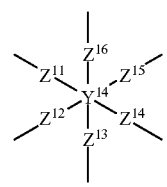
(6)

In Formula (6), $Y^4$ represents a hexavalent aliphatic hydrocarbon group having 2 to 35 carbon atoms, a hexavalent aromatic hydrocarbon group having 6 to 35 carbon atoms, or a hexavalent heterocyclic group having 2 to 35 carbon atoms, which aliphatic hydrocarbon group is optionally interrupted by —COO—, —O—, —OCO—, —NHCO—, —NH—, or —CONH—; and $Z^{11}$ to $Z^{16}$ each independently have the same meaning as the groups represented by $Z^{11}$ to $Z^{13}$ in Formula (3).

By using an organic polymer [excluding the (B) ethylenically unsaturated compound] in the polymerizable composition of the present invention, the properties of a cured product of the polymerizable composition can be improved. Examples of the organic polymer include polystyrenes, polymethyl methacrylates, methyl methacrylate-ethyl acrylate copolymers, poly(meth)acrylic acids, styrene-(meth) acrylic acid copolymers, (meth)acrylic acid-methyl methacrylate copolymers, ethylene-vinyl chloride copolymers, ethylene-vinyl copolymers, polyvinyl chloride resins, ABS resins, nylon 6, nylon 66, nylon 12, urethane resins, polycarbonates, polyvinyl butyrals, cellulose esters, polyacrylamides, saturated polyesters, phenol resins, phenoxy resins, polyamide-imide resins, polyamic acid resins and epoxy resins, among which polystyrenes, (meth)acrylic acid-methyl methacrylate copolymers and epoxy resins are preferred. When an organic polymer is used, the amount thereof is preferably 10 to 500 parts by mass with respect to 100 parts by mass of a polymerizable compound having an ethylenically unsaturated bond.

As the chain transfer agent or the sensitizer, a sulfur atom-containing compound is generally used. Examples thereof include: mercapto compounds, such as thioglycolic acid, thiomalic acid, thiosalicylic acid, 2-mercaptopropionic acid, 3-mercaptopropionic acid, 3-mercaptobutyric acid, N-(2-mercaptopropionyl)glycine, 2-mercaptonicotinic acid, 3-[N-(2-mercaptoethyl)carbamoyl]propionic acid, 3-[N-(2-mercaptoethyl)amino]propionic acid, N-(3-mercaptopropionyl)alanine, 2-mercaptoethanesulfonic acid, 3-mercaptopropanesulfonic acid, 4-mercaptobutanesulfonic acid, dodecyl (4-methylthio)phenyl ether, 2-mercaptoethanol, 3-mercapto-1,2-propanediol, 1-mercapto-2-propanol, 3-mercapto-2-butanol, mercaptophenol, 2-mercaptoethylamine, 2-mercaptoimidazole, 2-mercaptobenzoimidazole, 2-mercapto-3-pyridinol, 2-mercaptobenzothiazole, mercaptoacetic acid, trimethylolpropane tris(3-mercaptopropionate), and pentaerythritol tetrakis(3-mercaptopropionate); disulfide compounds obtained by oxidizing the mercapto compounds; alkyl iodide compounds, such as iodoacetic acid, iodopropionic acid, 2-iodoethanol, 2-iodoethanesulfonic acid, and 3-iodopropanesulfonic acid; polyfunctional aliphatic thiol compounds, such as trimethylolpropane tris (3-mercaptoisobutyrate), butanediol bis(3-mercaptoisobutyrate), hexanedithiol, decanedithiol, 1,4-dimethylmercaptobenzene, butanediol bisthiopropionate, butanediol bisthioglycolate, ethylene glycol bisthioglycolate, trimethylolpropane tristhioglycolate, butanediol bisthiopropionate, trimethilolpropane tristhiopropionate, trimethylolpropane tristhioglycolate, pentaerythritol tetrakisthiopropionate, pentaerythritol tetrakisthioglycolate, trishydroxyethyl tristhiopropionate, diethylthioxanthone, diisopropylthioxanthone, the below-described compound No. C1, and trimercaptopropionate tris(2-hydroxyethyl)isocyanurate; and KARENZ MT BD1, PE1, and NR1, which are manufactured by Showa Denko K.K.

Compound No. C 1

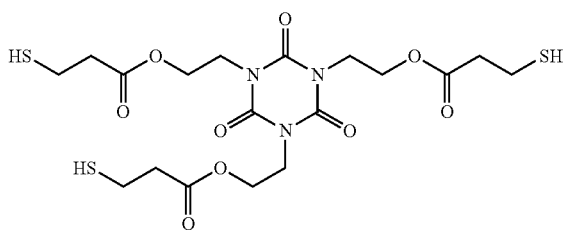

Examples of the surfactant that can be used include: fluorine surfactants, such as perfluoroalkyl phosphates and perfluoroalkyl carboxylates; anionic surfactants, such as higher fatty acid alkali salts, alkyl sulfonates, and alkyl sulfates; cationic surfactants, such as higher amine halogen acid salts and quaternary ammonium salts; nonionic surfactants, such as polyethylene glycol alkyl ethers, polyethylene glycol fatty acid esters, sorbitan fatty acid esters, and fatty acid monoglycerides; amphoteric surfactants; and silicone-based surfactants, and these surfactants may be used in combination.

Examples of the silane coupling agent that can be used include silane coupling agents manufactured by Shin-Etsu Chemical Co., Ltd., among which those having an isocyanate group, an acryloyl group, a methacryloyl group or an epoxy group, such as KBE-9007, KBM-5103, KBM-502 and KBE-403, are preferably used.

Examples of the melamine compound include compounds obtained by alkyl-etherification of all or some (at least two) of active methylol groups ($CH_2OH$ groups) in a nitrogen-containing compound such as (poly)methylol melamine, (poly)methylol glycoluril, (poly)methylol benzoguanamine, or (poly)methylolurea.

Examples of alkyl groups constituting the resulting alkyl ether include a methyl group, an ethyl group and a butyl group, and the alkyl groups may be the same or different. Moreover, methylol groups that have not been alkyl-etherified may form an oligomer component as a result of self-condensation in one molecule or condensation between two molecules.

Specifically, for example, hexamethoxymethyl melamine, hexabutoxymethyl melamine, tetramethoxymethyl glycoluril, and tetrabutoxymethyl glycoluril can be used. Thereamong, alkyl-etherified melamines such as hexamethoxymethyl melamine and hexabutoxymethyl melamine are preferred.

As the leveling agent, any existing leveling agent can be used as long as it has a leveling effect and, among such leveling agents, silicone-based leveling agents and fluorine-based leveling agents can be particularly preferably used.

As a silicone-based leveling agent, a commercially available silicone-based leveling agent can be used, and examples thereof include BYK-300, BYK-306, BYK-307, BYK-310, BYK-315, BYK-313, BYK-320, BYK-322, BYK-323, BYK-325, BYK-330, BYK-331, BYK-333, BYK-337, BYK-341, BYK-344, BYK-347, BYK-348, BYK-349, BYK-370, BYK-375, BYK-377, BYK-378, BYK-UV3500, BYK-UV3510, BYK-UV3570, BYK-3550, BYK-SILCLEAN 3700, and BYK-SILCLEAN 3720 (which are manufactured by BYK Japan K.K.); AC FS 180, AC FS 360, and AC S 20 (which are manufactured by Algin-Chemie); POLYFLOW KL-400X, POLYFLOW KL-400HF, POLYFLOW KL-401, POLYFLOW KL-402, POLYFLOW KL-403, and POLYFLOW KL-404 (which are manufactured by Kyoeisha Chemical Co., Ltd.); KP-323, KP-326, KP-341, KP-104, KP-110, and KP-112 (which are manufactured by Shin-Etsu Chemical Co., Ltd.); and LP-7001, LP-7002, 8032 ADDITIVE, 57 ADDITIVE, L-7604, FZ-2110, FZ-2105, 67 ADDITIVE, 8618 ADDITIVE, 3 ADDITIVE, and 56 ADDITIVE (which are manufactured by Dow Corning Toray Co., Ltd.).

As a fluorine-based leveling agent, a commercially available fluorine-based leveling agent can be used, and examples thereof include OPTOOL DSX and OPTOOL DAC-HP (which are manufactured by Daikin Industries, Ltd.); SURFLON S-242, SURFLON S-243, SURFLON 5-420, SURFLON 5-611, SURFLON 5-651, and SURFLON S-386 (which are manufactured by AGC Seimi Chemical Co., Ltd.); BYK-340 (manufactured by BYK Japan K.K.); AC 110a and AC 100a (which are manufactured by Algin-Chemie); MEGAFACE F-114, MEGAFACE F-410, MEGAFACE F-444, MEGAFACE EXP TP-2066, MEGAFACE F-430, MEGAFACE F-472SF, MEGAFACE F-477, MEGAFACE F-552, MEGAFACE F-553, MEGAFACE F-554, MEGAFACE F-555, MEGAFACE R-94, MEGAFACE RS-72-K, MEGAFACE RS-75, MEGAFACE F-556, MEGAFACE EXP TF-1367, MEGAFACE EXP TF-1437, MEGAFACE F-558, and MEGAFACE EXP TF-1537 (which are manufactured by DIC Corporation); FC-4430 and FC-4432 (which are manufactured by Sumitomo 3M Ltd.); FTERGENT 100, FTERGENT 100C, FTERGENT 110, FTERGENT 150, FTERGENT 150CH, FTERGENT A-K, FTERGENT 501, FTERGENT 250, FTERGENT 251, FTERGENT 222F, FTERGENT 208C5 FTERGENT 300, FTERGENT 310, and FTERGENT 400SW (which are manufactured by Neos Co., Ltd.); and PF-136A, PF-156A, PF-151N, PF-636, PF-6320, PF-656, PF-6520, PF-651, PF-652, and PF-3320 (which are manufactured by Kitamura Chemicals, Co., Ltd.).

In the polymerizable composition of the present invention, the amount of the optional components excluding the above-described (A) polymerization initiator, (B) ethylenically unsaturated compound, (C) colorant, (D) alkali-developable compound, solvent, inorganic compound, and organic polymer is selected as appropriate in accordance with the intended purpose thereof and is not particularly restricted; however, a total content of the optional components is preferably 50 parts by mass or less with respect to 100 parts by mass of the (B) ethylenically unsaturated compound.

The cured product of the present invention is obtained by curing the polymerizable composition of the present invention or the alkali-developable photosensitive resin composition of the present invention.

The polymerizable composition, alkali-developable photosensitive resin composition, and cured product of the present invention can be used in a variety of applications including, but not particularly limited to: photocurable paints and varnishes; photocurable adhesives; printed boards; color filters used in color liquid-crystal display elements of display devices, (e.g., color televisions, PC monitors, portable information terminals, and digital cameras); color filters of CCD image sensors; electrode materials for plasma display panels; powder coatings; printing inks; printing plates; adhesives; dental compositions; gel coats; photoresists for electronics; electroplating resists; etching resists; dry films; solder resists; resists for the formation of various display device structures; compositions for enclosing electric and electronic components; solder resists; magnetic recording materials; micromachine components; waveguides; optical switches; plating masks; etching masks; color testing systems; glass fiber cable coatings; screen printing stencils; materials for the production of three-dimensional objects by stereolithography; materials for holographic recording; image recording materials; nanoelectronic circuits; decoloring materials; decoloring materials for image recording materials; decoloring materials for image recording materials using microcapsules; photoresist materials for printed wiring boards; photoresist materials for direct imaging systems using UV and visible lasers; and photoresist materials or protective films that are used for the dielectric layer formation in sequential lamination on printed circuit boards.

The polymerizable composition and alkali-developable photosensitive resin composition of the present invention can yield cured products having a high brightness and are, therefore, useful as polymerizable compositions for color filters.

The polymerizable composition and alkali-developable photosensitive resin composition of the present invention can also be used for the formation of a spacer for a liquid-crystal display panel and the formation of projections for a vertical alignment-type liquid-crystal display element. The polymerizable composition and alkali-developable photosensitive resin composition of the present invention are particularly useful as polymerizable compositions for the simultaneous formation of projections and spacer for a vertical alignment-type liquid-crystal display element.

Next, a method of producing a cured product of the polymerizable composition or alkali-developable photosensitive resin composition of the present invention will be described in detail.

The polymerizable composition or alkali-developable photosensitive resin composition of the present invention can be applied onto a support substrate, such as a soda glass, a quartz glass, a semiconductor substrate, a metal substrate, a piece of paper or a plastic substrate, using a known means such as a spin coater, a roll coater, a bar coater, a die coater or a curtain coater, or various printing or immersion means. Further, the polymerizable composition or alkali-developable photosensitive resin composition of the present invention can be once applied onto a support substrate such as a film and then transferred onto another support substrate, and the method thereof is not restricted.

The production of a cured product of the polymerizable composition of the present invention includes the step of irradiating the polymerizable composition with light, or the step of curing the polymerizable composition by heating.

Examples of a light source that can be utilized in the step of irradiating the polymerizable composition with light include those generating an electromagnetic energy ray having a wavelength of 2,000 Å to 7,000 Å or a high-energy ray (e.g., electron beam, X-ray, or radiation), such as an ultrahigh-pressure mercury lamp, a high-pressure mercury lamp, a medium-pressure mercury lamp, a low-pressure mercury lamp, a mercury vapor arc lamp, a xenon arc lamp, a carbon arc lamp, a metal halide lamp, a fluorescent lamp, a tungsten lamp, an excimer lamp, a sterilizing lamp, a light-emitting diode or a CRT light source, and it is preferred to use an ultrahigh-pressure mercury lamp, a mercury vapor arc lamp, a carbon arc lamp, a xenon arc lamp or the like that emits a light having a wavelength of 300 to 450 nm.

Further, a laser direct imaging method in which an image is formed directly from digital information transmitted from a computer or the like by using a laser light as an exposure light source without a mask is useful since it improves not only the productivity but also the resolution, the positional accuracy and the like. As the laser light, a light having a wavelength of 340 to 430 nm is preferably used, and a light source which emits a light of the visible to infrared region, such as an excimer laser, a nitrogen laser, an argon ion laser, a helium cadmium laser, a helium neon laser, a krypton ion laser, a semiconductor laser or a YAG laser, can also be used. When any of these lasers is used, a sensitizing dye that absorbs the light of the visible to infrared region is added.

The step of curing the polymerizable composition of the present invention by heating will now be described. The heating temperature can be set as appropriate in accordance with the thickness of the resulting coating film or cured product of the composition to be treated, the polymerization initiation temperature of a thermal polymerization initiator and the like, and the heating temperature can be, for example, 50° C. to 250° C., preferably 100° C. to 200° C., particularly preferably 100° C. to 150° C. In the method of producing a cured product according to the present invention, the heating temperature refers to, for example, the surface temperature of the above-described polymerizable composition or cured product. Further, the heating time may be 10 minutes to 2 hours. The heating time refers to a duration of continuously maintaining a prescribed temperature after the composition or cured product reached the prescribed temperature.

The above-mentioned spacer for a liquid-crystal display panel is preferably formed by (1) the step of forming a coating film of the polymerizable composition of the present invention on a substrate; (2) the step of irradiating the coating film with radiation through a mask having a prescribed pattern shape; (3) the post-exposure baking step; (4) the step of developing the thus exposed film; and (5) the step of heating the thus developed film.

The polymerizable composition of the present invention to which an ink repellent has been added is useful as partition-forming resin composition for ink-jet system, and the composition is used for a color filter, particularly preferably for partition walls of an ink-jet color filter that has a profile angle of 500 or larger. As the ink repellent, a fluorine-based surfactant or a composition containing a fluorine-based surfactant is preferably used.

An optical element is produced by a method in which partition walls formed from the polymerizable composition of the present invention divide a transfer object, and droplets are applied to recesses on the thus divided transfer object by an ink-jet method to form an image area. In this process, it is preferred that the droplets contain a colorant and the image area be colored. An optical element produced by the above-described optical element production method, which has at least a pixel group composed of plural colored regions and partition walls separating the colored regions of the pixel group on a substrate, can be preferably used.

EXAMPLES

The present invention will now be described in more detail by way of Examples and Comparative Examples; however, the present invention is not restricted to the following Examples by any means.

Production Example 1: Production of Compound No. 1-1

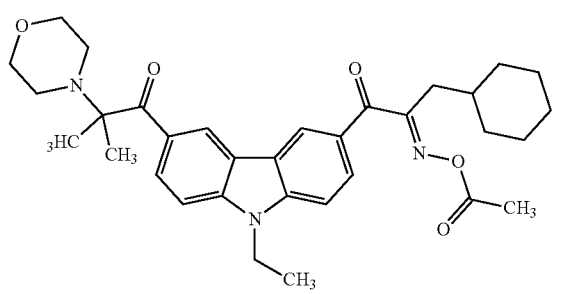

Compound No. 1-1

(1) Production of Intermediate 1-A

Aluminum chloride (16.8 g, 126 mmol) and 120.0 g of dichloroethane were added to a four-necked flask, and ethylcarbazole (23.4 g, 120 mmol) and 3-cyclohexylpropanoyl chloride (16.8 g, 126 mmol) were sequentially added thereto with ice cooling. These materials were allowed to react at room temperature for 1 hour, after which the resulting reaction solution was poured into ice water to perform oil-water separation. The resulting organic layer was washed with ion-exchanged water three times and the solvent was subsequently removed, whereby an intermediate 1-A was obtained in the form of a pale-yellow solid (32.4 g, yield: 81%).

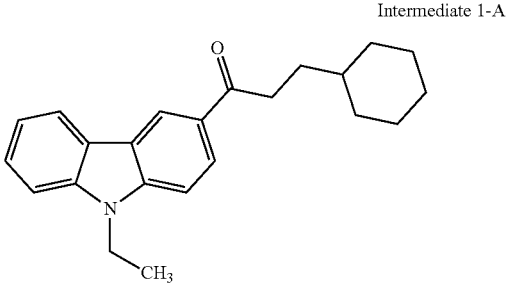 [SMILES: CCn1c2ccccc2c2cc(C(=O)CCC3CCCCC3)ccc21]

Intermediate 1-A (2) Production of Intermediate 1-B

Aluminum chloride (17.4 g, 131 mmol) and 90.0 g of dichloroethane were added to a four-necked flask, and the intermediate 1-A (20.7 g, 62.2 mmol) and 2-bromoisobutyryl bromide (15.0 g, 65.3 mmol) were sequentially added thereto with ice cooling. These materials were allowed to react at room temperature for 1 hour, after which the resulting reaction solution was poured into ice water to perform oil-water separation. The resulting organic layer was washed with ion-exchanged water three times and the solvent was subsequently removed, whereby an intermediate 1-B was obtained in the form of a pale-yellow solid (27.0 g, yield: 90%).

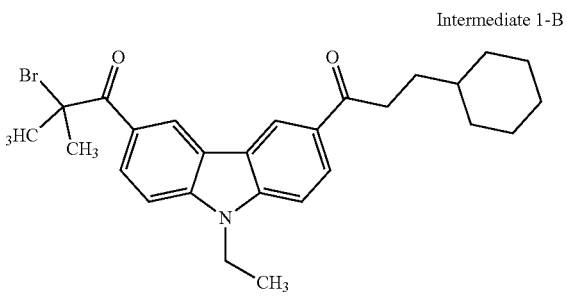

Intermediate 1-B (3) Production of Intermediate 1-C

The intermediate 1-B (30.0 g, 62.2 mmol), xylene (54.2 g), methanol (27.1 g), and potassium carbonate (17.2 g, 124.4 mmol) were added and stirred at room temperature for 3 hours. The resulting inorganic salt was recovered by filtration and the solvent was removed from the filtrate, whereby an intermediate 1-C was obtained in the form of a pale-yellow oil (27.1 g, yield: 100%).

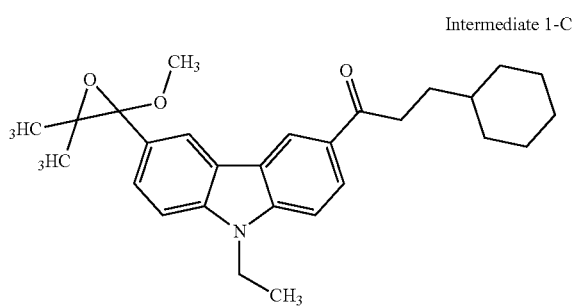

Intermediate 1-C (4) Production of Intermediate 1-D

In a four-necked flask, the intermediate 1-C (27.1 g, 62.2 mmol) and 81.3 g of morpholine were added and refluxed in a nitrogen stream. After the resultant was allowed to react for 12 hours with stirring, the solvent was removed. Ethyl acetate and 1% hydrochloric acid were further added and the resultant was stirred, followed by oil-water separation. The resulting organic layer was washed with water three times and the solvent was subsequently removed, whereby an intermediate 1-D was obtained in the form of a pale-yellow oil (28.9 g, yield: 95%).

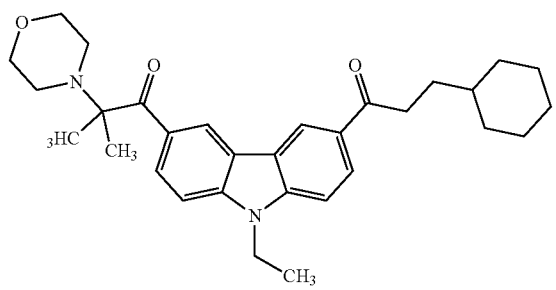

Intermediate 1-D (5) Production of Intermediate 1-E

While stirring the intermediate 1-D (8.73 g, 17.8 mmol) and 30.0 g of DMF in a four-necked flask at 5° C., 4.0 g of 35% hydrochloric acid and isobutyl nitrite (3.87 g, 37.5 mmol) were added and allowed to react at room temperature for 12 hours. Ethyl acetate was further added and, after oil-water separation, the resulting organic layer was washed with water three times and the solvent was subsequently removed, whereby an intermediate 1-E was obtained (9.0 g, yield: 97%).

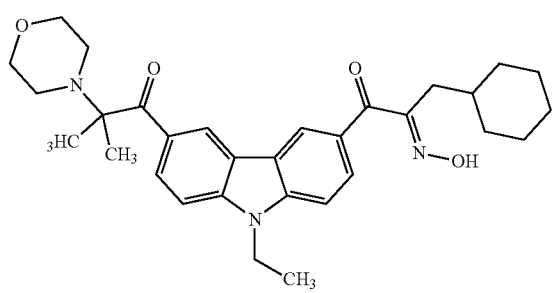

Intermediate 1-E (6) Production of Compound No. 1-1

The intermediate 1-E (9.24 g, 17.9 mmol) and 30.0 g of ethyl acetate were added to a four-necked flask, and acetyl chloride (1.54 g, 19.7 mmol) and triethylamine (1.99 g, 19.7 mmol) were sequentially added thereto dropwise with ice cooling. After stirring these materials at room temperature for 1 hour, ion-exchanged water was added to perform oil-water separation. The resulting organic layer was washed with water three times and the solvent was subsequently removed, after which the resultant was applied to a silica gel column (ethyl acetate/hexane=3/10), whereby a compound No. 1-1 was obtained (2.1 g, yield: 21%). The NMR data of the thus obtained compound No. 1-1 is shown in [Table 1].

Production Example 2: Production of Compound No. 1-7

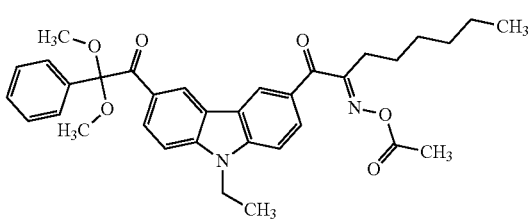

Compound No. 1-7

(1) Production of Intermediate 1-7-A

An intermediate 1-7-A was obtained in the same manner as in Production Example 1, except that 3-cyclohexylpropanoyl chloride used in the production of the intermediate 1-A was changed to benzoylformyl chloride and the acid chloride used in the production of the intermediate 1-B was changed to octanoyl chloride.

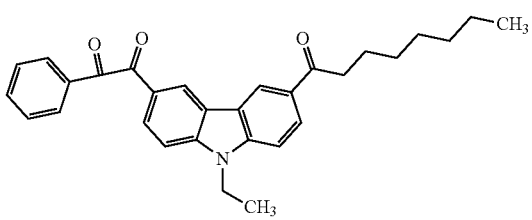

Intermediate 1-7-A (2) Production of Intermediate 1-7-B

The intermediate 1-7-A (9.1 g, 20.0 mmol), dioxane (30.0 g), and dimethyl sulfate (3.2 g, 60.0 mmol) were added, and sodium methylate (3.2 g, 60.0 mmol) was further added while maintaining room temperature. After allowing these materials to react at room temperature for 5 hours, ethyl acetate and ion-exchanged water were added to perform oil-water separation. The resulting organic layer was washed with water three times and the solvent was subsequently removed, after which the resultant was applied to a silica gel column, whereby an intermediate 1-7-B was obtained.

Intermediate 1-7-B

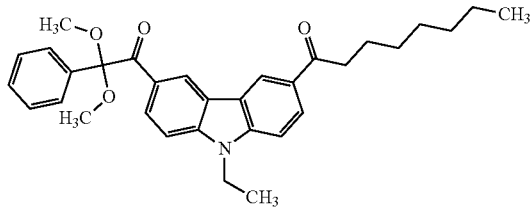

(3) Production of Compound No. 1-7

A compound No. 1-7 was obtained in the same manner as in Production Example 1, except that the intermediate 1-D was changed to the intermediate 1-7-B.

Production Example 3: Production of Compound No. 1-14

Compund No. 1-14

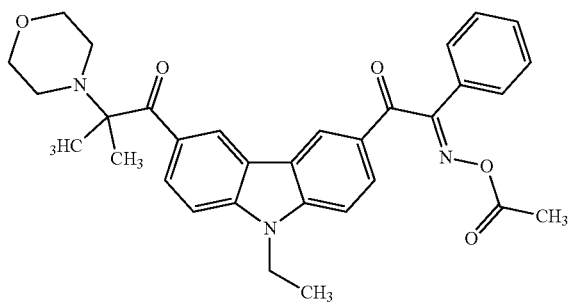

A compound No. 1-14 was obtained in the same manner as in Production Example 1, except that 3-cyclohexylpropanoyl chloride used in the production of the intermediate 1-A was changed to phenylacetyl chloride. The NMR data of the thus obtained compound No. 1-14 is shown in [Table 1].

Production Example 4: Production of Compound No. 1-70

Compound No. 1-70

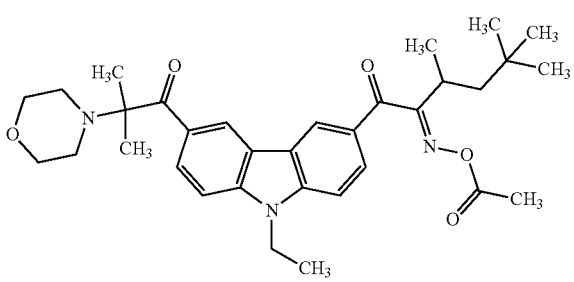

A compound No. 1-70 was obtained in the same manner as in Production Example 1, except that 3-cyclohexylpropanoyl chloride used in the production of the intermediate 1-A was changed to 3,5,5-trimethylhexanoyl chloride. The NMR data of the thus obtained compound No. 1-70 is shown in [Table 1].

Production Example 5: Production of Compound No. 1-71

Compound No. 1-71

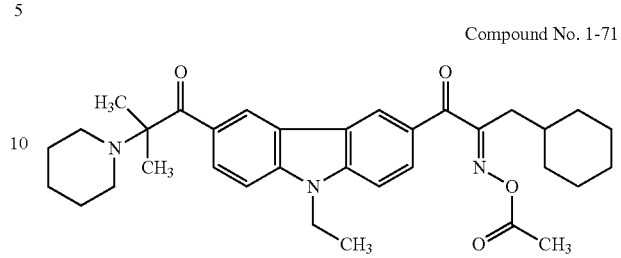

A compound No. 1-71 was obtained in the same manner as in Production Example 1, except that morpholine used in the production of the intermediate 1-D was changed to piperidine. The NMR data of the thus obtained compound No. 1-71 is shown in [Table 1].

Production Example 6: Production of Compound No. 1-72

Compound No. 1-72

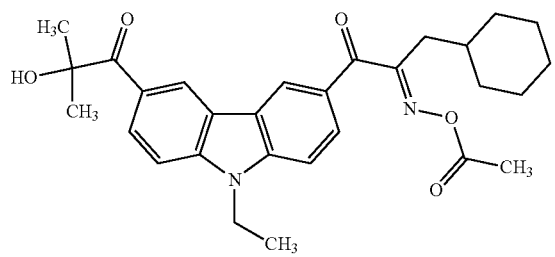

(1) Production of Intermediate 1-72-A

The compound 1-B (5.75 g, 11.9 mmol), THF (17.2 g), ion-exchanged water (17.2 g), and 48% aqueous sodium hydroxide solution (1.1 g) were added and allowed to react at room temperature for 24 hours. Extraction was performed with ethyl acetate and the resulting organic layer was washed with water three times, after which the solvent was removed, whereby an intermediate 1-72-A was obtained.

Compound No. 1-72-A

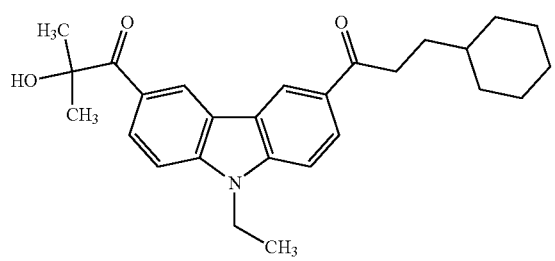

(2) Production of Compound No. 1-72

Thereafter, a compound No. 1-72 was obtained in the same manner as in Production Example 1. The NMR data of the thus obtained compound No. 1-72 is shown in [Table 1].

Production Example 7: Production of Compound No. 1-73

Compound No. 1-73

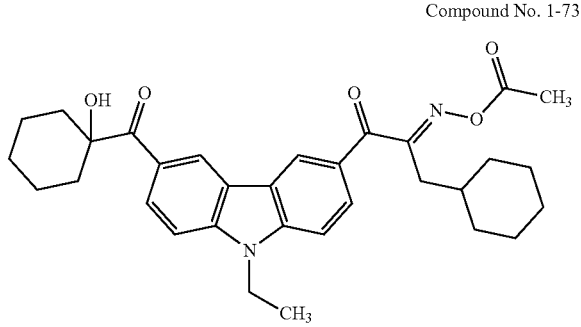 [SMILES: CCn1c2ccc(C(=O)/C(CC3CCCCC3)=N/OC(C)=O)cc2c2cc(C(=O)C3(O)CCCCC3)ccc21]

(1) Production of Intermediate 1-73-A

An intermediate 1-73-A was obtained in the same manner as in Example 1, except that the acid chloride used in the production of the intermediate 1-B was changed to cyclohexane carbonyl chloride.

Intermediate 1-73-A

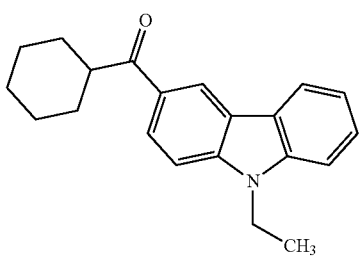

(2) Production of Intermediate 1-73-B

The intermediate 1-73-A (11.9 g, 39.0 mmol) and methylene chloride (50 g) were added, and bromine (6.8 g, 42.9 mmol) was slowly added thereto with ice cooling. These materials were allowed to react at room temperature for 1 hour, and the solvent was subsequently removed, whereby an intermediate 1-73-B was obtained.

Intermediate 1-73-B

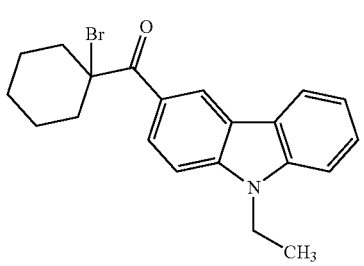

(3) Production of Intermediate 1-73-C

The intermediate 1-73-B (5.9 g, 15.6 mmol), THF (12.0 g), ion-exchanged water (12.0 g), and 48% aqueous sodium hydroxide solution (1.9 g) were added and allowed to react at room temperature for 24 hours. Extraction was performed with ethyl acetate and the resulting organic layer was washed with water three times, after which the solvent was removed, whereby an intermediate 1-73-C was obtained.

Intermediate 1-73-C

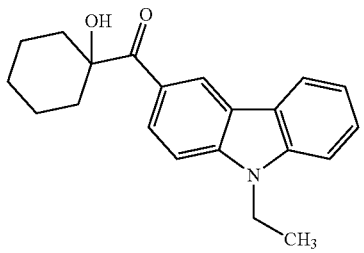

(4) Production of Intermediate 1-73-D

An intermediate 1-73-D was obtained in the same manner as in the production of the intermediate 1-A, except that ethylcarbazole was changed to the intermediate 1-73-C and 3-cyclohexylpropanoyl chloride was changed to octanoyl chloride.

Intermediate 1-73-D

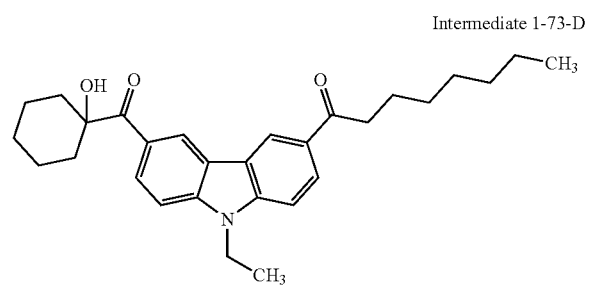 [SMILES: CCCCCCCC(=O)c1ccc2c(c1)c1cc(C(=O)C3(O)CCCCC3)ccc1n2CC]

(5) Production of Compound No. 1-73

A compound No. 1-73 was obtained in the same manner as in Production Example 1, except that the intermediate 1-D was changed to the intermediate 1-73-D.

Production Example 8: Production of Compound No. 1-74

Compound No. 1-74

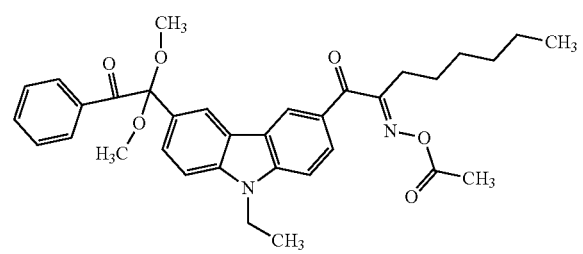

(1) Production of Intermediate 1-74-A

An intermediate 1-74-A was obtained as an isomer in the same manner as in the production of the intermediate 1-7-B. It is noted here that the intermediate 1-7-B of the compound No. 1-7 and the intermediate 1-74-A of the compound No. 1-74 are isomers produced by the same method and were purified and isolated using a silica gel column.

Intermediate 1-74-A

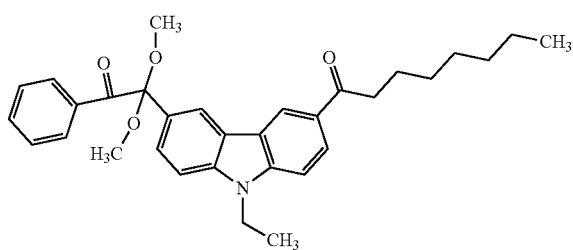

(2) Production of Compound No. 1-74

A compound No. 1-74 was obtained in the same manner as in Production Example 1, except that the intermediate 1-D was changed to the intermediate 1-74-A.

Production Example 9: Production of Compound No. 1-75

Compound No. 1-75

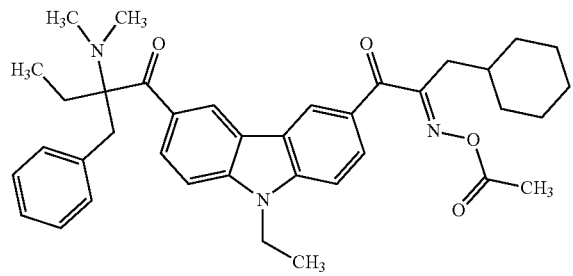

(1) Production of Intermediate 1-75-A

Intermediate 1-75-A

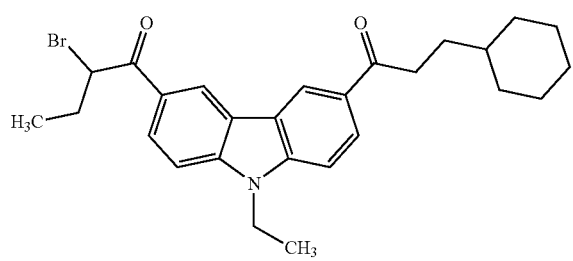

An intermediate 1-75-A was obtained in the same manner as the intermediate 1-B, except that 2-bromoisobutyryl bromide was changed to 2-bromobutyryl bromide.

(2) Production of Intermediate 1-75-B

Intermediate 1-75-B

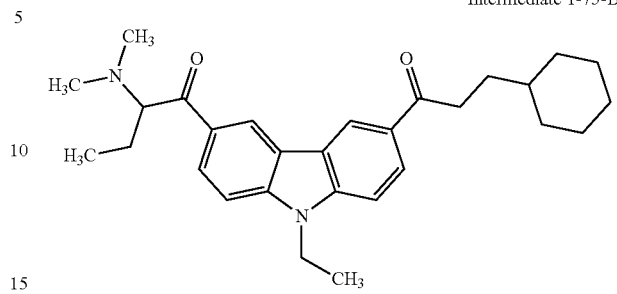

The intermediate 1-75-A (10.0 g, 20.7 mmol), acetone (30.0 g), 50% aqueous dimethylamine solution (5.6 g, 62.2 mol), and potassium carbonate (4.3 g, 31.1 mmol) were added and stirred at room temperature for 4 hours. After the reaction, ethyl acetate and ion-exchanged water were added to perform oil-water separation. The resulting organic layer was washed with water three times, and the solvent was subsequently removed, whereby an intermediate 1-75-B was obtained.

(3) Production of Intermediate 1-75-C

Intermediate 1-75-C

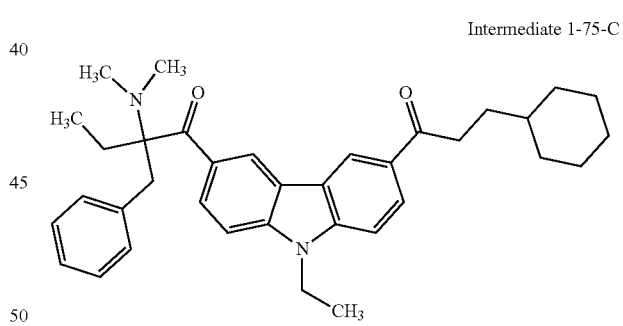

The intermediate 1-75-B (8.3 g, 18.6 mmol), ethyl acetate (30.0 g), ion-exchanged water (30.0 g), benzyl bromide (3.5 g, 20.5 mmol), and 48% sodium hydroxide (1.7 g, 20.5 mmol) were added and allowed to react at room temperature for 3 hours. After the reaction, ethyl acetate and ion-exchanged water were added to perform oil-water separation. The resulting organic layer was washed with water three times and the solvent was subsequently removed, after which the resultant was applied to a silica gel column, whereby an intermediate 1-75-C was obtained.

(4) Production of Compound No. 1-75

A compound No. 1-75 was obtained in the same manner as in Production Example 1, except that the intermediate 1-D was changed to the intermediate 1-75-C.

Production Example 10: Production of Compound No. 1-76

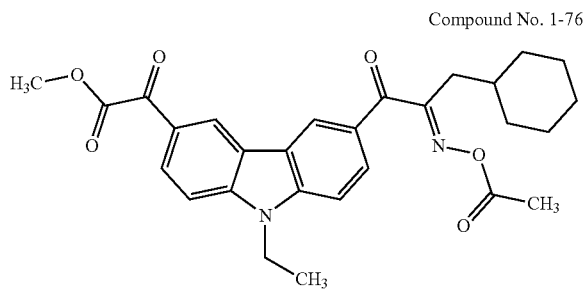 [SMILES: CCn1c2ccc(C(=O)C(=O)OC)cc2c2cc(C(=O)/C(CC3CCCCC3)=N/OC(C)=O)ccc21]

Compound No. 1-76

(1) Production of Intermediate 1-76-A

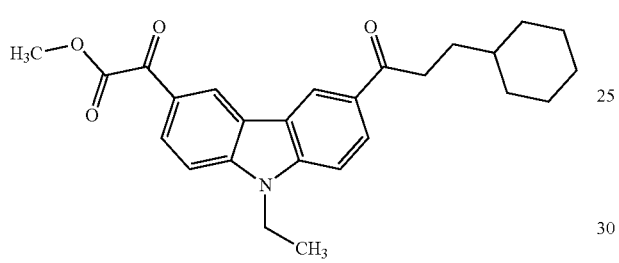

Intermediate 1-76-A

An intermediate 1-76-A was obtained in the same manner as the intermediate 1-B, except that 2-bromoisobutyryl bromide was changed to methyl chloroglyoxylate.

(2) Production of Compound No. 1-76

A compound No. 1-76 was obtained in the same manner as in Production Example 1, except that the intermediate 1-D was changed to the intermediate 1-76-A. The NMR data of the thus obtained compound No. 1-76 is shown in [Table 1].

Production Example 11: Production of Compound No. 2-1

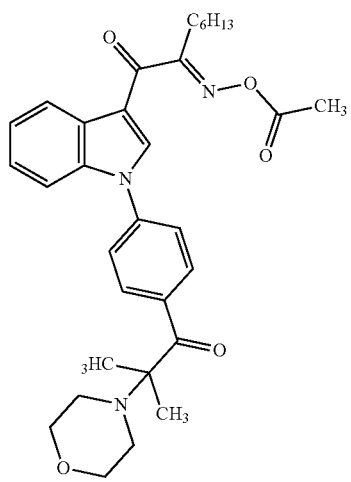

Compound No. 2-1

(1) Production of Intermediate 2-C

In a four-necked flask, the intermediate 2-A (12.7 g, 47.4 mmol), the intermediate 2-B (10.5 g, 43.1 mol), potassium carbonate (11.9 g, 86.3 mmol), and 60.0 g of dimethylformacetamide were added and heated to reflux for 12 hours in a nitrogen stream. After cooling the resultant to room temperature, ion-exchanged water and ethyl acetate were added to perform oil-water separation at 60° C. The resulting organic layer was washed with water three times while being heated to 60° C., and this organic layer was subsequently cooled to room temperature, after which the resulting precipitate was recovered by filtration to obtain an intermediate 2-C (8.5 g, yield: 57%).

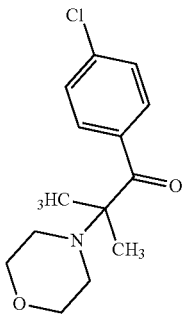

Intermediate 2-A

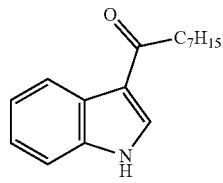

Intermediate 2-B

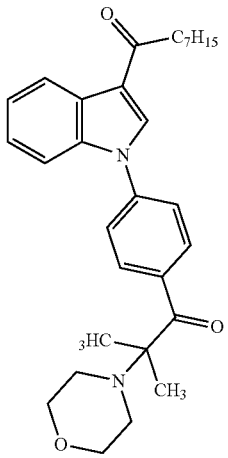

Intermediate 2-C (2) Production of compound No. 2-1

The intermediate 2-C (4.35 g, 9.16 mmol) and DMF (40.0 g) were added to a four-necked round-bottom flask, and 35% hydrochloric acid (2.00 g) and isobutyl nitrite (1.98 g, 10.1 mol) were added thereto dropwise with stirring and ice cooling, followed by 30-hour stirring at 40° C. Ion-exchanged water and ethyl acetate were added to the resultant to perform oil-water separation, and the resulting organic layer was washed with water three times. Subsequently, acetyl chloride (1.51 g, 19.2 mmol) and triethylamine (1.95 g, 19.2 mmol) were added to the organic layer with ice cooling. After stirring the resultant at room temperature for 1 hour, ion-exchanged water was added to perform oil-water separation, and the resulting organic layer was washed with water three times. After removing the solvent, the resultant was applied to a silica gel column (ethyl acetate/hexane=2/10), whereby a compound No. 2-1 was obtained (2.1 g, yield: 45%). The NMR data of the thus obtained compound No. 2-1 is shown in [Table 1].

Production Example 12: Production of Compound No. 3-1

Compound No. 3-1

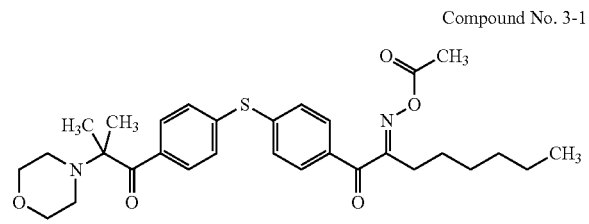 [SMILES: CCCCCC/C(=N\OC(C)=O)C(=O)c1ccc(Sc2ccc(C(=O)C(C)(C)N3CCOCC3)cc2)cc1]

A compound No. 3-1 was obtained in the same manner as in Production Example 1 except that, in the production of the intermediate 1-A, ethylcarbazole was changed to diphenyl sulfide and 3-cyclohexylpropanoyl chloride was changed to octanoyl chloride. The NMR data of the thus obtained compound No. 3-1 is shown in [Table 1].

Production Example 13: Production of Compound No. 4-71

Compound No. 4-71

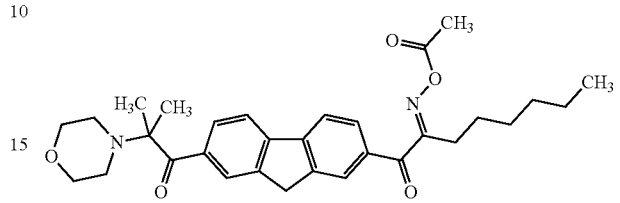

A compound No. 4-71 was obtained in the same manner as in Production Example 1 except that, in the production of the intermediate 1-A, ethylcarbazole was changed to fluorene and 3-cyclohexylpropanoyl chloride was changed to octanoyl chloride. The NMR data of the thus obtained compound No. 4-71 is shown in [Table 1].

Production Example 14: Production of Compound No. 4-72

Compound No. 4-72

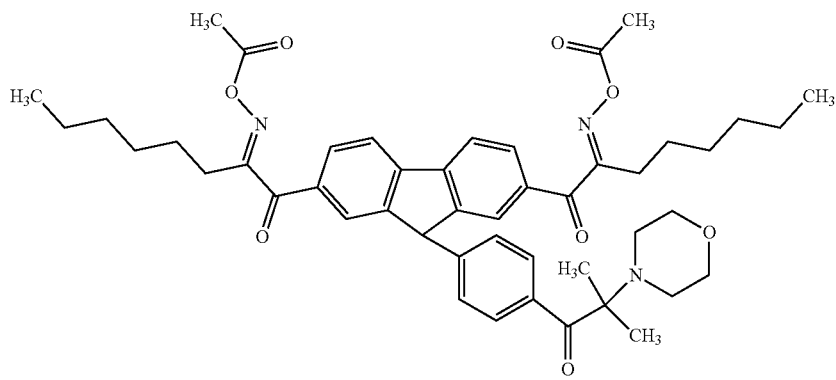

(1) Production of Intermediate 4-72-A

Aluminum chloride (309.56 g, 71.7 mmol) and 30.0 g of dichloroethane were added, and fluorene (3.97 g, 23.9 mmol) and octanoyl chloride (7.97 g, 49.0 mmol) were sequentially added thereto with ice cooling. These materials were allowed to react at room temperature for 1 hour, after which the resulting reaction solution was poured into ice water and the thus formed precipitate was recovered by filtration. This precipitate was washed with ion-exchanged water and methanol to obtain an intermediate 4-72-A.

Intermediate 4-72-A

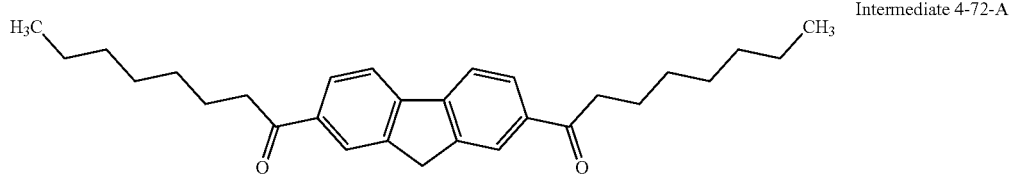 [SMILES: CCCCCCCC(=O)c1ccc2c(c1)Cc1cc(C(=O)CCCCCCC)ccc1-2]

(2) Production of Intermediate 4-72-B

Using the thus obtained intermediate 4-72-A, an intermediate 4-72-B was obtained in the same manner as in the synthesis of the intermediate 2-C.

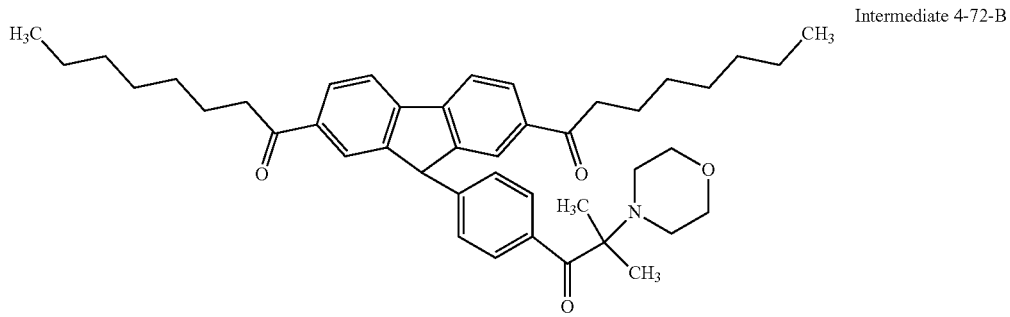 [SMILES: CCCCCCCC(=O)c1ccc2c(c1)C(c1ccc(C(=O)C(C)(C)N3CCOCC3)cc1)c1cc(C(=O)CCCCCCC)ccc1-2]

Intermediate 4-72-B (3) Production of Compound No. 4-72

A compound No. 4-72 was obtained in the same manner as in the production of the compound No. 2-1. The NMR data of the thus obtained compound No. 4-72 is shown in [Table 1].

Production Example 15: Production of Compound No. 6-1

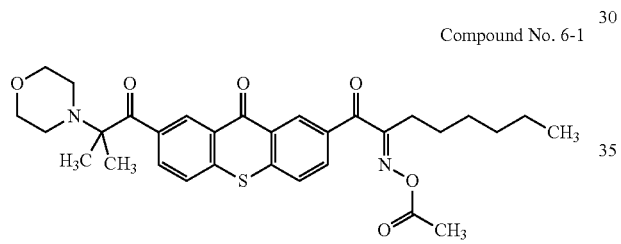

Compound No. 6-1

A compound No. 6-1 was obtained by the same method except that, in the production of the intermediate 1-A, ethylcarbazole was changed to thioxanthone and 3-cyclohexylpropanoyl chloride was changed to octanoyl chloride.

TABLE 1

| | Chemical shift/ppm (multiplicity, number of protons) |
|---|---|
| Compound No. 1-1 | 9.70 (s, 1H), 8.98 (s, 1H), 8.73 (d, 1H), 8.34 (d, 1H), 7.48 (d, 1H), 7.46 (d, 1H), 4.42 (q, 2H), 3.74 (m, 4H), 2.84 (d, 2H), 2.68 (m, 4H), 2.30 (s, 3H), 1.80-1.05 (m, 20H) |
| Compound No. 1-14 | 9.60 (s, 1H), 8.76 (d, 1H), 8.72 (s, 1H), 8.10 (d, 1H), 7.82 (d, 2H), 7.40-7.50 (m, 5H), 4.42 (q, 2H), 3.68 (m, 4H), 2.65 (m, 4H), 2.01 (s, 3H), 1.50 (t, 3H), 1.41 (s, 6H) |
| Compound No. 1-70 | 9.67 (s, 1H), 8.92 (s, 1H), 8.75 (d, 1H), 8.27 (d, 1H), 7.47 (d, 1H), 7.45 (d, 1H), 4.43 (q, 2H), 3.74 (m, 4H), 3.50 (m, 1H), 2.67 (d, 4H), 2.30 (s, 3H), 1.93 (q, 1H), 1.55-1.35 (m, 13H), 0.95 (s, 9H) |
| Compound No. 1-71 | 9.70 (s, 1H), 8.93 (s, 1H), 8.73 (d, 1H), 8.34 (d, 1H), 7.48 (d, 1H), 7.45 (d, 1H), 4.43 (g, 2H), 2.84 (d, 2H), 2.53 (m, 4H), 2.30 (s, 3H), 1.80-1.05 (m, 26H) |
| Compound No. 1-72 | 9.04 (s, 1H), 8.94 (s, 1H), 8.33 (d, 1H), 8.28 (d, 1H), 7.48 (m, 2H), 4.43 (q, 2H), 4.35 (s, 1H), 2.83 (d, 2H), 2.31 (s, 3H), 1.77 (s, 6H), 1.75-1.00 (m, 14H) |
| Compound No. 1-76 | 9.02 (s, 1H), 8.88 (s, 1H), 8.39 (d, 1H), 8.26 (d, 1H), 7.55 (s, 1H), 7.53 (s, 1H), 4.47 (q, 2H), 4.09 (s, 3H), 2.85 (m, 2H), 2.33 (s, 3H), 1.75-1.00 (m, 14H) |
| Compound No. 2-1 | 8.79 (d, 2H), 8.62 (s, 1H), 8.54 (d, 1H), 7.63 (d, 2H), 7.58 (d, 1H), 7.38 (m, 2H), 3.74 (m, 4H), 2.81 (t, 2H), 2.63 (m, 4H), 2.28 (s, 3H), 2.58 (m, 2H), 1.38 (s, 6H), 1.40-1.30 (m, 6H), 3.43 (m, 3H) |
| Compound No. 3-1 | 8.53 (d, 2H), 8.03 (d, 2H), 7.42 (d, 2H), 7.40 (d, 2H), 3.70 (q, 4H), 2.77 (t, 2H), 2.58 (d, 4H), 2.26 (s, 3H), 1.55 (m, 2H), 1.40-1.20 (m, 12H), 0.87 (t, 3H) |
| Compound No. 4-71 | 8.75 (d, 1H), 8.71 (s, 1H), 8.29 (s, 1H), 7.16 (d, 1H), 7.92 (d, 1H), 7.88 (d, 1H), 4.03 (s, 2H), 3.72 (m, 4H), 2.82 (t, 2H), 2.62 (m, 4H), 2.29 (s, 3H), 1.60 (m, 2H), 1.45-1.25 (m, 12H), 0.87 (t, 3H) |

TABLE 1-continued

| | Chemical shift/ppm (multiplicity, number of protons) |
|---|---|
| Compound No. 4-72 | 8.49 (d, 2H), 8.16 (d, 2H), 8.07 (s, 2H), 7.84 (d, 2H), 7.42 (d, 2H), 3.67 (m, 4H), 2.84 (s, 1H), 2.76 (t, 4H), 2.55 (m, 4H), 2.20 (s, 6H), 1.54 (m, 4H), 1.35-1.20 (m, 18H), 0.86 (t, 6H) |

[Production of Blue Pigment Dispersion No. 1]

As a dispersant and a colorant, DISPERBYK-161 (12.5 parts by mass; manufactured by BYK Japan K.K.) and PIGMENT BLUE 15:6 (15 parts by mass), respectively, were dispersed in PGMEA (72.5 parts by mass) using a bead mill to produce a blue pigment dispersion.

Examples 1 to 15 and Comparative Examples 1 to 4

Preparation of Polymerizable Compositions

Components were prepared in accordance with the respective formulations shown in [Table 2] and [Table 3] to obtain polymerizable compositions of Examples 1 to 15 and Comparative Examples 1 to 4. It is noted here that the numbers in these tables are in parts by mass.

A-1: Compound No. 1-1
A-2: Compound No. 1-7
A-3: Compound No. 1-14
A-4: Compound No. 1-70
A-5: Compound No. 1-71
A-6: Compound No. 1-72
A-7: Compound No. 1-73
A-8: Compound No. 1-74
A-9: Compound No. 1-75
A-10: Compound No. 1-76
A-11: Compound No. 2-1
A-12: Compound No. 3-1
A-13: Compound No. 4-71
A-14: Compound No. 4-72
A-15: Compound No. 6-1
A'-1: Compound No. A2-9
A'-2: 2-methyl-1-[4-(methylthio)phenyl]-2-morpholinopropan-1-one
B-1: SPC-3000 (carboxyl group-containing polymer; manufactured by Showa Denko K.K., solid content: 42.7%, PGMEA solution)
C-1: KAYARAD DPHA (ethylenically unsaturated compound; manufactured by Nippon Kayaku Co., Ltd.)
D-1: blue pigment dispersion No. 1
E-1: KBE-403 (coupling agent; manufactured by Shin-Etsu Chemical Co., Ltd.)
F-1: PGMEA (solvent)

[Evaluation of Cured Products Obtained from Polymerizable Compositions]

For the thus obtained polymerizable compositions and cured products thereof, the sensitivity and the brightness were evaluated by the following procedures. The results thereof are shown together in [Table 2] and [Table 3].

(Sensitivity)

Each polymerizable composition was spin-coated on a glass substrate (post-baking chromaticity coordinates (x, y)=(0.135, 0.098)), and the thus coated glass substrate was pre-baked at 90° C. for 120 seconds using a hot plate, followed by cooling at 23° C. for 60 seconds. Subsequently, the substrate was exposed to light (exposure gap=100 µm, exposure dose=40 mJ/cm$^2$) through a photomask (mask opening=30 µm) using a ultrahigh-pressure mercury lamp. The substrate was developed using a 0.04%-by-mass aqueous KOH solution as a developer, after which the substrate was thoroughly washed with water and post-baked at 230° C. for 20 minutes in a clean oven to fix a pattern. The thus obtained pattern was observed under an electron microscope, and the line width of the part corresponding to the mask opening was measured.

The pattern was evaluated as "A+" when the line width was 35 µm or greater, "A" when the line width was 32.5 µm or greater but less than 35 µm, "A−" when the line width was 30 µm or greater but less than 32.5 µm, or "B" when the line width was less than 30 µm. A greater line width means a higher sensitivity, and a substrate having a sensitivity of A+, A or A− can be preferably used as a color filter. A substrate having a sensitivity of A+ or A is more preferred, and a substrate having a sensitivity of A+ is particularly preferred. A substrate having a sensitivity of B cannot be used as a color filter.

(Brightness)

Each polymerizable composition was spin-coated on a glass substrate (post-baking chromaticity coordinates (x, y)=(0.135, 0.098)), and the thus coated glass substrate was pre-baked at 90° C. for 120 seconds using a hot plate, followed by cooling at 23° C. for 60 seconds. Subsequently, the substrate was exposed to light at 150 mJ/cm$^2$ using a ultrahigh-pressure mercury lamp and post-baked at 230° C. for 20 minutes in a clean oven to prepare an evaluation sample. From the transmittance at 380 to 780 nm of the thus obtained sample, the Y value was determined in accordance with JIS Z8701. A larger Y value means a higher brightness and a higher transmittance in the visible-light region, making the substrate more useful. A substrate having a Y value of 9.5 or higher can be used as a color filter, and a substrate having a Y value of 11.0 or higher can be particularly preferably used, while a substrate having a Y value of lower than 9.5 is not suitable as a color filter.

TABLE 2

| | Example 1 | Example 2 | Example 3 | Example 4 | Example 5 | Example 6 | Example 7 | Example 8 | Example 9 | Example 10 |
|---|---|---|---|---|---|---|---|---|---|---|
| A-1 | 1.9 | — | — | — | — | — | — | — | — | — |
| A-2 | — | 1.9 | — | — | — | — | — | — | — | — |
| A-3 | — | — | 1.9 | — | — | — | — | — | — | — |
| A-4 | — | — | — | 1.9 | — | — | — | — | — | — |
| A-5 | — | — | — | — | 1.9 | — | — | — | — | — |
| A-6 | — | — | — | — | — | 1.9 | — | — | — | — |
| A-7 | — | — | — | — | — | — | 1.9 | — | — | — |

TABLE 2-continued

| | Example 1 | Example 2 | Example 3 | Example 4 | Example 5 | Example 6 | Example 7 | Example 8 | Example 9 | Example 10 |
|---|---|---|---|---|---|---|---|---|---|---|
| A-8 | — | — | — | — | — | — | — | 1.9 | — | — |
| A-9 | — | — | — | — | — | — | — | — | 1.9 | — |
| A-10 | — | — | — | — | — | — | — | — | — | 1.9 |
| A-11 | — | — | — | — | — | — | — | — | — | — |
| A-12 | — | — | — | — | — | — | — | — | — | — |
| A-13 | — | — | — | — | — | — | — | — | — | — |
| A-14 | — | — | — | — | — | — | — | — | — | — |
| A-15 | — | — | — | — | — | — | — | — | — | — |
| A'-1 | — | — | — | — | — | — | — | — | — | — |
| A'-2 | — | — | — | — | — | — | — | — | — | — |
| B-1 | 100.0 | 100.0 | 100.0 | 100.0 | 100.0 | 100.0 | 100.0 | 100.0 | 100.0 | 100.0 |
| C-1 | 12.6 | 12.6 | 12.6 | 12.6 | 12.6 | 12.6 | 12.6 | 12.6 | 12.6 | 12.6 |
| D-1 | 120.1 | 120.1 | 120.1 | 120.1 | 120.1 | 120.1 | 120.1 | 120.1 | 120.1 | 120.1 |
| E-1 | 1.7 | 1.7 | 1.7 | 1.7 | 1.7 | 1.7 | 1.7 | 1.7 | 1.7 | 1.7 |
| F-1 | 186.0 | 186.0 | 186.0 | 186.0 | 186.0 | 186.0 | 186.0 | 186.0 | 186.0 | 186.0 |
| Total | 422.3 | 422.3 | 422.3 | 422.3 | 422.3 | 422.3 | 422.3 | 422.3 | 422.3 | 422.3 |
| Brightness | 11.0 | 11.0 | 11.0 | 11.0 | 11.0 | 11.0 | 11.0 | 11.1 | 11.1 | 11.1 |
| Sensitivity | A+ | A+ | A+ | A+ | A+ | A+ | A+ | A+ | A+ | A+ |

TABLE 3

| | Example 11 | Example 12 | Example 13 | Example 14 | Example 15 | Comparative Example 1 | Comparative Example 2 | Comparative Example 3 | Comparative Example 4 |
|---|---|---|---|---|---|---|---|---|---|
| A-1 | — | — | — | — | — | — | — | — | — |
| A-2 | — | — | — | — | — | — | — | — | — |
| A-3 | — | — | — | — | — | — | — | — | — |
| A-4 | — | — | — | — | — | — | — | — | — |
| A-5 | — | — | — | — | — | — | — | — | — |
| A-6 | — | — | — | — | — | — | — | — | — |
| A-7 | — | — | — | — | — | — | — | — | — |
| A-8 | — | — | — | — | — | — | — | — | — |
| A-9 | — | — | — | — | — | — | — | — | — |
| A-10 | — | — | — | — | — | — | — | — | — |
| A-11 | 1.9 | — | — | — | — | — | — | — | — |
| A-12 | — | 1.9 | — | — | — | — | — | — | — |
| A-13 | — | — | 1.9 | — | — | — | — | — | — |
| A-14 | — | — | — | 1.9 | — | — | — | — | — |
| A-15 | — | — | — | — | 1.9 | — | — | — | — |
| A'-1 | — | — | — | — | — | 1.9 | 3.8 | — | — |
| A'-2 | — | — | — | — | — | — | — | 1.9 | 9.5 |
| B-1 | 100.0 | 100.0 | 100.0 | 100.0 | 100.0 | 100.0 | 100.0 | 100.0 | 100.0 |
| C-1 | 12.6 | 12.6 | 12.6 | 12.6 | 12.6 | 12.6 | 12.6 | 12.6 | 12.6 |
| D-1 | 120.1 | 120.1 | 120.1 | 120.1 | 120.1 | 120.1 | 120.1 | 120.1 | 120.1 |
| E-1 | 1.7 | 1.7 | 1.7 | 1.7 | 1.7 | 1.7 | 1.7 | 1.7 | 1.7 |
| F-1 | 186.0 | 186.0 | 186.0 | 186.0 | 186.0 | 186.0 | 186.0 | 186.0 | 186.0 |
| Total | 422.3 | 422.3 | 422.3 | 422.3 | 422.3 | 422.3 | 424.2 | 422.3 | 429.9 |
| Brightness | 11.1 | 11.1 | 11.1 | 11.1 | 10.9 | 10.5 | 9.4 | 11.0 | 11.0 |
| Sensitivity | A | A− | A− | A | A | B | A− | B | B |

It is apparent from [Table 2] and [Table 3] that the polymerizable compositions according to the present invention were highly sensitive and the cured products according to the present invention had a high brightness. The oxime ester compound of the present invention is useful as a polymerization initiator since it yields a polymerizable composition and a cured product.

(Heat Resistance)

The compounds shown in [Table 4] were collected as samples, and the thermal weight reduction was measured for about 5 to 10 mg of each sample that was heated using a thermogravimetry/differential thermal analyzer (manufactured by SII NanoTechnology Inc., model: EXSTAR TG/DTA6200) in a nitrogen atmosphere of 200 mL/min at a heating initiation temperature of 30° C., a heating termination temperature of 500° C. and a heating rate of 10° C./min. The temperature at which the sample weight at 30° C. had been reduced by 10% was defined as "10% weight reduction temperature". It is noted here that a compound having a 10% weight reduction temperature of 230° C. or higher can be used as a photoradical polymerization initiator having excellent heat resistance.

TABLE 4

| | 10% thermal weight reduction temperature (° C.) |
|---|---|
| Compound No. 1-1 | 243 |
| Compound No. 1-14 | 240 |
| Compound No. 1-71 | 233 |

TABLE 4-continued

| | 10% thermal weight reduction temperature (° C.) |
|---|---|
| Compound No. 4-71 | 230 |
| Compound No. 4-72 | 234 |
| A'-2 | 220 |

It is apparent from [Table 4] that the oxime ester compound of the present invention has a high heat resistance; therefore, the oxime ester compound of the present invention is particularly useful as a photoradical polymerization initiator for an application that requires heat resistance.

The invention claimed is:

1. An oxime ester compound comprising, a structure represented by the following Formula (II):

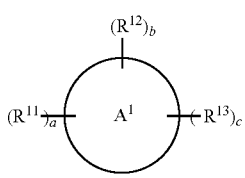

(II)

wherein, $A^1$ represents an aromatic ring having 6 to 20 carbon atoms;

$R^{11}$ represents a group represented by the following Formula (I);

$R^{12}$ represents a photoradical cleavable group containing no oxime ester group represented by the following Formula (IVα), (IVβ), (IVγ), (IVδ), (IVε), (IVζ), or (IVθ); a hydrocarbon group having 1 to 20 carbon atoms which is substituted with the photoradical cleavable group containing no oxime ester group; or a heterocycle-containing group having 2 to 20 carbon atoms which is substituted with the photoradical cleavable group containing no oxime ester group:

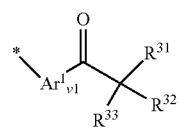

(IV α)

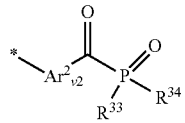

(IV β)

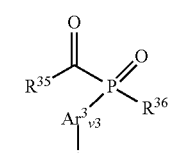

(IV γ)

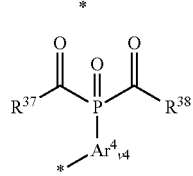

(IV δ)

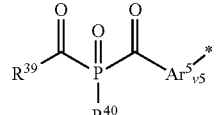

(IV ε)

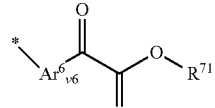

(IV ζ)

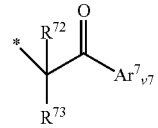

(IV θ)

in Formulae (IVα) to (IVθ), $R^{31}$ represents $OR^{41}$, $NR^{42}R^{43}$, or a heterocycle-containing group having 2 to 20 carbon atoms;

$R^{32}$ and $R^{33}$ each represent $R^{41}$ or $OR^{41}$;

$R^{32}$ and $R^{33}$ are optionally bound together to form a ring;

$R^{41}$ represents a hydrogen atom or a hydrocarbon group having 1 to 20 carbon atoms;

$R^{42}$ and $R^{43}$ each represent a hydrocarbon group having 1 to 20 carbon atoms;

$R^{71}$ represents a hydrocarbon group having 1 to 20 carbon atoms;

$R^{72}$ and $R^{73}$ each represent $R^{41}$ or $OR^{41}$;

$R^{34}$, $R^{35}$, $R^{36}$, $R^{37}$, $R^{38}$, $R^{39}$, $R^{40}$, $Ar^1$, $Ar^2$, $Ar^3$, $Ar^4$, $Ar^5$, $Ar^6$, and $Ar^7$ each represent an aryl group having 6 to 20 carbon atoms;

v1, v2, v3, v4, v5, and v6 each represent 0 or 1;

v7 represents 1; and

* represents a bond;

$R^{13}$ each independently represents a halogen atom, a nitro group, a cyano group, a hydrocarbon group having 1 to 20 carbon atoms, or a heterocycle-containing group having 2 to 20 carbon atoms;

one or more hydrogen atoms in the groups represented by $R^{12}$ and $R^{13}$ are optionally substituted with a halogen atom, a nitro group, a cyano group, a hydroxy group, an amino group, a carboxyl group, a methacryloyl group, an acryloyl group, an epoxy group, a vinyl group, a vinyl ether group, a mercapto group, an isocyanate group, or a heterocycle-containing group having 2 to 20 carbon atoms;

one or more methylene groups in the groups represented by $R^{12}$ are optionally substituted with —O—, —CO—, —COO—, —OCO—, —NR$^{14}$—, —NR$^{14}$CO—, —CS—, —SO$_2$—, —SCO—, —COS—, —OCS—, or CSO—, provided that oxygen atoms are not arranged adjacent to one another;

one or more methylene groups in the groups represented by $R^{13}$ are optionally substituted with —O—, —CO—, —COO—, —OCO—, —NR$^{14}$—, —NR$^{14}$CO—, —S—, —CS—, —SO$_2$—, —SCO—, —COS—, —OCS—, or CSO—, provided that oxygen atoms are not arranged adjacent to one another;

$R^{14}$ represents a hydrogen atom or a hydrocarbon group having 1 to 20 carbon atoms;

a represents an integer of 1 to 20 and, when a is an integer of 2 or larger, plural $R^{11}$s are optionally the same or different;

b represents an integer of 1 to 20 and, when b is an integer of 2 or larger, plural $R^{12}$s are optionally the same or different;

c represents an integer of 0 to 20 and, when c is an integer of 2 or larger, plural $R^{13}$s are optionally the same or different; and (a+b+c) is 20 or less;

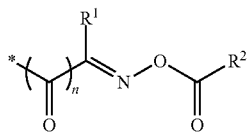 (I)

wherein, $R^1$ and $R^2$ each independently represent a hydrogen atom, a halogen atom, a nitro group, a cyano group, a hydrocarbon group having 1 to 20 carbon atoms, or a heterocycle-containing group having 2 to 20 carbon atoms;

one or more hydrogen atoms in the groups represented by $R^1$ and $R^2$ are optionally substituted with a halogen atom, a nitro group, a cyano group, a hydroxy group, an amino group, a carboxyl group, a methacryloyl group, an acryloyl group, an epoxy group, a vinyl group, a vinyl ether group, a mercapto group, an isocyanate group, or a heterocycle-containing group having 2 to 20 carbon atoms;

one or more methylene groups in the groups represented by $R^1$ and $R^2$ are optionally substituted with —O—, —CO—, —COO—, —OCO—, —$NR^3$—, —$NR^3$CO—, —S—, —CS—, —$SO_2$—, —SCO—, —COS—, —OCS—, or CSO—, provided that oxygen atoms are not arranged adjacent to one another;

$R^3$ represents a hydrogen atom or a hydrocarbon group having 1 to 20 carbon atoms;

n represents 0 or 1; and

* represents a bond.

2. The oxime ester compound according to claim 1, wherein $A^1$ is a structure represented by the following Formula (IIIα) or (IIIβ):

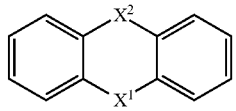 (III α)

in Formula (IIIα), $X^1$ represents an oxygen atom, a sulfur atom, a selenium atom, $CR^{21}R^{22}$, CO, or $NR^{23}$;

$X^2$ represents a single bond, no bond, an oxygen atom, a sulfur atom, a selenium atom, $CR^{21}R^{22}$, CO, or $NR^{23}$;

$R^{21}$, $R^{22}$, $R^{23}$ and $R^{24}$ each independently represent a hydrogen atom, a hydrocarbon group having 1 to 20 carbon atoms, or a heterocycle-containing group having 2 to 20 carbon atoms;

hydrogen atoms in the groups represented by $R^{21}$, $R^{22}$, $R^{23}$ and $R^{24}$ are optionally substituted with a halogen atom, a nitro group, a cyan group, a hydroxy group, a carboxyl group, or a heterocyclic group having 2 to 20 carbon atoms; and one or more methylene groups in the groups represented by $R^{21}$, $R^{22}$, $R^{23}$ and $R^{24}$ are optionally substituted with —O—, provided that oxygen atoms are not arranged adjacent to one another; or

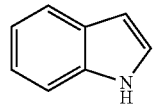 (III β)

3. The oxime ester compound according to claim 1, wherein $R^{12}$ in Formula (II) is the photoradical cleavable group containing no oxime ester group.

4. A polymerization initiator, comprising the oxime ester compound according to claim 1.

5. A polymerizable composition, comprising:
   (A) the polymerization initiator according to claim 4; and
   (B) an ethylenically unsaturated compound.

6. The polymerizable composition according to claim 5, further comprising (C) a colorant.

7. A cured product obtained from the polymerizable composition according to claim 5.

8. A color filter, comprising the cured product according to claim 7.

9. A display device, comprising the color filter according to claim 8.

10. A method of producing a cured product, the method comprising irradiating with light or curing by heating the polymerizable composition according to claim 5.

11. The oxime ester compound according to claim 2, wherein $R^{12}$ in Formula (II) is the photoradical cleavable group containing no oxime ester group.

12. A polymerization initiator, comprising the oxime ester compound according to claim 2.

13. A polymerization initiator, comprising the oxime ester compound according to claim 3.

* * * * *